United States Patent
Johnson et al.

(10) Patent No.: US 10,023,536 B2
(45) Date of Patent: Jul. 17, 2018

(54) SUPRAMETALLOGELS AND USES THEREOF

(71) Applicant: Massachusetts Institute of Technology, Cambridge, MA (US)

(72) Inventors: Jeremiah A. Johnson, Boston, MA (US); Niels Holten-Andersen, Allston, MA (US); Scott Charles Grindy, Cambridge, MA (US); Ken Kawamoto, Cambridge, MA (US); Aleksandr V. Zhukhovitskiy, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/270,959

(22) Filed: Sep. 20, 2016

(65) Prior Publication Data
US 2017/0073311 A1  Mar. 16, 2017

Related U.S. Application Data

(63) Continuation of application No. 14/617,747, filed on Feb. 9, 2015, now Pat. No. 9,447,129.

(60) Provisional application No. 61/937,052, filed on Feb. 7, 2014.

(51) Int. Cl.
| | |
|---|---|
| *A61K 47/22* | (2006.01) |
| *C07D 213/30* | (2006.01) |
| *C07F 15/00* | (2006.01) |
| *C07F 15/02* | (2006.01) |
| *C07F 15/04* | (2006.01) |
| *C08G 83/00* | (2006.01) |

(52) U.S. Cl.
CPC ............ *C07D 213/30* (2013.01); *A61K 47/22* (2013.01); *C07F 15/006* (2013.01); *C07F 15/0066* (2013.01); *C07F 15/02* (2013.01); *C07F 15/04* (2013.01); *C08G 83/008* (2013.01)

(58) Field of Classification Search
CPC .................... C07F 15/0066; A61K 47/22
See application file for complete search history.

(56) References Cited

U.S. PATENT DOCUMENTS

| | | |
|---|---|---|
| 4,359,425 A | 11/1982 | Totani et al. |
| 5,811,515 A | 9/1998 | Grubbs et al. |
| 8,067,505 B2 | 11/2011 | Harris et al. |
| 9,381,253 B2 | 7/2016 | Johnson et al. |
| 9,447,129 B2 | 9/2016 | Johnson et al. |
| 2003/0065023 A1 | 4/2003 | Swindell et al. |
| 2005/0109976 A1* | 5/2005 | Fuchs ................. B82Y 25/00 252/62.54 |

(Continued)

OTHER PUBLICATIONS

Extended European Search Report for EP 14782253.0, dated Nov. 11, 2016.

(Continued)

*Primary Examiner* — Timothy R Rozof
(74) *Attorney, Agent, or Firm* — Wolf, Greenfield & Sacks, P.C.

(57) ABSTRACT

The disclosure provides nanostructures (e.g., nanospheres and nano-paddlewheels) formed through transition metal-ligand (e.g., Pd(II)-, Ni(II)-, or Fe(II)-ligand of Formula (A)) coordination and junction self-assembly. The disclosure also provides supramolecular complexes that include the nanostructures connected by divalent linkers Y. The provided supramolecular complexes are able to form gels (e.g., hydrogels). The gels are suprametallogels and exhibited excellent mechanical properties without sacrificing self-healing and showed high robustness and storage modulus. The present disclosure further provides compositions (e.g., gels) that include the nanostructures or supramolecular complexes and optionally an agent (e.g., small molecule), where the nanostructures and the nanostructure moieties of the supramolecular complexes may encapsulate and slowly release the agent. The nanostructures, supramolecular complex, and compositions may be useful in delivering an agent to a subject, tissue, or cell, as super-absorbent materials, and in treating a disease (e.g., a genetic diseases, proliferative disease (e.g., cancer or benign neoplasm), hematological disease, neurological disease, gastrointestinal disease (e.g., liver disease), spleen disease, respiratory disease (e.g., lung disease), painful condition, genitourinary disease, musculoskeletal condition, infectious disease, inflammatory disease, autoimmune disease, psychiatric disorder, or metabolic disorder).

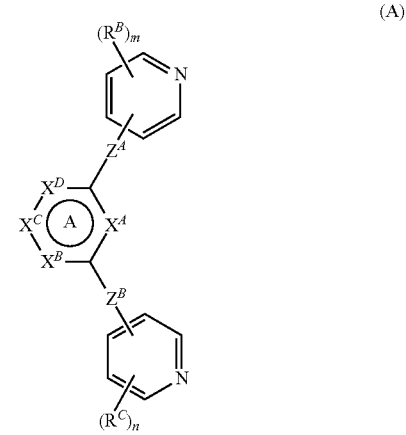

35 Claims, 34 Drawing Sheets

(56) References Cited

U.S. PATENT DOCUMENTS

| | | |
|---|---|---|
| 2011/0300219 A1 | 12/2011 | Lippard et al. |
| 2015/0225438 A1 | 8/2015 | Johnson et al. |
| 2016/0296631 A1 | 10/2016 | Johnson et al. |
| 2017/0073311 A1 | 3/2017 | Johnson et al. |

OTHER PUBLICATIONS

International Search Report and Written Opinion for Application No. PCT/US2014/033554, dated Aug. 29, 2014.

International Preliminary Report on Patentability for Application No. PCT/US2014/033554, dated Oct. 22, 2015.

International Search Report and Written Opinion for Application No. PCT/US2015/015032, dated May 8, 2015.

International Preliminary Report on Patentability for Application No. PCT/US2015/015032, dated Aug. 18, 2016.

Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.

Amouri et al., Host-guest interactions: design strategy and structure of an unusual cobalt cage that encapsulates a tetrafluoroborate anion. Angew Chem Int Ed Engl. Jul. 18, 2005;44(29):4543-6.

Anderson, Late Transition Metal Complexes of Pentafluorophenylphosphino-Pincer Ligands. Doctoral Thesis. Victoria University of Wellington. 2012:ii, iii, 32.

Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.

Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.

Barbour et al., an intermolecular (H2O)10 cluster in a solid-state supramolecular complex. Nature. 1998;393(6686): 671-673.

Barrett et al., pH-Based Regulation of Hydrogel Mechanical Properties Through Mussel-Inspired Chemistry and Processing. Advanced Functional Materials. Mar. 6, 2013;23(9):1111-1119.

Beck et al., Multistimuli, multiresponsive metallo-supramolecular polymers. J Am Chem Soc. Nov. 19, 2003;125(46):13922-3.

Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.

Bunzen et al., Self-assembly of M24L48 polyhedra based on empirical prediction. Angew Chem Int Ed Engl. Mar. 26, 2012;51(13):3161-3. doi: 10.1002/anie.201108731.

Burnworth et al., Decoupling Optical Properties in Metallo-Supramolecular Poly (p-phenylene ethynylene)s. Macromolecules. 2008;41(6):2157-2163.

Burts et al., Using EPR to Compare PEG-branch-nitroxide "Bivalent-Brush Polymers" and Traditional PEG Bottle-Brush Polymers: Branching Makes a Difference. Macromolecules. 2012;45(20):8310-18.

Caiolfa et al., Polymer-bound camptothecin: initial biodistribution and antitumour activity studies. J Control Release. Mar. 1, 2000;65(1-2):105-19.

Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.

Campos-Fernández et al., Fine-tuning the ring-size of metallacyclophanes: a rational approach to molecular pentagons. J Am Chem Soc. Jan. 31, 2001;123(4):773-4.

Castilla et al., Stereochemistry in subcomponent self-assembly. Acc Chem Res. Jul. 15, 2014;47(7):2063-73. doi: 10.1021/ar5000924. Epub May 2, 2014.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Chifotides et al., Anion-π interactions in supramolecular architectures. Acc Chem Res. Apr. 16, 2013;46(4):894-906. doi: 10.1021/ar300251k. Epub Mar. 11, 2013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4– Guest Anions. European Journal of Inorganic Chemistry. Oct. 2009;(29-30):4396-4400. doi: 10.1002/ejic.200900606.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Duncan, The dawning era of polymer therapeutics. Nat Rev Drug Discov. May 2003;2(5):347-60.

Eryazici et al., Two Large-Pore Metal-Organic Frameworks Derived from a Single Polytopic Strut. Crystal Growth & Design. Mar. 7, 2012;12(3):1075-1080.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2012;137(30):9722-9. doi: 10.1021/jacs.5b05507. Epub Jul. 23, 2015.

Fullenkamp et al., Mussel-Inspired Histidine-Based Transient Network Metal Coordination Hydrogels. Macromolecules. Jan. 18, 2013;46(3):1167-1174.

Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Greenwald et al., Effective drug delivery by PEGylated drug conjugates. Adv Drug Deliv Rev. Feb. 10, 2003;55(2):217-50.

(56) References Cited

OTHER PUBLICATIONS

Grumbley et al., Photoresponsive Polymers Containing Nitrobenzyl Esters via Ring-Opening Metathesis Polymerization. Macromolecules. 2011;44(20):7956-61.

Hackelbusch et al., Chain Dynamics in Supramolecular Polymer Networks. Macromolecules. 2013;46(15):6273-6286.

Hackelbusch et al., Multiresponsive Polymer Hydrogels by Orthogonal Supramolecular Chain Cross-Linking. Macromolecules. 2014;47(12):4028-4036.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Hirakawa et al., Removal of Perchlorate Anion from an Aqueous Solution by Encapsulation in an Anion-templated Self-assembled Molecular Capsule. Chemistry Letters. 2009;38(3):290-291.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huinink et al., Topotecan versus paclitaxel for the treatment of recurrent epithelial ovarian cancer. J Clin Oncol. Jun. 1997;15(6):2183-93.

Huynh, Novel Polymeric Micelles via RAFT Polymerization for Platinum Drug Delivery. Doctoral Thesis. The University of New South Wales. 2012:i, 57-58.

Jamieson et al., Structure, Recognition, and Processing of Cisplatin-DNA Adducts. Chem Rev. Sep. 8, 1999;99(9):2467-98.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Lee et al., Mussel-Inspired Adhesives and Coatings. Annu Rev Mater Res. Aug. 1, 2011;41:99-132.

Lee et al., Single-molecule mechanics of mussel adhesion. Proc Natl Acad Sci U S A. Aug. 29, 2006;103(35):12999-3003. Epub Aug. 18, 2006.

Leininger et al., Self-assembly of discrete cyclic nanostructures mediated by transition metals. Chem Rev. Mar. 8, 2000;100(3):853-908.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Surface Properties of Bottlebrush Polymer Thin Films. Macromolecules. 2012;45(17):7118-7127.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 4, 2010.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

(56) References Cited

OTHER PUBLICATIONS

Liu et al., Particles without a Box: Brush-first Synthesis of Photodegradable PEG Star Polymers under Ambient Conditions. J Vis Exp. 2013;80:e50874, doi:10.3791/50874.

Loveless et al., Chemoresponsive viscosity switching of a metallosupramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Moghimi et al., Long-circulating and target-specific nanoparticles: theory to practice. Pharmacol Rev. Jun. 2001;53(2):283-318.

Nair et al., Modulating mechanical properties of self-assembled polymer networks by multi-functional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nishiyama et al., Novel cisplatin-incorporated polymeric micelles can eradicate solid tumors in mice. Cancer Res. Dec. 15, 2003;63(24):8977-83.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sengupta et al., Temporal targeting of tumour cells and neovasculature with a nanoscale delivery system. Nature. Jul. 28, 2005;436(7050):568-72.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Tam et al., Recent advances in metallogels. Chem Soc Rev. Feb. 21, 2013;42(4):1540-67. doi: 10.1039/c2cs35354g. Epub Jan. 8, 2013.

Tominaga et al., Finite, spherical coordination networks that self-organize from 36 small components. Angew Chem Int Ed Engl. Oct. 25, 2004;43(42):5621-5.

Tsuji et al., Facile Palladium catalyzed decarboxylative allylation of active methylene compounds under neutral conditions using allylic carbonates. Tetrahedron Letters. 1982;23(46):4809-12.

Wang et al., Advances of cancer therapy by nanotechnology. Cancer Res Treat. Mar. 2009;41(1):1-11. doi: 10.4143/crt.2009.41.1.1. Epub Mar. 31, 2009.

Weng et al., Control of Gel Morphology and Properties of a Class of Metallo-Supramolecular Polyers by Good/Poor Solvent Environments. Macromolecules. 2009;42(1):236-246.

Weng et al., Effect of monomer structure on the gelation of a class of metallo-supramolecular polymers. Soft Matter. 2009;5(23):4647-4657.

Weng et al., Structural origin of the thixotropic behavior of a class of metallosupramolecular gels. Tetrahedron. Jul. 30, 2007;63(31):7419-7431.

Weng et al., Understanding the mechanism of gelation and stimuli-responsive nature of a class of metallo-supramolecular gels. J Am Chem Soc. Sep. 6, 2006;128(35):11663-72.

Westhaus et al., Triggered release of calcium from lipid vesicles: a bioinspired strategy for rapid gelation of polysaccharide and protein hydrogels. Biomaterials. Mar. 2001;22(5):453-62.

Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.

Xing et al., A stable metal coordination polymer gel based on a calix[4]arene and its 'uptake' of non-ionic organic molecules from the aqueous phase. Chem Commun (Camb). Feb. 21, 2002;(4):362-3.

Xing et al., Design of coordination polymer as stable catalytic systems. Chemistry. Nov. 4, 2002;8(21):5028-32.

Xing et al., Spontaneous Enrichment of Organic Molecules from Aqueous and Gas Phases into a Stable Metallogel. Langmuir. 2002;18:9654-9658.

Xu et al., Mechanism of Shear Thickening in Reversibly Cross-linked Supramolecular Polymer Networks. Macromolecules. Apr. 13, 2010;43(7):3556-3565.

Xu et al., Scaling Laws in Supramolecular Polymer Networks. Macromolecules. 2011;44(13):5465-5472.

Xu et al., Strain Hardening and Strain Softening of Reversibly Cross-linked Supramolecular Polymer Networks. Macromolecules. Sep. 27, 2011;44(18):7478-7488.

Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.

Yan et al., Particle carriers for combating multidrug-resistant cancer. ACS Nano. Nov. 26, 2013;7(11):9512-7. doi: 10.1021/nn405632s. Epub Nov. 11, 2013.

Yan et al., Supramolecular polymers with tunable topologies via hierarchical coordination-driven self-assembly and hydrogen bond-

(56) References Cited

OTHER PUBLICATIONS ing interfaces. Proc Natl Acad Sci U S A. Sep. 24, 2013;110(39):15585-90. doi: 10.1073/pnas.1307472110. Epub Sep. 9, 2013.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
Yount et al., Small-molecule dynamics and mechanisms underlying the macroscopic mechanical properties of coordinatively cross-linked polymer networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.
Zhang et al., Active cross-linkers that lead to active gels. Angew Chem Int Ed Engl. Oct. 25, 2013;52(44):11494-8. doi: 10.1002/anie.201304437. Epub Sep. 12, 2013.
Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.
Zhao et al., Rheological Behavoir of Shear-Responsive Metallo-Supramolecular Gels. Macromolecules. 2004;37(10):3529-3531.
Zhou et al., Counting primary loops in polymer gels. Proc Natl Acad Sci U S A. Nov. 20, 2012;109(47):19119-24. doi: 10.1073/pnas.1213169109. Epub Nov. 6, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
Allen et al., Chemically crosslinked isoreticular metal-organic frameworks. Chem Commun (Camb). Apr. 21, 2013;49(31):3200-2. doi: 10.1039/c3cc40635k. Epub Mar. 14, 2013.
Allen et al., Exploration of chemically cross-linked metal-organic frameworks. Inorg Chem. Jul. 7, 2014;53(13):7014-9. doi: 10.1021/ic500951b. Epub Jun. 19, 2014.
Altintas et al., ATRP-based polymers with modular ligation points under thermal and thermomechanical stress. Polym. Chem., Feb. 2015;6:2854-68.
Binauld et al., Precise Synthesis of Molecularly Defined Oligomers and Polymers by Orthogonal Iterative Divergent/Convergent Approaches. Macromol. Rapid Commun., 32: 147-168. doi:10.1002/marc.201000548.
Brown et al., Halide-induced supramolecular ligand rearrangement. J Am Chem Soc. Nov. 10, 2004;126(44):14316-7.
Burnworth et al., Optically healable supramolecular polymers. Nature. Apr. 21, 2011;472(7343):334-7. doi: 10.1038/nature09963.
Calvez et al., One step synthesis of MOF-polymer composites. RSC Adv., 2016;6:17314-7.
Chakrabarty et al., Supramolecular coordination: self-assembly of finite two- and three-dimensional ensembles. Chem Rev. Nov. 9, 2011;111(11):6810-918. doi: 10.1021/cr200077m. Epub Aug. 24, 2011.
Cook et al., Biomedical and biochemical applications of self-assembled metallacycles and metallacages. Acc Chem Res. Nov. 19, 2013;46(11):2464-74. doi: 10.1021/ar400010v. Epub Jun. 20, 2013.
Cook et al., Metal-organic frameworks and self-assembled supramolecular coordination complexes: comparing and contrasting the design, synthesis, and functionality of metal-organic materials. Chem Rev. Jan. 9, 2013;113(1):734-77. doi: 10.1021/cr3002824. Epub Nov. 2, 2012.
Cook et al., Recent Developments in the Preparation and Chemistry of Metallacycles and Metallacages via Coordination. Chem Rev. Aug. 12, 2015;115(15):7001-45. doi: 10.1021/cr5005666. Epub Mar. 27, 2015.
Eryazici et al., Square-planar Pd(II), Pt(II), and Au(III) terpyridine complexes: their syntheses, physical properties, supramolecular constructs, and biomedical activities. Chem Rev. Jun. 2008;108(6):1834-95. doi: 10.1021/cr0781059.
Fujita et al., Coordination assemblies from a Pd(II)-cornered square complex. Acc Chem Res. Apr. 2005;38(4):371-80.
Fujita et al., Metal-directed self-assembly of two- and three-dimensional synthetic receptors. Chem. Soc. Rev., 1998;27:417-25. doi: 10.1039/A827417Z.
Fujita et al., Self-Assembly of M30L60 Icosidodecahedron. Chem 2016;1:91.
Fujita et al., Self-assembly of ten molecules into nanometre-sized organic host frameworks. Nature Nov. 1995;378:469-71. doi:10.1038/378469a0.
Furukawa et al., Structuring of metal-organic frameworks at the mesoscopic/macroscopic scale. Chem Soc Rev. Aug. 21, 2014;43(16):5700-34. doi: 10.1039/c4cs00106k.
Furukawa et al., The chemistry and applications of metal-organic frameworks. Science. Aug. 30, 2013;341(6149):1230444. doi: 10.1126/science.1230444.
Gamage et al., MOF-5-Polystyrene: Direct Production from Monomer, Improved Hydrolytic Stability, and Unique Guest Adsorption. Angew Chem Int Ed Engl. Sep. 19, 2016;55(39):12099-103. doi: 10.1002/anie.201606926. Epub Aug. 24, 2016.
Hardy et al., Generation of metallosupramolecular polymer gels from multiply functionalized grid-type complexes. New J. Chem., 2012;36:668-73.
Hosono et al., Metal-Organic Polyhedral Core as a Versatile Scaffold for Divergent and Convergent Star Polymer Synthesis. J Am Chem Soc. May 25, 2016;138(20):6525-31. doi: 10.1021/jacs.6b01758. Epub May 11, 2016.
Jansze et al., Ligand Aspect Ratio as a Decisive Factor for the Self-Assembly of Coordination Cages. J Am Chem Soc. Feb. 17, 2016;138(6):2046-54. doi: 10.1021/jacs.5b13190. Epub Feb. 8, 2016.
Jiang et al., Thiophene-coated functionalized M12L24 spheres: synthesis, characterization, and electrochemical properties. Chem Asian J. Oct. 2012;7(10):2230-4. doi: 10.1002/asia.201200413. Epub Jul. 9, 2012.
Johnson et al., Construction of Linear Polymers, Dendrimers, Networks, and Other Polymeric Architectures by Copper-Catalyzed Azide-Alkyne Cycloaddition "Click" Chemistry. Macromol Rapid Commun Jul. 2008;29(12-13):1052-72.
Johnson et al., Synthesis of degradable model networks via ATRP and click chemistry. J Am Chem Soc. May 24, 2006;128(20):6564-5.
Kawamoto et al., Dual Role for 1,2,4,5-Tetrazines in Polymer Networks: Combining Diels-Alder Reactions and Metal Coordination to Generate Functional Supramolecular Gels. ACS Macro Letters 2015;4(4):458-61. doi: 10.1021/acsmacrolett.5b00221.
Kikuchi et al., Stepwise DNA condensation by a histone-mimic peptide-coated M12L24 spherical complex. Chem. Sci., 2014;5:3257-60.
Kuppler et al., Potential applications of metal-organic frameworks. Coord. Chem. Rev. 2009;253:3042-66.
Li et al., Cross-linked supramolecular polymer gels constructed from discrete multi-pillar[5]arene metallacycles and their multiple stimuli-responsive behavior. J Am Chem Soc. Jun. 18, 2014;136(24):8577-89. doi: 10.1021/ja413047r. Epub Mar. 11, 2014.
Li et al., Design and synthesis of an exceptionally stable and highly porous metal-organic framework. Nature Nov. 1999;402:276-79. doi:10.1038/46248.
Li et al., Metallo/clusto hybridized supramolecular polymers. Soft Matter. Dec. 7, 2014;10(45):9038-53. doi: 10.1039/c4sm01684j.

(56) References Cited

OTHER PUBLICATIONS

Liu et al., Composites of metal-organic frameworks and carbon-based materials: preparations, functionalities and applications. J. Mater. Chem. A, 2016;4:3584-616.

Lutz et al., From precision polymers to complex materials and systems. Nat Rev Mat, 2016;1:1. doi:10.1038/natrevmats.2016.24.

Matyjaszewski et al., Nanostructured functional materials prepared by atom transfer radical polymerization. Nat Chem. Jul. 2009;1(4):276-88. doi: 10.1038/nchem.257. Epub Jun. 22, 2009.

McConnell et al., Stimuli-Responsive Metal-Ligand Assemblies. Chem Rev. Aug. 12, 2015;115(15):7729-93. doi: 10.1021/cr500632f. Epub Apr. 16, 2015.

McDonald et al., Polymer@MOF@MOF: "grafting from" atom transfer radical polymerization for the synthesis of hybrid porous solids. Chem. Commun. 2015;51:11994-6.

Meng et al., Controlling the transmission of stereochemical information through space in terphenyl-edged Fe4L6 cages. J Am Chem Soc. Aug. 31, 2011;133(34):13652-60. doi: 10.1021/ja205254s. Epub Aug. 9, 2011.

Nitschke et al., Construction, substitution, and sorting of metallo-organic structures via subcomponent self-assembly. Acc Chem Res. Feb. 2007;40(2):103-12.

Olenyuk et al., Self-assembly of nanoscale cuboctahedra by coordination chemistry. Nature. Apr. 29, 1999;398(6730):796-9.

Oliveri et al., Heteroligated supramolecular coordination complexes formed via the halide-induced ligand rearrangement reaction. Acc Chem Res. Dec. 2008;41(12):1618-29. doi: 10.1021/ar800025w.

Pluth et al., Proton-mediated chemistry and catalysis in a self-assembled supramolecular host. Acc Chem Res. Oct. 20, 2009;42(10):1650-9. doi: 10.1021/ar900118t.

Pollino et al., Cross-linked and functionalized 'universal polymer backbones' via simple, rapid, and orthogonal multi-site self-assembly. Tetrahedron, 60(34), 7205-7215. DOI: 10.1016/j.tet.2004.05.055.

Reboul et al., Mesoscopic architectures of porous coordination polymers fabricated by pseudomorphic replication. Nat Mater. Jun. 24, 2012;11(8):717-23. doi: 10.1038/nmat3359.

Rodenas et al., Metal-organic framework nanosheets in polymer composite materials for gas separation. Nat Mater. Jan. 2015;14(1):48-55. doi: 10.1038/nmat4113. Epub Nov. 2, 2014.

Sato et al., Remarkable stabilization of M(12)L(24) spherical frameworks through the cooperation of 48 Pd(II)-pyridine interactions. J Am Chem Soc. May 6, 2009;131(17):6064-5. doi: 10.1021/ja900676f.

Semino et al., Microscopic Model of the Metal-Organic Framework/Polymer Interface: A First Step toward Understanding the Compatibility in Mixed Matrix Membranes. ACS Appl Mater Interfaces. Jan. 13, 2016;8(1):809-19. doi: 10.1021/acsami.5b10150. Epub Dec. 22, 2015.

Seredyuk et al., Spin-crossover and liquid crystal properties in 2D cyanide-bridged Fe(II)-M(I/II) metalorganic frameworks. Inorg Chem. Nov. 1, 2010;49(21):10022-31. doi: 10.1021/ic101304v.

Smulders et al., Integrative self-sorting synthesis of a Fe8Pt6L24 cubic cage. Angew Chem Int Ed Engl. Jul. 2, 2012;51(27):6681-5. doi: 10.1002/anie.201202050. Epub Jun. 5, 2012.

Stadler et al., Formation of RACK- and grid-type metallosupramolecular architectures and generation of molecular motion by reversible uncoiling of helical ligand strands. Chemistry. Jun. 2, 2006;12(17):4503-22.

Stang et al., Self-Assembly, Symmetry, and Molecular Architecture: Coordination as the Motif in the Rational Design of Supramolecular Metallacyclic Polygons and Polyhedra. Acc. Chem. Res., 1997;30(12):502-18. DOI: 10.1021/ar9602011.

Stock et al., Synthesis of Metal-Organic Frameworks (MOFs): Routes to Various MOF Topologies, Morphologies, and Composites. Chem. Rev., 2012;112(2):933-69.

Uemura et al., Polymerization reactions in porous coordination polymers. Chem Soc Rev. May 2009;38(5):1228-36. doi: 10.1039/b802583p. Epub Feb. 3, 2009.

Wang et al., A supramolecular approach to combining enzymatic and transition metal catalysis. Nat Chem. Feb. 2013;5(2):100-3. doi: 10.1038/nchem.1531. Epub Jan. 6, 2013.

Wang et al., Block Co-PolyMOCs by Stepwise Self-Assembly. J Am Chem Soc. Aug. 24, 2016;138(33):10708-15. doi: 10.1021/jacs.6b06712. Epub Aug. 16, 2016.

Wang et al., Star PolyMOCs with Diverse Structures, Dynamics, and Functions by Three-Component Assembly. Angew Chem Int Ed Engl. Jan. 2, 2017;56(1):188-192. doi: 10.1002/anie.201609261. Epub Dec. 5, 2016.

Wood et al., Two-stage directed self-assembly of a cyclic [3]catenane. Nat Chem. Apr. 2015;7(4):354-8. doi: 10.1038/nchem.2205.

Xie et al., Construction of a highly symmetric nanosphere via a one-pot reaction of a tristerpyridine ligand with Ru(II). J Am Chem Soc. Jun. 11, 2014;136(23):8165-8. doi: 10.1021/ja502962j. Epub May 22, 2014.

Xie et al., Hydrophobic-Driven, Metallomacrocyclic Assembly— Towards Quantitative Construction. Eur. J. Inorg. Chem. 2016;11:1671-7.

Xie et al., Precise Molecular Fission and Fusion: Quantitative Self-Assembly and Chemistry of a Metallo-Cuboctahedron. Angew. Chem., 2015;54:9224-9. doi:10.1002/ange.201503609.

Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.

Yang et al., Supramolecular Polymers: Historical Development, Preparation, Characterization, and Functions. Chem Rev. Aug. 12, 2015;115(15):7196-239. doi: 10.1021/cr500633b. Epub Mar. 13, 2015.

Zhang et al., Challenges and recent advances in MOF-polymer composite membranes for gas separation. Inorg. Chem. Front., 2016;3:896-909. DOI: 10.1039/C6QI00042H.

Zhang et al., Metal-organic gels: From discrete metallogelators to coordination polymers. Coordination Chemistry Reviews Apr. 2013:257(7-8):1373-1408.

Zhang et al., Polymer-Metal-Organic Frameworks (polyMOFs) as Water Tolerant Materials for Selective Carbon Dioxide Separations. J Am Chem Soc. Jan. 27, 2016;138(3):920-5. doi: 10.1021/jacs.5b11034. Epub Jan. 13, 2016.

Zhao et al., Chiral amide directed assembly of a diastereo- and enantiopure supramolecular host and its application to enantioselective catalysis of neutral substrates. J Am Chem Soc. Dec. 18, 2013;135(50):18802-5. doi: 10.1021/ja411631v. Epub Dec. 5, 2013.

Zheng et al., Construction of Smart Supramolecular Polymeric Hydrogels Cross-linked by Discrete Organoplatinum(II) Metallacycles via Post-Assembly Polymerization. J Am Chem Soc. Apr. 13, 2016;138(14):4927-37. doi: 10.1021/jacs.6b01089. Epub Mar. 29, 2016.

Zhou et al., Introduction to metal-organic frameworks. Chem Rev. Feb. 8, 2012;112(2):673-4. doi: 10.1021/cr300014x. Epub Jan. 26, 2012.

Zhukhovitskiy et al., Highly branched and loop-rich gels via formation of metal-organic cages linked by polymers. Nat Chem. Jan. 2016;8(1):33-41. doi: 10.1038/nchem.2390. Epub Nov. 16, 2015.

Zhukhovitskiy et al., Polymer Structure Dependent Hierarchy in PolyMOC Gels. Macromolecules, 2016;49(18):6896-902.

* cited by examiner

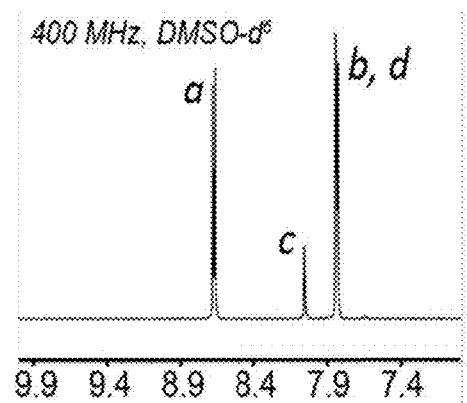
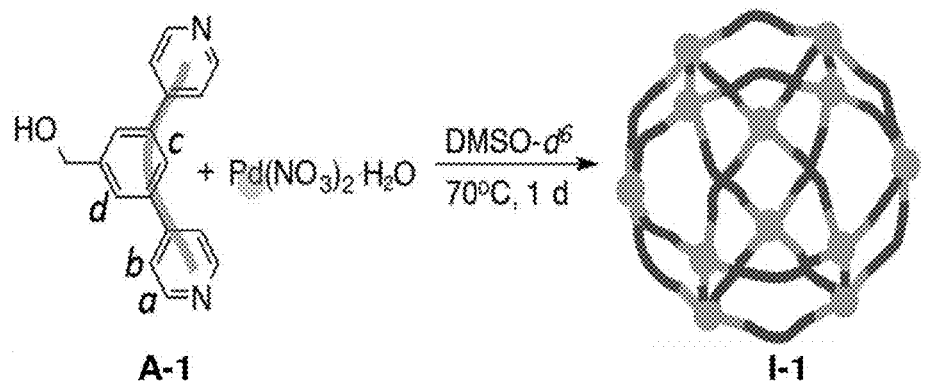
Figure 1B
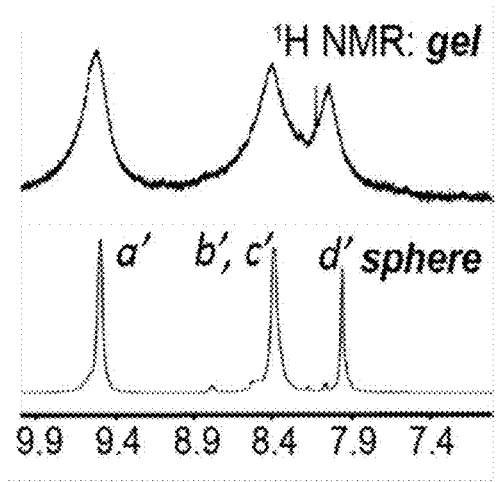
Figure 1C

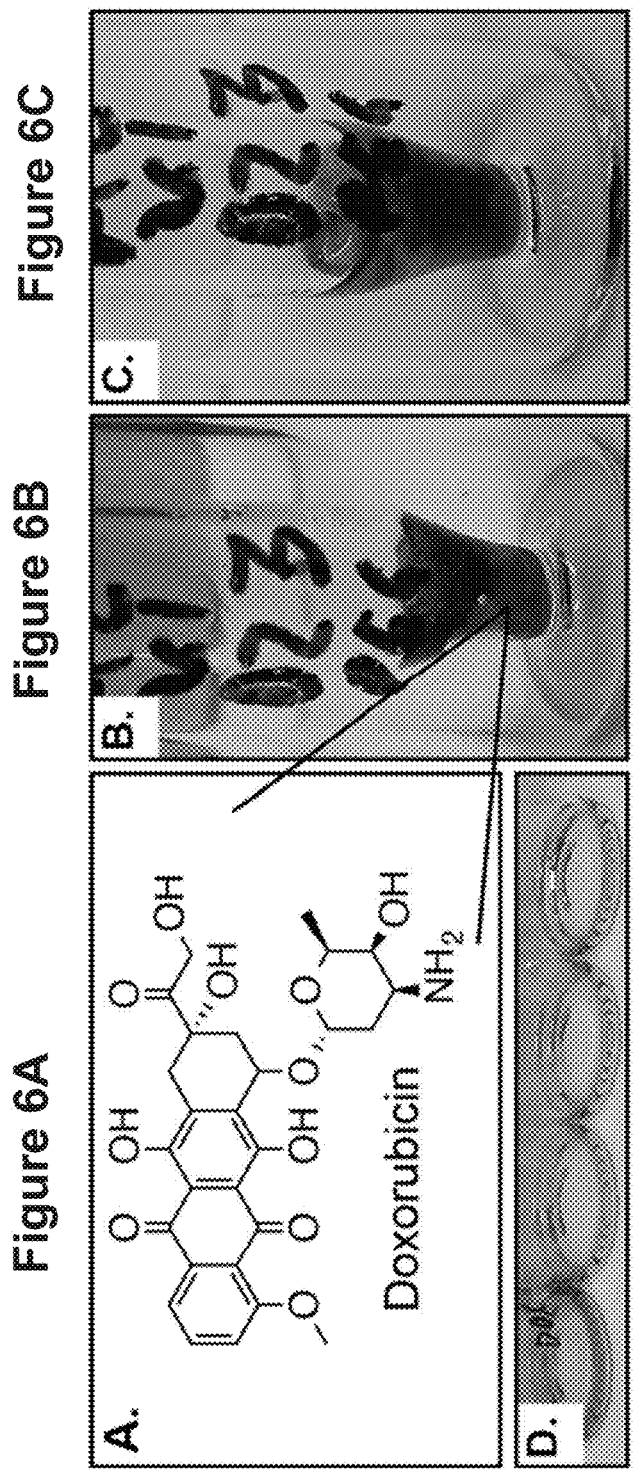

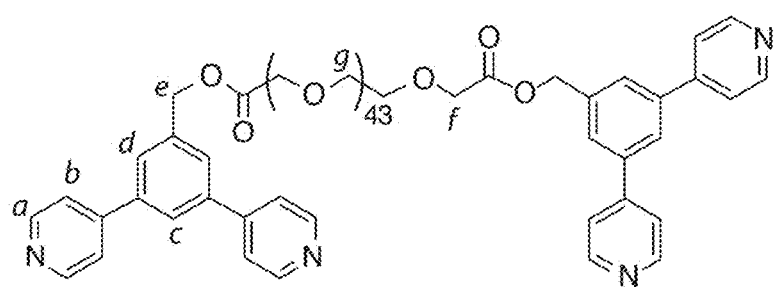
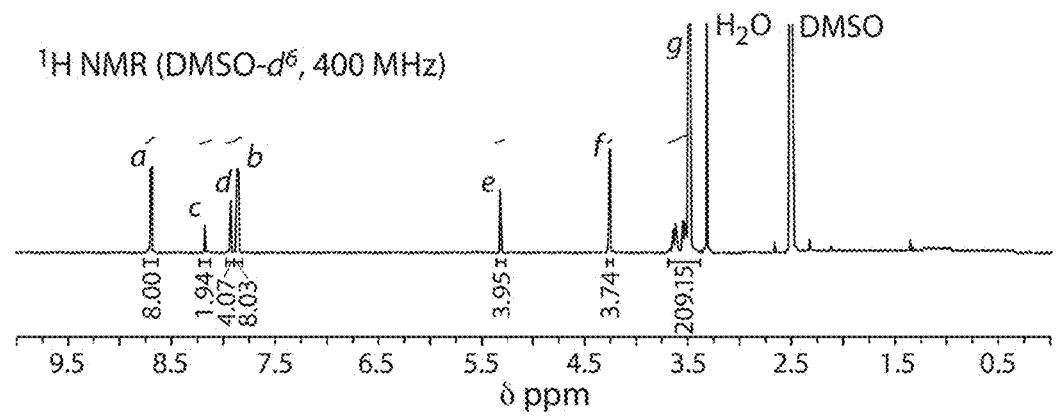
Figure 12

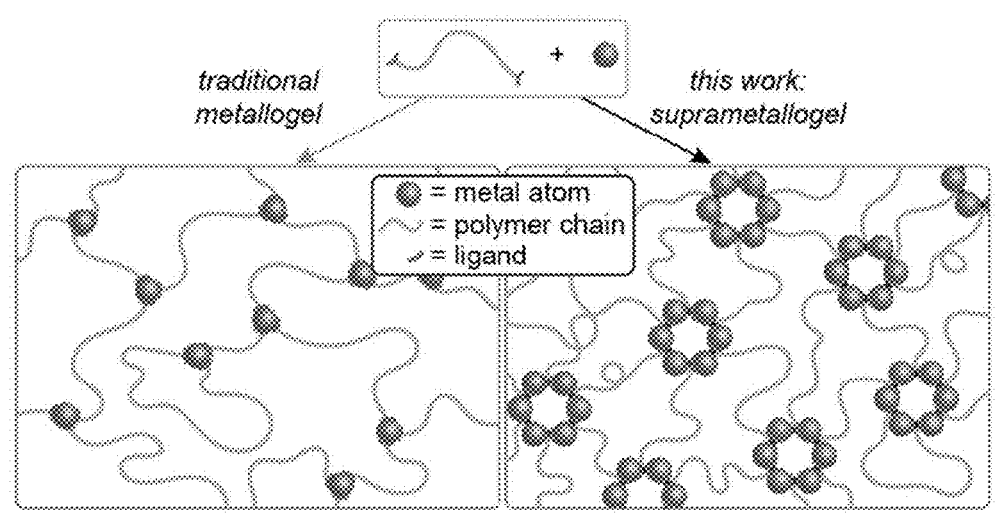
Figure 16A
Figure 16B
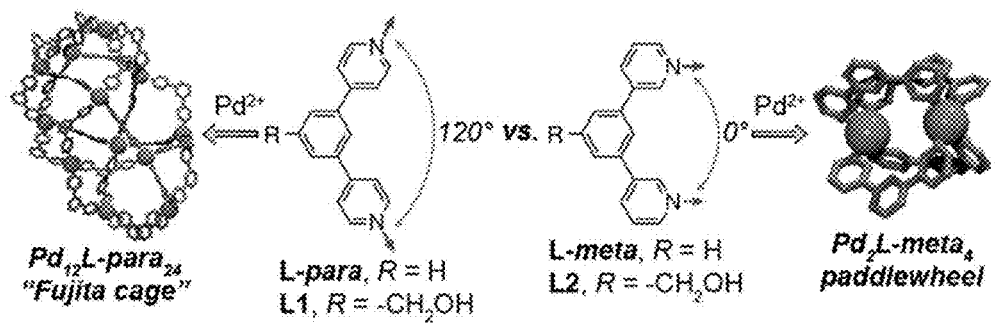
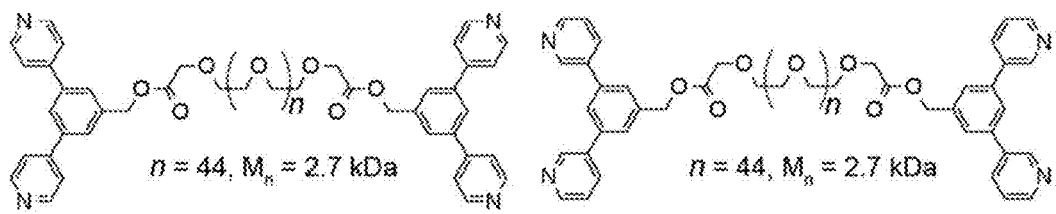
Figure 16C

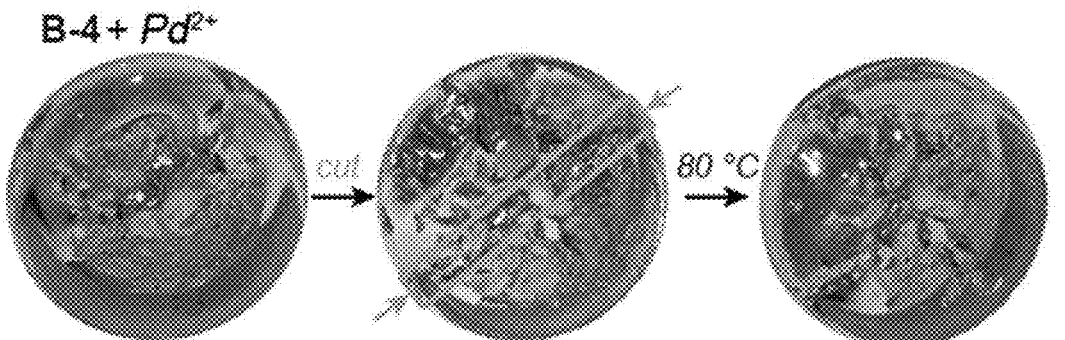
Figure 22A  Figure 22B  Figure 22C complete healing
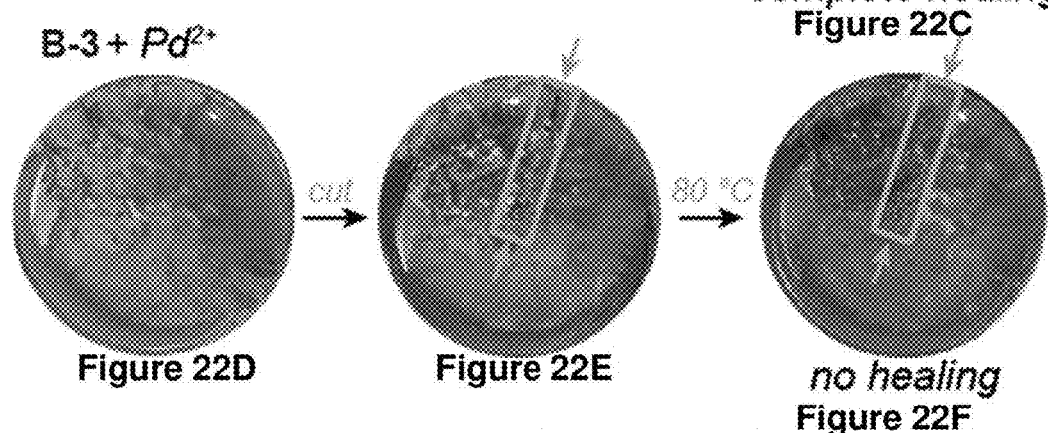
Figure 22D  Figure 22E  Figure 22F no healing
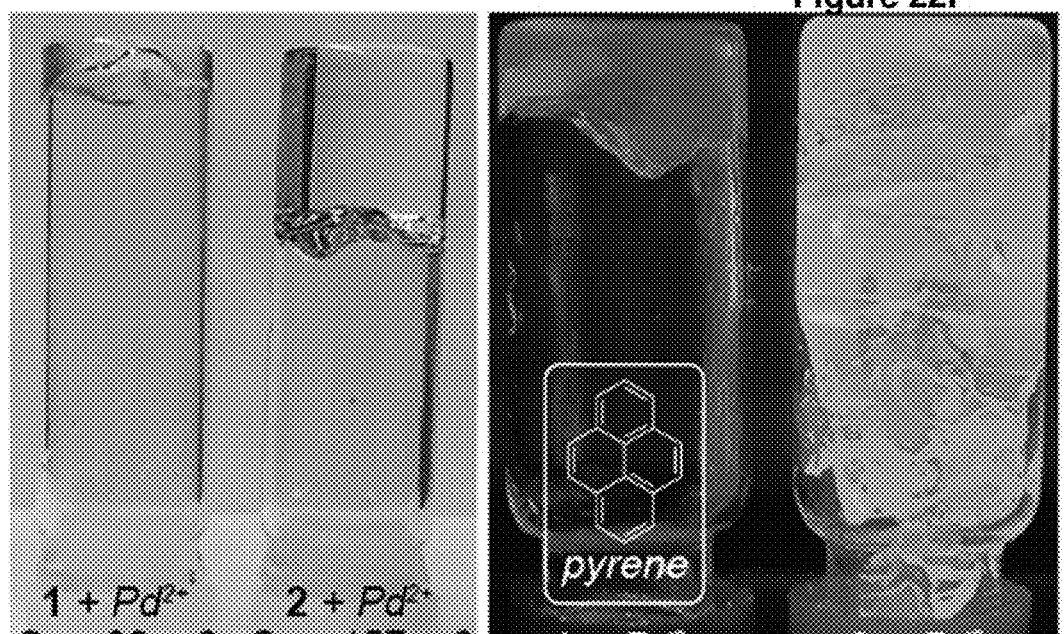
Figure 22G  Figure 22H (I-A)

(I-B)

SUPRAMETALLOGELS AND USES THEREOF

RELATED APPLICATIONS

The present application is a continuation of and claims priority under 35 U.S.C. § 120 to U.S. patent application Ser. No. 14/617,747, filed Feb. 9, 2015, and now issued as U.S. Pat. No. 9,447,129, which claims priority under 35 U.S.C. § 119(e) to U.S. provisional patent application, U.S. Ser. No. 61/937,052, filed Feb. 7, 2014, each of which is incorporated herein by reference.

GOVERNMENT SUPPORT

This invention was made with Government support under grant number CHE-1334703 awarded by the National Science Foundation. The Government has certain rights in the invention.

BACKGROUND OF THE INVENTION

Synthetic gels (e.g., synthetic hydrogels) constitute a class of materials useful in biomedicine. One of the first such applications for hydrogels was soft contact lenses invented by Wichterle and Lim. The gel used by Wichterle and Lim was composed of a covalently crosslinked poly(hydroxyethyl methacrylate (p(HEMA)). Such covalently-linked gels typically are typically quite robust but suffer from inability to self-heal when damaged. They also cannot be injected because they don't flow at relevant timescales, even under a high shear stress.

To complement these materials, metal-ligand coordination-linked gels have been developed where coordination complexation between metal ions and ligands were one or the sole crosslinking motif (Holten-Andersen et al., *Proceedings of the National Academy of Sciences of the United States of America*, 2011, 108, 2651-2655; Holten-Andersen et al., *Journal of Materials Chemistry B*, 2014, 2, 2467-2472; Barrett et al., *Advanced functional materials*, 2013, 23, 1111-1119; Fullenkamp et al., *Macromolecules*, 2013, 46, 1167-1174; Menyo et al., *Soft matter*, 2013, 9:10314-10323). In particular, much of the work thus far has focused primarily on demonstrating the mechanical properties of gels using different metal-ligand pairs. For example, Fullenkamp et al. studied histidine hydrogels with $Zn^{2+}$, $Cu^{2+}$, $Co^{2+}$, and $Ni^{2+}$ as the central atoms in coordination complexes (Fullenkamp et al., *Macromolecules*, 2013, 46, 1167-1174); Holten-Andersen et al. studied 3,4-dihydroxyphenylalanine (DOPA) hydrogels with $Fe^{3+}$, $V^{3+}$, and $Al^{3+}$ the central atoms (Holten-Andersen et al., *Journal of Materials Chemistry B*, 2014, 2, 2467-2472); and Menyo et al. studied hydrogels using DOPA and chemical modifications of DOPA using $Fe^{3+}$ as metal centers (Menyo et al., *Soft matter*, 2013, 9:10314-10323). While these metal-ligand coordination-linked gels are able to flow at a high shear stress and to self-heal due to the dynamic nature of the coordination bonding, they typically lack robustness and storage modulus of covalently linked gels. Therefore, there remains a need for new gels with improved properties.

SUMMARY OF THE INVENTION

Synthetic gels are typically formed through the use of strong, static covalent bonds or relatively weak, dynamic hydrogen bonds, van der Waals, hydrophobic or ionic interactions, or metal-ligand coordination. Gels formed entirely from the former suffer from an inability to shear-thin or heal upon fracture, while those formed from the latter are generally subject to viscous flow even under weak forces. Hierarchical assembly of multivalent dynamic species within a gel network can potentially overcome these limitations and introduce novel material properties. The present disclosure provides suprametallogels that form via metallosupramolecular assembly. Compared to conventional metallogels, the suprametallogels described herein behave as elastic solids at low oscillatory angular frequencies and exhibit high storage moduli. The suprametallogels bridge the gap between traditional metallogels and discrete metallosupramolecular assemblies.

In one aspect, the present disclosure provides nanostructures (e.g., nanospheres (nanocages) and nano-paddlewheels) formed through metal-ligand (e.g., transition metal-ligand of Formula (A)) coordination and junction self-assembly. The present disclosure also provides supramolecular complexes that include nanostructures described herein connected by divalent linkers Y. The provided supramolecular complexes are able to swell in various solvents (including water) without dissolution and to form a new class of gels, "suprametallogels." The gels described herein exhibited better mechanical properties without sacrificing self-healing than conventional gels and showed higher robustness and storage modulus than conventional nanostructures. The nanostructures, and the nanostructure moieties of a supramolecular complex or gel described herein, may encapsulate and slowly release an agent (e.g., a small molecule). The nanostructures, supramolecular complex, and compositions (e.g., gels) may be useful in delivering effectively and efficiently an agent to a subject, tissue, or cell. The supramolecular complexes and compositions (e.g., gels) may also be able to absorb a large amount of a fluid (e.g., absorb at least 100 times by weight of the fluid, compared to the weight of the supramolecular complex or the dry weight of the composition (weight of the composition minus the weight of the fluid included in the composition) and, therefore, may be useful as super-absorbent materials.

In one aspect, the present disclosure provides nanostructures comprising:
(i) a plurality of a transition metal ion; and
(ii) a plurality of a ligand;
wherein each instance of the transition metal ion and two or more instances of the ligand form through coordination bonds a coordination complex; and
wherein the average outer diameter of the nanostructure is between about 1 nm and about 100 nm, inclusive.

In certain embodiments, a nanostructure described herein comprises:
(i) x instances of a transition metal ion, wherein x is an integer between 2 and 60, inclusive; and
(ii) 2x instances of a ligand of Formula (A):

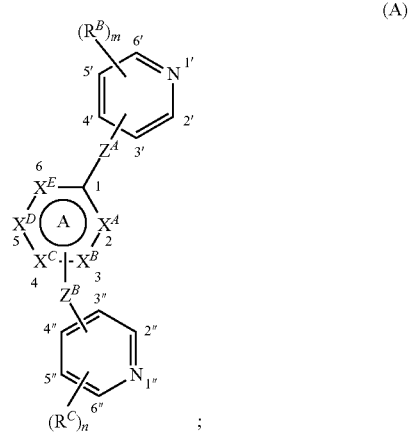

(A)

;

wherein:

Ring A is a substituted or unsubstituted phenyl ring or a substituted or unsubstituted, 5- or 6-membered, monocyclic heteroaryl ring;

each instance of $X^A$, $X^B$, $X^C$, and $X^D$ is independently O, S, N, $NR^{A1}$, C, or $CR^{A2}$;

$X^E$ is absent, N, or $CR^{A2}$;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)O$R^a$, —C(=O)N($R^a$)$_2$, or a nitrogen protecting group;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

m is 0, 1, 2, 3, or 4;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

n is 0, 1, 2, 3, or 4;

$Z^A$ is a bond or a substituted or unsubstituted $C_{1-4}$ hydrocarbon chain, optionally wherein one or more chain atoms are independently replaced with —O—, —S—, —N$R^{ZA}$—, —N=, or =N—, wherein each instance of $R^{ZA}$ is independently hydrogen, substituted or unsubstituted $C_{1-6}$ alkyl, or a nitrogen protecting group;

$Z^B$ is a bond or a substituted or unsubstituted $C_{1-4}$ hydrocarbon chain, optionally wherein one or more chain atoms are independently replaced with —O—, —S—, or —N$R^{ZB}$—, wherein each instance of $R^{ZB}$ is independently hydrogen, substituted or unsubstituted $C_{1-6}$ alkyl, or a nitrogen protecting group;

wherein each instance of the transition metal ion and two instances of the ligand of Formula (A) form through coordination bonds a coordination complex;

wherein each of the coordination bonds is formed between an instance of the transition metal ion and the nitrogen atom labeled with 1' or 1" of an instance of the ligand of Formula (A);

wherein the x instances of the transition metal ion and the 2x instances of the ligand of Formula (A) form through the coordination bonds a substantially spherical or substantially paddlewheel structure; and wherein the average outer diameter of the nanostructure is between about 1 nm and about 100 nm, inclusive.

In certain embodiments, the x instances of the transition metal ion and the 2x instances of the ligand of Formula (A) form through the coordination bonds a substantially spherical structure. When the x instances of the transition metal ion and the 2x instances of the ligand of Formula (A) form through the coordination bonds a substantially spherical structure, the nanostructure is a nanosphere. In certain embodiments, the x instances of the transition metal ion and the 2x instances of the ligand of Formula (A) form through the coordination bonds a substantially paddlewheel structure. When the x instances of the transition metal ion and the 2x instances of the ligand of Formula (A) form through the coordination bonds a substantially paddlewheel structure, the nanostructure is a nano-paddlewheel.

In certain embodiments, the nanosphere has icosidodecahedral symmetry. In certain embodiments, a nanosphere described herein is of Formula (I-A) as shown in FIG. 29, or a salt thereof, wherein each instance of the black dot represents the transition metal ion, each instance of the gray line represents the ligand of Formula (A), and each black line represents the coordination bond.

In certain embodiments, the nanosphere has icosidodecahedral symmetry. In certain embodiments, a nanosphere described herein is of Formula (I-B) as shown in FIG. 30, or a salt thereof, wherein each instance of the black dot represents the transition metal ion, and each instance of the gray line represents the ligand of Formula (A).

In another aspect, the present disclosure provides supramolecular complexes comprising:

(a) two or more instances of a nanostructure described herein; and (b) at least one instance of Y, wherein each instance of Y is independently a substituted or unsubstituted, saturated or unsaturated $C_{30-3000}$ hydrocarbon chain, optionally wherein one or more chain atoms are independently replaced with —O—, —S—, —N$R^Y$—, =N—, or —N=, wherein each instance of $R^a$ is independently hydrogen, substituted or unsubstituted $C_{1-6}$ alkyl, or a nitrogen protecting group;

wherein each instance of Y is independently directly covalently attached to an instance of the ligand of Formula (A) and directly covalently attached to another instance of the ligand of Formula (A), and at least two instances of the nanostructure are directly covalently connected by at least one instance of Y.

In certain embodiments, a supramolecular complex described herein forms a gel (suprametallogel) upon contact with a fluid (e.g., water). In certain embodiments, a nanostructure or supramolecular complex described herein may further comprise at least one instance of an anionic counterion.

In another aspect, the present disclosure provides methods of preparing the nanostructures, the methods including reacting a ligand of Formula (A), or a salt thereof, with a transition metal salt.

In another aspect, the present disclosure provides methods of preparing the supramolecular complexes, the methods including complexing a macromer of Formula (B) or (C), or a salt thereof, with a transition metal salt:

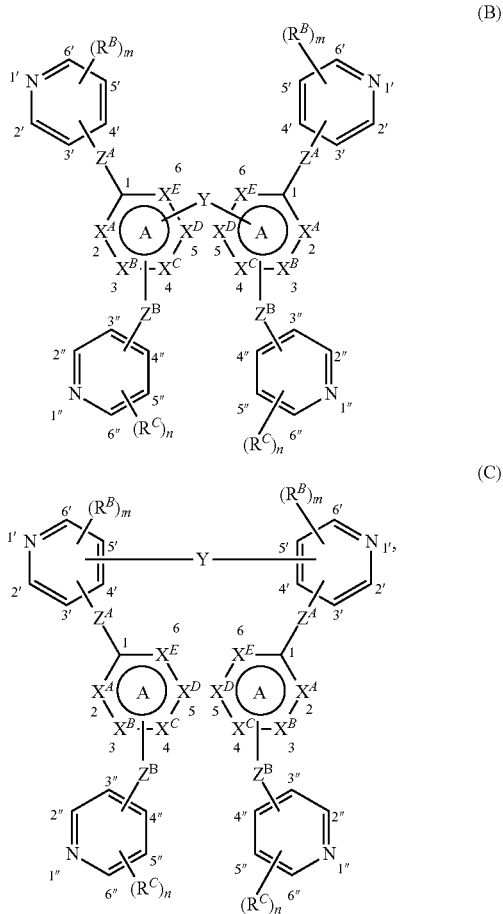

in the presence of a fluid and optionally an agent.

The transition metal of the transition metal ion or transition metal salt may be Pd(II), Ni(II), Fe(II), Rh(I), Ir(I), Pt(II), or Au(III).

In another aspect, the present disclosure provides methods of preparing the gels, the methods comprising complexing a macromer of Formula (B) or (C) with a transition metal salt in the presence of a fluid and optionally an agent (i.e., agent to be delivered).

In yet another aspect, the present disclosure provides compositions (e.g., pharmaceutical compositions) comprising a nanostructure or supramolecular complex described herein, optionally an agent (e.g., a small molecule), and optionally an excipient (e.g., a pharmaceutically acceptable excipient). In certain embodiments, a composition described herein is in the form of a gel (e.g., hydrogel). The described compositions are thought to be useful for delivering an agent to a subject, tissue, or cell. An agent may be encapsulated within the nanostructures or the nanostructure moieties of a supramolecular complex and may get transported through the cell membranes (e.g., into or out of a cell). The nanostructures or nanostructure moieties of a supramolecular complex may dissociate and release the agent to a cell (e.g., a target cell) or tissue (e.g., a target tissue).

The compositions described herein (e.g., pharmaceutical compositions) may be useful in treating a variety of diseases (e.g., genetic diseases, proliferative diseases (e.g., cancers and benign neoplasms), hematological diseases, neurological diseases, gastrointestinal diseases (e.g., liver diseases), spleen diseases, respiratory diseases (e.g., lung diseases), painful conditions, genitourinary diseases, musculoskeletal conditions, infectious diseases, inflammatory diseases, autoimmune diseases, psychiatric disorders, and metabolic disorders) in a subject in need thereof. In certain embodiments, a composition described herein includes a therapeutically effective amount of the agent.

The compositions described herein (e.g., pharmaceutical compositions) may also be useful in preventing a range of diseases (e.g., genetic diseases, proliferative diseases (e.g., cancers and benign neoplasms), hematological diseases, neurological diseases, gastrointestinal diseases (e.g., liver diseases), spleen diseases, respiratory diseases (e.g., lung diseases), painful conditions, genitourinary diseases, musculoskeletal conditions, infectious diseases, inflammatory diseases, autoimmune diseases, psychiatric disorders, and metabolic disorders) in a subject. In certain embodiments, a composition described herein includes a prophylactically effective amount of the agent.

Another aspect of the present disclosure relates to methods of delivering an agent to a subject. In certain embodiments, the method of delivering an agent comprises administering to a subject (e.g., a human) a composition (e.g., gel) described herein.

Another aspect of the present disclosure relates to methods of delivering an agent to a tissue. In certain embodiments, the method of delivering an agent comprises contacting a tissue (e.g., a liver, spleen, or lung) with a composition (e.g., gel) described herein. In certain embodiments, the agent is selectively delivered to a target tissue, compared to the delivery of the agent to a non-target tissue. For example, the agent may be delivered to a target tissue at 5 times, 10 times, 50 times, or 100 times greater than delivery to a non-target tissue.

Another aspect of the present disclosure relates to methods of delivering an agent to a cell. In certain embodiments, the method of delivering an agent comprises contacting a cell with a composition (e.g., gel) described herein. The cell may be in vitro or in vivo. In certain embodiments, the agent is selectively delivered to a target cell compared to the delivery of the agent to a non-target cell.

Another aspect of the disclosure relates to methods of increasing the exposure or concentration of an agent in a subject, tissue, or cell.

In another aspect, the present disclosure provides methods of treating a disease in a subject in need thereof. In certain embodiments, the methods of treating a disease comprise administering to the subject a therapeutically effective amount of a composition described herein.

In still another aspect, the present disclosure provides methods of preventing a disease in a subject in need thereof. In certain embodiments, the methods of preventing a disease comprise administering to the subject a prophylactically effective amount of a composition described herein.

In certain embodiments, the disease that is treated or prevented by a described method is a genetic diseases, proliferative disease (e.g., cancer or benign neoplasm), hematological disease, neurological disease, gastrointestinal disease (e.g., liver disease), spleen disease, respiratory disease (e.g., lung disease), painful condition, genitourinary disease, musculoskeletal condition, infectious disease, inflammatory disease, autoimmune disease, psychiatric disorder, or metabolic disorder. In certain embodiments, the disease is hepatic carcinoma, hypercholesterolemia, refractory anemia, or familial amyloid neuropathy.

In yet another aspect, the present disclosure provides nanostructures, supramolecular complexes, and compositions described herein for use in a method of the present disclosure (e.g., a method of delivering an agent to a subject; a method of delivering an agent to a tissue; a method of delivering an agent to a cell; a method of increasing the exposure or concentration of an agent in a subject, tissue, or cell; a method of treating a disease in a subject in need thereof; or a method of preventing a disease in a subject).

Another aspect of the present disclosure relates to kits comprising a container with: a transition metal salt, ligand of Formula (A), macromer of Formula (B), macromer of Formula (C), nanostructure, supramolecular complex, composition described herein, or a combination thereof. The kits may include a single dose or multiple doses of the nanostructure, supramolecular complex, or composition. The kits may be useful in a method described herein. In certain embodiments, a kit of the disclosure further includes instructions for preparing and/or using the inventive nanostructures, supramolecular complexes, and/or compositions thereof (e.g., for administering the nanostructures, supramolecular complexes, or compositions to a subject (e.g., as required by a regulatory agency)).

The details of one or more embodiments of the disclosure are set forth herein. Other features, objects, and advantages of the disclosure will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds (e.g., ligands) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$), and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is unspecified (e.g., —CH=CHCH$_3$ or 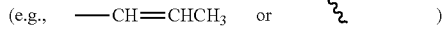 )

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-6}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3{}^+$X$^-$, —N(OR$^{cc}$)R$^{bb}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate,p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

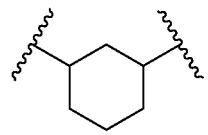 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

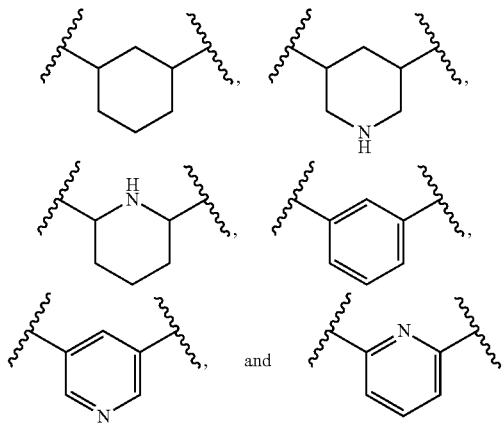

are all examples of a hydrocarbon chain. In contrast, in certain embodiments,

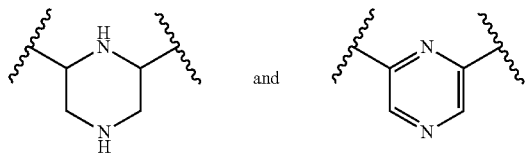 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

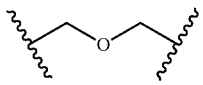 [SMILES: *COC*]

is a $C_3$ hydrocarbon chain wherein one chain atom is replaced with an oxygen atom.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·y H$_2$O, wherein R is the compound and wherein y is a number greater than 0. A given compound may form more than one type of hydrates, including, e.g., monohydrates (y is 1), lower hydrates (y is a number greater than 0 and smaller than 1, e.g., hemihydrates (R·0.5 H$_2$O)), and polyhydrates (y is a number greater than 1, e.g., dihydrates (R·2 H$_2$O) and hexahydrates (R·6 H$_2$O)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the disclosure. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

The term "polymer" refers to a compound comprising eleven or more covalently connected repeating units. In certain embodiments, a polymer is naturally occurring. In certain embodiments, a polymer is synthetic (i.e., not naturally occurring).

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. § § 330.5, 331 through 361, and 440 through 460, incorporated herein by reference; drugs for veterinary use are listed by the FDA under 21 C.F.R. § § 500 through 589, incorporated herein by reference. All listed drugs are considered acceptable for use in accordance with the present disclosure.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. The proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the subject will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bemoist et al., *Nature,* 290, 304-310, (1981); Yamamoto et al., *Cell,* 22, 787-797, (1980); Wagner et al., *Proc. Natl. Acad. Sci. U.S.A.* 78, 1441-1445, (1981); Brinster et al., *Nature* 296, 39-42, (1982)). Any type of plasmid, cosmid, yeast artificial chromosome, or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoramidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning,* second edition, Cold Spring Harbor Laboratory, Plainview, N.Y.; (1989), or Ausubel et al., *Current Protocols in Molecular Biology,* Current Protocols (1989), and *DNA Cloning: A Practical Approach,* Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "sphere" or "spherical" refers to a cage-like structure, which is hollow and has at least one reflectional symmetry, rotational symmetry, or a combination thereof. The term "nanosphere" refers to a sphere, wherein the maximum diameter of the sphere is between 1 nanometer (nm) and about 1 micrometer ($\mu$m) (e.g., between about 1 nm and about 300 nm, between about 1 nm and about 100 nm, between about 1 nm and about 30 nm, between about 1 nm and about 10 nm, or between about 1 nm and about 3 nm), inclusive).

The term "paddlewheel" refers to a coordination complex comprising m instances of ligands and two metal centers (metal atoms or metal ions), wherein there is an axis of symmetry connecting the two metal centers, and the overall symmetry of the coordination complex falls into the Dmh point group. In certain embodiments, m is 4, and the point group is D4h (e.g., there is a four-fold axis of symmetry when looking down the metal centers). In certain embodiments, the geometry of each of the metal centers is substantially square planar. In certain embodiments, m is 3. The term "nano-paddlewheel" refers to a paddlewheel, wherein the maximum diameter of the paddlewheel is between 1 nanometer (nm) and about 1 micrometer ($\mu$m) (e.g., between about 1 nm and about 300 nm, between about 1 nm and about 100 nm, between about 1 nm and about 30 nm, between about 1 nm and about 10 nm, or between about 1 nm and about 3 nm), inclusive). In certain embodiments, a nano-paddlewheel described herein is of the formula depicted in Scheme 8.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average (e.g., mean) characteristic dimension of about not more than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having an average (e.g., mean) dimension (e.g., diameter) of between about 1 nanometer (nm) and about 1 micrometer ($\mu$m) (e.g., between about 1 nm and about 300 nm, between about 1 nm and about 100 nm, between about 1 nm and about 30 nm, between about 1 nm and about 10 nm, or between about 1 nm and about 3 nm), inclusive.

The term "microparticle" refers to a particle having an average (e.g., mean) dimension (e.g., diameter) of between about 1 micrometer ($\mu$m) and about 1 millimeter (mm) (e.g., between about 1 $\mu$m and about 100 $\mu$m, between about 1 $\mu$m and about 30 $\mu$m, between about 1 $\mu$m and about 10 $\mu$m, or between about 1 $\mu$m and about 3 $\mu$m), inclusive.

The term "fluid" refers to a substance that, under a shear stress at 25° C., continually flows (e.g., at a velocity of 1 millimeter per second) along a solid boundary. Examples of fluids include liquids (e.g., solvents and solutions), gases, and suspensions (where solids are suspended in a liquid or gas). In certain embodiments, a fluid is water. In certain embodiments, a fluid is DMSO or acetonitrile. In certain embodiments, a fluid is water, DMSO, acetonide, or a mixture thereof. A "nonfluid" is a substance that is not a fluid.

The term "gel" is a nonfluid colloidal network or nonfluid polymer network that is expanded throughout its whole volume by a fluid (e.g., a solvent (e.g., water) or a solution (e.g., an aqueous solution)). A gel has a finite, usually rather small, yield stress. A gel may contain: (i) a covalent molecular network (e.g., polymer network), e.g., a network formed by crosslinking molecules (e.g., polymers) or by nonlinear polymerization; (ii) a molecular network (e.g., polymer network) formed through non-covalent aggregation of molecules (e.g., polymers), caused by complexation (e.g., coordination bond formation between a ligand and a metal, the resulting gel referring to a "metallogel"), electrostatic interactions, hydrophobic interactions, hydrogen bonding, van der Waals interactions, π-π stacking, or a combination thereof, that results in regions of local order acting as the network junction points. The term "thermoreversible gel" refers to a gel where the regions of local order in the gel are thermally reversible; (iii) a polymer network formed through glassy junction points, e.g., one based on block copolymers. If the junction points are thermally reversible glassy domains, the resulting swollen network may also be termed a thermoreversible gel; (iv) lamellar structures including mesophases, e.g., soap gels, phospholipids, and clays; or (v) particulate disordered structures, e.g., a flocculent precipitate usually consisting of particles with large geometrical anisotropy, such as in $V_2O_5$ gels and globular or fibrillar protein gels. The term "hydrogel" refers to a gel, in which the fluid is water.

The term "interstructural" refers to a divalent linker Y directly covalently attached to two different instances of a nanostructure.

The term "intrastructural" refers to a divalent linker Y directly covalently attached to the same instance of a nanostructure.

The terms "composition" and "formulation" are used interchangeably.

The term "toxic" refers to a substance showing detrimental, deleterious, harmful, or otherwise negative effects on a subject, tissue, or cell when or after administering the substance to the subject or contacting the tissue or cell with the substance, compared to the subject, tissue, or cell prior to administering the substance to the subject or contacting the tissue or cell with the substance. In certain embodiments, the effect is death or destruction of the subject, tissue, or cell. In certain embodiments, the effect is a detrimental effect on the metabolism of the subject, tissue, or cell. In certain embodiments, a toxic substance is a substance that has a median lethal dose ($LD_{50}$) of not more than 500 milligrams per kilogram of body weight when administered orally to an albino rat weighing between 200 and 300 grams, inclusive. In certain embodiments, a toxic substance is a substance that has an $LD_{50}$ of not more than 1,000 milligrams per kilogram of body weight when administered by continuous contact for 24 hours (or less if death occurs within 24 hours) with the bare skin of an albino rabbit weighing between two and three kilograms, inclusive. In certain embodiments, a toxic substance is a substance that has an $LC_{50}$ in air of not more than 2,000 parts per million by volume of gas or vapor, or not more than 20 milligrams per liter of mist, fume, or dust, when administered by continuous inhalation for one hour (or less if death occurs within one hour) to an albino rat weighing between 200 and 300 grams, inclusive. The term "non-toxic" refers to a substance that is not toxic.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "target tissue" refers to any biological tissue of a subject (including a group of cells, a body part, or an organ) or a part thereof, including blood and/or lymph vessels, which is the object to which a compound, particle, and/or composition of the disclosure is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. In certain embodiments, the target tissue is the spleen. A "non-target tissue" is any biological tissue of a subject (including a group of cells, a body part, or an organ) or a part thereof, including blood and/or lymph vessels, which is not a target tissue.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer, anal cancer, angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer, breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer, epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer, gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrim's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer, rhabdomyosarcoma; salivary gland cancer, skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer, sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer, and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, postsurgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barre syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder, autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder, cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor, Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster, Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; ministrokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

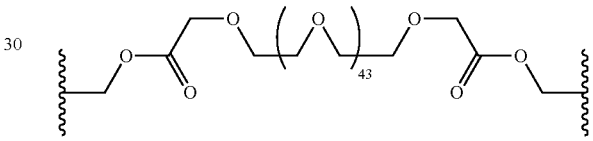

were omitted for clarity. FIG. 1B, top panel, shows an exemplary proton nuclear magnetic resonance ($^1$H NMR) spectrum (400 MHz, DMSO-d$_6$) of ligand A-1. FIG. 1B, bottom panel, shows that ligand A-1 and Pd(NO$_3$)$_2$ formed nanosphere I-1. FIG. 1C shows an exemplary $^1$H NMR spectrum (400 MHz) of a gel formed by heating at 80° C. overnight a solution of ligand B-2 (0.01 M) and Pd(NO$_3$)$_2$ in DMSO-d$_6$ (top panel) and an exemplary $^1$H NMR spectrum (400 MHz, DMSO-d$_6$) of nanosphere I-1 (bottom panel).

Figure 1A:
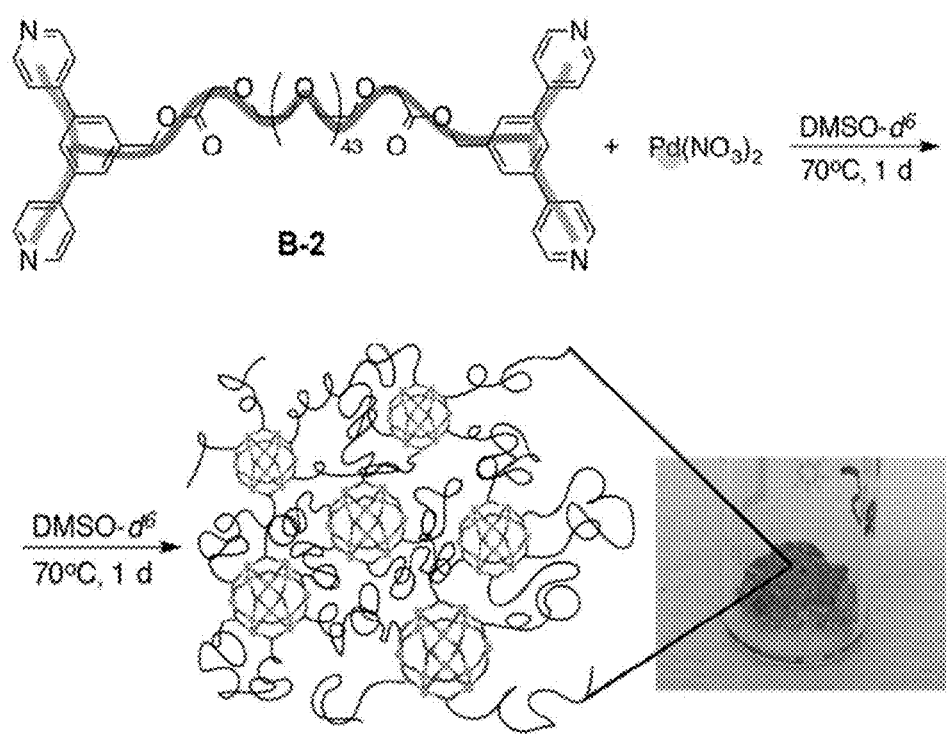
FIG. 1A shows that ligand B-2 and Pd(NO$_3$)$_2$ formed a gel. Some instances of divalent linker
Figure 2A:
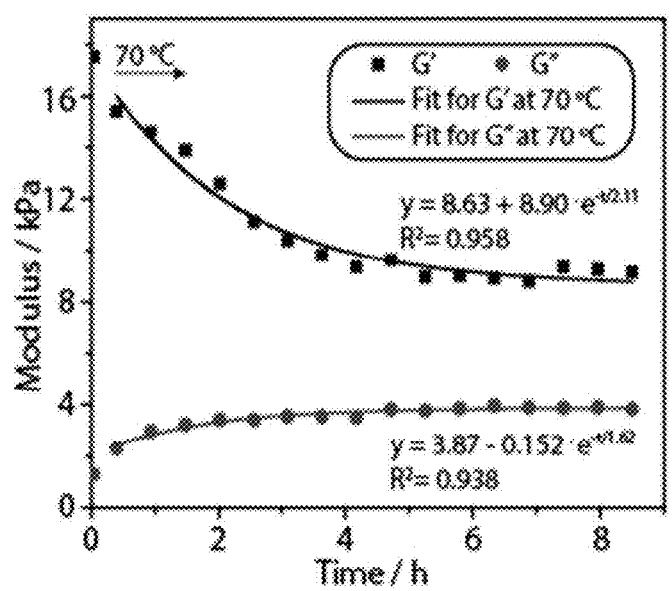
Figure 2B:
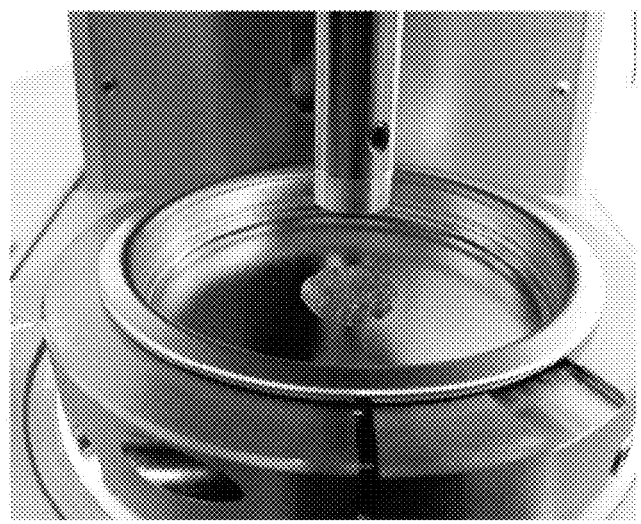
Figure 2C:
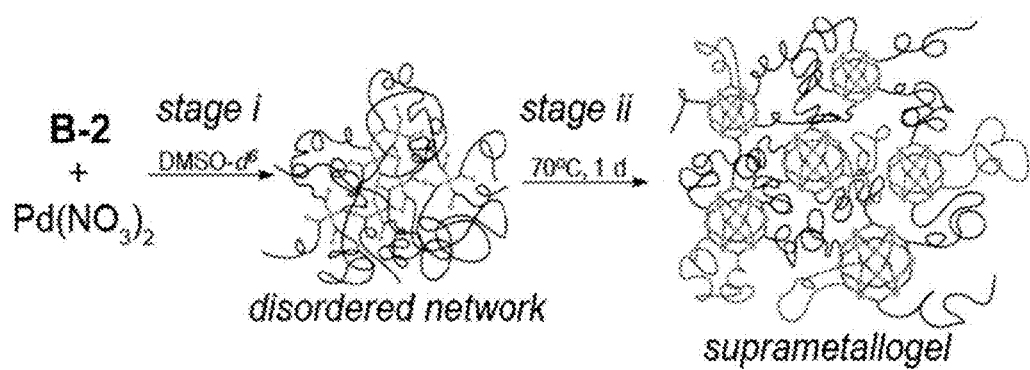

FIG. 2A shows exemplary gelation kinetics results of a reaction (gelation) mixture of FIG. 1A as indicated by rheology of the reaction mixture at different reaction times. The concentration of ligand B-2 in DMSO-d$_6$ was 0.024 M; w was 10 rad/s; 1% strain. G': shear storage modulus. G": shear loss modulus. FIG. 2B shows an image of the equipment employed in FIG. 2A. FIG. 2C shows a proposed two-stage mechanism of the gelation of FIG. 2A. Stage i: initial disordered network formation. Stage ii: thermal equilibration to form the gel. Primary loops formed in the process are highlighted in red.

Figure 3A:
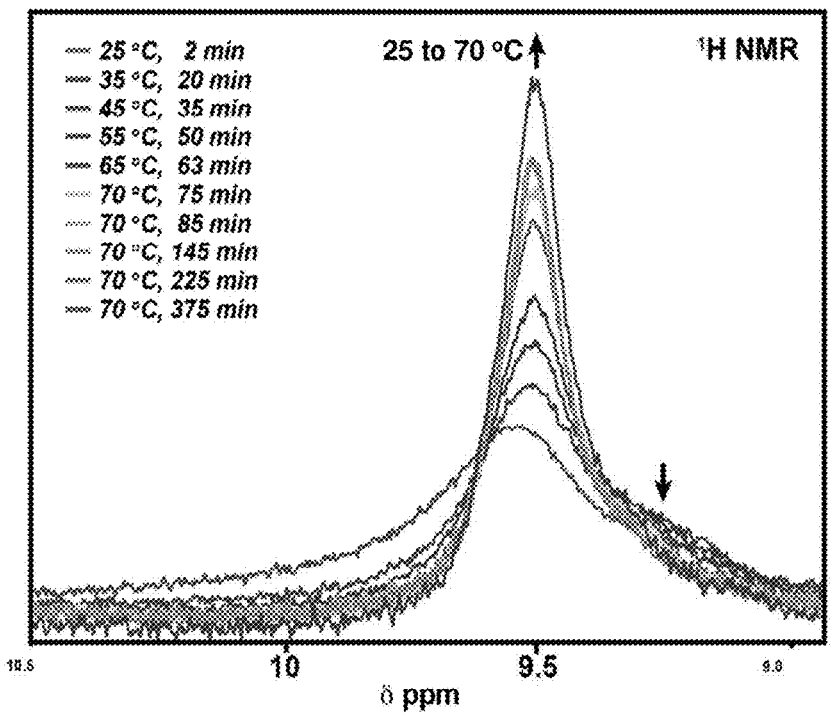
Figure 3B:
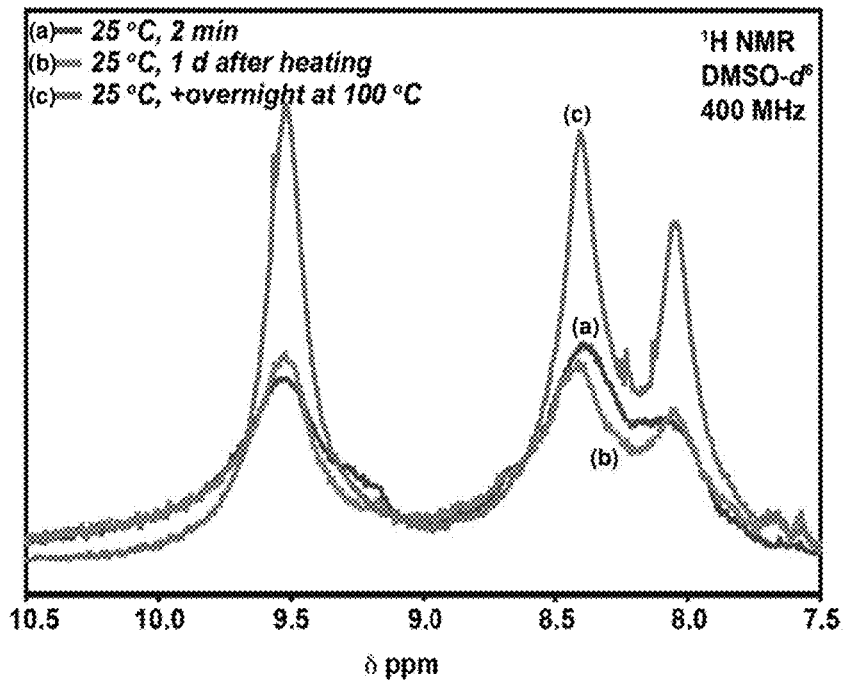

FIGS. 3A and 3B show exemplary $^1$H NMR spectra of the reaction mixtures of FIG. 1A, except the reaction temperature and time duration, which were as provided in FIGS. 3A and 3B.

Figures 4A, 4B:
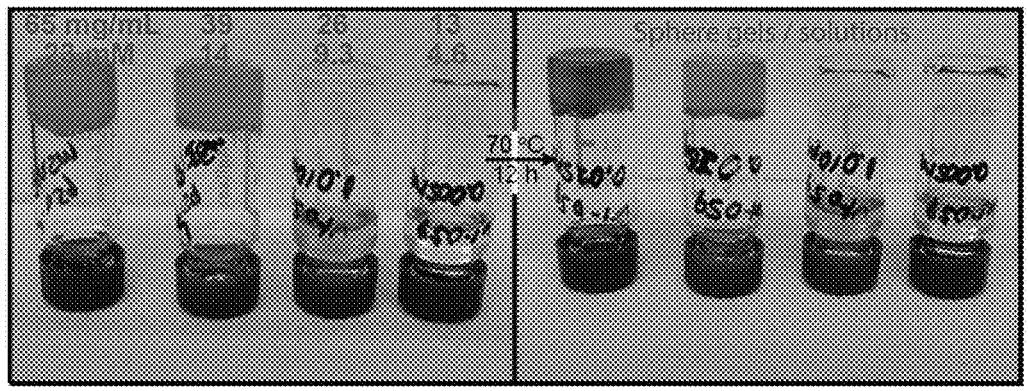
Figure 4C:
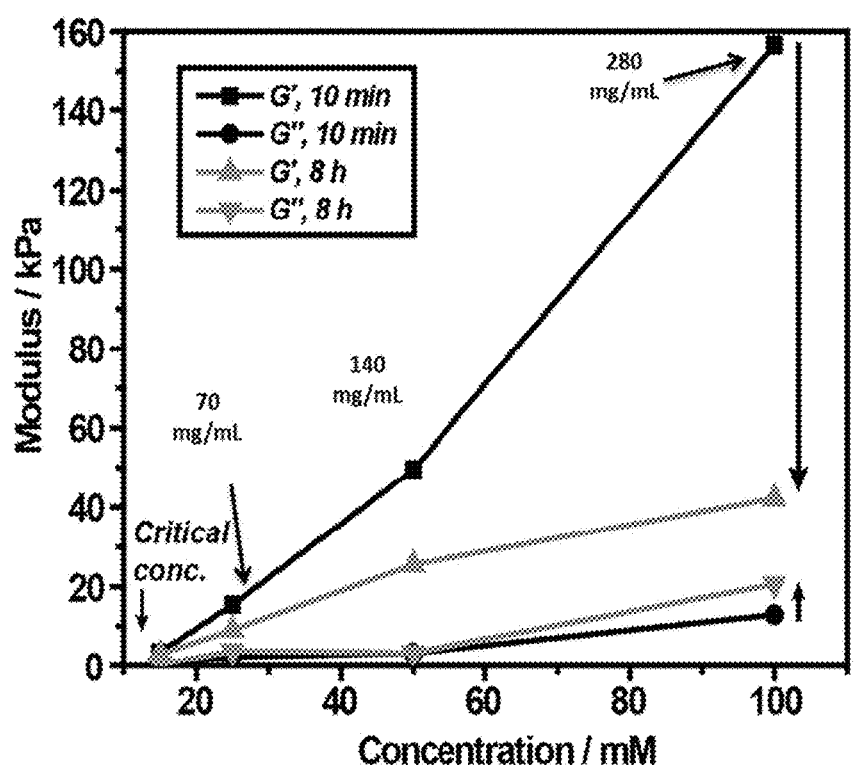

FIG. 4A shows the effects of concentration (in millimoles of ligand B-2 per liter of DMSO-d$_6$) on gelation of reactions of FIG. 1A, wherein the reaction temperature was room temperature. FIG. 4B shows the effects of concentration (in millimoles of ligand B-2 per liter of DMSO-d$_6$) on gelation of reactions of FIG. 1A. Gels at room temperature remained gels after annealing. Gelation took place at concentrations as low as 0.014 M. FIG. 4C shows the dependence of storage and loss modulus of a gel on the concentration of ligand B-2 of the gel.

Figure 5A:
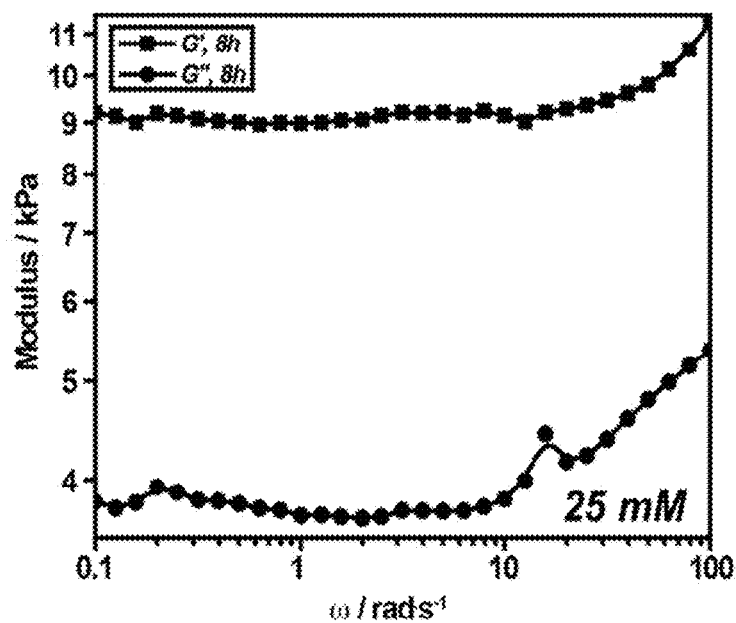
Figure 5B:
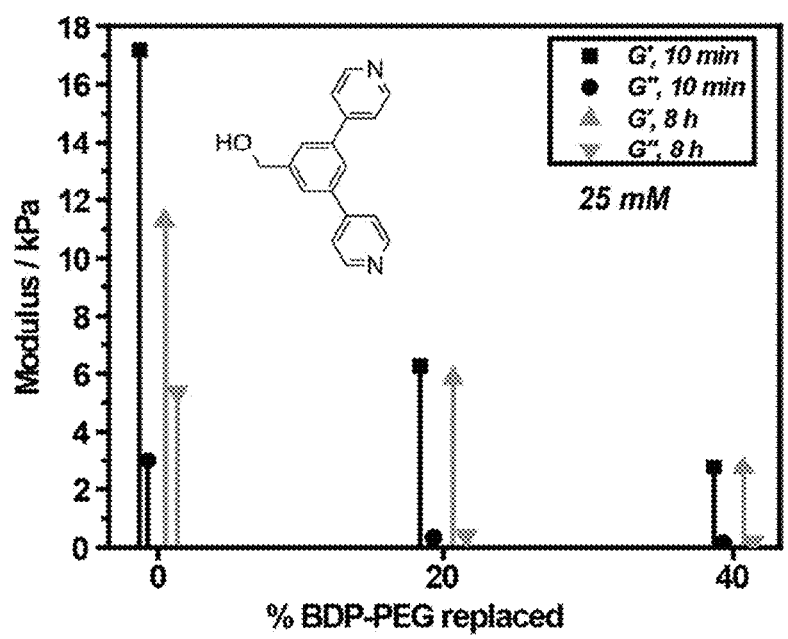
Figure 5C:
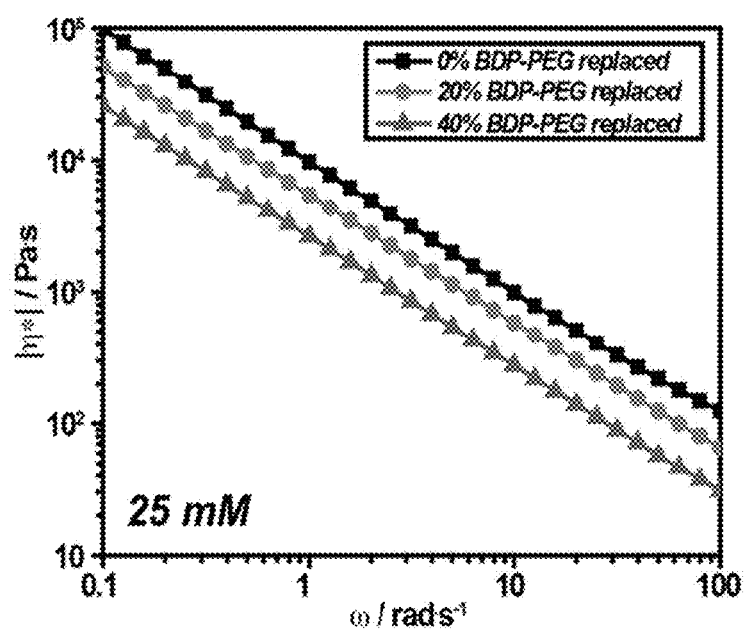

FIG. 5A shows exemplary rheology of gels formed from macromer B-2. FIG. 5B shows the storage and loss modulus of a gel formed by a reaction of FIG. 1A, wherein ligand B-2 was partially replaced with ligand A-1, wherein the mole amount of ligand A-1 was twice the mole amount of ligand B-2 that was replaced by ligand A-1. FIG. 5C shows the shear viscosity of the gels of FIG. 5B.

FIG. 6A shows the chemical structure of doxorubicin. FIG. 6B is a photograph of a gel formed by heating in DMSO-$d_6$ at 70° C. for 1 day a solution of ligand B-2 (100 mM) and Pd(NO$_3$)$_2$ in the presence of doxorubicin (12 equivalents relative to the expected amount of the nanospheres ($M_{12}L_{24}$) formed from B-2 and Pd(NO$_3$)$_2$; 100 mM). FIG. 6C is a photograph of the gel after extracting the gel of FIG. 6B four times with DMSO-$d_6$. FIG. 6D are photographs of the four extracts of FIG. 6C. From left to right; the first to fourth extracts.

Figure 7:
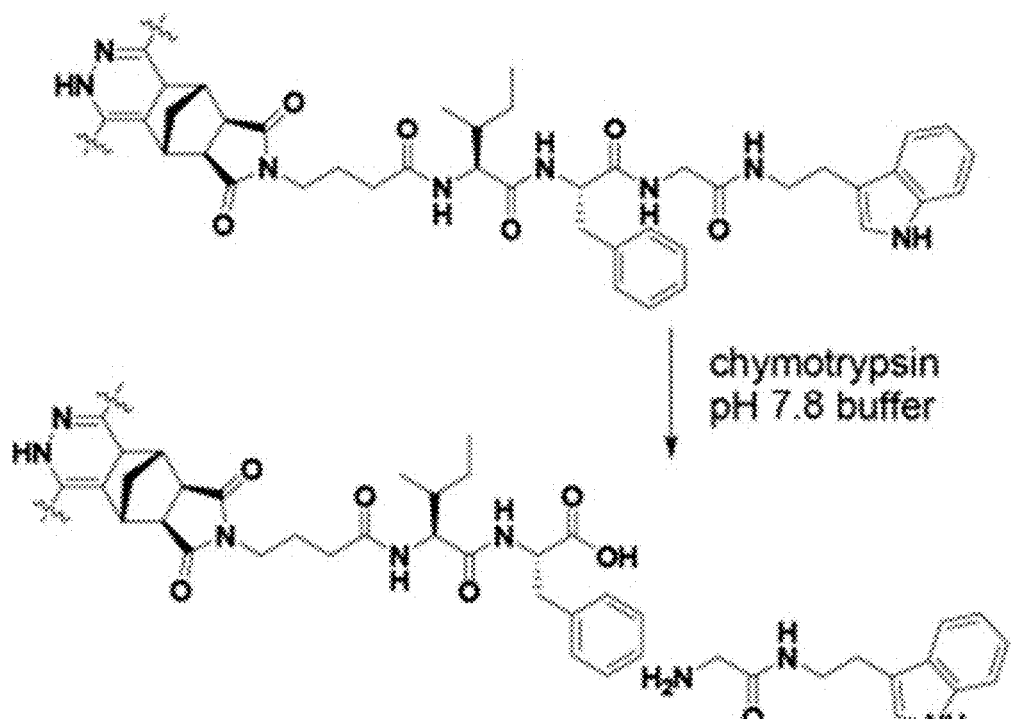

FIG. 7: a scheme showing the release of tryptamine glycnamide from a gel of Example 18 by treating the gel with chymotrypsin. The details are shown in Example 19.

Figure 8:
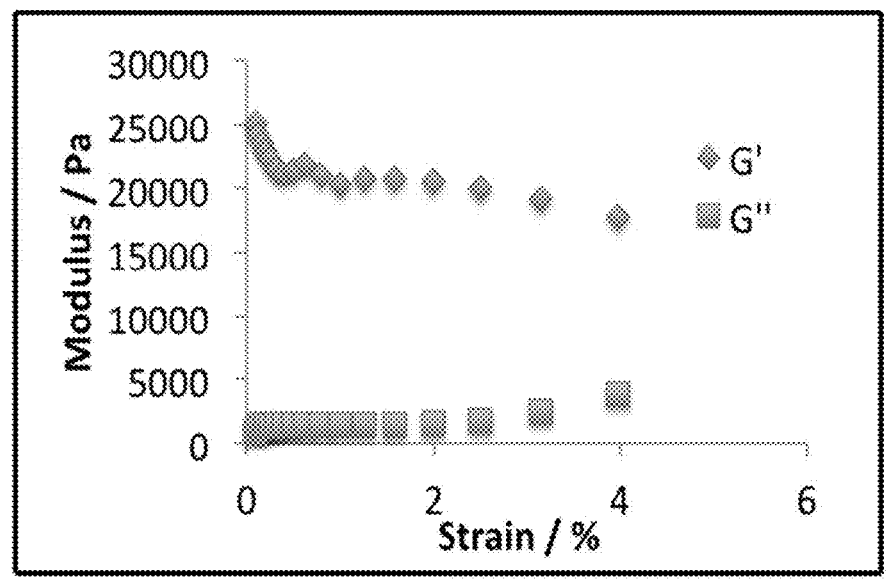

FIG. 8 shows exemplary strain sweeps at ω=100 rad/s of a gel formed at room temperature. The reactants were B-2 and Pd(NO$_3$)$_2$.2H$_2$O, which were mixed in DMSO-$d_6$ at room temperature to form a gel where the concentration of B-2 is 0.024 M. G': shear storage modulus. G": shear loss modulus.

Figure 9A:
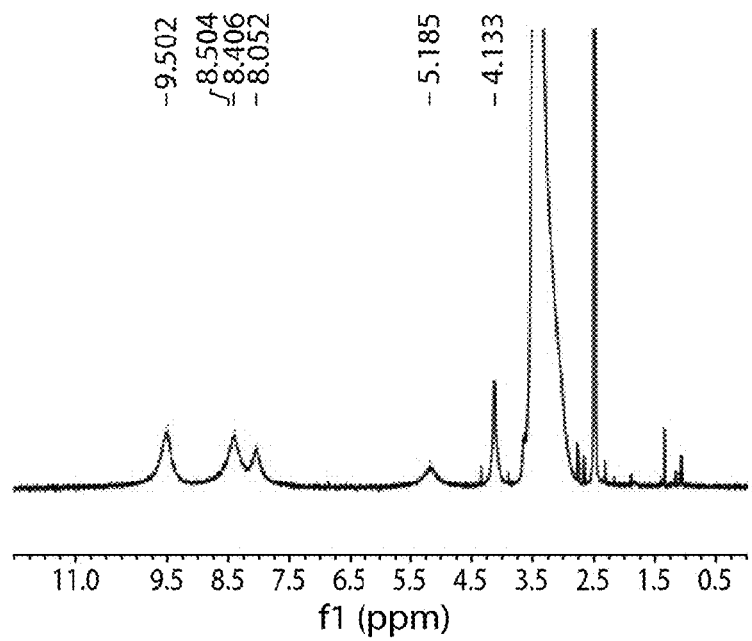
Figure 9B:
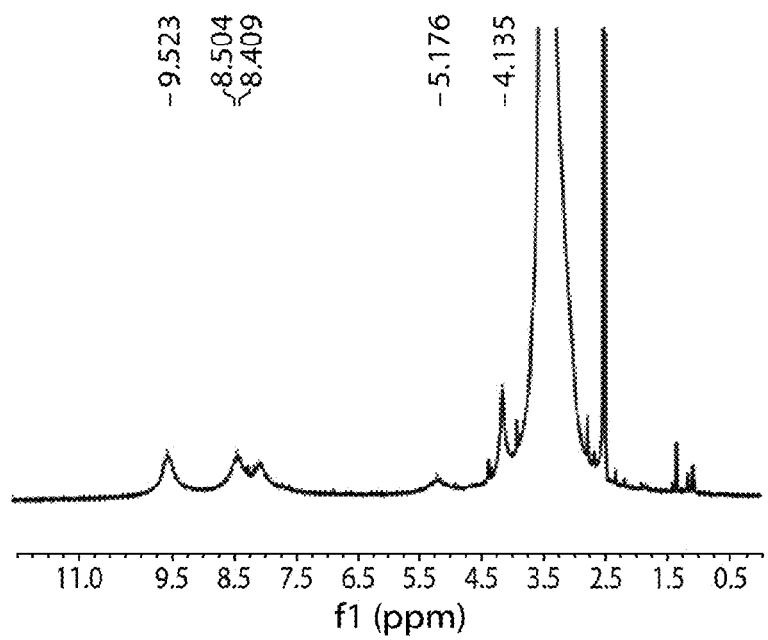

FIGS. 9A and 9B show exemplary $^1$H NMR spectra (DMSO-$d_6$) of gels III-5 (FIG. 9A) and III-6 (FIG. 9B).

Figure 10:
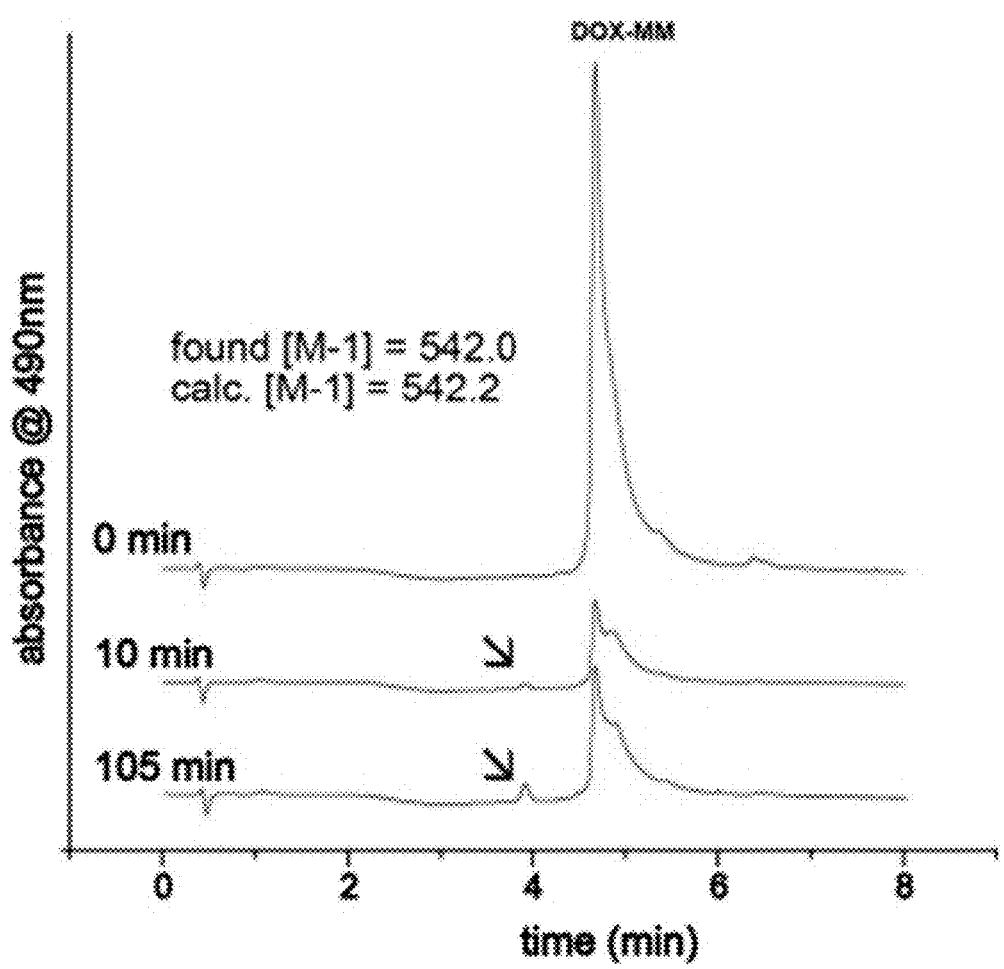

FIG. 10: release of doxorubicin from the gel of Example 17. The details are shown in Example 18.

Figure 11A:
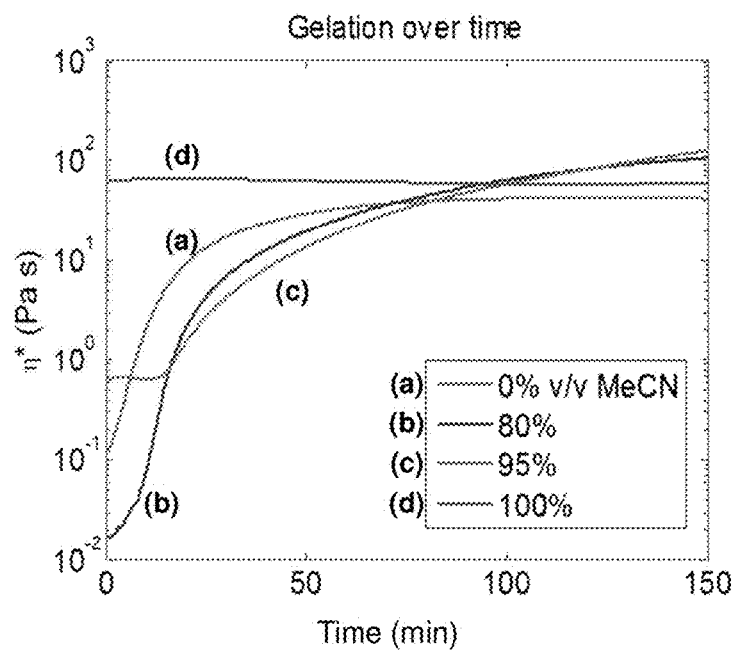
Figure 11B:
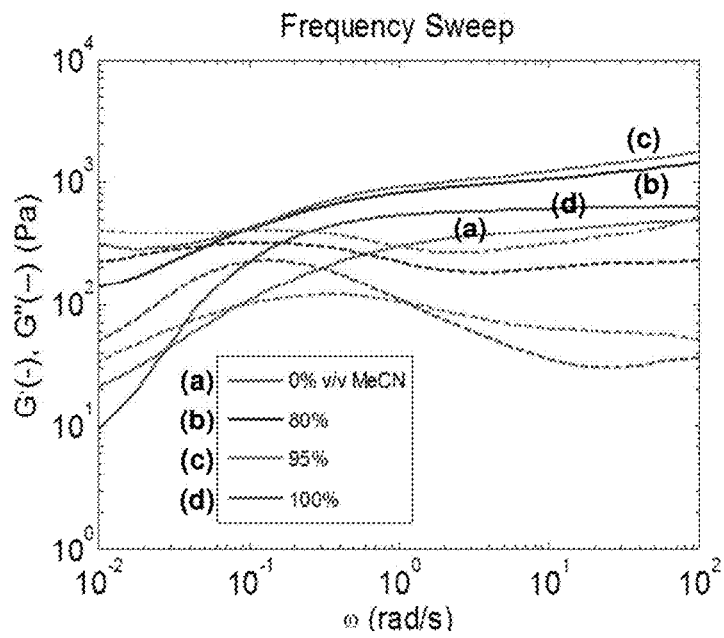
Figure 15A:
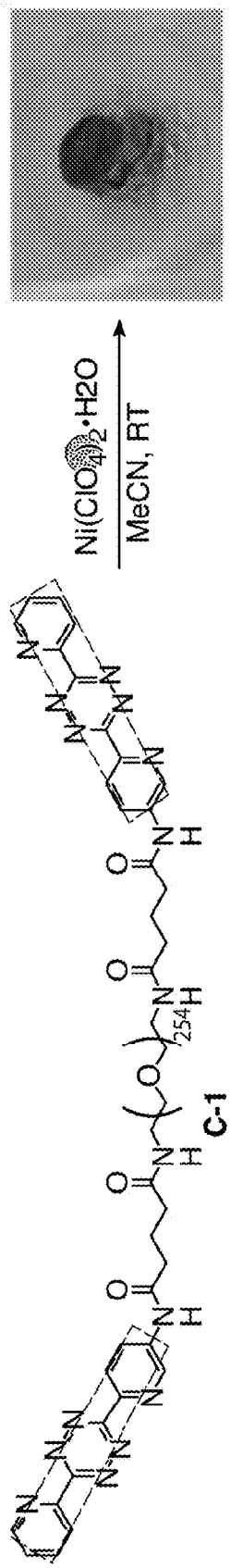

FIG. 11A shows the changes in shear viscosity of a reaction mixture of FIG. 15A over reaction time. FIG. 11B is a plot of storage modulus (G') and loss modulus (G") of a gel of FIG. 15A versus the strain (ω) of the gel.

FIG. 12 is an exemplary $^1$H NMR spectrum (DMSO-$d_6$, 400 MHz) of ligand B-1.

Figure 13A:
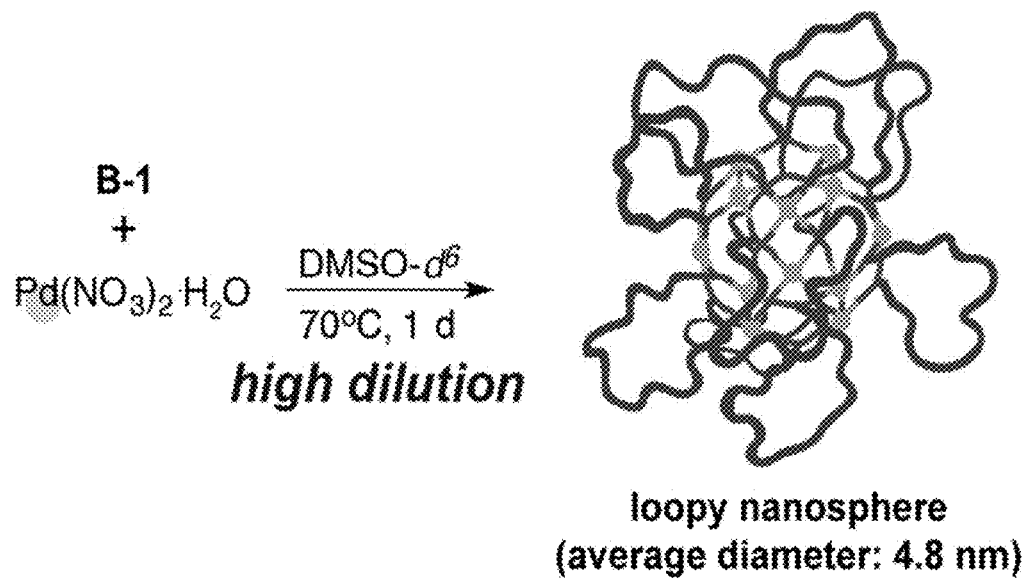
Figure 13B:
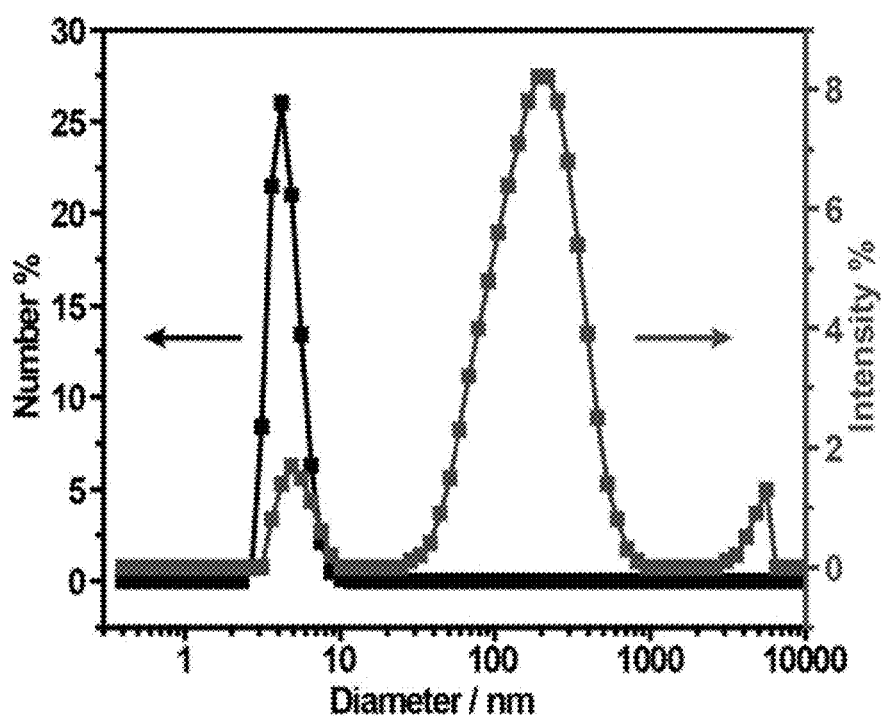

FIG. 13A illustrates the formation of a loopy nanosphere by reacting ligand B-1 with Pd(NO$_3$)$_2$.H$_2$O. FIG. 13B shows exemplary dynamic light scattering (DLS) results of dialyzed loopy nanospheres.

Figure 14:
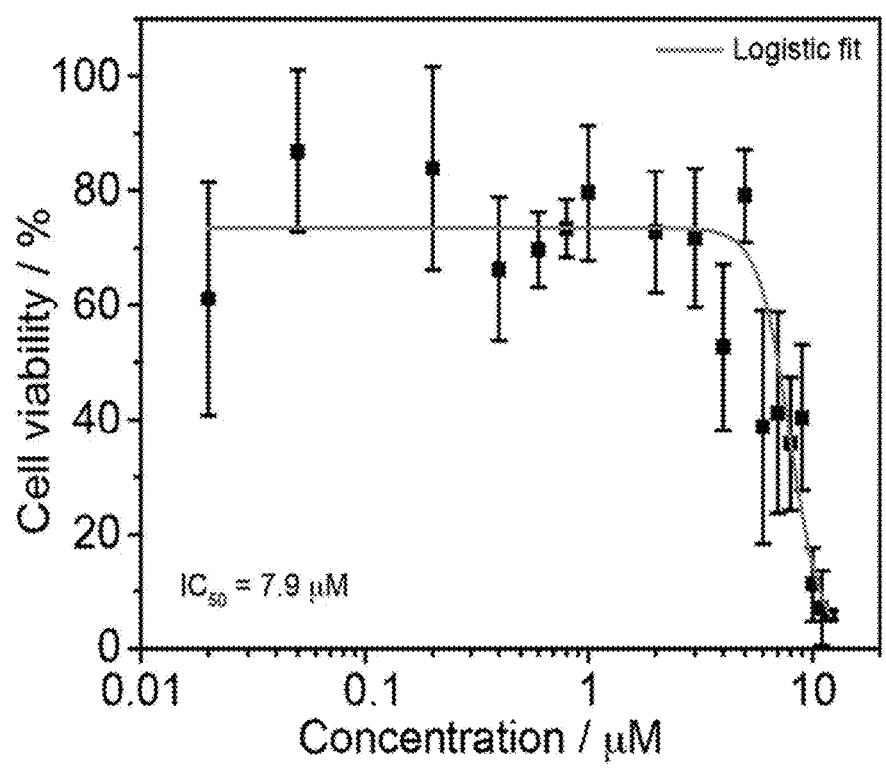

FIG. 14 shows exemplary MTT proliferation assay results of nanosphere I-1 using HeLa cells.

Figure 15B:
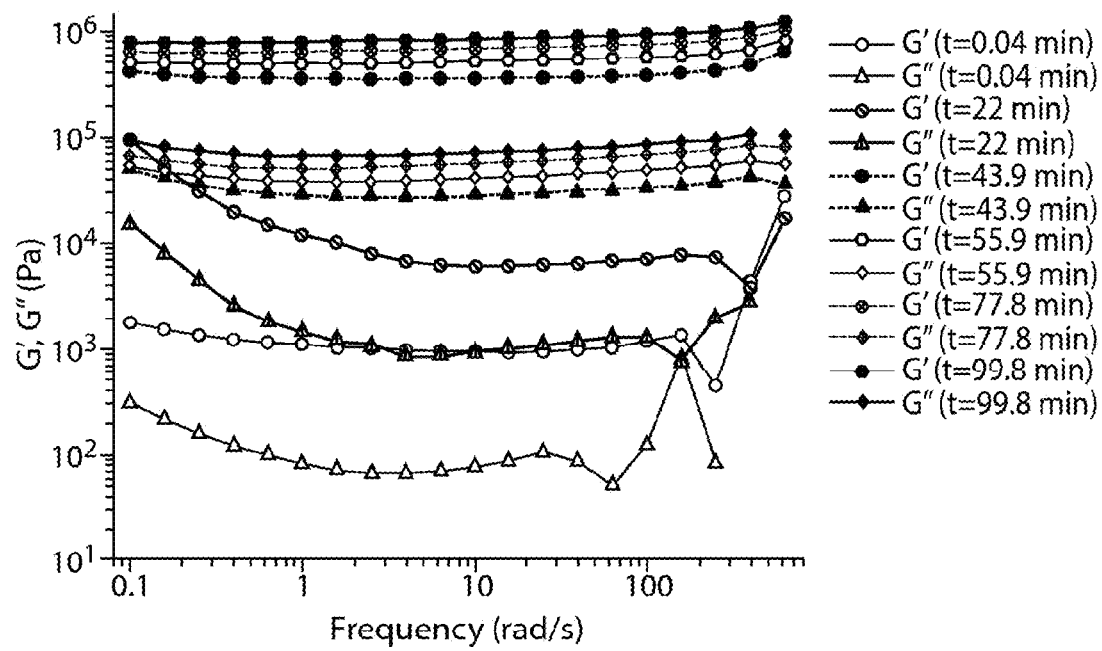
Figure 15C:
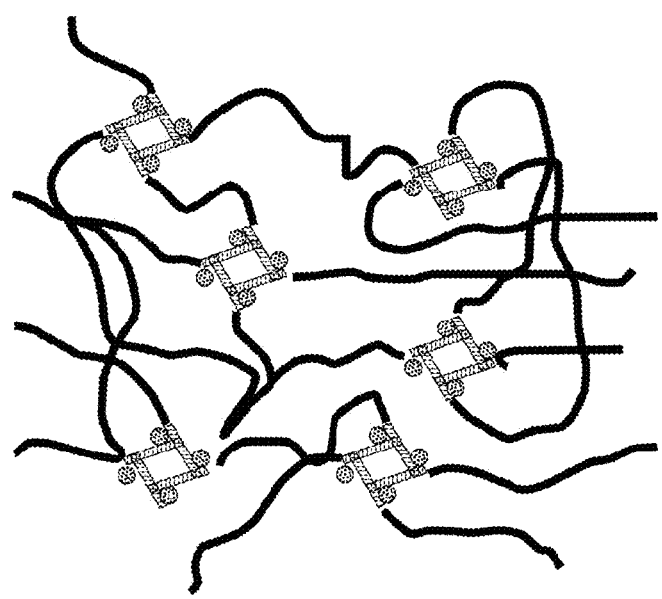

FIG. 15A shows the formation of supramolecular complexes and gels using ligand C-1 and Ni(ClO$_4$)$_2$. FIG. 15B shows exemplary frequency sweep results of the reaction mixture at different reaction times. FIG. 15C is a cartoon illustrating a proposed structure of the formed supramolecular complexes and gels, where the black bands represent divalent linkers of the formula:

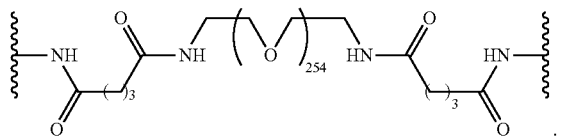

FIG. 16A: Schematic representations of traditional polymer metallogels (left panel) compared to suprametallogels (right panel). FIG. 16B: Chemical structures of exemplary ligands described herein along with the effect of ligand bite angle on the self-assembly of these ligands into supramolecular nanostructures. The "Fujita cage" and paddlewheel structures (far left panel and far right panel, respectively) were obtained from molecular dynamics simulations. FIG. 16C: Chemical structures of exemplary macromers B-3 (left panel) and B-4 (right panel) described herein.

Figure 17A:
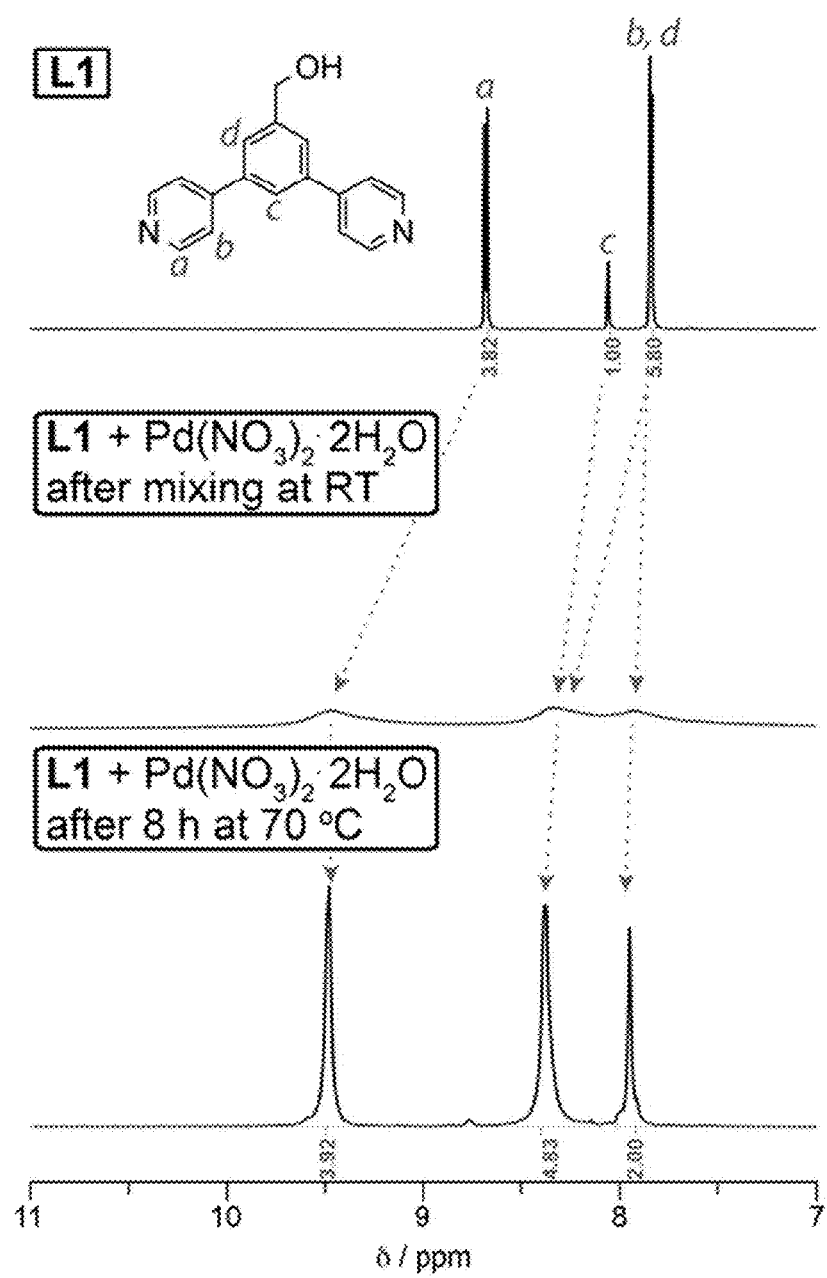
Figure 17B:
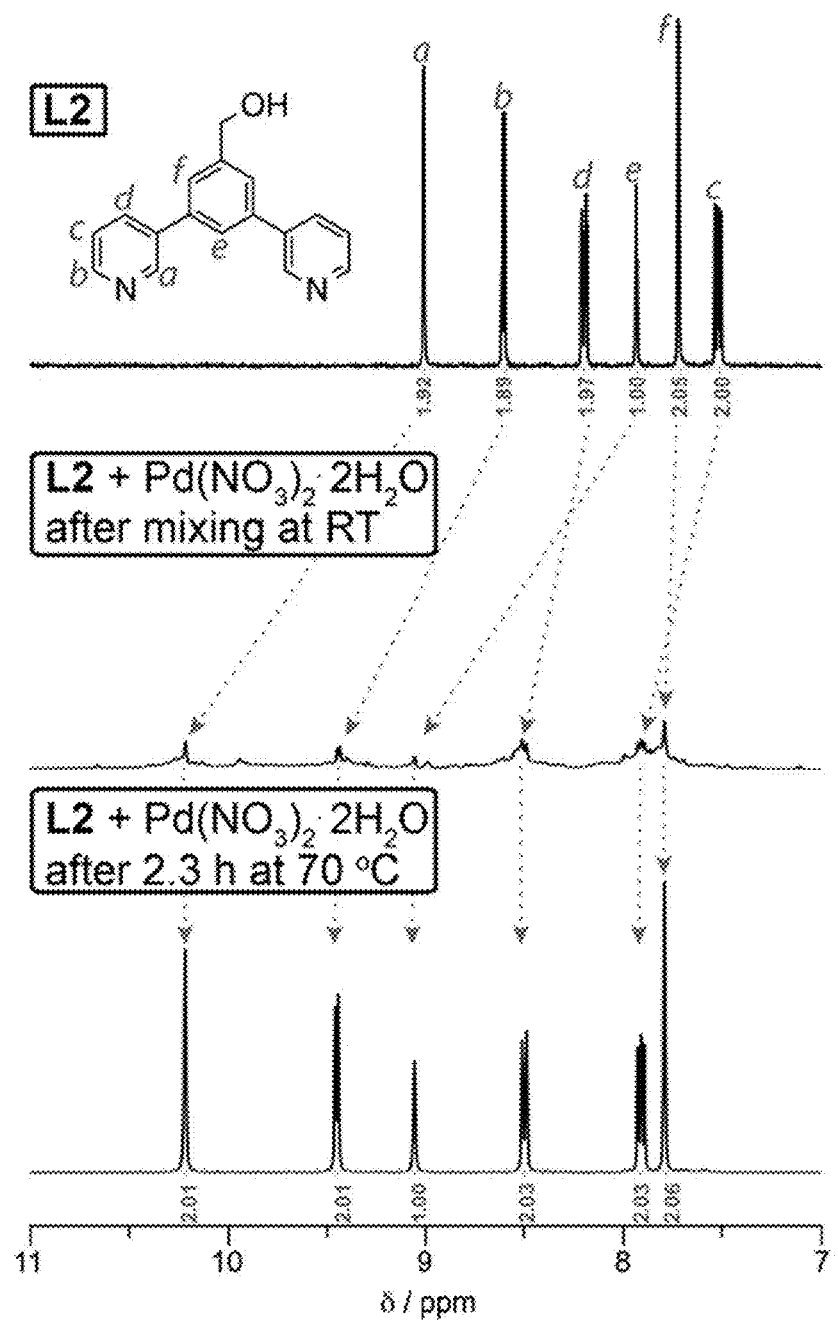
Figure 17C:
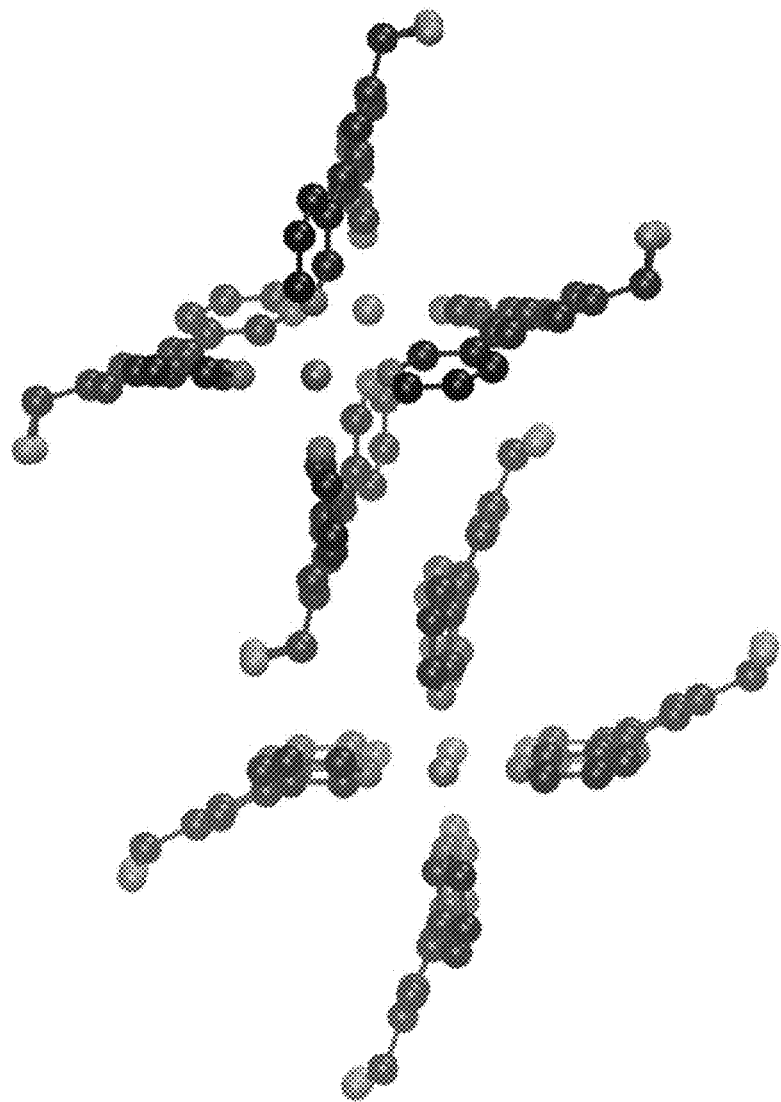

FIG. 17A: Aromatic regions of the $^1$H NMR spectra (400 MHz, DMSO-$d^6$, 25° C.) of, from top to bottom, L1, the initial mixture of L1 and Pd(NO$_3$)$_2$.2H$_2$O prepared at room temperature, and the same mixture after thermal annealing. FIG. 17B: Aromatic regions of the $^1$H NMR spectra (400 MHz, DMSO-$d^6$, 25° C.) of, from top to bottom, L2, the initial mixture of L2 and Pd(NO$_3$)$_2$.2H$_2$O prepared at room temperature, and the same mixture after thermal annealing. FIG. 17C: Low-quality crystal structure of (L2)$_4$Pd$^{II}{}_2$. Note that due to significant disorder this structure was not used to analyze bond lengths and/or angles. However, the paddlewheel connectivity of the complex was confidently assigned.

Figure 18:
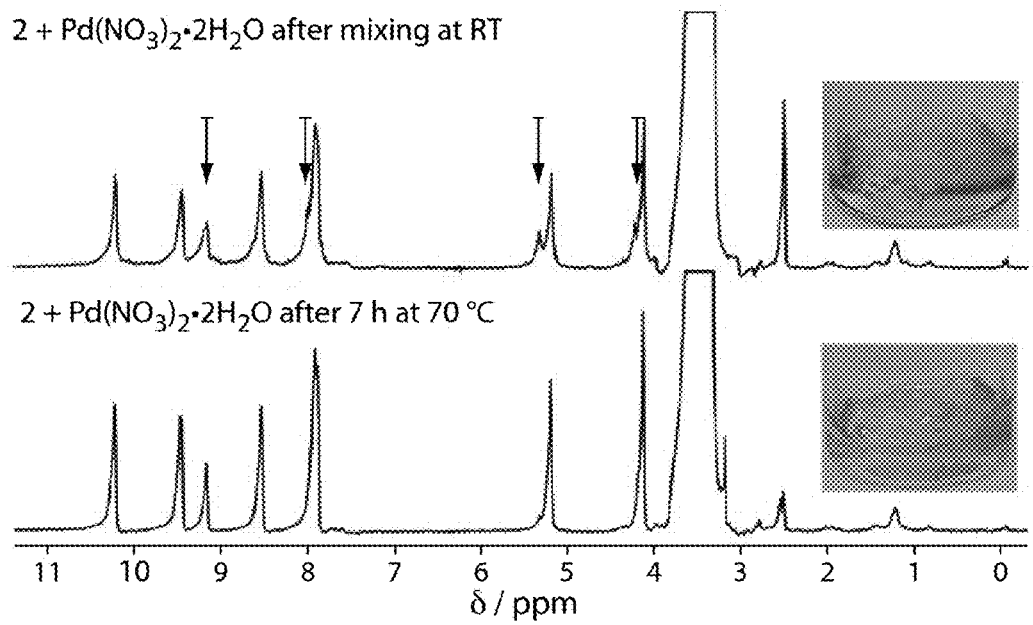

FIG. 18: VT $^1$H ssNMR spectroscopy (500 MHz, DMSO-$d^6$, magic angle spinning at 10 kHz) of the gel derived from paddlewheel-former B-4 ([B-4]=24 mM) before (top panel) and after (bottom panel) annealing. "2": B-4.

Figure 19A:
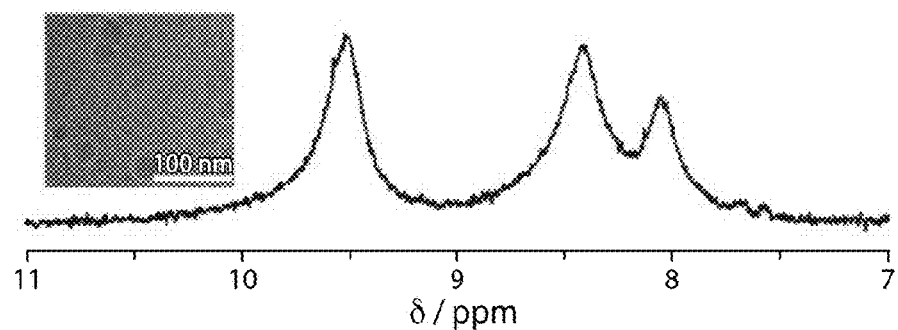
Figure 19B:
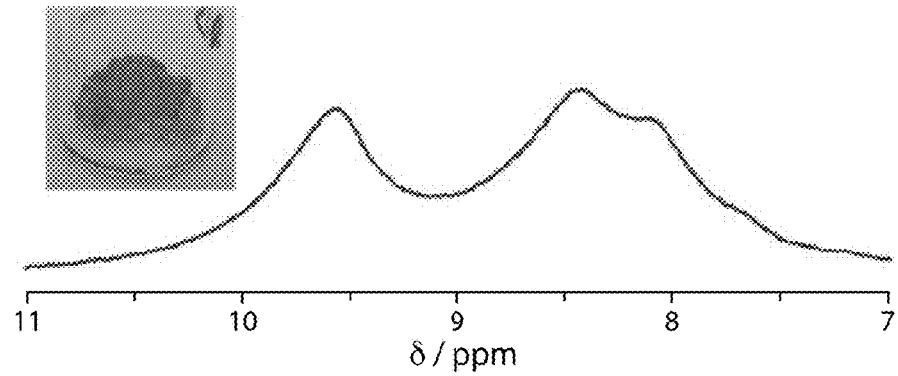

FIG. 19A: Aromatic region of the $^1$H NMR (400 MHz, DMSO-$d^6$) spectrum of the $M_{12}L_{24}$ spheres derived from B-3 at high dilution (4.4 mM). Inset: Cryo-TEM image of the soluble aggregates of $M_{12}L_{24}$ spheres dialyzed against Millipore water exhibits ~30-nm spherical particles. FIG. 19B: Aromatic region of the $^1$H ssNMR (500 MHz, DMSO-$d^6$, magic angle spinning at 10 kHz) spectrum of the corresponding gel when [B-3]=24 mM. Inset: a picture of the gel.

Figure 20A:
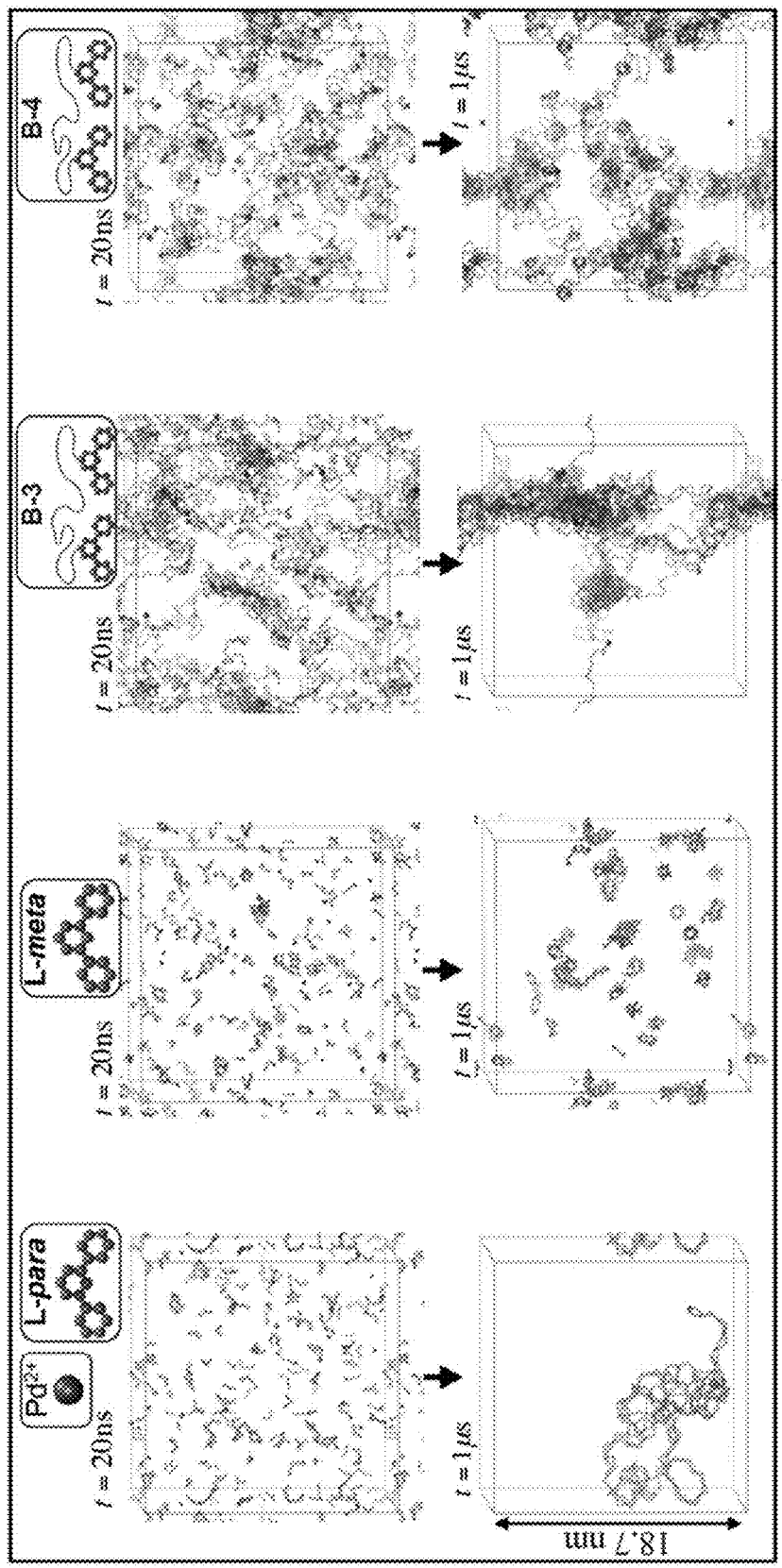

FIG. 20A: Snapshots illustrating the assembly of metal-ligand clusters for different ligand species, each initialized from random configurations at time t=0. Images from left to right correspond to the assembly of Pd$^{2+}$ and L-para, L-meta, B-3, and B-4, respectively. For the suprametallogels prepared from macromers B-3 and B-4, grey lines indicate a likely configuration of the 2.2 kDa PEG chain, which is described implicitly in the simulations.

Figure 20B:
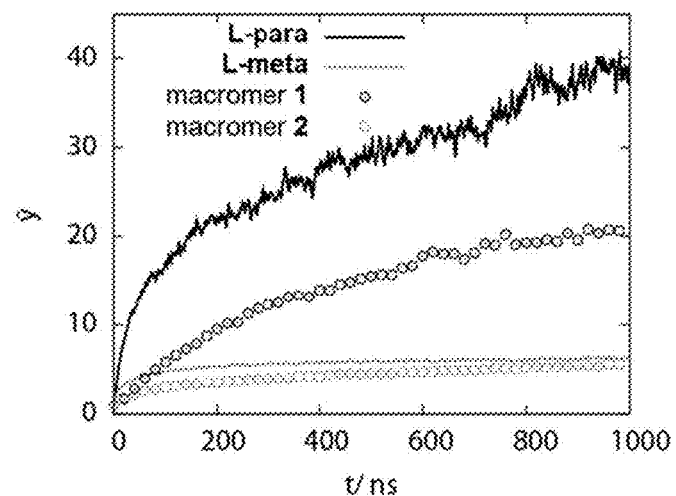

FIG. 20B: Average cluster size as a function of time for systems with L-para, L-meta, and macromers B-3 and B-4. Data is plotted in black or grey to indicate L-para or L-meta based ligands, respectively. Lines or points (circles and squares) are used to differentiate free ligands from macromers, respectively. "Macromer 1": B-3. "Macromer 2": B-4.

Figure 20C:
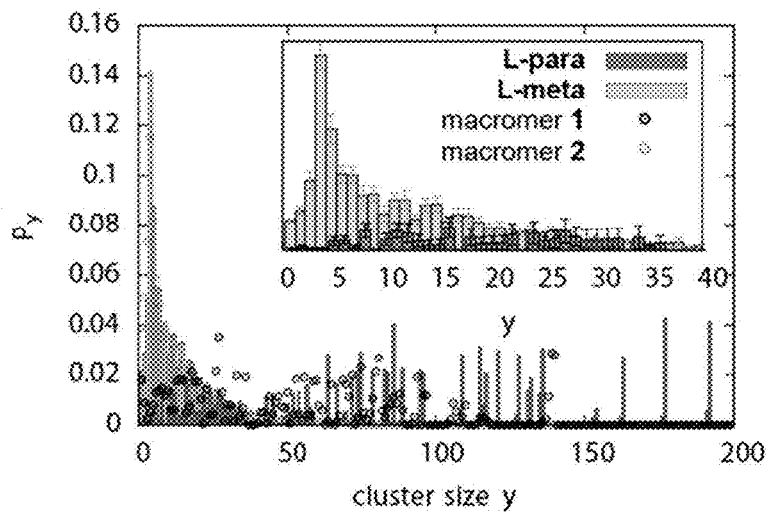

FIG. 20C: Distribution of cluster sizes for systems with L-para and L-meta ligands are plotted with black or grey bars, respectively. The data representing suprametallogels from macromers B-3 and B-4 are plotted with points using the same color and symbol conventions as in FIG. 20B. Inset highlights a narrower data range for the free ligands L-para and L-meta only. "Macromer 1": B-3. "Macromer 2": B-4.

Figure 20D:
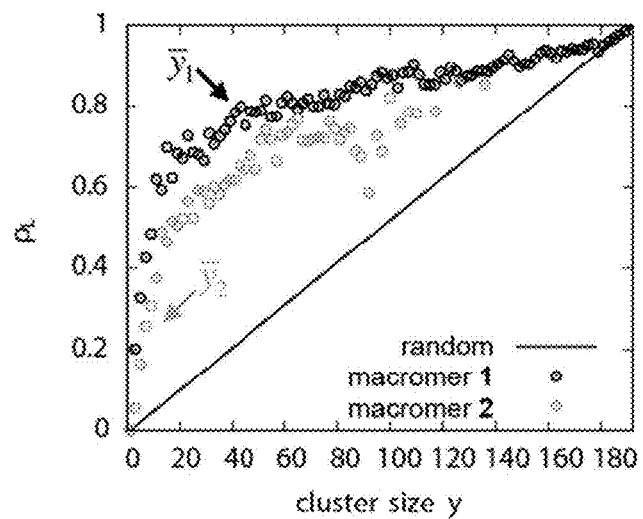

FIG. 20D: Average density of primary loops as a function of cluster size in suprametallogels from macromers B-3 and B-4 plotted using the same color and symbol convention as in FIG. 20B. The black line indicates the predicted density of loops if clusters are assembled from randomly selected ligands. Arrows provide the approximate y (cluster size) after 1 μs for suprametallogels prepared from B-3 and B-4 (as obtained from FIG. 20B); they indicate the fraction of looped chains in the respective suprametallogel. "Macromer 1": B-3. "Macromer 2": B-4.

Figures 21A, 21B, 21C, 21D:
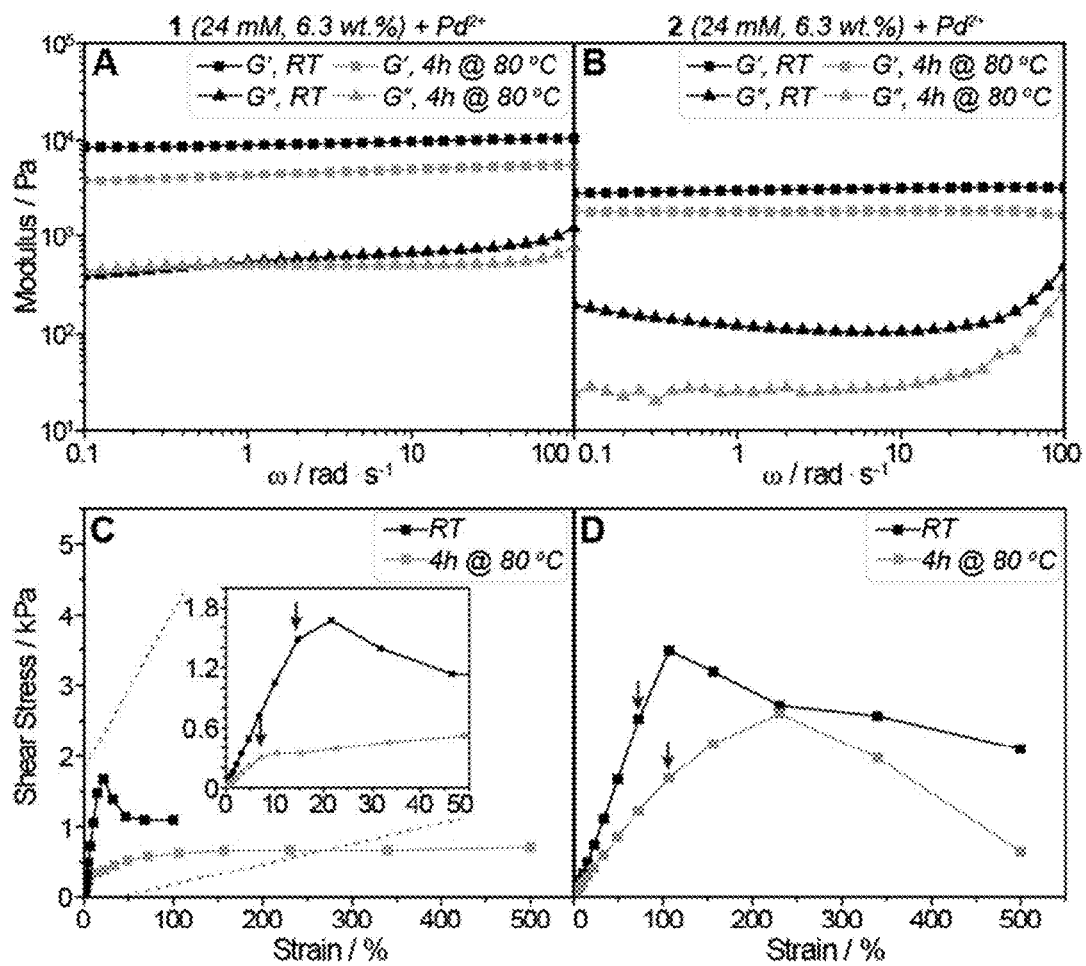

FIGS. 21A and 21B: Frequency sweeps in oscillatory rheology at 1.0% strain amplitude before and after annealing for 4 h at 80° C. for gels derived from B-3 ([B-3]=24 mM, FIG. 21A) and B-4 ([B-4]=24 mM, FIG. 21B). Stress vs. strain plots before and after thermal annealing for gels derived from B-3 ([B-3]=24 mM, FIG. 21C) and B-4

([B-4]=24 mM, FIG. 21D). Black arrows indicate points used for the determination of the yield stresses and strains. "1": B-3. "2": B-4.

FIG. 22A to 22C show images of a gel derived from B-3 ([B-3]=24 mM) as prepared (FIG. 22A), after cutting (FIG. 22B), and after annealing for 4 h at 80° C. (FIG. 22C), respectively. The damage emphasized by the grey box was not healed. FIG. 22D to 22F show images of a gel derived from B-4 ([B-4]=24 mM) as prepared (FIG. 22D), after cutting (FIG. 22E), and after annealing for 4 h at 80° C. (FIG. 22F), respectively. The damage emphasized by the grey box was healed. In all cases, the images shown are photographs of the bottom of 1-dram vials containing the gels. No solvent was added or pressure applied to facilitate healing. FIG. 22G: representative images of suprametallogels from B-3 and B-4 after swelling for 5 days in DMSO. The swelling ratios ($S_1$ and $S_2$=mass of swollen gel/mass of dry gel) are provided. FIG. 22H: images of suprametallogels derived from B-3 and B-4 in the presence of pyrene. Images were taken after continuous washing of the gels with fresh DMSO for two days. Superior retention of pyrene in the paddlewheel-based gel is readily observed. "1": B-3. "2": B-4.

Figure 23A:

FIG. 23A: images of gels formed from mixing C-1 and iron perchlorate (left panel) or nickel perchlorate (right panel) in acetonitrile.

Figure 23B:

FIG. 23B: an image of a liquid mixture formed after 25 μL of a 0.05 M $K_4$EDTA aqueous solution was added to the gel shown in FIG. 23A left panel (left panel); and an image of a liquid mixture formed after 25 μL of a 0.05 M $K_4$EDTA aqueous solution was added to the gel shown in FIG. 23A right panel (right panel).

Figure 24A:
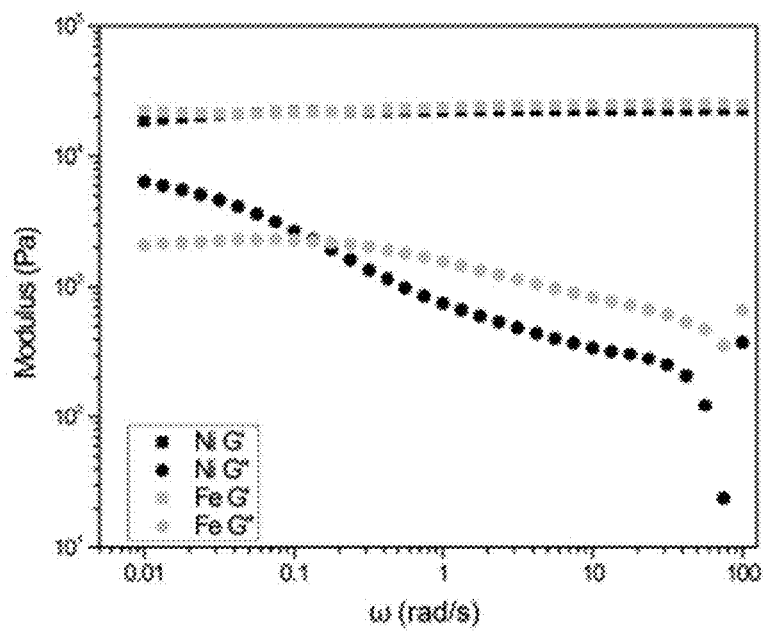
Figure 24B:
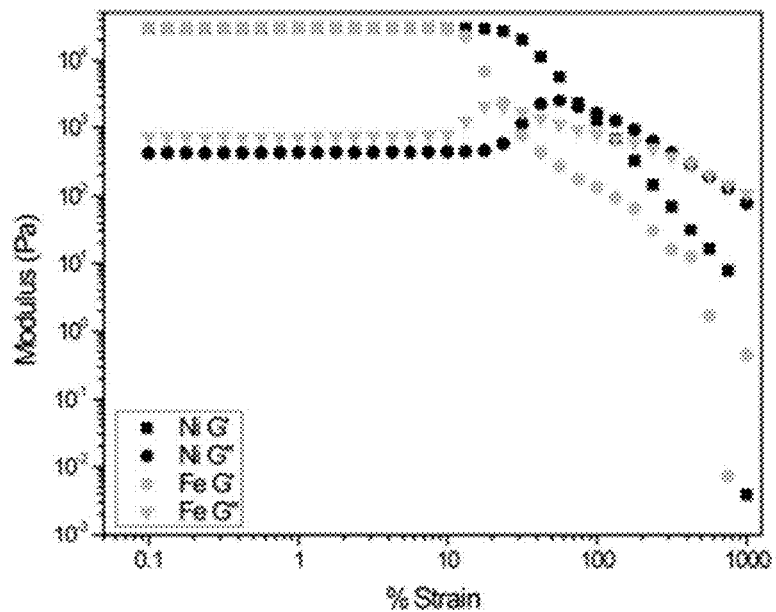

FIGS. 24A and 24B: mechanical properties of gels formed from C-1 and Ni(ClO$_4$)$_2$ ("Ni") and Fe(ClO$_4$)$_2$("Fe") in acetonitrile were characterized by oscillatory rheology.

Figure 25A:
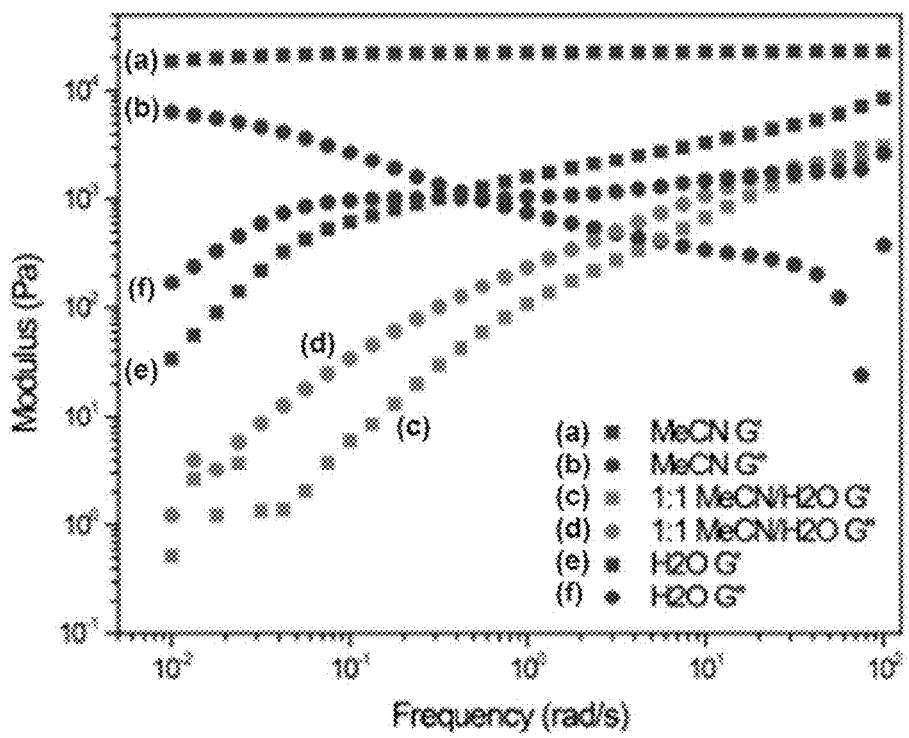
Figure 25B:
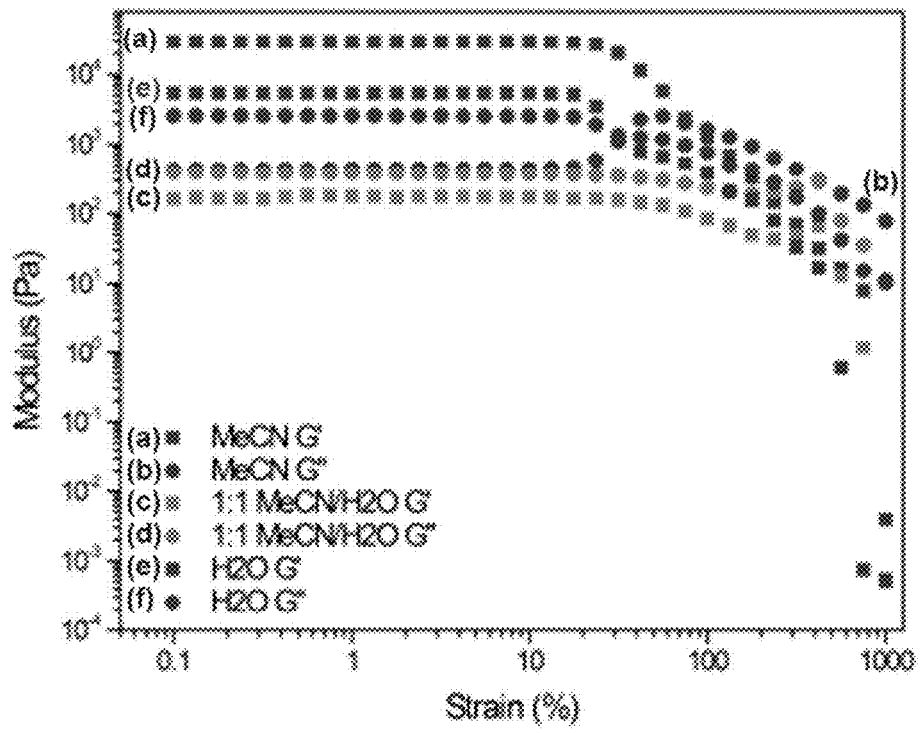

FIGS. 25A and 25B: effects of solvents on gelation of the gels formed from macromer C-1 and Ni(ClO$_4$)$_2$ hydrate.

Figure 26:
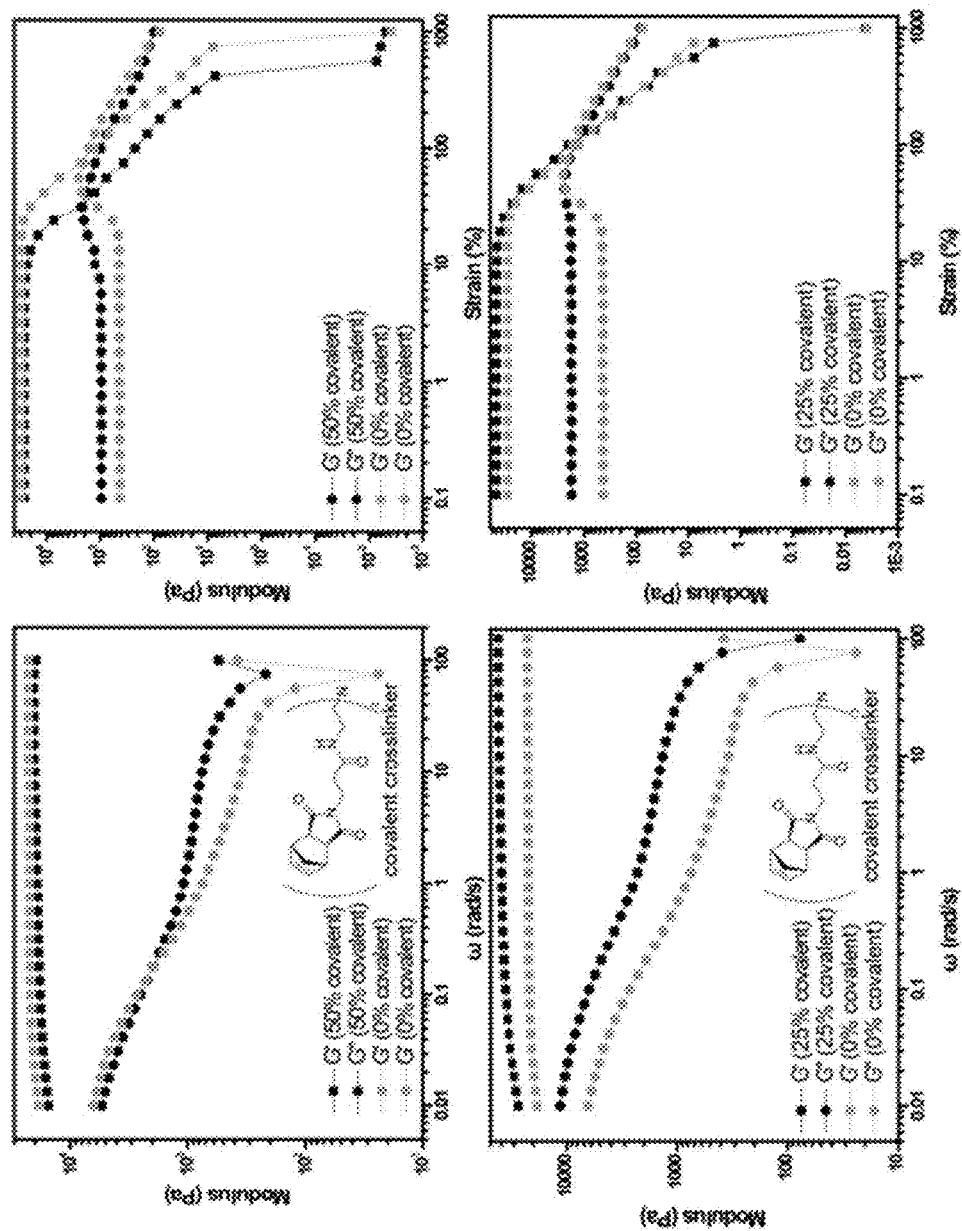

FIG. 26: oscillatory rheology of the gels of Example 15.

Figure 27:
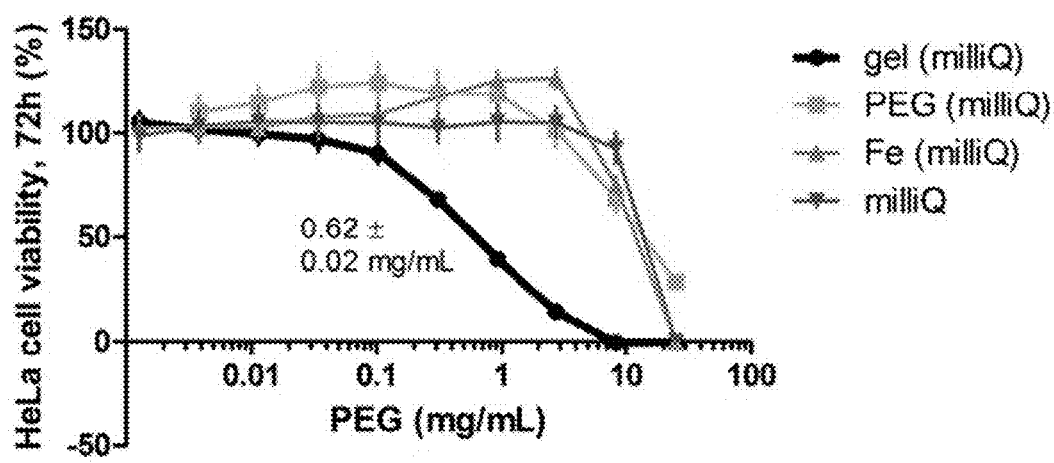

FIG. 27: cytotoxicities of (1) a gel formed from C-2 and $Fe^{2+}$ ("gel"), (2) PEG, and (3) $Fe^{2+}$ ("Fe") against HeLa cells. MILLIQ water ("milliQ") used as a control.

Figure 28:
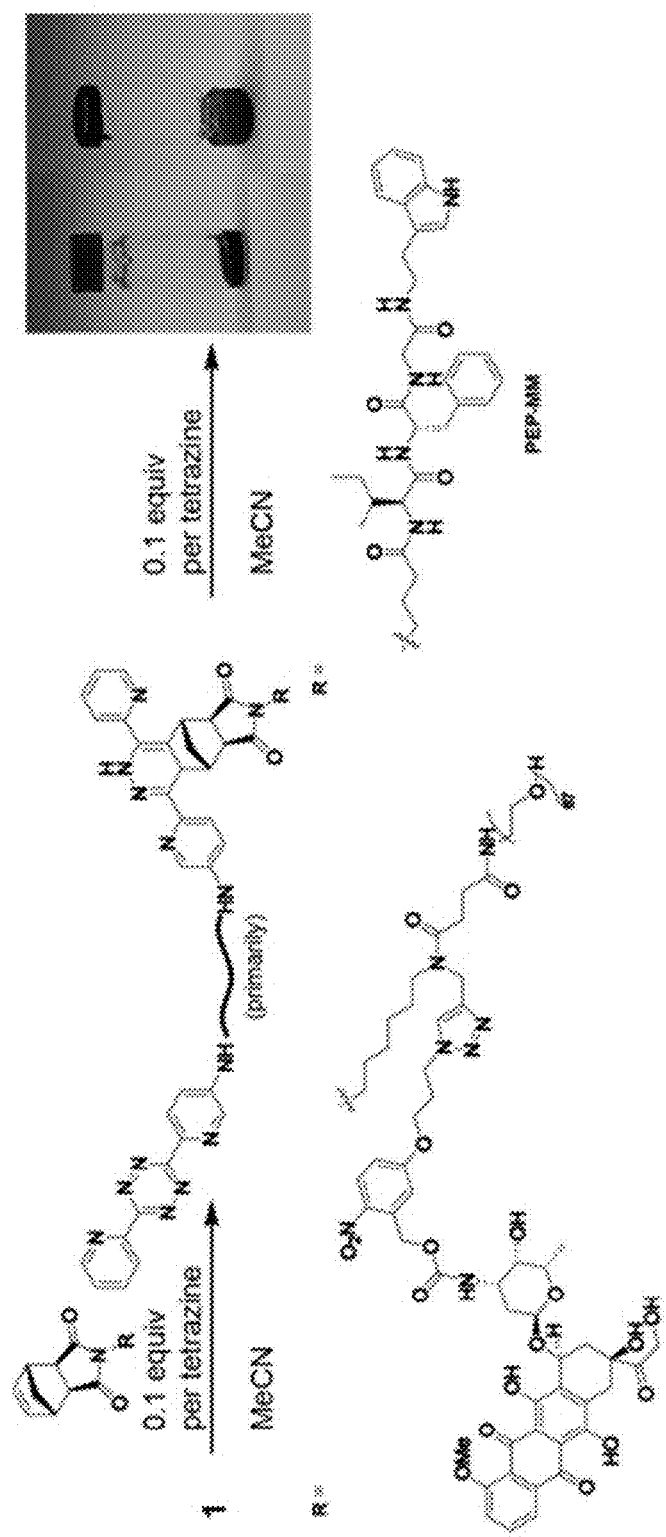

FIG. 28: preparation of the gel of Example 17, where the gel contains covalently attached doxorubicin. Inset: an image of the gel.

Figure 29:
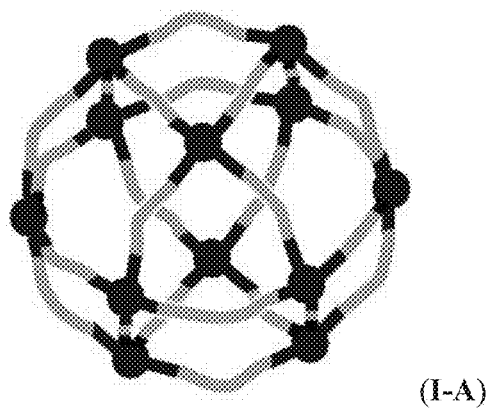

FIG. 29 shows Formula (I-A), wherein each instance of the black dot represents a transition metal ion, each instance of the gray line represents a ligand of Formula (A), and each black line represents a coordination bond.

Figure 30:
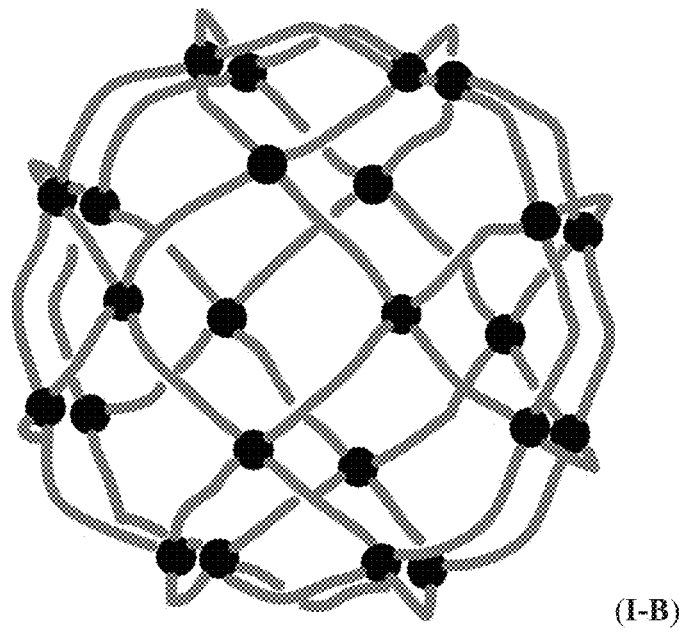

FIG. 30 shows Formula (I-B), wherein each instance of the black dot represents a transition metal ion, and each instance of the gray line represents a ligand of Formula (A).

Figure 31:
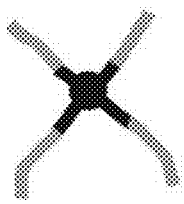

FIG. 31 shows a moiety of a nanosphere described herein.

Figure 32:

FIG. 32 shows Scheme 8, which shows exemplary synthesis of a paddlewheel (e.g., nano-paddlewheel described herein).

DETAILED DESCRIPTION OF CERTAIN EMBODIMENTS OF THE INVENTION

Reversible metal-ligand coordination has emerged as a powerful tool for the formation of a broad array of materials. In the realm of soft materials (e.g., gels), reversible metal-ligand coordination is a tool for the formation of self-healing molecular networks. In the area of hard materials, reversible metal-ligand coordination enables the formation of metal-organic frameworks (MOFs) and related metallosupramolecular assemblies.

The present disclosure provides, in one aspect, nanostructures formed through metal-ligand coordination and junction self-assembly. The present disclosure also provides supramolecular complexes that include nanostructures described herein connected by divalent linkers Y. The provided supramolecular complexes are able to swell in various solvents (including water) without dissolution and to form gels. Advantageous over conventional gels (e.g., conventional metallogels), the gels described herein exhibited excellent mechanical properties without sacrificing self-healing. Compared to conventional gels (e.g., conventional metallogels), the gels described herein behaved as elastic solids at low oscillatory angular frequencies and showed higher robustness (e.g., showed higher storage moduli). The nanostructures, and the nanostructure moieties of a supramolecular complex or gel described herein, may encapsulate and slowly release an agent (e.g., a small molecule, a peptide or protein, or a polynucleotide). The nanostructures, supramolecular complex, and compositions (e.g., gels) may be useful in delivering effectively and efficiently an agent to a subject, tissue, or cell, as bulk materials (e.g., as super-absorbent materials and/or bioactive materials), and/or in increasing the toughness of composite materials.

Nanostructures

Fujita et al. have reported banana-shaped organic molecules that self-organize into "Fujita spheres," which are finite, spherical coordination networks with a diameter in the order of nanometers (e.g., Tominaga et al., *Angew. Chem., Int. Ed.*, 2004, 43, 5621-5625; Bunzen et al. *Angew. Chem., Int. Ed.* 2012, 51, 3161; Sun et al., *Science*, 2010, 328, 1144). One of such reported Fujita spheres consists of 12 equivalents of a central metal ion (e.g., Pd(II)) and 24 equivalents of a bidentate ligand and has cuboctahedral symmetry. Hupp et al. has reported metal-organic frameworks prepared from a hexacarboxylated ligand and a transition metal ion (e.g., Cu(II) or Zn(II)) (Eryazici et al., *Crystal Growth & Design*, 2012, 12, 1075).

One aspect of the present disclosure relates to novel nanostructures, including, but not limited to, nanospheres and nano-paddlewheels. In certain embodiments, provide herein are nanospheres comprising:

(i) a plurality of a transition metal ion; and
(ii) a plurality of a ligand;

wherein each instance of the transition metal ion and two or more instances of the ligand form through coordination bonds a coordination complex;

wherein the plurality of a transition metal ion and the plurality of a ligand form through the coordination bonds one substantially spherical structure; and wherein the average outer diameter of the nanosphere is between about 1 nm and about 100 nm, inclusive.

In certain embodiments, provide herein are nano-paddlewheels comprising:

(i) a plurality of a transition metal ion; and
(ii) a plurality of a ligand;

wherein each instance of the transition metal ion and two or more instances of the ligand form through coordination bonds a coordination complex;

wherein the plurality of a transition metal ion and the plurality of a ligand form through the coordination bonds one substantially paddlewheel structure; and wherein the average outer diameter of the nano-paddlewheel is between about 1 nm and about 100 nm, inclusive.

In certain embodiments, each instance of the ligand is a monodentate ligand. In certain embodiments, each instance of the ligand is a polydentate (e.g., bidentate, tridentate, or tetradentate) ligand. In certain embodiments, each instance of the ligand comprises two or more pyridinyl moieties. In certain embodiments, each instance of the ligand comprises at least a first pyridinyl moiety and second pyridinyl moiety, wherein the angle (bite angle) between (1) the lone electron pair of the nitrogen atom of the first pyridinyl moiety and (2) the lone electron pair of the nitrogen atom of the second pyridinyl moiety, along the long axes of the lone electron pairs, is between 30° and 180°, inclusive, when the ligand is in the minimum energy conformation. In certain embodiments, the bite angle is between 60° and 160°, inclusive (e.g., about 90°, about 120°, about 127°, or about 149°). In certain embodiments, each instance of the ligand is a polydentate ligand, wherein the shortest distance between two chelation sites of the ligand is between about 5 Å and about 20 Å (e.g., between about 5 Å and about 10 Å), inclusive, when the ligand is in the minimum energy conformation.

In certain embodiments, a nanostructure described herein comprises x instances of a transition metal ion and 2x instances of a ligand of Formula (A):

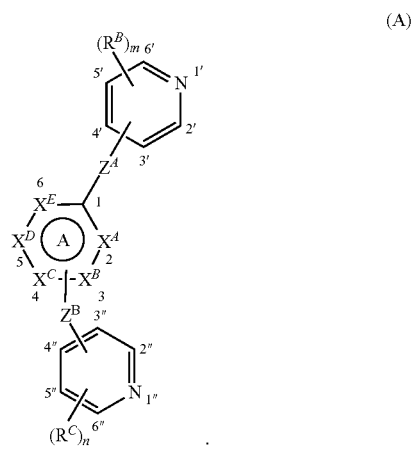

A nanostructure described herein includes x instances of a transition metal ion. In certain embodiments, all instances of the transition metal ion in a nanostructure are the same. In certain embodiments, x is an integer (e.g., an even integer) between 2 and 48, inclusive. In certain embodiments, x is an integer (e.g., an even integer) between 2 and 30, inclusive. In certain embodiments, x is an integer (e.g., an even integer) between 2 and 24, inclusive. In certain embodiments, x is an integer (e.g., an even integer) between 2 and 18, inclusive. In certain embodiments, x is 2. In certain embodiments, x is 4. In certain embodiments, x is 6. In certain embodiments, x is 12. In certain embodiments, x is 18. In certain embodiments, x is 24. In certain embodiments, x is 30. In certain embodiments, x is 48. In certain embodiments, x is 60. In certain embodiments, x is 12; and the nanostructure is a nanosphere. In certain embodiments, x is 24; and the nanostructure is a nanosphere. In certain embodiments, x is 2; and the nanostructure is a nano-paddlewheel. In certain embodiments, each instance of the transition metal ion is Pd (e.g., Pd(II)). In certain embodiments, each instance of the transition metal ion is Rh (e.g., Rh(I)). In certain embodiments, each instance of the transition metal ion is Ir (e.g., Ir(I)). In certain embodiments, each instance of the transition metal ion is Ni (e.g., Ni(II)). In certain embodiments, each instance of the transition metal ion is Pt (e.g., Pt(II)). In certain embodiments, each instance of the transition metal ion is Fe (e.g., Fe(II) or Fe(III)). In certain embodiments, each instance of the transition metal ion is Au (e.g., Au(III)). In certain embodiments, each instance of the transition metal ion is Cd (e.g., Cd(II)), Co (e.g., Co(III)), or Cu (e.g., Cu(I) or Cu(II)). In certain embodiments, each instance of the transition metal ion is Zn(II). In certain embodiments, each instance of the transition metal ion is not Zn(II).

A nanostructure described herein also includes 2x instances of a ligand of Formula (A). In certain embodiments, all instances of the ligand of Formula (A) in a nanostructure are the same. In other embodiments, at least two instances of the ligand of Formula (A) in a nanostructure are different.

Formula (A) includes Ring A that includes $X^A$, $X^B$, $X^C$, $X^D$, and $X^E$ in the ring system and is unsubstituted (e.g., each instance of $R^{41}$ and $R^{42}$ is hydrogen) or substituted with one or more substituents $R^{41}$ and/or $R^{42}$ (e.g., at least one instance of $R^{41}$ or $R^{42}$ is not hydrogen). In certain embodiments, each instance of $X^A$, $X^B$, $X^C$, $X^D$, and $X^E$ is independently C or $CR^{42}$, and Ring A is a substituted or unsubstituted phenyl ring. In certain embodiments, Ring A is of the formula:

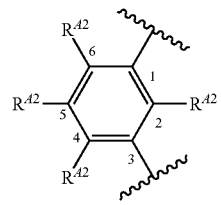

In certain embodiments, Ring A is of the formula:

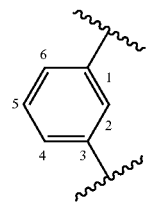

In certain embodiments, Ring A is of the formula:

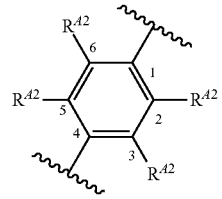

In certain embodiments, Ring A is of the formula:

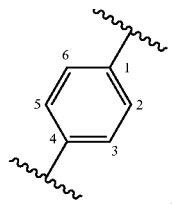

In certain embodiments, each instance of $X^A$, $X^B$, $X^C$, and $X^D$ is independently O, S, N, $NR^{A1}$, C, or $CR^{A2}$; at least one of $X^A$, $X^B$, $X^C$, and $X^D$ is not C or $CR^{A2}$; $X^E$ is absent; and Ring A is a substituted or unsubstituted, 5-membered, monocyclic heteroaryl ring. In certain embodiments, Ring A is a substituted or unsubstituted furanyl, substituted or unsubstituted thienyl, or substituted or unsubstituted pyrrolyl ring. In certain embodiments, Ring A is of the formula:

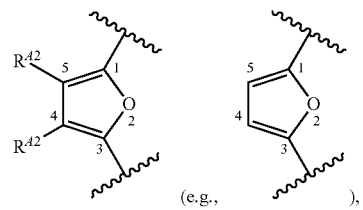

(e.g., ),

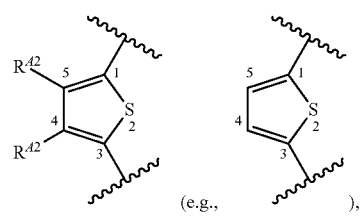

(e.g., ),

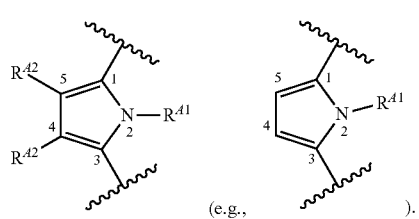

(e.g., ).

In certain embodiments, Ring A is a pyrazolyl, imidazolyl, oxazolyl, isoxazolyl, thiazolyl, or isothiazolyl ring, each of which is unsubstituted or substituted with $R^{A2}$. In certain embodiments, each instance of $X^A$, $X^B$, $X^C$, and $X^D$ is independently O, S, N, $NR^{A1}$, C, or $CR^{A2}$; $X^E$ is N, C, or $CR^{A2}$; at least one of $X^A$, $X^B$, $X^C$, $X^D$, and $X^E$ is not C or $CR^{A2}$; and Ring A is a substituted or unsubstituted, 6-membered, monocyclic heteroaryl ring. In certain embodiments, Ring A is a substituted or unsubstituted pyridyl ring. In certain embodiments, Ring A is of the formula:

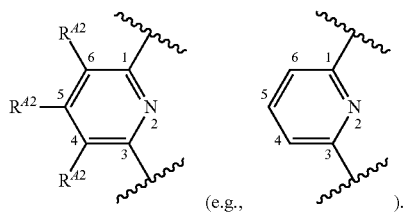

(e.g., ).

In certain embodiments, Ring A is a substituted or unsubstituted pyrazinyl, substituted or unsubstituted pyrimidinyl, or substituted or unsubstituted pyridazinyl ring. In certain embodiments, Ring A is of the formula:

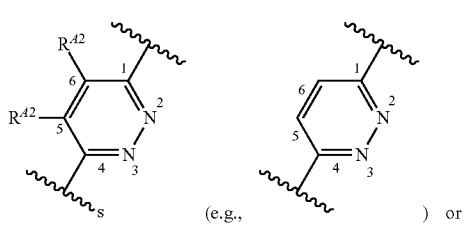

(e.g., ) or

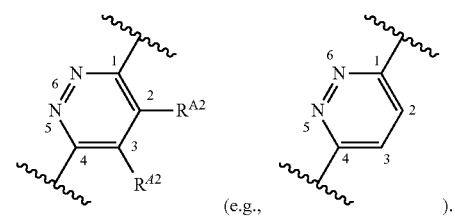

(e.g., ).

In certain embodiments, Ring A is of the formula:

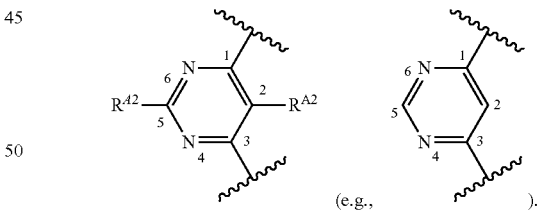

(e.g., ).

In certain embodiments, Ring A is of the formula:

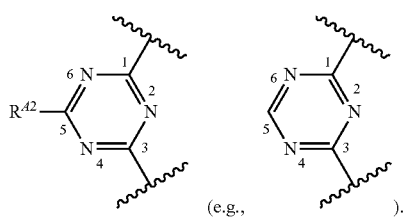

(e.g., ).

In certain embodiments, Ring A is of the formula:

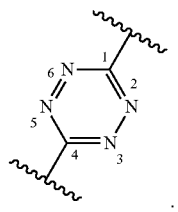 [SMILES: *c1nnc(*)nn1]

In certain embodiments, at least two instances of $R^{A1}$ are different from each other. In certain embodiments, all instances of $R^{A1}$ are the same. In certain embodiments, at least one instance of $R^{A1}$ is hydrogen. In certain embodiments, each instance of $R^{A1}$ is hydrogen. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is unsubstituted $C_{1-6}$ alkyl. In certain embodiments, all instances of $R^{A1}$ are unsubstituted $C_{1-6}$ alkyl. In certain embodiments, at least one instance of $R^{A1}$ is substituted $C_{1-6}$ alkyl. In certain embodiments, at least one instance of $R^{A1}$ is $C_{1-6}$ alkyl substituted with at least one halogen. In certain embodiments, at least one instance of $R^{A1}$ is —$CH_3$. In certain embodiments, all instances of $R^{A1}$ are —$CH_3$. In certain embodiments, at least one instance of $R^{A1}$ is substituted methyl. In certain embodiments, at least one instance of $R^{A1}$ is —$CH_2F$, —$CHF_2$, or —$CF_3$. In certain embodiments, at least one instance of $R^{A1}$ is ethyl, propyl, butyl, pentyl, or hexyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is saturated carbocyclyl. In certain embodiments, at least one instance of $R^{A1}$ is unsaturated carbocyclyl. In certain embodiments, at least one instance of $R^{A1}$ is monocyclic carbocyclyl. In certain embodiments, at least one instance of $R^{A1}$ is 3- to 7-membered, monocyclic carbocyclyl. In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is saturated heterocyclyl. In certain embodiments, at least one instance of $R^{A1}$ is unsaturated heterocyclyl. In certain embodiments, at least one instance of $R^{A1}$ is heterocyclyl, wherein one, two, or three atoms in the heterocyclic ring system are independently selected from the group consisting of nitrogen, oxygen, and sulfur. In certain embodiments, at least one instance of $R^{A1}$ is monocyclic heterocyclyl. In certain embodiments, at least one instance of $R^{A1}$ is 3- to 7-membered, monocyclic heterocyclyl. In certain embodiments, at least one instance of $R^{A1}$ is substituted aryl. In certain embodiments, at least one instance of $R^{A1}$ is unsubstituted aryl. In certain embodiments, at least one instance of $R^{A1}$ is 6- to 10-membered aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is substituted heteroaryl. In certain embodiments, at least one instance of $R^{A1}$ is unsubstituted heteroaryl. In certain embodiments, at least one instance of $R^{A1}$ is heteroaryl, wherein one, two, three, or four atoms in the heteroaryl ring system are independently selected from the group consisting of nitrogen, oxygen, and sulfur. In certain embodiments, at least one instance of $R^{A1}$ is monocyclic heteroaryl. In certain embodiments, at least one instance of $R^{A1}$ is 5-membered, monocyclic heteroaryl. In certain embodiments, at least one instance of $R^{A1}$ is 6-membered, monocyclic heteroaryl. In certain embodiments, at least one instance of $R^{A1}$ is bicyclic heteroaryl, wherein the point of attachment may be on any atom of the bicyclic heteroaryl ring system, as valency permits. In certain embodiments, at least one instance of $R^{A1}$ is 9- or 10-membered, bicyclic heteroaryl. In certain embodiments, at least one instance of $R^{A1}$ is —$C(=O)R^a$ (e.g., —$C(=O)$(substituted or unsubstituted $C_{1-6}$ alkyl)), —$C(=O)OR^a$ (e.g., —$C(=O)O$(substituted or unsubstituted $C_{1-6}$ alkyl)), or —$C(=O)N(R^a)_2$ (e.g., —$C(=O)NH_2$, —$C(=O)NH$(substituted or unsubstituted $C_{1-6}$ alkyl), or —$C(=O)N$(substituted or unsubstituted $C_{1-6}$ alkyl)-(substituted or unsubstituted $C_{1-6}$ alkyl)). In certain embodiments, at least one instance of $R^{A1}$ is a nitrogen protecting group. In certain embodiments, at least one instance of $R^{A1}$ is Bn, Boc, Cbz, Fmoc, trifluoroacetyl, triphenylmethyl, acetyl, or Ts.

Each instance of $R^{A1}$, $R^{A2}$, $R^B$, and $R^C$ may independently include one or more substituents $R^a$. In certain embodiments, all instances of $R^a$ are the same. In certain embodiments, at least two instances of R are different from each other. In certain embodiments, at least one instance of $R^a$ is H. In certain embodiments, each instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted $C_{1-6}$ alkyl). In certain embodiments, at least one instance of $R^a$ is —$CH_3$. In certain embodiments, at least one instance of $R^a$ is —$CF_3$, unsubstituted ethyl, perfluoroethyl, unsubstituted propyl, perfluoropropyl, unsubstituted butyl, or perfluorobutyl. In certain embodiments, at least one instance of $R^a$ is substituted or unsubstituted alkenyl (e.g., substituted or unsubstituted $C_{1-6}$ alkenyl). In certain embodiments, at least one instance of $R^a$ is substituted or unsubstituted alkynyl (e.g., substituted or unsubstituted $C_{1-6}$ alkynyl). In certain embodiments, at least one instance of $R^a$ is substituted or unsubstituted carbocyclyl (e.g., substituted or unsubstituted, monocyclic, 3- to 7-membered carbocyclyl). In certain embodiments, at least one instance of $R^a$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^a$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$ are joined to form a substituted or unsubstituted heterocyclic ring (e.g., substituted or unsubstituted, monocyclic, 5- to 6-membered heterocyclic ring, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, monocyclic, 5- to 6-membered heteroaryl ring, wherein one, two, three, or four atoms in the heteroaryl ring system are independently nitrogen, oxygen, or sulfur).

In certain embodiments, at least two instances of $R^{A2}$ are different from each other. In certain embodiments, all instances of $R^{A2}$ are the same. In certain embodiments, at least one instance of $R^{A2}$ is hydrogen. In certain embodiments, each instance of $R^{A2}$ is hydrogen. In certain embodiments, at least one instance of $R^{A2}$ is halogen. In certain embodiments, at least one instance of $R^{A2}$ is F. In certain embodiments, at least one instance of $R^{A2}$ is Cl. In certain embodiments, at least one instance of $R^{A2}$ is Br. In certain embodiments, at least one instance of $R^{A2}$ is I (iodine). In certain embodiments, at least one instance of $R^{A2}$ is substituted alkyl. In certain embodiments, at least one instance of $R^{A2}$ is unsubstituted alkyl. In certain embodiments, at least one instance of $R^{A2}$ is unsubstituted $C_{1-6}$ alkyl. In certain embodiments, all instances of $R^{A2}$ are unsubstituted $C_{1-6}$ alkyl. In certain embodiments, at least one instance of $R^{A2}$ is substituted $C_{1-6}$ alkyl. In certain embodiments, at least one instance of $R^{A2}$ is $C_{1-6}$ alkyl substituted with at least one halogen. In certain embodiments, at least one instance of $R^{A2}$ is —$CH_3$. In certain embodiments, all instances of $R^{A2}$ are —$CH_3$. In certain embodiments, at least one instance of $R^{A2}$ is substituted methyl. In certain embodiments, at least one instance of $R^{A2}$ is —$CH_2F$, —$CHF_2$, or —$CF_3$. In certain embodiments, at least one instance of $R^{A2}$ is ethyl, propyl, butyl, pentyl, or hexyl. In certain embodiments, at least one instance of $R^{A2}$ is substituted alkenyl. In certain embodiments, at least one instance of $R^{A2}$ is unsubstituted alkenyl. In certain embodiments, at least one instance of $R^{A2}$ is substituted alkynyl. In certain embodiments, at least one instance of $R^{A2}$ is unsubstituted alkynyl. In certain embodiments, at least one instance of $R^{A2}$ is substituted carbocyclyl. In certain embodiments, at least one instance of $R^{A2}$ is unsubstituted carbocyclyl. In certain embodiments, at least one instance of $R^{A2}$ is saturated carbocyclyl. In certain embodiments, at least one instance of $R^{A2}$ is unsaturated carbocyclyl. In certain embodiments, at least one instance of $R^{A2}$ is monocyclic carbocyclyl. In certain embodiments, at least one instance of $R^{A2}$ is 3- to 7-membered, monocyclic carbocyclyl. In certain embodiments, at least one instance of $R^{A2}$ is substituted heterocyclyl. In certain embodiments, at least one instance of $R^{A2}$ is unsubstituted heterocyclyl. In certain embodiments, at least one instance of $R^{A2}$ is saturated heterocyclyl. In certain embodiments, at least one instance of $R^{A2}$ is unsaturated heterocyclyl. In certain embodiments, at least one instance of $R^{A2}$ is heterocyclyl, wherein one, two, or three atoms in the heterocyclic ring system are independently selected from the group consisting of nitrogen, oxygen, and sulfur. In certain embodiments, at least one instance of $R^{A2}$ is monocyclic heterocyclyl. In certain embodiments, at least one instance of $R^{A2}$ is 3- to 7-membered, monocyclic heterocyclyl. In certain embodiments, at least one instance of $R^{A2}$ is substituted aryl. In certain embodiments, at least one instance of $R^{A2}$ is unsubstituted aryl. In certain embodiments, at least one instance of $R^{A2}$ is 6- to 10-membered aryl. In certain embodiments, at least one instance of $R^{A2}$ is substituted phenyl. In certain embodiments, at least one instance of $R^{A2}$ is unsubstituted phenyl. In certain embodiments, at least one instance of $R^2$ is substituted heteroaryl. In certain embodiments, at least one instance of $R^{A2}$ is unsubstituted heteroaryl. In certain embodiments, at least one instance of $R^{A2}$ is heteroaryl, wherein one, two, three, or four atoms in the heteroaryl ring system are independently selected from the group consisting of nitrogen, oxygen, and sulfur. In certain embodiments, at least one instance of $R^{A2}$ is monocyclic heteroaryl. In certain embodiments, at least one instance of $R^{A2}$ is 5-membered, monocyclic heteroaryl. In certain embodiments, at least one instance of $R^{A2}$ is 6-membered, monocyclic heteroaryl. In certain embodiments, at least one instance of $R^{A2}$ is bicyclic heteroaryl, wherein the point of attachment may be on any atom of the bicyclic heteroaryl ring system, as valency permits. In certain embodiments, at least one instance of $R^{A2}$ is 9- or 10-membered, bicyclic heteroaryl. In certain embodiments, at least one instance of $R^{A2}$ is —$OR^a$. In certain embodiments, at least one instance of $R^{A1}$ is —OH. In certain embodiments, at least one instance of $R^{A2}$ is —O(substituted or unsubstituted $C_{1-6}$ alkyl). In certain embodiments, at least one instance of $R^{A2}$ is —OMe. In certain embodiments, at least one instance of $R^{A2}$ is —OEt, —OPr, or —OBu. In certain embodiments, at least one instance of $R^{A2}$ is —OBn or —OPh. In certain embodiments, at least one instance of $R^{A2}$ is —SR. In certain embodiments, at least one instance of $R^{A2}$ is —SH. In certain embodiments, at least one instance of $R^{A2}$ is —SMe. In certain embodiments, at least one instance of $R^{A1}$ is —$N(R^a)_2$. In certain embodiments, at least one instance of $R^{A2}$ is —$NH_2$. In certain embodiments, at least one instance of $R^{A2}$ is —NHMe. In certain embodiments, at least one instance of $R^2$ is —$NMe_2$. In certain embodiments, at least one instance of $R^{A2}$ is —CN. In certain embodiments, at least one instance of $R^{A2}$ is —SCN. In certain embodiments, at least one instance of $R^{A2}$ is —$C(=NR^a)R^a$, —$C(=NR^a)OR^a$, or —$C(=NR^a)N(R^a)_2$. In certain embodiments, at least one instance of $R^{A2}$ is —$C(=O)R^a$ or —$C(=O)OR^a$. In certain embodiments, at least one instance of $R^{A2}$ is —$C(=O)N(R^a)_2$. In certain embodiments, at least one instance of $R^{A2}$ is —$C(=O)NMe_2$, —$C(=O)NHMe$, or —$C(=O)NH_2$. In certain embodiments, at least one instance of $R^{A2}$ is —$NO_2$. In certain embodiments, at least one instance of $R^{A2}$ is —$NR^aC(=O)R^a$, —$NR^aC(=O)OR^a$, or —$NR^aC(=O)N(R^a)_2$. In certain embodiments, at least one instance of $R^{A2}$ is —$OC(=O)R^a$, —$OC(=O)OR^a$, or —$OC(=O)N(R^a)_2$.

Formula (A) includes as Ring B a pyridyl ring that is unsubstituted (e.g., when m is 0) or substituted with one or more substituents $R^B$ (e.g., when m is 1, 2, 3, or 4). In certain embodiments, Ring B is of the formula:

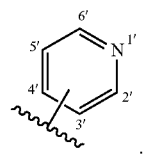

In certain embodiments, Ring B is of the formula:

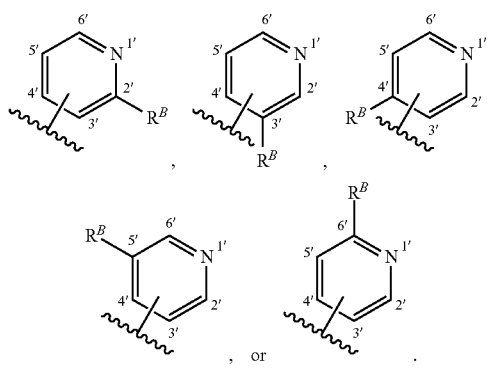

, or

In certain embodiments, Ring B is of the formula:

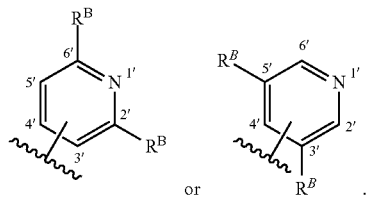

In certain embodiments, Ring B is of the formula:

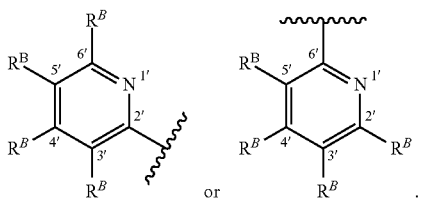

In certain embodiments, Ring B is of the formula:

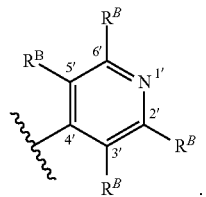

In certain embodiments, Ring B is of the formula:

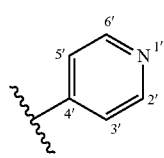

In certain embodiments, Ring B is of the formula:

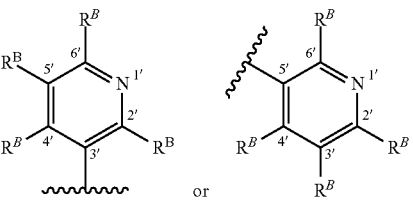

In certain embodiments, Ring B is of the formula:

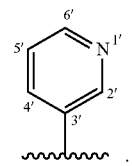

In certain embodiments, at least two instances of $R^B$ are different from each other. In certain embodiments, all instances of $R^B$ are the same. In certain embodiments, at least one instance of $R^B$ is halogen. In certain embodiments, at least one instance of $R^B$ is F. In certain embodiments, at least one instance of $R^B$ is Cl. In certain embodiments, at least one instance of $R^B$ is Br. In certain embodiments, at least one instance of $R^B$ is I (iodine). In certain embodiments, at least one instance of $R^B$ is substituted alkyl. In certain embodiments, at least one instance of $R^B$ is unsubstituted alkyl. In certain embodiments, at least one instance of $R^B$ is unsubstituted $C_{1-6}$ alkyl. In certain embodiments, all instances of $R^B$ are unsubstituted $C_{1-6}$ alkyl. In certain embodiments, at least one instance of $R^B$ is substituted $C_{1-6}$ alkyl. In certain embodiments, at least one instance of $R^B$ is $C_{1-6}$ alkyl substituted with at least one halogen. In certain embodiments, at least one instance of $R^B$ is —$CH_3$. In certain embodiments, all instances of $R^B$ are —$CH_3$. In certain embodiments, at least one instance of $R^B$ is substituted methyl. In certain embodiments, at least one instance of $R^B$ is —$CH_2F$, —$CHF_2$, or —$CF_3$. In certain embodiments, at least one instance of $R^B$ is ethyl, propyl, butyl, pentyl, or hexyl. In certain embodiments, at least one instance of $R^B$ is substituted alkenyl. In certain embodiments, at least one instance of $R^B$ is unsubstituted alkenyl. In certain embodiments, at least one instance of $R^B$ is substituted alkynyl. In certain embodiments, at least one instance of $R^B$ is unsubstituted alkynyl. In certain embodiments, at least one instance of $R^B$ is substituted carbocyclyl. In certain embodiments, at least one instance of $R^B$ is unsubstituted carbocyclyl. In certain embodiments, at least one instance of $R^B$ is saturated carbocyclyl. In certain embodiments, at least one instance of $R^B$ is unsaturated carbocyclyl. In certain embodiments, at least one instance of $R^B$ is monocyclic carbocyclyl. In certain embodiments, at least one instance of $R^B$ is 3- to 7-membered, monocyclic carbocyclyl. In certain embodiments, at least one instance of $R^B$ is substituted heterocyclyl. In certain embodiments, at least one instance of $R^B$ is unsubstituted heterocyclyl. In certain embodiments, at least one instance of $R^B$ is saturated heterocyclyl. In certain embodiments, at least one instance of $R^B$ is unsaturated heterocyclyl. In certain embodiments, at least one instance of $R^B$ is heterocyclyl, wherein one, two, or three atoms in the heterocyclic ring system are independently selected from the group consisting of nitrogen, oxygen, and sulfur. In certain embodiments, at least one instance of $R^B$ is monocyclic heterocyclyl. In certain embodiments, at least one instance of $R^B$ is 3- to 7-membered, monocyclic heterocyclyl. In certain embodiments, at least one instance of $R^B$ is substituted aryl. In certain embodiments, at least one instance of $R^B$ is unsubstituted aryl. In certain embodiments, at least one instance of $R^B$ is 6- to 10-membered aryl. In certain embodiments, at least one instance of $R^B$ is substituted phenyl. In certain embodiments, at least one instance of $R^B$ is unsubstituted phenyl. In certain embodiments, at least one instance of $R^B$ is substituted heteroaryl. In certain embodiments, at least one instance of $R^B$ is unsubstituted heteroaryl. In certain embodiments, at least one instance of $R^B$ is heteroaryl, wherein one, two, three, or four atoms in the heteroaryl ring system are independently selected from the group consisting of nitrogen, oxygen, and sulfur. In certain embodiments, at least one instance of $R^B$ is monocyclic heteroaryl. In certain embodiments, at least one instance of $R^B$ is 5-membered, monocyclic heteroaryl. In certain embodiments, at least one instance of $R^B$ is 6-membered, monocyclic heteroaryl. In certain embodiments, at least one instance of $R^B$ is bicyclic heteroaryl, wherein the point of attachment may be on any atom of the bicyclic heteroaryl ring system, as valency permits. In certain embodiments, at least one instance of $R^B$ is 9- or 10-membered, bicyclic heteroaryl. In certain embodiments, at least one instance of $R^B$ is —$OR^a$. In certain embodiments, at least one instance of $R^B$ is —OH. In certain embodiments, at least one instance of $R^B$ is —O(substituted or unsubstituted $C_{1-6}$ alkyl). In certain embodiments, at least one instance of $R^B$ is —OMe. In certain embodiments, at least one instance of $R^B$ is —OEt, —OPr, or —OBu. In certain embodiments, at least one instance of $R^B$ is —OBn or —OPh. In certain embodiments, at least one instance of $R^B$ is —SR. In certain embodiments, at least one instance of $R^B$ is —SH. In certain embodiments, at least one instance of $R^B$ is —SMe. In certain embodiments, at least one instance of $R^B$ is —N($R^a$)$_2$. In certain embodiments, at least one instance of $R^B$ is —NH$_2$. In certain embodiments, at least one instance of $R^B$ is —NHMe. In certain embodiments, at least one instance of $R^B$ is —NMe$_2$. In certain embodiments, at least one instance of $R^B$ is —CN. In certain embodiments, at least one instance of $R^B$ is —SCN. In certain embodiments, at least one instance of $R^B$ is —C(=N$R^a$)$R^a$, —C(=N$R^a$)O$R^a$, or —C(=N$R^a$)N($R^a$)$_2$. In certain embodiments, at least one instance of $R^B$ is —C(=O)$R^a$ or —C(=O)O$R^a$. In certain embodiments, at least one instance of $R^B$ is —C(=O)N($R^a$)$_2$. In certain embodiments, at least one instance of $R^B$ is —C(=O)NMe$_2$, —C(=O)NHMe, or —C(=O)NH$_2$. In certain embodiments, at least one instance of $R^B$ is —NO$_2$. In certain embodiments, at least one instance of $R^B$ is —N$R^a$C(=O)$R^a$, —N$R^a$C(=O)O$R^a$, or —N$R^a$C(=O)N($R^a$)$_2$. In certain embodiments, at least one instance of $R^B$ is —OC(=O)$R^a$, —OC(=O)O$R^a$, or —OC(=O)N($R^a$)$_2$.

In certain embodiments, m is 0. In certain embodiments, m is 1. In certain embodiments, m is 2. In certain embodiments, m is 3. In certain embodiments, m is 4.

Formula (A) includes as Ring C a pyridyl ring that is unsubstituted (e.g., when n is 0) or substituted with one or more substituents $R^C$ (e.g., when n is 1, 2, 3, or 4). In certain embodiments, Ring C is of the formula:

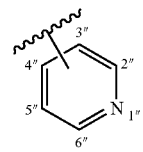

In certain embodiments, Ring C is of the formula:

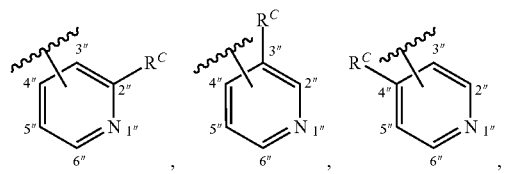

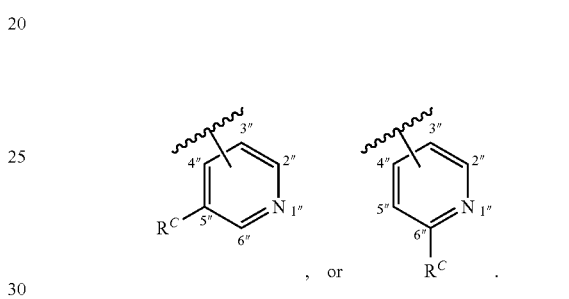

In certain embodiments, Ring C is of the formula:

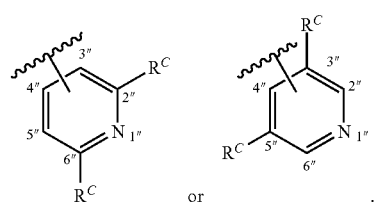

In certain embodiments, Ring C is of the formula:

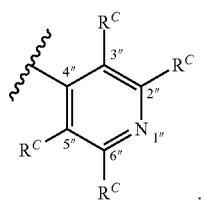

In certain embodiments, Ring C is of the formula:

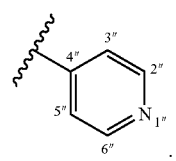

In certain embodiments, Ring C is of the formula:

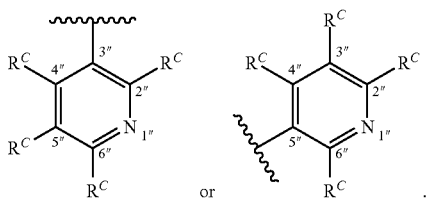

In certain embodiments, Ring C is of the formula:

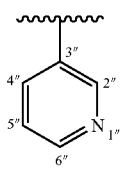

In certain embodiments, at least two instances of $R^C$ are different from each other. In certain embodiments, all instances of $R^C$ are the same. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted alkyl. In certain embodiments, at least one instance of $R^C$ is unsubstituted alkyl. In certain embodiments, at least one instance of $R^C$ is unsubstituted $C_{1-6}$ alkyl. In certain embodiments, all instances of $R^C$ are unsubstituted $C_{1-6}$ alkyl. In certain embodiments, at least one instance of $R^C$ is substituted $C_{1-6}$ alkyl. In certain embodiments, at least one instance of $R^C$ is $C_{1-6}$ alkyl substituted with at least one halogen. In certain embodiments, at least one instance of $R^C$ is —$CH_3$. In certain embodiments, all instances of $R^C$ are —$CH_3$. In certain embodiments, at least one instance of $R^C$ is substituted methyl. In certain embodiments, at least one instance of $R^C$ is —$CH_2F$, —$CHF_2$, or —$CF_3$. In certain embodiments, at least one instance of $R^C$ is ethyl, propyl, butyl, pentyl, or hexyl. In certain embodiments, at least one instance of $R^C$ is substituted alkenyl. In certain embodiments, at least one instance of $R^C$ is unsubstituted alkenyl. In certain embodiments, at least one instance of $R^C$ is substituted alkynyl. In certain embodiments, at least one instance of $R^C$ is unsubstituted alkynyl. In certain embodiments, at least one instance of $R^C$ is substituted carbocyclyl. In certain embodiments, at least one instance of $R^C$ is unsubstituted carbocyclyl. In certain embodiments, at least one instance of $R^C$ is saturated carbocyclyl. In certain embodiments, at least one instance of $R^C$ is unsaturated carbocyclyl. In certain embodiments, at least one instance of $R^C$ is monocyclic carbocyclyl. In certain embodiments, at least one instance of $R^C$ is 3- to 7-membered, monocyclic carbocyclyl. In certain embodiments, at least one instance of $R^C$ is substituted heterocyclyl. In certain embodiments, at least one instance of $R^C$ is unsubstituted heterocyclyl. In certain embodiments, at least one instance of $R^C$ is saturated heterocyclyl. In certain embodiments, at least one instance of $R^C$ is unsaturated heterocyclyl. In certain embodiments, at least one instance of $R^C$ is heterocyclyl, wherein one, two, or three atoms in the heterocyclic ring system are independently selected from the group consisting of nitrogen, oxygen, and sulfur. In certain embodiments, at least one instance of $R^C$ is monocyclic heterocyclyl. In certain embodiments, at least one instance of $R^C$ is 3- to 7-membered, monocyclic heterocyclyl. In certain embodiments, at least one instance of $R^C$ is substituted aryl. In certain embodiments, at least one instance of $R^C$ is unsubstituted aryl. In certain embodiments, at least one instance of $R^C$ is 6- to 10-membered aryl. In certain embodiments, at least one instance of $R^C$ is substituted phenyl. In certain embodiments, at least one instance of $R^C$ is unsubstituted phenyl. In certain embodiments, at least one instance of $R^C$ is substituted heteroaryl. In certain embodiments, at least one instance of $R^C$ is unsubstituted heteroaryl. In certain embodiments, at least one instance of $R^C$ is heteroaryl, wherein one, two, three, or four atoms in the heteroaryl ring system are independently selected from the group consisting of nitrogen, oxygen, and sulfur. In certain embodiments, at least one instance of $R^C$ is monocyclic heteroaryl. In certain embodiments, at least one instance of $R^C$ is 5-membered, monocyclic heteroaryl. In certain embodiments, at least one instance of $R^C$ is 6-membered, monocyclic heteroaryl. In certain embodiments, at least one instance of $R^C$ is bicyclic heteroaryl, wherein the point of attachment may be on any atom of the bicyclic heteroaryl ring system, as valency permits. In certain embodiments, at least one instance of $R^C$ is 9- or 10-membered, bicyclic heteroaryl. In certain embodiments, at least one instance of $R^C$ is —$OR^a$. In certain embodiments, at least one instance of $R^C$ is —OH. In certain embodiments, at least one instance of $R^C$ is —O(substituted or unsubstituted $C_{1-6}$ alkyl). In certain embodiments, at least one instance of $R^C$ is —OMe. In certain embodiments, at least one instance of $R^C$ is —OEt, —OPr, or —OBu. In certain embodiments, at least one instance of $R^C$ is —OBn or —OPh. In certain embodiments, at least one instance of $R^C$ is —$SR^a$. In certain embodiments, at least one instance of $R^C$ is —SH. In certain embodiments, at least one instance of $R^C$ is —SMe. In certain embodiments, at least one instance of $R^C$ is —$N(R^a)_2$. In certain embodiments, at least one instance of $R^C$ is —$NH_2$. In certain embodiments, at least one instance of $R^C$ is —NHMe. In certain embodiments, at least one instance of $R^C$ is —$NMe_2$. In certain embodiments, at least one instance of $R^C$ is —CN. In certain embodiments, at least one instance of $R^C$ is —SCN. In certain embodiments, at least one instance of $R^C$ is —$C(=NR^a)R^a$, —$C(=NR^a)OR^a$, or —$C(=NR^a)N(R^a)_2$. In certain embodiments, at least one instance of $R^C$ is —C(=O)R'' or —$C(=O)OR^a$. In certain embodiments, at least one instance of $R^C$ is —$C(=O)N(R^a)_2$. In certain embodiments, at least one instance of $R^C$ is —$C(=O)NMe_2$, —C(=O)NHMe, or —$C(=O)NH_2$. In certain embodiments, at least one instance of $R^C$ is —$NO_2$. In certain embodiments, at least one instance of $R^C$ is —$NR^aC(=O)R^a$, —$NR^aC(=O)OR^a$, or —$NR^aC(=O)N(R^a)_2$. In certain embodiments, at least one instance of $R^C$ is —$OC(=O)R^a$, —$OC(=O)OR^a$, or —$OC(=O)N(R^a)_2$.

In certain embodiments, n is 0. In certain embodiments, n is 1. In certain embodiments, n is 2. In certain embodiments, n is 3. In certain embodiments, n is 4.

In certain embodiments, at least one instance of $R^B$ and at least one instance of $R^C$ are different from each other. In certain embodiments, the instance of $R^B$ at the carbon atom labeled with w' is the same as the instance of $R^C$ at the carbon atom labeled with w", wherein w is 2, 3, 4, 5, or 6. In certain embodiments, m and n are different from each other. In certain embodiments, m and n are the same. In certain embodiments, each of m and n is 0.

Formula (A) includes a divalent linker $Z^A$ that directly covalently connects Ring A and Ring B. In certain embodiments, $Z^A$ is a bond. In certain embodiments, $Z^A$ is a substituted or unsubstituted $C_{1-4}$ hydrocarbon chain, optionally wherein one or more chain atoms are independently replaced with —O—, —S—, —NR$^{ZA}$—, —N═, or ═N—. In certain embodiments, when $Z^A$ is a substituted or unsubstituted $C_{1-6}$ hydrocarbon chain, $Z^A$ consists of a chain, and optionally one or more hydrogen atoms and/or one or more substituents (e.g., ═O) on the chain, where any two substituents may optionally be joined to form a ring. In certain embodiments, $Z^A$ does not include unsaturated bonds in the chain. In certain embodiments, $Z^A$ consists of one or two unsaturated bonds in the chain. In certain embodiments, $Z^A$ is a substituted (e.g., substituted with at least one instance of halogen) $C_{1-6}$ hydrocarbon chain. In certain embodiments, $Z^A$ is an unsubstituted $C_{1-4}$ hydrocarbon chain. In certain embodiments, the molecular weight of $Z^A$ is not more than about 150 g/mol, not more than about 100 g/mol, not more than 80 g/mol, not more than about 50 g/mol, or not more than about 30 g/mol. In certain embodiments, $Z^A$ consists of not more than about 50 atoms, not more than about 40 atoms, not more than about 30 atoms, not more than about 20 atoms, or not more than about 10 atoms. In certain embodiments, $Z^A$ is —C≡C— or —C≡C—C≡C—. In certain embodiments, $Z^A$ is of the formula:

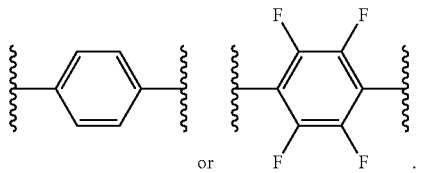

or

In certain embodiments, all instances of $R^{ZA}$ are the same. In certain embodiments, at least two instances of $R^{A2}$ are different from each other. In certain embodiments, at least one instance of $R^{ZA}$ is hydrogen. In certain embodiments, all instances of $R^{ZA}$ are hydrogen. In certain embodiments, at least one instance of $R^{ZA}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{ZA}$ is a nitrogen protecting group (e.g., Bn, Boc, Cbz, Fmoc, trifluoroacetyl, triphenylmethyl, acetyl, or Ts).

In certain embodiments, $Z^A$ is directly covalently attached to the carbon atom labeled with 2' or 6' of Ring B. In certain embodiments, $Z^A$ is directly covalently attached to the carbon atom labeled with 3' or 5' of Ring B. In certain embodiments, $Z^A$ is directly covalently attached to the carbon atom labeled with 4' of Ring B.

Formula (A) includes a divalent linker $Z^B$ that directly covalently connects Ring A and Ring C. In certain embodiments, $Z^B$ is a bond. In certain embodiments, $Z^B$ is a substituted or unsubstituted $C_{1-4}$ hydrocarbon chain, optionally wherein one or more chain atoms are independently replaced with —O—, —S—, —NR$^{ZB}$—, —N═, or ═N—. In certain embodiments, when $Z^B$ is a substituted or unsubstituted $C_{1-4}$ hydrocarbon chain, $Z^B$ consists of a chain, and optionally one or more hydrogen atoms and/or one or more substituents (e.g., ═O) on the chain, where any two substituents may optionally be joined to form a ring. In certain embodiments, $Z^B$ does not include unsaturated bonds in the chain. In certain embodiments, $Z^B$ consists of one or two unsaturated bonds in the chain. In certain embodiments, $Z^B$ is a substituted (e.g., substituted with at least one instance of halogen) $C_{1-6}$ hydrocarbon chain. In certain embodiments, $Z^B$ is an unsubstituted $C_{1-4}$ hydrocarbon chain. In certain embodiments, the molecular weight of $Z^B$ is not more than about 150 g/mol, not more than about 100 g/mol, not more than 80 g/mol, not more than about 50 g/mol, or not more than about 30 g/mol. In certain embodiments, $Z^B$ consists of not more than about 50 atoms, not more than about 40 atoms, not more than about 30 atoms, not more than about 20 atoms, or not more than about 10 atoms. In certain embodiments, $Z^B$ is —C≡C— or —C≡C—C≡C—. In certain embodiments, $Z^B$ is of the formula:

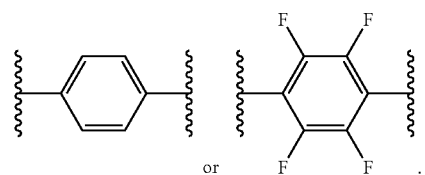

or

In certain embodiments, all instances of $R^{ZB}$ are the same. In certain embodiments, at least two instances of $R^{ZB}$ are different from each other. In certain embodiments, at least one instance of $R^{ZB}$ is hydrogen. In certain embodiments, all instances of $R^{ZB}$ are hydrogen. In certain embodiments, at least one instance of $R^{ZB}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{ZB}$ is a nitrogen protecting group (e.g., Bn, Boc, Cbz, Fmoc, trifluoroacetyl, triphenylmethyl, acetyl, or Ts).

In certain embodiments, $Z^B$ is directly covalently attached to the carbon atom labeled with 2 or 6 of Ring A. In certain embodiments, $Z^B$ is directly covalently attached to the carbon atom labeled with 3 or 5 of Ring A. In certain embodiments, $Z^B$ is directly covalently attached to the carbon atom labeled with 4 of Ring A.

In certain embodiments, $Z^B$ is directly covalently attached to the carbon atom labeled with 2" or 6" of Ring C. In certain embodiments, $Z^B$ is directly covalently attached to the carbon atom labeled with 3" or 5" of Ring C. In certain embodiments, $Z^B$ is directly covalently attached to the carbon atom labeled with 4" of Ring C.

In certain embodiments, $Z^A$ and $Z^B$ are different from each other. In certain embodiments, $Z^A$ and $Z^B$ are the same. In certain embodiments, each of $Z^A$ and $Z^B$ is a bond.

In certain embodiments, $Z^A$ is directly covalently attached to the carbon atom labeled with 2' or 6' of Ring B; and $Z^B$ is directly covalently attached to the carbon atom labeled with 2" or 6" of Ring C. In certain embodiments, $Z^A$ is directly covalently attached to the carbon atom labeled with 3' or 5' of Ring B; and $Z^B$ is directly covalently attached to the carbon atom labeled with 3" or 5" of Ring C. In certain embodiments, $Z^A$ is directly covalently attached to the carbon atom labeled with 4' of Ring B; and $Z^B$ is directly covalently attached to the carbon atom labeled with 4" of Ring C.

In certain embodiments, the ligand of Formula (A) is of the formula:

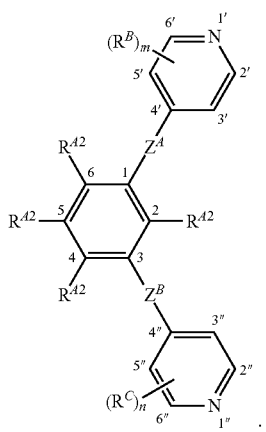

In certain embodiments, the ligand of Formula (A) is of the formula:

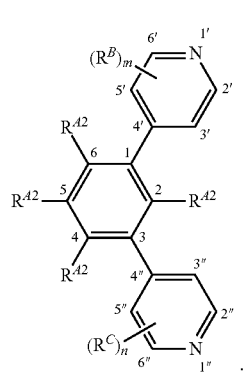

In certain embodiments, the ligand of Formula (A) is of the formula:

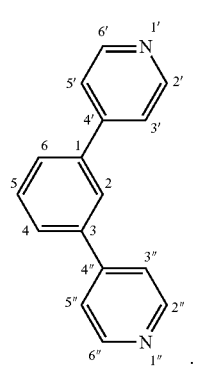 [SMILES: c1cc(-c2ccncc2)cc(-c2ccncc2)c1]

In certain embodiments, the ligand of Formula (A) is of the formula:

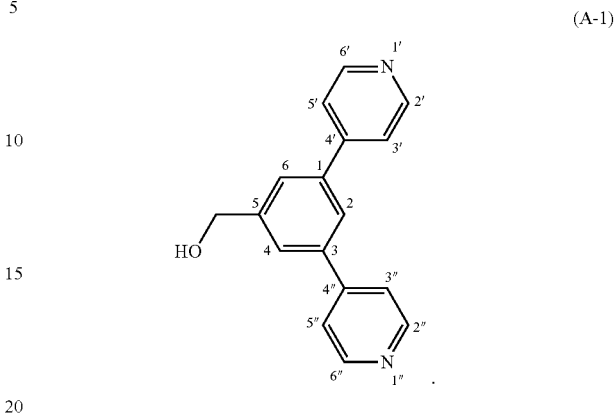

(A-1)

In certain embodiments, the ligand of Formula (A) is of the formula:

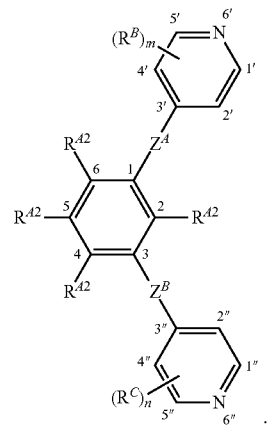

In certain embodiments, the ligand of Formula (A) is of the formula:

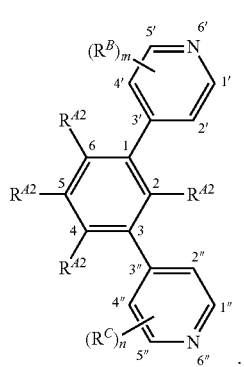

In certain embodiments, the ligand of Formula (A) is of the formula:

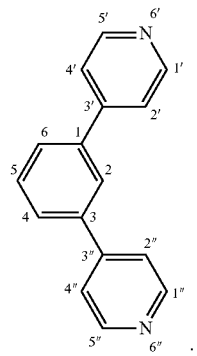 [SMILES: c1cc(-c2ccncc2)cc(-c2ccncc2)c1]

In certain embodiments, the ligand of Formula (A) is of the formula:

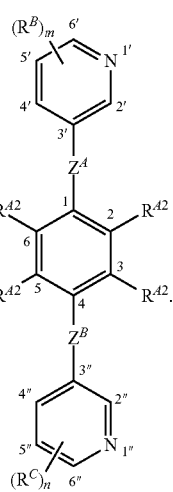

In certain embodiments, the ligand of Formula (A) is of the formula:

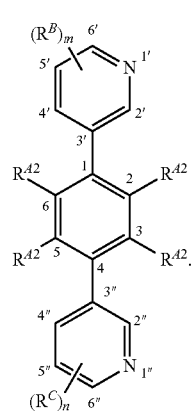

In certain embodiments, the ligand of Formula (A) is of the formula:

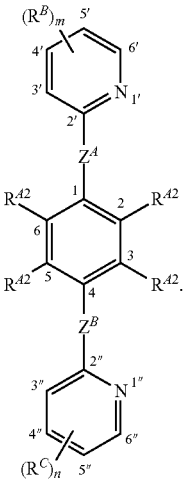

In certain embodiments, the ligand of Formula (A) is of the formula:

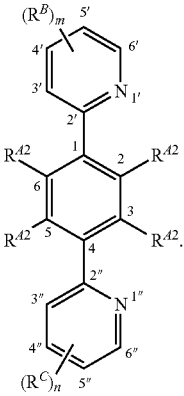

In certain embodiments, the ligand of Formula (A) is of the formula:

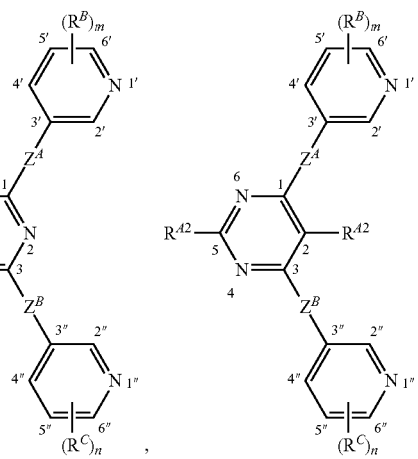
, or

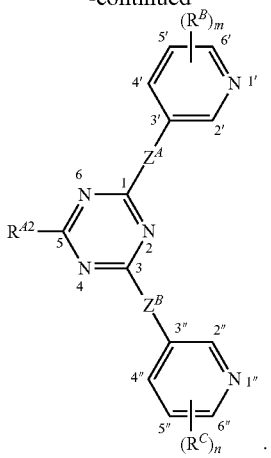
In certain embodiments, the ligand of Formula (A) is of the formula:
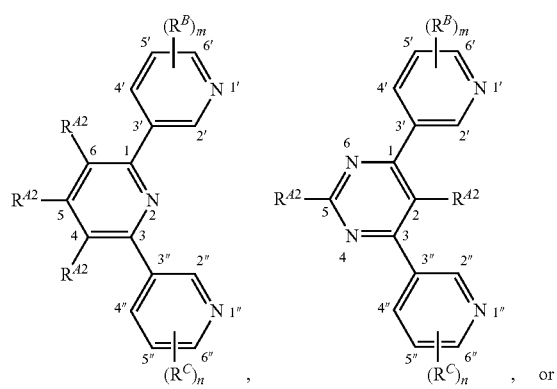
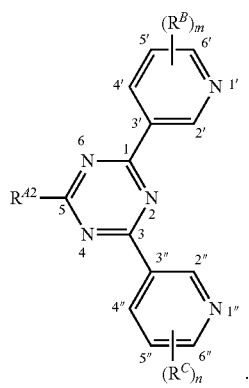
In certain embodiments, the ligand of Formula (A) is of the formula:
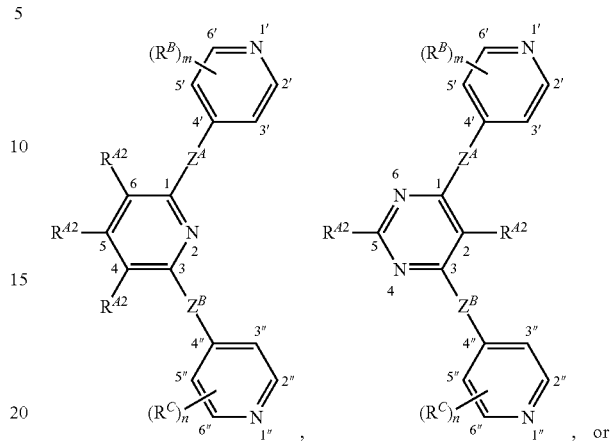
In certain embodiments, the ligand of Formula (A) is of the formula:
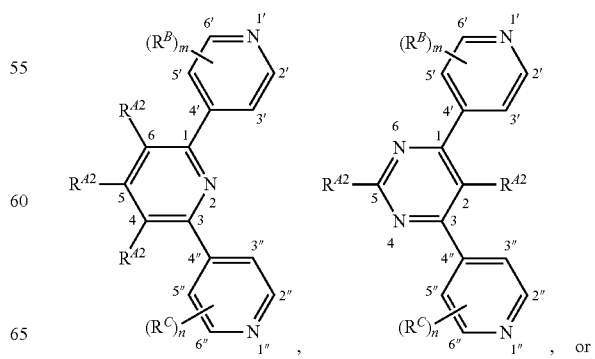

-continued
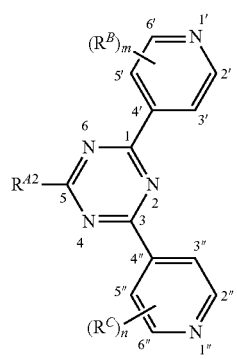
In certain embodiments, the ligand of Formula (A) is of the formula:
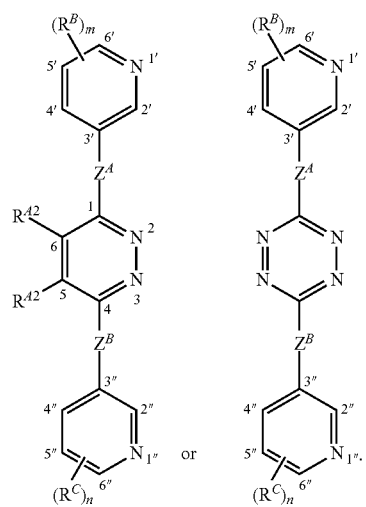
In certain embodiments, the ligand of Formula (A) is of the formula:
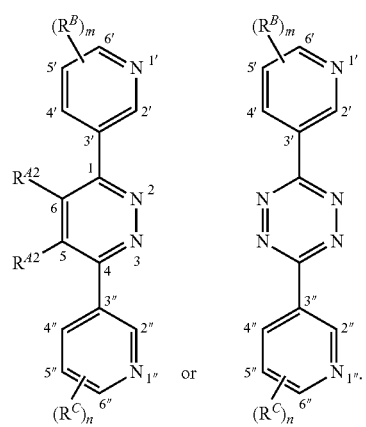
In certain embodiments, the ligand of Formula (A) is of the formula:
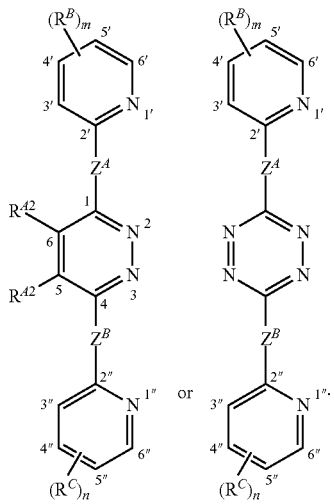
In certain embodiments, the ligand of Formula (A) is of the formula:
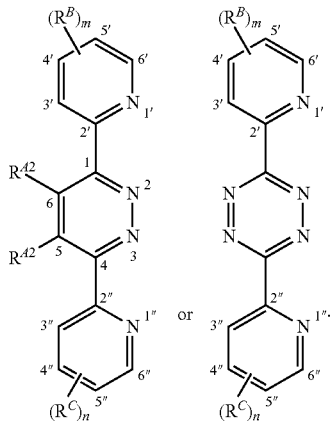
In certain embodiments, the ligand of Formula (A) is of the formula:
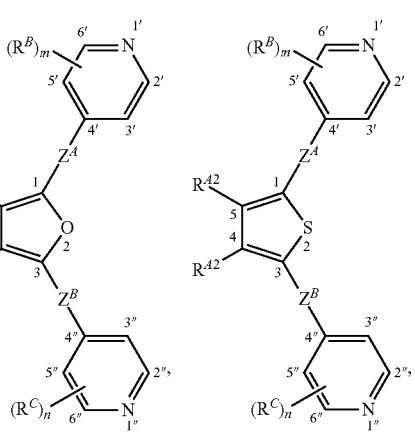

-continued
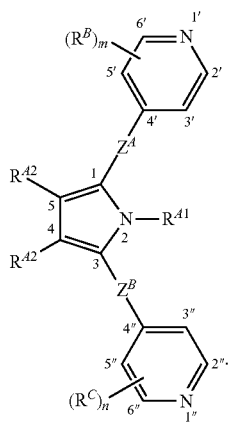
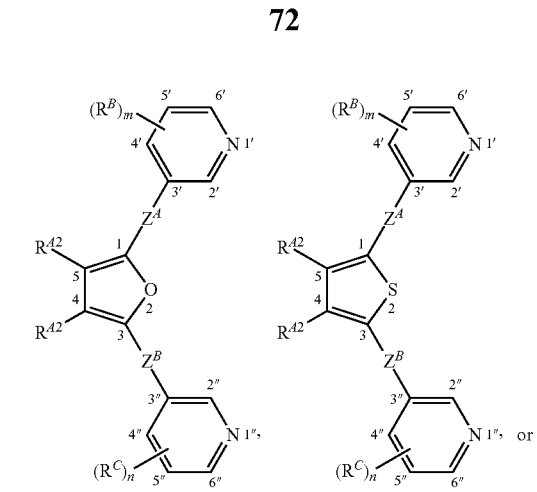
In certain embodiments, the ligand of Formula (A) is of the formula:
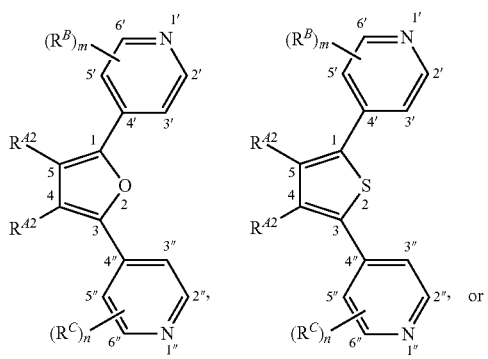
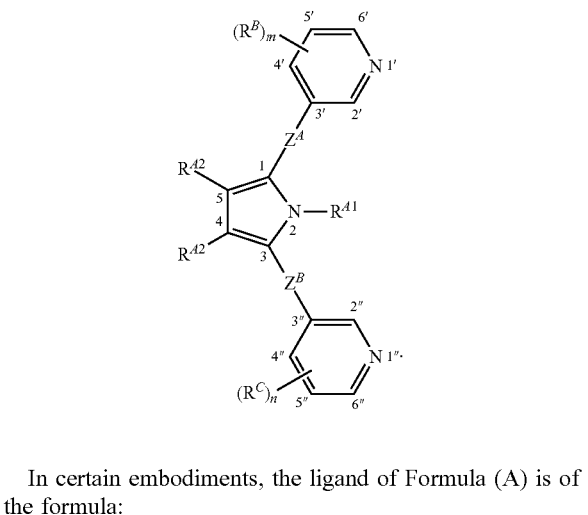
In certain embodiments, the ligand of Formula (A) is of the formula:
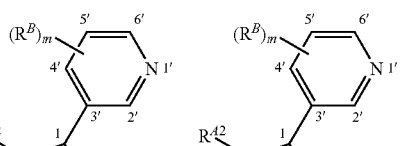
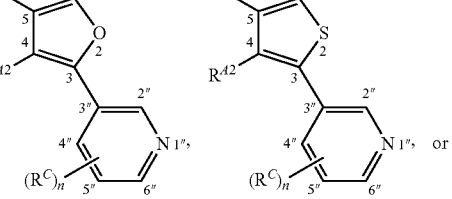
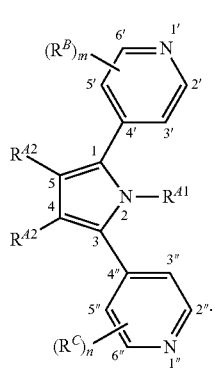
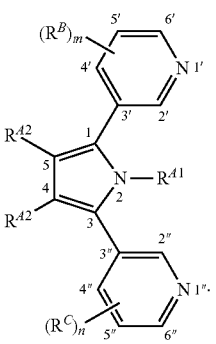
In certain embodiments, the ligand of Formula (A) is of the formula:

In a nanostructure described herein, each instance of the transition metal ion and two instances of the ligand of Formula (A) form through coordination bonds a coordination complex. In certain embodiments, each instance of the ligand of Formula (A) forms through coordination bonds a coordination complex with one instance of the transition metal ion. In certain embodiments, an instance of the coordination bonds is formed between an instance of the transition metal ion and the nitrogen atom labeled with 1' of an instance of the ligand of Formula (A). In certain embodiments, an instance of the coordination bonds is formed between an instance of the transition metal ion and the nitrogen atom labeled with 1" of an instance of the ligand of Formula (A). In certain embodiments, an instance of the coordination bonds is formed between an instance of the transition metal ion and the nitrogen atom labeled with 1' of an instance of the ligand of Formula (A), and another instance of the coordination bonds is formed between the instance of the transition metal ion and the nitrogen atom labeled with 1" of the instance of the ligand of Formula (A).

In a nanostructure described herein, each instance of the coordination complex may be in a square planar molecular geometry. In a nanostructure described herein, each instance of the coordination complex may also be in a pseudo square planar molecular geometry.

A nanostructure described herein may be a nanosphere. In certain embodiments, the nanosphere has quasi-regular polyhedral symmetry. In certain embodiments, the nanosphere has cuboctahedral symmetry. In certain embodiments, the nanosphere has icosidodecahedral symmetry. In certain embodiments, the nanosphere has regular polyhedral symmetry (e.g., cubic (regular hexahedral) or dodecahedral symmetry).

A nanostructure described herein may be a nano-paddlewheel.

A nanostructure described herein is hollow (e.g., including a cavity). In certain embodiments, the average (e.g., mean) outer diameter of a nanostructure described herein is not more than about 100 nm, not more than about 60 nm, not more than about 30 nm, not more than about 10 nm, not more than about 5 nm, not more than about 3 nm, or not more than about 1 nm. In certain embodiments, the average outer diameter of the a nanostructure described herein is at least about 1 nm, at least about 2 nm, at least about 5 nm, at least about 10 nm, at least about 30 nm, at least about 60 nm, or at least about 100 nm. Combinations of the above ranges (e.g., at least about 1 nm and not more than about 100 nm or at least about 1 nm and not more than about 10 nm) are also within the scope of the present disclosure. The average inner diameter of a nanostructure described herein is the average diameter of the cavity of the nanostructure. In certain embodiments, the average inner diameter of a nanostructure described herein is not more than about 100 nm, not more than about 60 nm, not more than about 30 nm, not more than about 10 nm, not more than about 5 nm, not more than about 3 nm, or not more than about 1 nm. In certain embodiments, the average inner diameter of the nanostructure described herein is at least about 1 nm, at least about 2 nm, at least about 5 nm, at least about 10 nm, at least about 30 nm, at least about 60 nm, or at least about 100 nm. Combinations of the above ranges (e.g., at least about 1 nm and not more than about 60 nm or at least about 1 nm and not more than about 5 nm) are also within the scope of the present disclosure.

In certain embodiments, a nanostructure described herein is not a polymer or does not include a polymeric moiety.

In certain embodiments, a nanosphere described herein is of Formula (I-A), or a salt thereof.

In certain embodiments, a nanosphere described herein is of Formula (I-B), or a salt thereof.

In certain embodiments, a nanosphere described herein (nanosphere I-1) is of Formula (I-A), wherein each instance of the gray line is ligand A-1. In Formula (I-A), each instance of the moiety shown in FIG. 31 is of the formula:

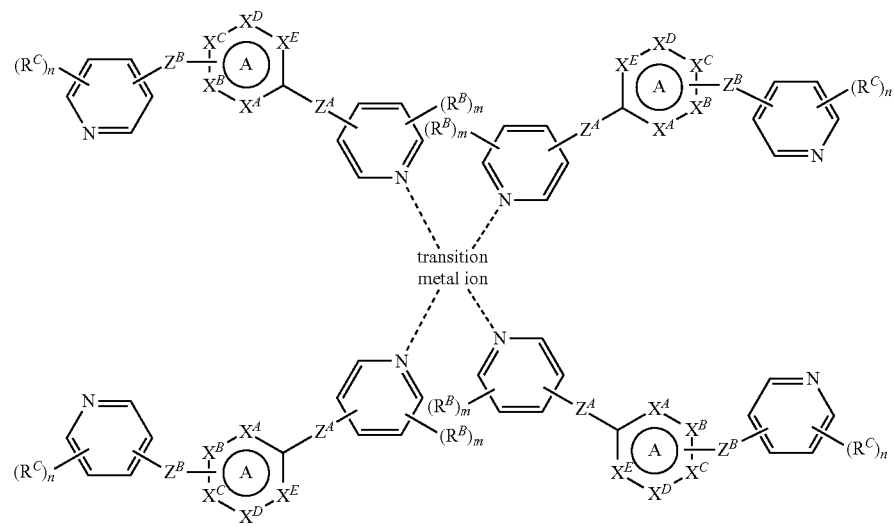

In certain embodiments, each instance of the moiety shown in FIG. 31 is of the formula:

[Chemical structure diagram showing four pyridine-containing ligands coordinating to a transition metal ion]

In certain embodiments, a nano-paddlewheel described herein is of the formula depicted in Scheme 8.

Supramolecular Complexes

Another aspect of the present disclosure relates to supramolecular complexes that include nanostructures described herein covalently connected by divalent linkers Y. In certain embodiments, a supramolecular complex described herein includes two or more (e.g., at least 10, at least 100, at least 1,000, or at least 10,000) instances of a nanostructure described herein and at least one instance of Y.

Each instance of Y consists of a chain, and optionally one or more hydrogen atoms and/or one or more substituents (e.g., =O, halogen, and substituted or unsubstituted $C_{1-6}$ alkyl) on the chain, wherein any two substituents may optionally be joined to form a ring. In certain embodiments, at least two instances of Y are different from each other. In certain embodiments, all instances of Y are the same. In certain embodiments, at least one instance of Y does not include unsaturated bonds in the chain. In certain embodiments, at least one instance of Y consists of one or more unsaturated bonds in the chain. In certain embodiments, at least one instance of Y is a substituted or unsubstituted $C_{30-3000}$ (e.g., $C_{100-3000}$, $C_{200-2500}$, $C_{300-2000}$, $C_{400-1500}$, $C_{70-1500}$, $C_{500-1000}$, $C_{100-1000}$, $C_{30-500}$, $C_{40-400}$, $C_{60-300}$, or $C_{80-200}$) hydrocarbon chain, optionally wherein one or more chain atoms are independently replaced with —O—, —S—, —NR$^Y$—, —N=, or =N—. In certain embodiments, at least one instance of Y is a substituted or unsubstituted $C_{80-1000}$ hydrocarbon chain, optionally wherein one or more chain atoms are independently replaced with —O—, —S—, —NR$^Y$—, —N=, or =N—. In certain embodiments, each chain atom, with any substituents thereon, of at least one instance of Y is independently —CH$_2$—, —CH(substituted or unsubstituted $C_{1-6}$ alkyl)-, —C(substituted or unsubstituted $C_{1-6}$ alkyl)$_2$-, —C(=O)—, —O—, —NH—, —N(substituted or unsubstituted $C_{1-6}$ alkyl)-, or —N(nitrogen protecting group)-. In certain embodiments, each chain atom, with any substituents thereon, of at least one instance of Y is independently —CH$_2$—, —CF$_2$—, —C(=O)—, —O—, —NH—, or —NMe—. In certain embodiments, each chain atom, with any substituents thereon, of at least one instance of Y is independently —CH$_2$—, —C(=O)—, or —O—. In certain embodiments, at least one instance of Y comprises at least one instance of the moiety —C(=O)O— or —OC(=O)—. In certain embodiments, each instance of Y is independently of the formula:

[Chemical structure with subscripts 0-20, 1-20, 20-500, 1-20, 0-20] or

[Chemical structure with subscripts 0-20, 1-20, 20-500, 1-20, 0-20].

In certain embodiments, each instance of Y is independently of the formula:

[Chemical structure with subscript 30-60]

In certain embodiments, each instance of Y is independently of the formula:

[Chemical structure with subscripts 0-20, 1-20, 20-500, 1-20, 0-20]

In certain embodiments, each instance of Y is independently of the formula:

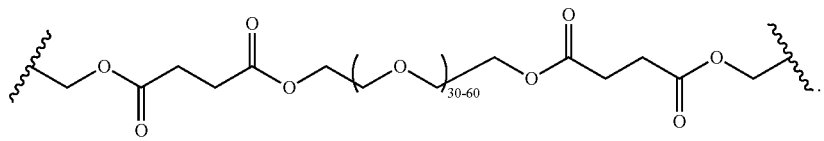

In certain embodiments, each instance of Y is independently of the formula:

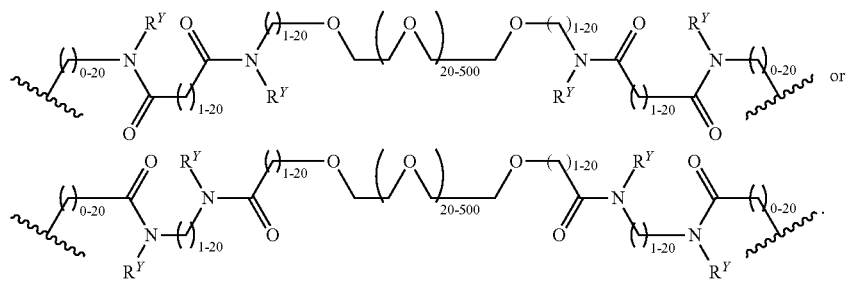

In certain embodiments, each instance of Y is independently of the formula:

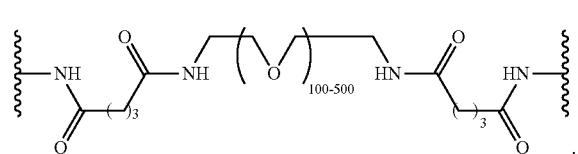

In certain embodiments, each instance of Y is independently of the formula:

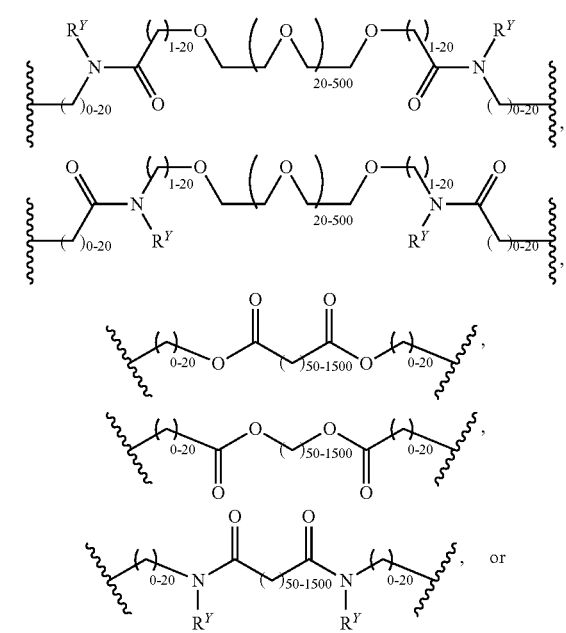

-continued

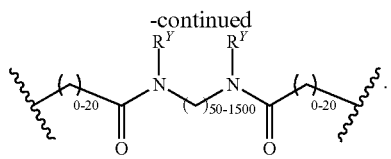

In certain embodiments, the molecular weight of at least one instance of Y (calculated by subtracting 2 from the molecular weight of the molecule YH$_2$) is not more than about 100,000 g/mol, not more than about 30,000 g/mol, not more than 10,000 g/mol, not more than about 3,000 g/mol, not more than about 1,000 g/mol, not more than about 300 g/mol, or not more than about 100 g/mol. In certain embodiments, the molecular weight of at least one instance of Y is at least about 100 g/mol, at least about 300 g/mol, at least about 1,000 g/mol, at least about 3,000 g/mol, at least about 10,000 g/mol, at least about 30,000 g/mol, or at least about 100,000 g/mol. Combinations of the above ranges (e.g., between about 300 and about 30,000 g/mol) are also within the scope of the present disclosure. In certain embodiments, at least one instance of Y consists of not more than about 30,000 atoms, not more than about 10,000 atoms, not more than about 3,000 atoms, not more than about 1,000 atoms, not more than about 300 atoms, not more than about 100 atoms, or not more than about 30 atoms. In certain embodiments, at least one instance of Y consists of at least about 30 atoms, at least about 100 atoms, at least about 300 atoms, at least about 1,000 atoms, at least about 3,000 atoms, at least about 10,000 atoms, or at least about 30,000 atoms. Combinations of the above ranges (e.g., between about 30 and about 10,000 g/mol) are also within the scope of the present disclosure.

In certain embodiments, at least one instance of Y is hydrolytically unstable under physiological conditions. In certain embodiments, at least one instance of Y includes a hydrolytically unstable moiety (e.g., —C(=O)O— or —C(=O)O—) in the chain of Y. In certain embodiments, at least one instance of Y is hydrolytically stable under physiological conditions.

In certain embodiments, all instances of $R^Y$ are the same. In certain embodiments, at least two instances of $R^Y$ are different from each other. In certain embodiments, at least one instance of $R^Y$ is hydrogen. In certain embodiments, all instances of $R^Y$ are hydrogen. In certain embodiments, at least one instance of $R^Y$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, at least one instance of $R^Y$ is a nitrogen protecting group (e.g., Bn, Boc, Cbz, Fmoc, trifluoroacetyl, triphenylmethyl, acetyl, or Ts).

An instance of Y may be directly covalently attached to an instance of the ligand of Formula (A) (e.g., by removing a hydrogen atom from the instance of the ligand of Formula (A) to form a radical (ligand radical) and directly covalently attaching one of the two radicals of the instance of Y to the ligand radical). Each instance of Y is independently directly covalently attached to an instance of the ligand of Formula (A) and directly covalently attached to another instance of the ligand of Formula (A). In certain embodiments, each instance of the ligand of Formula (A) is covalently attached to w instances of Y, wherein w is 1. In certain embodiments, each instance of the ligand of Formula (A) is covalently attached to w instances of Y, wherein w is 2. In certain embodiments, at least one instance of Y is directly covalently attached to the atom labeled with 2, 3, 4, 5, or 6 (e.g., 3, 4, or 5) of an instance of the ligand of Formula (A) and directly covalently attached to the atom labeled with 2, 3, 4, 5, or 6 (e.g., 3, 4, or 5) of another instance of the ligand of Formula (A). In certain embodiments, at least one instance of Y is directly covalently attached to the atom labeled with 2', 3', 4', 5', or 6' (e.g., 3', 4', or 5') of an instance of the ligand of Formula (A) and directly covalently attached to the atom labeled with 2', 3', 4', 5', or 6' (e.g., 3', 4', or 5') of another instance of the ligand of Formula (A). In certain embodiments, at least one instance of Y is directly covalently attached to the atom labeled with 2", 3", 4", 5", or 6" (e.g., 3", 4", or 5") of an instance of the ligand of Formula (A) and directly covalently attached to the atom labeled with 2", 3", 4", 5", or 6" (e.g., 3", 4", or 5") of another instance of the ligand of Formula (A). In a supramolecular complex described herein, at least two instances of the nanostructure are directly covalently connected by at least one instance of Y. In certain embodiments, at least about 50% (e.g., at least about 60%, at least about 70%, at least about 80%, or at least about 90%) of all instances of Y directly covalently attached to an instance of the nanostructure are directly covalently attached to other instances of the nanostructure.

A nanostructure or supramolecular complex described herein may further comprise at least one instance of an anionic counterion. The anionic counterions may reduce the overall electric charge of the nanostructure or supramolecular complex, each of which includes transition metal ions that are positively charged. In certain embodiments, at least two instances of the anionic counterion are different. In certain embodiments, all instances of the anionic counterion are the same. In certain embodiments, the nanostructure or supramolecular complex is substantially electrically neutral. In certain embodiments, the nanostructure or supramolecular complex is slightly positively charged. In certain embodiments, the ζ-potential of the nanostructure or supramolecular complex is between about 0 and about +30 mV, inclusive (e.g., between about 0 and about 10 mV, inclusive). In certain embodiments, the nanostructure or supramolecular complex is slightly negatively charged. In certain embodiments, the ζ-potential of the nanostructure or supramolecular complex is between about −30 and about 0 mV, inclusive (e.g., between about −10 and about 0 mV, inclusive). In certain embodiments, at least one instance of the anionic counterion is a non-coordinating anionic counterion (e.g., $ClO_4^-$, $NO_3^-$, $TfO^-$, $BF_4^-$, $PF_4^-$, $PF_6^-$, $AsF_6^-$, or $SbF_6^-$). In certain embodiments, at least one instance (e.g., each instance) of the anionic counterion is $NO_3^-$. In certain embodiments, at least one instance of the anionic counterion is $AcO^-$, $F^-$, $Cl^-$, $Br^-$, or $I^-$. In certain embodiments, at least one instance of the anionic counterion is a coordinating anionic counterion. In certain embodiments, at least one instance (e.g., each instance) of the anionic counterion is at the outer surface of an instance of the nanostructure. In certain embodiments, at least one instance of the anionic counterion is at the inner surface of an instance of the nanostructure. In certain embodiments, at least one instance of the anionic counterion is encapsulated by an instance of the nanostructure.

Macromers

In another aspect, the present disclosure provides macromers of Formula (B), and salts thereof:

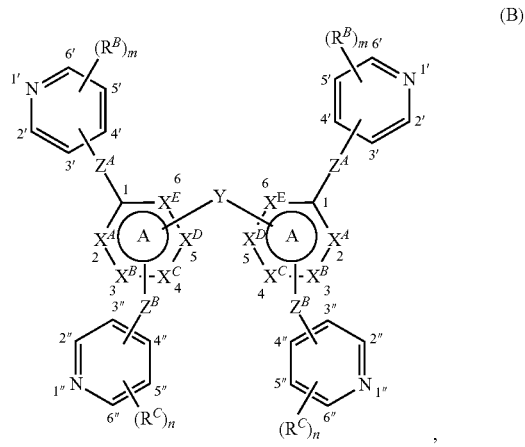

(B)

wherein Ring A, $X^A$, $X^B$, $X^C$, $X^D$, $X^E$, Y, $Z^A$, $Z^B$, $R^B$, $R^C$, m, and n are as described herein.

In certain embodiments, the macromer of Formula (B) is of the formula:

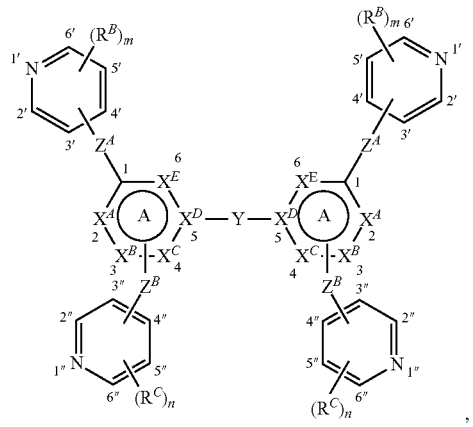

or a salt thereof, wherein each instance of $X^D$ is N or C.

In certain embodiments, the macromer of Formula (B) is of the formula:
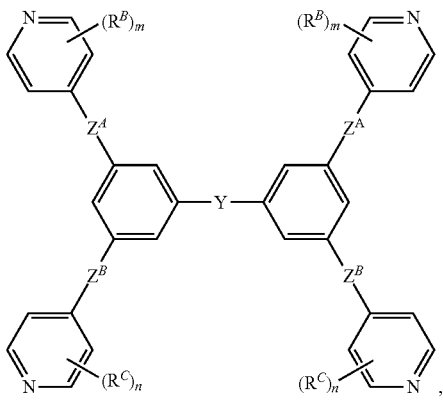
or a salt thereof.
In certain embodiments, the macromer of Formula (B) is of the formula:
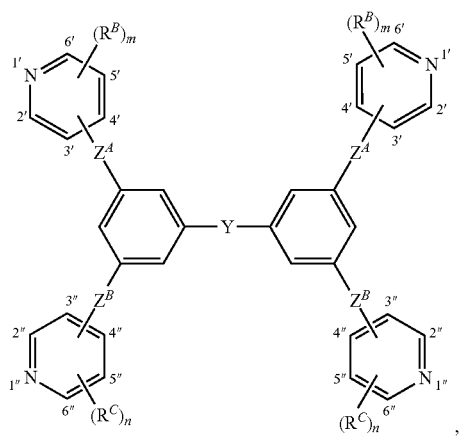
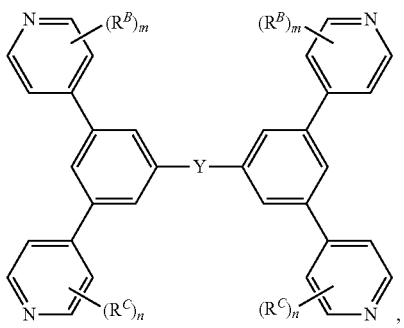
or a salt thereof.
In certain embodiments, the macromer of Formula (B) is of the formula:
or a salt thereof.
In certain embodiments, the macromer of Formula (B) is of the formula:
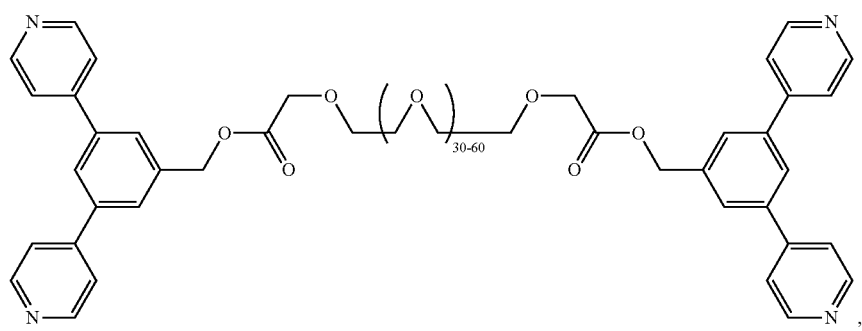
or a salt thereof.

In certain embodiments, the macromer of Formula (B) is of Formula (B-1), (B-2), or (B-3):
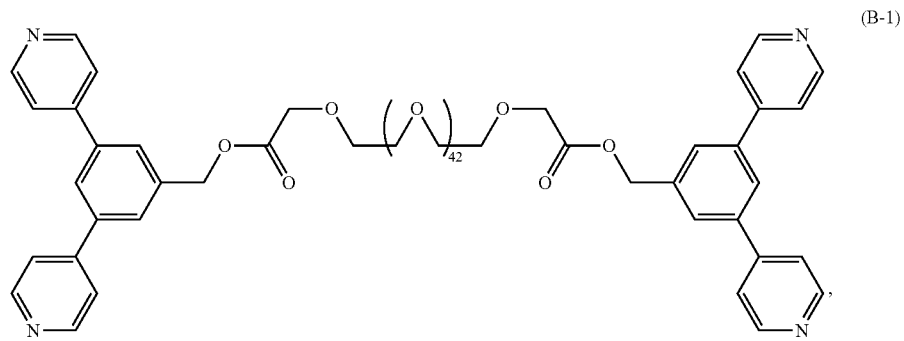
(B-1)
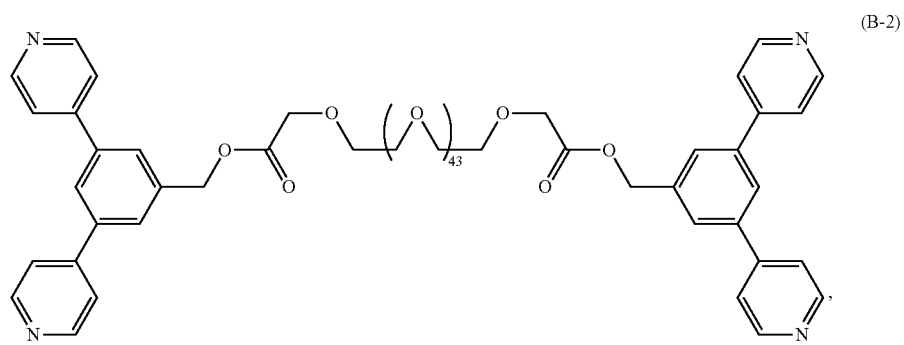
(B-2)
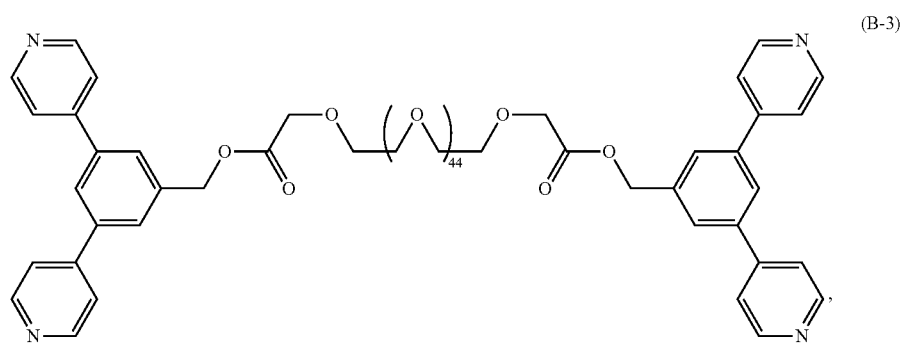
(B-3)
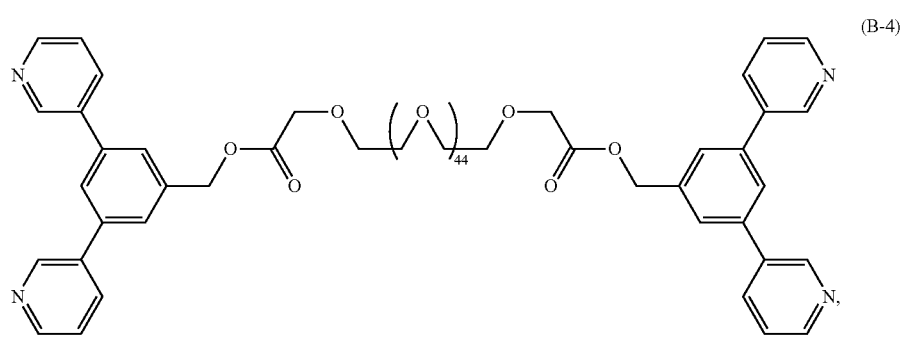
(B-4)
or a salt thereof.

In another aspect, the present disclosure provides macromers of Formula (C), and salts thereof:

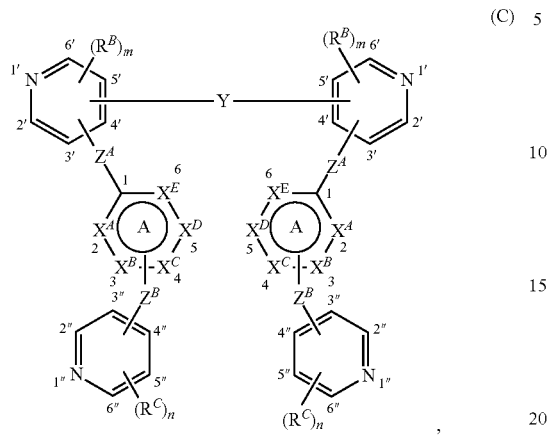
(C)

wherein Ring A, $X^A$, $X^B$, $X^C$, $X^D$, $X^E$, Y, $Z^A$, $Z^B$, $R^B$, $R^C$, m, and n are as described herein.

In certain embodiments, the macromer of Formula (C) is of the formula:

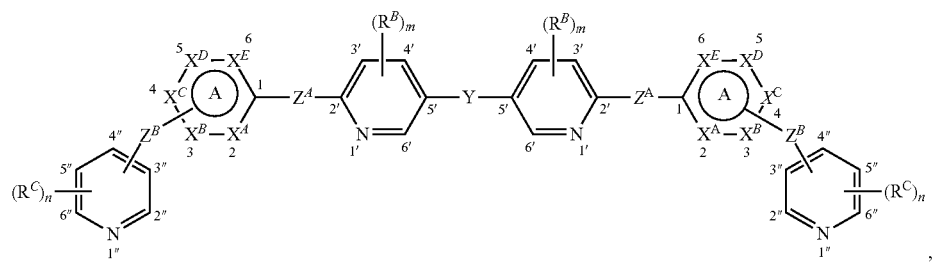

or a salt thereof.

In certain embodiments, the macromer of Formula (C) is of the formula:

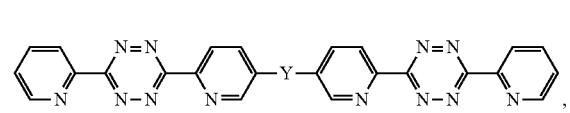

or a salt thereof.

In certain embodiments, the macromer of Formula (C) is of the formula:

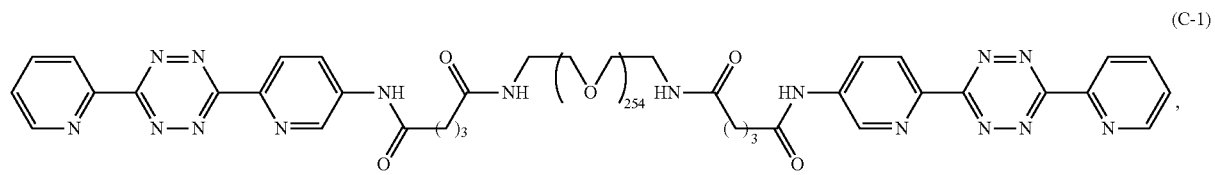
(C-1)

(C-2)

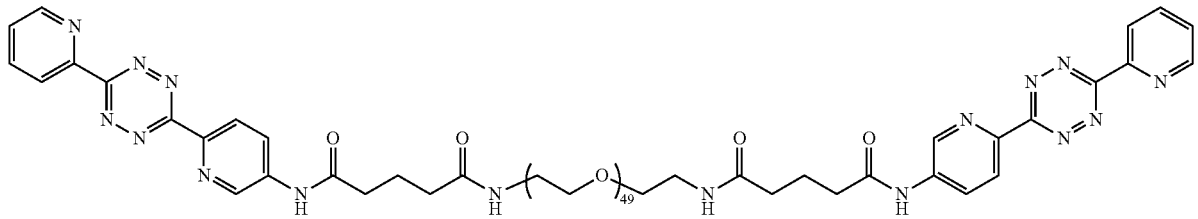

or a salt thereof.

Compositions

In another aspect, the present disclosure provides compositions comprising a nanostructure described herein and optionally an excipient. A composition described herein may further comprise a solvent (e.g., a suitable solvent described herein, such as water or DMSO). The solvent may be encapsulated inside a nanostructure and/or be present outside of any nanostructure in the composition.

In still another aspect, the present disclosure provides compositions comprising a supramolecular complex described herein and optionally an excipient.

The excipient included in a composition described herein may be a pharmaceutically acceptable excipient, cosmetically acceptable excipient, dietarily acceptable excipient, or nutraceutically acceptable excipient.

A composition described herein may further comprise an agent (e.g., a pharmaceutical agent or diagnostic agent). In a composition described herein, an agent may form an adduct (e.g., through covalent attachment and/or non-covalent interactions) with a nanostructure described herein (including a nanostructure moiety of a supramolecular complex described herein). In certain embodiments, a composition described herein is useful in the delivery of the agent (e.g., an effective amount of the agent) to a subject, tissue, or cell.

A composition described herein may further comprise a fluid (e.g., a solvent, e.g., water, DMSO, acetonitrile, or a mixture thereof)

Compositions of the disclosure may improve or increase the delivery of an agent described herein to a subject, tissue, or cell. In certain embodiments, the compositions increase the delivery of the agent to a target tissue or target cell. In certain embodiments, the target tissue is liver, spleen, or lung. In certain embodiments, the target tissue is pancreas, kidney, uterus, ovary, heart, thymus, fat, or muscle. In certain embodiments, the target cell is a liver cell, spleen cell, lung cell, pancreas cell, kidney cell, uterus cell, ovary cell, heart cell, thymus cell, or muscle cell. In certain embodiments, the compositions selectively deliver the agent to the target tissue or target cell (e.g., the compositions deliver the agent to the target tissue in a greater quantity in unit time than to a non-target tissue or deliver the agent to the target cell in a greater quantity in unit time than to a non-target cell).

The delivery of an agent described herein may be characterized in various ways, such as the exposure, concentration, and bioavailability of the agent. The exposure of an agent in a subject, tissue, or cell may be defined as the area under the curve (AUC) of the concentration of the agent in the subject, tissue, or cell after administering or dosing the agent. In general, an increase in exposure may be calculated by first taking the difference in: (1) a first AUC, which is the AUC measured in a subject, tissue, or cell administered or dosed with a composition described herein; and (2) a second AUC, which is the AUC measured in a subject, tissue, or cell administered or dosed with a control composition; and then by dividing the difference by the second AUC. Exposure of an agent may be measured in an appropriate animal model. The concentration of an agent and, when appropriate, its metabolite(s), in a subject, tissue, or cell is measured as a function of time after administering or dosing the agent.

Concentration of an agent, and, when appropriate, of its metabolite(s), in a subject, tissue, or cell, may be measured as a function of time in vivo using an appropriate animal model. In certain embodiments, the concentration of the agent is the concentration of the agent in a target tissue or target cell. One exemplary method of determining the concentration of an agent involves dissecting of a tissue. The concentration of the agent may be determined by HPLC or LC/MS analysis.

In some embodiments, a composition of the disclosure increases the delivery of an agent described herein to a subject, tissue, or cell by due to the presence of a nanostructure described herein. In some embodiments, a composition of the disclosure increases the delivery of an agent described herein to a subject, tissue, or cell by due to the presence of a supramolecular complex described herein. In some embodiments, the composition increases the delivery of the agent due to the presence of an adduct formed between the nanostructure (including a nanostructure moiety of a supramolecular complex) and the agent. In some embodiments, the presence of a nanostructure or supramolecular complex described herein increase the delivery of the agent by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, or at least about 1000-fold. In certain embodiments, a nanostructure or supramolecular complex described herein is present in the composition in an amount sufficient to increase the delivery of the agent by an amount described herein when administered in the composition compared to the delivery of the agent when administered in the absence of the nanostructure or supramolecular complex.

Compositions described herein may deliver an agent selectively to a tissue or cell. In certain embodiments, the tissue or cell to which the agent is selectively delivered is a target tissue or target cell, respectively. In certain embodiments, the compositions deliver at least about 10%, at least about 20%, at least about 30%, at least about 40%, at least about 50%, at least about 70%/o, at least about 100%, at least about 3-fold, at least about 10-fold, at least about 30-fold, at least about 100-fold, at least about 300-fold, or at least about 1000-fold more amount of the agent in unit time to a target tissue than to a non-target tissue or to a target cell than to a non-target cell. The amount of agent may be measured by the exposure, concentration, and/or bioavailability of the agent in a tissue or cell as described herein.

The compositions described herein (e.g., pharmaceutical compositions) including one or more agents (e.g., pharmaceutical agents) may be useful in treating and/or preventing a disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing a gastrointestinal disease. In certain embodiments, the compositions are useful for treating and/or preventing a liver disease. In certain embodiments, the compositions are useful for treating and/or preventing a spleen disease. In certain embodiments, the compositions are useful for treating and/or preventing a respiratory disease. In certain embodiments, the compositions are useful for treating and/or preventing a lung disease. In certain embodiments, the compositions are useful for treating and/or preventing hepatic carcinoma, hypercholesterolemia, refractory anemia, or familial amyloid neuropathy. In certain embodiments, the compositions are useful for treating and/or preventing a painful condition. In certain embodiments, the compositions are useful for treating and/or preventing a genitourinary disease. In certain embodiments, the compositions are useful for treating and/or preventing a musculoskeletal condition. In certain embodiments, the compositions are useful for treating and/or preventing an infectious disease. In certain embodiments, the compositions are useful for treating and/or preventing a psychiatric disorder. In certain embodiments, the compositions are useful for treating and/or preventing a metabolic disorder.

The agents may be provided in an effective amount in a composition described herein. In certain embodiments, the effective amount is a therapeutically effective amount. In certain embodiments, the effective amount is a prophylactically effective amount. In certain embodiments, the effective amount is an amount effective for treating a disease described herein. In certain embodiments, the effective amount is an amount effective for preventing a disease described herein.

An effective amount of an agent may vary from about 0.001 mg/kg to about 1000 mg/kg in one or more dose administrations for one or several days (depending on the mode of administration). In certain embodiments, the effective amount per dose varies from about 0.001 to about 1000 mg/kg, from about 0.01 to about 750 mg/kg, from about 0.1 to about 500 mg/kg, from about 1.0 to about 250 mg/kg, and from about 10.0 to about 150 mg/kg.

In certain embodiments, a composition described herein is in the form of gels. In certain embodiments, the gels result from self-assembly of the components of the composition. The agent to be delivered by the gel may be in the form of a gas, liquid, or solid. The nanostructures and/or supramolecular complexes described herein may be combined with polymers (synthetic or natural), surfactants, cholesterol, carbohydrates, proteins, lipids, lipidoids, etc. to form gels. The gels may be further combined with an excipient to form the composition. The gels are described in more detail herein.

The compositions described herein (e.g., pharmaceutical compositions) can be prepared by any method known in the art (e.g., pharmacology). In certain embodiments, such preparatory methods include the steps of bringing a nanostructure or supramolecular complex described herein into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A unit dose is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition described herein will vary, depending upon the identity, size, and/or condition of the subject to whom the composition is administered and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, and mixtures thereof.

Exemplary chelating agents include ethylenediaminetetraacetic acid (EDTA) and salts and hydrates thereof (e.g., sodium edetate, disodium edetate, trisodium edetate, calcium disodium edetate, and dipotassium edetateke), citric acid and salts and hydrates thereof (e.g., citric acid monohydrate), fumaric acid and salts and hydrates thereof, malic acid and salts and hydrates thereof, phosphoric acid and salts and hydrates thereof, tartaric acid and salts and hydrates thereof, and mixtures thereof.

Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, thimerosal, and mixtures thereof.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, sorbic acid, and mixtures thereof.

Exemplary alcohol preservatives include ethanol, polyethylene glycol, phenol, phenolic compounds, bisphenol, chlorobutanol, hydroxybenzoate, phenylethyl alcohol, and mixtures thereof.

Exemplary acidic preservatives include vitamin A, vitamin C, vitamin E, beta-carotene, citric acid, acetic acid, dehydroacetic acid, ascorbic acid, sorbic acid, phytic acid, and mixtures thereof.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip®, methylparaben, Germall® 115, Germaben® II, Neolone®, Kathon®, Euxyl®, and mixtures thereof.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms.* Mol Ther. 18(7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophore, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a composition of this disclosure may include ointments, pastes, creams, lotions, gels, powders, solutions, sprays, inhalants, and/or patches. Generally, the active ingredient is admixed under sterile conditions with a carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Ballistic powder/ particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the active ingredient. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Nanostructures and supramolecular complexes described herein are typically formulated in dosage unit form for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder, the activity of the specific active ingredient employed, the specific composition employed, the age, body weight, general health, sex, and diet of the subject, the time of administration, route of administration, and rate of excretion of the specific active ingredient employed, the duration of the treatment, drugs used in combination or coincidental with the specific active ingredient employed, and like factors well known in the medical arts.

The compositions described herein can be administered by any suitable route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In certain embodiments, the compositions are administered by oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

Compositions described herein may further include a hydrophilic polymer (e.g., polyethylene glycol (PEG)). The compositions described herein may further include a lipid (e.g., a steroid, a substituted or unsubstituted cholesterol, or a polyethylene glycol (PEG)-containing material). In certain embodiments, the lipid included in the compositions is a triglyceride, a driglyceride, a PEGylated lipid, dimyristoyl-PEG2000 (DMG-PEG2000), a phospholipid (e.g., 1,2-distearoyl-sn-glycero-3-phosphocholine (DSPC)), dioleoyl-phosphatidylethanolamine (DOPE), a substituted or unsubstituted cholesterol, a steroid an apolipoprotein, or a combination thereof. In certain embodiments, the compositions include two components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include three components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include at least four components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include a hydrophilic polymer, a phospholipid, a steroid, and a substituted or unsubstituted cholesterol. In certain embodiments, the compositions include PEG, DSPC, and substituted or unsubstituted cholesterol. In certain embodiments, the additional materials are approved by a regulatory agency, such as the U.S. FDA, for human and/or veterinary use.

Compositions described herein may be useful in other applications, e.g., non-medical applications. Nutraceutical compositions described herein may be useful in the delivery of an effective amount of a nutraceutical, e.g., a dietary supplement, to a subject in need thereof. Cosmetic compositions described herein may be formulated as a cream, ointment, balm, paste, film, or liquid, etc., and may be useful in the application of make-up, hair products, and materials useful for personal hygiene, etc. Compositions described herein may be useful for other non-medical applications, e.g., such as an emulsion, emulsifier, or coating, useful, for example, as a food component, for extinguishing fires, for disinfecting surfaces, for oil cleanup, and/or as a bulk material.

Agents to be Delivered

Agents that are delivered by the systems (e.g., pharmaceutical compositions) described herein may be pharmaceutical (e.g., therapeutic or prophylactic), diagnostic, cosmetic, or nutraceutical agents. Any chemical compound to be administered to a subject or to be contacted with a tissue or cell may be delivered using the nanostructures, supramolecular complexes, and/or compositions described herein. The agent may be a small molecule (e.g., a small organic molecule or small inorganic molecule), protein, peptide, polynucleotide, targeting agent, isotopically labeled chemical compound, vaccine, or immunological agent. The agent may be an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a tissue or cell may be delivered to the subject, tissue, or cell using the compositions described herein.

Exemplary agents that may be included in a composition described herein include, but are not limited to, small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, agents useful in bioprocessing, and mixtures thereof. The targeting agents are described in more detail herein. In certain embodiments, the agents are nutraceutical agents. In certain embodiments, the agents are pharmaceutical agents (e.g., a therapeutic or prophylactic agent). In certain embodiments, the agent is an antibiotic agent (e.g., an anti-bacterial, anti-viral, or anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, and Freund's adjuvant, etc. In certain embodiments, the agent is a small molecule. In certain embodiments, the agent is an anti-cancer agent (e.g., an anti-cancer agent disclosed in U.S. Patent Application Publication No. US 2003/065023). In certain embodiments, the agent is doxorubicin.

In certain embodiments, an agent described herein is a polynucleotide. In certain embodiments, the agent is plasmid DNA (pDNA). In certain embodiments, the agent is single-stranded DNA (ssDNA), double-stranded DNA (dsDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, the agent is RNA. In certain embodiments, the agent is small interfering RNA (siRNA). In certain embodiments, the agent is messenger RNA (mRNA). In certain embodiments, the agent is single-stranded RNA (ssRNA), double-stranded RNA (dsRNA), small interfering RNA (siRNA), precursor messenger RNA (pre-mRNA), small hairpin RNA or short hairpin RNA (shRNA), micro-RNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, upon delivery of an RNA into a subject, tissue, or cell, the RNA is able to interfere with the expression of a specific gene in the subject, tissue, or cell. In certain embodiments, the agent is a pDNA, siRNA, mRNA, or a combination thereof.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

The RNA and/or RNAi described herein can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, RNA, 13:1765; Yiu et al., 2005, *Bioinformatics*, 21:144; and Jia et al., 2006, *BMC Bioinformatics*, 7: 271.

The polynucleotide included in a composition described herein may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes not more than about 10,000, not more than about 3,000, not more than about 1,000, not more than about 300, not more than about 100, or not more than about 30 base pairs. Combinations of the above ranges (e.g., at least about 100 and not more than about 1,000) are also within the scope of the disclosure. The polynucleotide may be provided by any suitable means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and/or end-capping, etc. In certain embodiments, the modifications lead to increased stability of the polynucleotide.

Wherever a polynucleotide is employed in the present disclosure, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any suitable means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, or an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, or insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from bacterial organisms, such as *Streptococccus pneumoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi,* and *Camphylobacter jejuni*; from viruses, such as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, and hepatitis E virus; and from fungal, protozoan, or parasitic organisms, such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis,* and *Schistosoma mansoni*.

An agent described herein may be covalently or non-covalently attached to (e.g., complexed to and/or encapsulated in) a nanostructure or supramolecular complex (e.g., attached to a nanostructure of the supramolecular complex) described herein, or included in a composition described herein. In certain embodiments, at least one instance of the nanostructure encapsulates the agent. In certain embodiments, at least one molecule of the agent is not encapsulated in any instance of the nanostructure. In certain embodiments, upon delivery of the agent into a cell, the agent is able to interfere with the expression of a specific gene in the cell.

In certain embodiments, an agent described herein may be a mixture of two or more agents that may be useful as, e.g., combination therapies. A composition including the mixture can be used to achieve a synergistic effect. In certain embodiments, the composition including the mixture can be used to improve the activity and/or bioavailability, reduce and/or modify the metabolism, inhibit the excretion, and/or modify the distribution of at least one of the two or more agents in a subject, tissue, or cell to which the mixture is administered or dosed. It will also be appreciated that the composition including the mixture may achieve a desired effect for the same disorder, and/or it may achieve different effects. The two or more agents in the mixture may be useful for treating and/or preventing a same disease or different diseases described herein.

The compositions (e.g., pharmaceutical compositions) described herein can be administered concurrently with, prior to, or subsequent to the one or more agents (e.g., pharmaceutical agents). Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, a composition described herein may further include targeting moieties or targeting agents. In certain embodiments, a nanostructure described herein (including a nanostructure moiety of a supramolecular complex described herein) is modified to include targeting moieties or targeting agents. For example, a targeting moiety or targeting agent may be included throughout a nanostructure or supramolecular complex (e.g., throughout a nanostructure of the supramolecular complex) described herein or may be only at the surface (e.g., outer or inner surface) of the nanostructure or supramolecular complex (e.g., at the surface of a nanostructure of the supramolecular complex). A targeting agent may be a protein, peptide, carbohydrate, glycoprotein, lipid, small molecule, or polynucleotide, and a targeting moiety may be a fragment of the targeting agent. The targeting moiety or targeting agent may be used to target specific cells or tissues or may be used to promote endocytosis or phagocytosis of the nanostructure and/or supramolecular complex. The targeting moieties or targeting agents include the ones known in the art. See, e.g., Cotten et al., *Methods Enzym.* 217:618, 1993. Examples of the targeting moieties and targeting agents include, but are not limited to, antibodies, proteins, peptides, carbohydrates, small molecules, metals, receptor ligands, sialic acid, aptamers, and fragments thereof. If a targeting moiety or targeting agent is included throughout a nanostructure or supramolecular complex, the targeting agent may be included in the mixture that is used to form the nanostructure or supramolecular complex. If the targeting agent is only on the surface of a nanostructure or supramolecular complex, the targeting agent may be associated with (e.g., by covalent or non-covalent (e.g., electrostatic, hydrophobic, hydrogen bonding, van der Waals, π-π stacking) interactions) the nanostructure or supramolecular complex using standard chemical techniques.

Adducts of a Nanostructure and an Agent

The present disclosure contemplates that the nanostructures described herein (including the nanostructure moieties of the supramolecular complexes described herein) are useful in the delivery of an agent described herein (e.g., a small molecule, peptide, protein, or a polynucleotide) to a subject, tissue, or cell. Without wishing to be bound by any particular theory, the nanostructures have several desirable properties that make a composition that includes the nanostructures and an agent suitable for delivering the agent to a subject, tissue, or cell. Encapsulation of an agent within a nanostructure described herein may have desirable properties for delivering an agent to a subject, tissue, or cell, including protection from degradation of the agent by ubiquitous nucleases, passive and active targeting, and/or evasion of endosomal Toll-like receptors. Other desirable properties include: 1) the ability of the nanostructures to form an adduct with and "protect" the agent that may otherwise be labile (e.g., labile at least due to chemical and/or enzymatical (e.g., by nucleases) degradation); 2) the ability of the nanostructures to buffer the pH in an endosome of the cell; 3) the ability of the nanostructures to act as a "proton sponge" and cause endosomolysis; and 4) the ability of the nanostructures to substantially neutralize the negative or positive charges of the agent. Challenges to the efficient delivery of an agent exist, including particle dissociation via serum proteins, cellular uptake, endosomal escape, and appropriate intracellular disassembly. To address some of these challenges, single parameter studies that evaluate the effect of chemical structure on a single biological property or on delivery performance have been reported. Furthermore, high-throughput synthetic methods have been exploited for the accelerated discovery of potent lipid nanoparticles (LNPs) and evaluation of structure activity relationships (SARs). In spite of these efforts, the relationships between physicochemical properties of nanoparticles and biological barriers, and that between biological barriers and gene silencing activity remain unclear. This lack of clarity has also resulted in poor in vitro-in vivo translation.

In certain embodiments, a nanostructure described herein encapsulates an agent described herein. In certain embodiments, the ratio of the amount of a nanostructure described herein to the amount of an agent encapsulated in the nanostructure is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the nanostructure or supramolecular complex to the agent is not more than about 500:1, not more than about 200:1, not more than about 100:1, not more than about 50:1, not more than about 20:1, not more than about 10:1, not more than about 5:1, not more than about 2:1, or not more than about 1:1 mol/mol. Combinations of the above ranges (e.g., at least about 1:1 and not more than about 100:1) are also within the scope of the disclosure.

A nanostructure and agent described herein may form an adduct. An adduct may be formed by covalently attaching an agent to a nanostructure or by non-covalent interactions (e.g., electrostatic interactions, hydrophobic interactions, hydrogen bonding, van der Waals interactions, and/or π-π stacking) between an agent and a nanostructure. An agent may be contacted with a nanostructure, or the components thereof (e.g., ligands of Formula (A) and transition metal ions, and optionally anionic counterions), under conditions suitable to form an adduct.

Micelles, Liposomes, and Lipoplexes

A composition including a nanostructure and agent described herein may be in the form of a micelle or liposome. In certain embodiments, the nanostructures are in the form of a micelle or liposome. An agent described herein may be inside a micelle or liposome, and a nanostructure described herein may be inside the micelle or liposome. In certain embodiments, in a micelle or liposome, an agent is encapsulated in a nanostructure. Micelles and liposomes are typically useful in delivering an agent, such as a hydrophobic agent, to a subject, tissue, or cell. When the micelle or liposome is complexed with (e.g., encapsulates or covers) a polynucleotide, the resulting complex may be referred to as a "lipoplex." Many techniques for preparing micelles and liposomes are known in the art, and any such method may be used to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This may prevent interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of lipsomes may involve preparing a nanostructure described herein for hydration, hydrating the nanostructures with agitation, and sizing the vesicles to achieve a homogenous distribution of liposomes. A nanostructure described herein may be first dissolved in a solvent in a container to result in a homogeneous mixture. The solvent is then removed to form a film. This film is thoroughly dried to remove residual amount of the solvent, e.g., by placing the container in vacuo for a period of time. Hydration of the film may be accomplished by adding an aqueous medium and agitating the resulting mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm. In certain embodiments, the amount of a nanostructure described herein in the liposome is between about 30 mol % and about 80 mol %, between about 40 mol % and about 70 mol %, or between about 60 mol % and about 70 mol %, inclusive. In certain embodiments, the nanostructures further complexes an agent, such as a small molecule.

Liposomes and micelles may also be prepared according to methods in the following scientific papers: Narang et al., "Cationic Lipids with Increased DNA Binding Affinity for Nonviral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Gels

Gels are much different from classical mechanics of materials, in that the timescale associated with the imposed stress or strain can affect the mechanical response by several orders of magnitude. These viscoelastic characteristics of gels are significant to many applications, and better understanding of the spatial and temporal mechanisms which effect desirable mechanical properties will lead to better materials designs. In gels, the timescales over which mechanical interactions occur are highly important; materials can have apparent fluid-like properties at long timescales yet apparent solid-like properties at short timescales. Typically, gels possess little long-range spatial ordering. Instead, the molecules in the gels arrange themselves in a wide array of spatial conformations. This spatial heterogeneity effects a corresponding temporal heterogeneity: upon application of a stress, the material begins to relax by deforming. Each of the local conformations relax at a distinct timescale. The mechanical properties (e.g., viscoelastic properties) of gels are important for the gels to be used in various applications. For example, it has been shown that substrate elasticity can determine mesenchymal stem cell differentiation (Engler et al. Cell, 2006, 126, 677-689). There is a need for gels with "designer viscoelasticity," the ability to create gels with a specifically engineered viscoelastic spectrum. Conventional methods for designing the mechanical properties of gels include changing the molecular weight or molecular weight distribution of the polymer matrix, increasing the degree of crosslinking between polymer chains, changing the stiffness of the polymer backbone, and changing the bulkiness of the side groups. However, these conventional techniques alter the properties of the polymer matrix such that they add other features which may be undesirable.

Coordination chemistry typically features bonds between metals and ligands that are intermediate in bond-energy between covalent bonds and non-covalent interactions (e.g., van der Waals interactions and H-bonding). Such bonds can be reversible or dynamic under appropriate conditions; they have been extensively used for the formation of a class of gel networks—metallogels—that features stimuli-responsive properties.[1-32] Due to their low branch functionality and dynamic bonds, most metallogels are soft elastic materials (storage moduli of G'≤20 kPa at ~2-10 wt. % polymer network) that often display viscous flow behavior at low shear strain frequencies.[6,7,21,26,29] These weak mechanical properties severely limit the possible applications of metallogels; the desirable dynamic properties inevitably come at the expense of structural integrity.

Recently, transition metal-organic ligand complexes have been suggested to reinforce the mechanical properties and self-healing nature of marine mussel adhesion fibers ("byssi") (Harrington et al. *Science*, 2010, 328, 216-220; Harrington et al. *The Journal of Experimental Biology*, 2007, 210, 4307-4318; Holten-Andersen et al. *Nature Materials*, 2007, 6, 669-672; Lee et al. *Proceedings of the National Academy of Sciences of the United States of America*, 2006, 103, 12999-13003). Efforts have been made to mimic the extraordinary mechanical properties of the byssi using simplified synthetic analogs (Holten-Andersen et al. *Proceedings of the National Academy of Sciences of the United States of America*, 2011, 108, 2651-2655; Holten-Andersen et al., *Journal of Materials Chemistry B*, 2014, 2, 2467-2472; Lee et al. *Annual Review of Materials Research*, 2011, 41, 99-132; Barrett et al. *Advanced functional materials*, 2013, 23, 1111-1119; Fullenkamp et al. *Macromolecules*, 2013, 46, 1167-1174). Craig et al. has reported the formation and dynamic mechanical properties of metallo-supramolecular networks formed by mixtures of bis-Pd(II) and Pt(II) cross-linkers with poly(4-vinylpyridine) in DMSO. These networks have relaxation timescales that vary across several orders of magnitude. Also reported are that the kinetics of metal-ligand dissociation could be used to tune the apparent mechanical properties of a metallogel within a relevant timescale.[24-26] Furthermore, it has been shown that the thermodynamics of coordination can serve as a partially complementary parameter to tune the mechanical properties of gels.[26] Though manipulation of the kinetic and thermodynamic properties of individual metal-ligand bonds offers one way to modulate bulk properties, this strategy is ultimately limited in terms of the magnitude of changes that can be induced. Furthermore, it requires the design and synthesis of an assortment of ligand architectures and/or the use of different metals to induce changes in network behavior, which may not be compatible with a given application.

Tetrazine derivatives are another ligand that is useful in transition metal-ligand complexes. Interest in tetrazine reactivity has recently resurged largely due to its use in bioconjugate and polymer chemistry (Wollack, J. W.; Monson, B. J.; Dozier, J. K.; Dalluge, J. J.; Poss, K.; Hilderbrand, S. A.; Distefano, M. D. *Chemical Biology & Drug Design* 2014, 84, 140; Darko, A.; Wallace, S.; Dmitrenko, O.; Machovina, M. M.; Mehl, R. A.; Chin, J. W.; Fox, J. M. *Chemical Science* 2014, 5, 3770; Wu, H.; Cisneros, B. T.; Cole, C. M.; Devaraj, N. K. *Journal of the American Chemical Society* 2014, 136, 17942; Hansell, C. F.; Espeel, P.; Stamenović, M. M.; Barker, I. A.; Dove, A. P.; Du Prez, F. E.; O'Reilly, R. K. *Journal of the American Chemical Society* 2011, 133, 13828; Blackman, M. L.; Royzen, M.; Fox, J. M. *Journal of* the American Chemical Society 2008, 130, 13518; Cok, A. M.; Zhou, H.; Johnson, J. A. *Macromolecular Symposia* 2013, 329, 108; Zhou, H.; Woo, J.; Cok, A. M.; Wang, M.; Olsen, B. D.; Johnson, J. A. *Proceedings of the National Academy of Sciences* 2012). Certain tetrazine species are known for their binding to various metal ions; specifically, 3,6-bis(2-pyridyl)-1,2,4,5-tetrazines (bptz), has been studied for additional purposes by several groups as ligands in self-assembled structures. The Dunbar group reported the synthesis of molecular triangles, squares, and pentagons using bptz and various metal ions including $Fe^{2+}$, $Ni^{2+}$, and $Ag^+$, respectively. Additional accounts of using bptz include gold surface modification and its use as a ligand for rhenium to use its MLCT for study in photoinduced charge separation (Skomski, D.; Tempas, C. D.; Smith, K. A.; Tait, S. L. *Journal of the American Chemical Society* 2014, 136, 9862; Li, G.; Parimal, K.; Vyas, S.; Hadad, C. M.; Flood, A. H.; Glusac, K. D. *J. Am. Chem. Soc.* 2009, 131, 11656).

It has previously reported that covalent $A_2+B_3$ type end-linked polymer networks was synthesized using a tris-bptz trifunctional crosslinker and norbornene-terminated poly (ethylene glycol) (PEG) telechelic polymers (Hansell, C. F.; Espeel, P.; Stamenović, M. M.; Barker, I. A.; Dove, A. P.; Du Prez, F. E.; O'Reilly, R. K. *Journal of the American Chemical Society* 2011, 133, 13828; Cok, A. M.; Zhou, H.; Johnson, J. A. *Macromolecular Symposia* 2013, 329, 108; Zhou, H.; Woo, J.; Cok, A. M.; Wang, M.; Olsen, B. D.; Johnson, J. A. *Proceedings of the National Academy of Sciences* 2012; Zhou, H.; Johnson, J. A. *Angew. Chem., Int. Ed.* 2013, 52, 2235). Strained alkenes and tetrazines undergo facile inverse-electron demand Diels-Alder reactions with the extrusion of nitrogen, which make them useful for efficiently synthesizing catalyst-free, two component polymer networks. Subsequent work by Anseth and coworkers used this chemistry to construct cytocompatible gels that could be photochemically patterned (Alge, D. L.; Azagarsamy, M. A.; Donohue, D. F.; Anseth, K. S. *Biomacromolecules* 2013, 14, 949). However, there are no known references of bptz-metal coordination as a mode of crosslinking for the formation of end-linked polymer networks and the applications thereof.

A key component of polymer network structures that cannot be readily addressed by traditional metallogels is the network branch functionality, f, which is the average number of chains that emanate from junctions within a network. According to the phantom network model of rubber elasticity, the modulus of a gel increases with f.[33] In traditional metallogels, the junctions are single metal centers (FIG. 1A, left); f is dictated by the number of ligands that can bind to that metal, which is typically limited to values between two and four. Thus, metallogels are typically very soft materials, and it is very difficult to tune f without complete redesign of the network components.

It was envisioned that dramatic enhancements in f could be realized if network junctions were created through metal-ligand self-assembly into higher-order cage-like structures (FIG. 16A, right panel). Such "suprametallogels" would retain the dynamic properties of metallogels while potentially featuring broadly tunable branch architectures and enhanced mechanical properties. Indeed, Mother Nature uses hierarchical, multivalent assembly of weakly interacting species to produce biological gels with robust mechanical properties and dynamic behavior. Similar concepts have been adopted to increase the mechanical stability of synthetic networks;[34] however, to our knowledge, the use of programmed metallosupramolecular assembly for gelation has not been explored. As demonstrated here, such an approach is attractive because it enables tuning of gel properties over a wide range using the same metal and polymer, and very simple ligand modifications.

Numerous examples of ligand-metal combinations are known to provide discrete self-assembled cage-like structures.[35-48] Reports of Fujita and coworkers on the formation of $M_{12}L_{24}$ spherical cages from the assembly of twenty-four phenyl-3,5-bis-(para-pyridine) ligands (e.g., L-para and L1, FIG. 16B) and 12 $Pd^{2+}$ atoms were inspiring. In several studies, these authors have shown that these assemblies can be synthesized in quantitative yield, that they are robust towards a diverse range of ligand substitutions (R in FIG. 16B),[49,50] and that they can serve as small molecule hosts and nano-reactors.[36] Thus, incorporation of these supramolecular cages as junctions within a polymer network could afford suprametallogels with additional advantages—aside from mechanical ones—over conventional metallogels such as the ability to encapsulate and release species within the junction cages, or conduct reactions in confined spaces within the gel.

Two questions were to be answered. First, if bis-pyridyl moieties similar to those used by Fujita et al.[36] are appended onto the ends of linear polymer chains (e.g., macromers B-3 and B-4, FIG. 16C), will those polymer chains form suprametallogels in the presence of $Pd^{2+}$ through the self-assembly of the polymer chain ends? This question is non-trivial, because gelation has the potential to dramatically perturb the dynamics of cage self-assembly. Second, if an isomeric bis-pyridyl ligand, one that does not generate spherical cages but an alternative assembly, can be used to tune the network branch functionality in a rational manner? For example, in contrast to the defined 120° bite angle of the para-pyridine isomers, the corresponding meta isomers (L-meta and L2, FIG. 16B) have infinitely many possible bite angles between 0° and 240° depending on the relative orientation of the two pyridines. Ditopic ligands with similar geometry are known to self-assemble into $M_2L_4$ paddlewheels (FIG. 16B) with several types of metal ions, including $Pd^{2+}$.[51-65] The 1-hydroxymethyl derivative of L-meta (L2, FIG. 16B) was synthesized, and it was confirmed that it quantitatively forms $M_2L4$ paddlewheels in the presence of $Pd^{2+}$ ions. Thus, assuming no network defects and perfect self-assembly, polymers terminated with ligand L1 (macromer B-3, FIG. 16C) may provide suprametallogels with f=24 cage-like junctions, while analogous polymers terminated with ligand L2 (macromer B-4, FIG. 16C) may provide suprametallogels with f=4 paddlewheel junctions. In other words, a small difference in macromer ligand structure may provide materials with different bulk properties. Notably, this approach stands in stark contrast to gels that are formed via pre-assembly of metal-ligand-derived nanostructures that feature orthogonal groups for subsequent crosslinking.[66-68] Presented here are the first examples of gelation induced through metal-ligand bond formation and concomitant metallosupramolecular assembly (e.g., induced exclusively through metal-ligand bond formation and concomitant metallosupramolecular assembly).

The present disclosure also provides a new use of bptz as a ligand appended to PEG that binds to metals as a method for gelation. In addition, it has been shown that the bptz motif can act as a bifunctional moiety: first, as a ligand for coordinating metal ions and second, as a reactive site for functionalization.

Therefore, in another aspect, the present disclosure provides compositions that are gels or in the form of a gel (e.g., hydrogel), the compositions including a supramolecular complex and optionally an agent described herein. The gels described herein are suprametallogels. A supramolecular complex described herein and/or an adduct of a supramolecular complex and an agent (supramolecule-agent adduct) may be able to form a gel upon contacting a fluid. In certain embodiments, the fluid is a suitable solvent described herein (e.g., water). In certain embodiments, the supramolecular complex and/or supramolecule-agent adduct form a gel at least through the complexation of ligands of Formula (A) and transition metal ions and optionally also through other non-covalent interrelations (e.g., electrostatic interactions, hydrophobic interactions, hydrogen bonding, van der Waals interactions, and/or π-π stacking). A supramolecular complex and/or supramolecule-agent adduct described herein may form a gel upon contacting a fluid when the concentration of the supramolecular complex and/or supramolecule-agent adduct in the fluid is a suitable concentration described herein (e.g., between about 10 and about 500 millimoles of a reactant or reagent (e.g., a ligand of Formula (A); a macromer of Formula (B) or (C); or a transition metal salt) per liter of the fluid, inclusive). The structure of a gel described herein includes the primary structure (e.g., the structure of the nanostructure moieties of the gel) and secondary structure (e.g., the way how different instances of the nanostructure moieties are connected by divalent linkers Y and the degree of entanglement of the supramolecular complexes in the gel). In a supramolecular complex, an instance of divalent linker Y may be intrastructural or interstructural. An intrastructural instance of Y forms a loopy structure, whereas an interstructural instance of Y forms a chain structure. When all instances of divalent linker Y included in a gel described herein are intrastructural (e.g., when the concentration of the nanostructure moieties of a supramolecular complex in the fluid is below a critical concentration (in other words, under an overly high dilution), a "loopy nanostructure" forms. In certain embodiments, the critical concentration is about 5 mM, about 10 mM, about 15 mM, or about 25 mM. In certain embodiments, a gel described herein does not include loopy nanostructures. A supramolecular complex may include more than two instances of the nanostructure moiety covalently connected by more than one interstructural instance of Y. An instance of the supramolecular complex may entangle within itself, and two or more instances of the supramolecular complex may also entangle. The entangled supramolecular complex(es) form a molecular network that includes cavities, which may be filled with a fluid when the supramolecular complex(es) are contacted with the fluid, and the supramolecular complex(es) may retain the fluid and be swelled, rather than be dissolved, by the fluid to form a gel. A high degree of entanglement of the supramolecular complexes may be beneficial for the formation of a gel when the supramolecular complexes are contacted with a fluid. A high ratio of the number of interstructural divalent linkers Y to the number of intrastructural divalent linkers Y may also be beneficial for the formation of a gel at least because such a high ratio may increase the entanglement of the supramolecular complexes in the gel. In certain embodiments, at least about 50%, at least about 60%, at least about 70%, at least about 80%, or at least about 90% of all instances of divalent linker Y included in a gel described herein are interstructural.

Conventional gels (e.g., gels formed by swelling a covalently cross-linked polymer with a fluid) are typically not able to flow under a suitable stress (a suitable shear stress) and to self-heal when damaged. The gels described herein are advantageous over the conventional gels at least in that the gels described herein are able to flow under a suitable stress and to self-heal when damaged. While a conventional gel is usually thermally irreversible, the gels described herein are thermoreversible. A change in physical and/or chemical conditions (e.g., stress, temperature, and/or concentration) from a first condition to a second condition may result in a change in the degree of gelation of a gel described herein from a first degree of gelation to a second degree of gelation. A change in physical and/or chemical conditions (e.g., stress, temperature, and/or concentration) from the second condition to the first condition may result in a change in the degree of gelation of a gel described herein from the second degree of gelation to the first degree of gelation. The molecular network of a gel described herein may reversibly deform at least through weakening or strengthening, or breaking or reforming, the coordination bonds between the ligands of Formula (A) and the transition metal ions by changing physical and/or chemical conditions. In contrast, the covalent bonds in a conventional gel typically cannot be reversibly weakened or strengthened, or broken or reformed, by changing physical and/or chemical conditions. The aggregation of the molecules in a gel described herein is more dynamic, compared to the aggregation of the molecules in a conventional gel, and the more dynamic aggregation in a gel described herein is at least due to the non-covalent interactions between the molecules therein. Conventional gels typically cannot be easily characterized using spectroscopic techniques. In contrast, the gels described herein allow facile characterizations using readily available spectroscopic techniques (e.g., UV-vis absorption spectroscopy and Raman spectroscopy) under various conditions. Combination of chemical spectroscopy with mechanical tests will then beget spatial structure-temporal structure-mechanical property relationships; this allows for shape design criteria for engineering the mechanical properties of gels (vis-à-vis modulating the modes of the relaxation spectrum).

The gels described herein are also advantageous over conventional nanostructures (e.g., nanoparticles without divalent linkers that are covalently attached to different instances of the nanoparticles). Individual instances of a conventional nanostructure are not covalently linked to each other, and therefore, the conventional nanostructures typically lack robustness and storage modulus. Conversely, in a gel described herein, at least two instances of the nanostructure are covalently linked by at least one instance of divalent linker Y. The covalent bonding between the individual nanostructures in a gel described herein is stronger than the non-covalent interactions, if any, between the individual nanostructures in conventional nanostructures. Therefore, compared to conventional nanostructures, the gels described herein show higher robustness and/or higher storage modulus.

The supramolecular complexes and compositions (e.g., gels) may also be able to absorb a large amount of a fluid (e.g., absorb at least 100 times by weight of the fluid, compared to the weight of the supramolecular complex or the dry weight of the composition (weight of the composition minus the weight of the fluid included in the composition) and, therefore, may be useful as super-absorbent materials.

Kits

Also described herein are kits (e.g., packs). The kits provided may comprise (1) a transition metal salt, ligand of Formula (A); a macromer of Formula (B); a macromer of Formula (C); a nanostructure; a supramolecular complex; and/or a composition (e.g., gel) described herein; and (2) a container (e.g., a vial, ampule, bottle, syringe, and/or dispenser package, or other suitable container). In some embodiments, a kit described herein further includes a second container comprising an excipient for dilution or suspension of a nanostructure, supramolecular complex, or composition described herein. In some embodiments, the nanostructure, supramolecular complex, or composition provided in the first container and the nanostructure, supramolecular complex, or composition provided in the second container are combined to form one unit dosage form.

In certain embodiments, the kits described herein are useful for delivering an agent to a subject, tissue, or cell. In certain embodiments, the kits are useful for delivering an agent to a target tissue described herein. In certain embodiments, the kits are useful for treating a disease described herein. In certain embodiments, the kits are useful for preventing a disease described herein.

In certain embodiments, the described kits further include instructions for administering a nanostructure, supramolecular complex, or composition described herein. The kits may also include information as required by a regulatory agency such as the U.S. Food and Drug Administration (FDA). In certain embodiments, the information included in the kits is prescribing information. In certain embodiments, the kits, including the instructions, provide for delivering an agent described herein to a subject, tissue, or cell. In certain embodiments, the kits, including the instructions, provide for treating a disease described herein. In certain embodiments, the kits, including the instructions, provide for preventing a disease described herein. The kit described herein may include one or more agents described herein as a separate composition.

Methods of Preparing the Nanostructures, Supramolecular Complexes, and Gels; and the Nanostructures, Supramolecular Complexes, and Gels Prepared by the Methods The nanostructures, supramolecular complexes, and compositions (e.g., gels) described herein may be prepared by complexation reactions. In another aspect, the present disclosure provides methods of preparing a nanostructure (Method A), the methods including reacting a ligand of Formula (A), or a salt thereof, with a transition metal salt to provide the nanostructure.

In certain embodiments, the transition metal salt is salt of a transition metal ion described herein. In certain embodiments, the transition metal salt is a solvate (e.g., hydrate). In certain embodiments, the transition metal salt is not a solvate (e.g., is anhydrous). In certain embodiments, the transition metal salt is a Pd (e.g., Pd(II)) salt. In certain embodiments, the transition metal salt is a Ni (e.g., Ni(II)) salt. In certain embodiments, the transition metal salt is a Fe (e.g., Fe(II) or Fe(III)) salt. In certain embodiments, the transition metal salt is a Rh (e.g., Rh(I)) salt, Ir (e.g., Ir(I)) salt, Pt (e.g., Pt(II)) salt, or Au (e.g., Au(III)) salt. In certain embodiments, the transition metal salt is a Cd (e.g., Cd(II)) salt, Co (e.g., Co(III)) salt, or Cu (e.g., Cu(I) or Cu(II)) salt. In certain embodiments, the transition metal salt includes an anionic counterion described herein (e.g., $ClO_4^-$, $NO_3^-$, $TfO^-$, $BF_4^-$, $PF_4^-$, $PF_6^-$, $AsF_6^-$, $SbF_6^-$, $AcO^-$, $F^-$, $Cl^-$, $Br^-$, or $I^-$). In certain embodiments, the transition metal salt is $Pd(NO_3)_2$, or a solvate or hydrate thereof (e.g., $Pd(NO_3)_2 \cdot H_2O$ or $Pd(NO_3)_2 \cdot 2H_2O$). In certain embodiments, the transition metal salt is $Ni(ClO_4)_2$, or a solvate or hydrate thereof. In certain embodiments, the transition metal salt is $Fe(ClO_4)_2$, or a solvate or hydrate thereof.

In another aspect, the present disclosure provides methods of preparing a supramolecular complex (Method B), the methods including complexing a macromer of Formula (B) or (C), or a salt thereof, with a transition metal salt to provide the supramolecular complex.

In another aspect, the present disclosure provides methods of preparing a gel (Method C), the methods including complexing a macromer of Formula (B) or (C), or a salt thereof, with a transition metal salt in the presence of a fluid to provide the gel. In certain embodiments, the step of complexing of Method C further comprises the presence of an agent (e.g., a small molecule, such as an anticancer agent (e.g., doxorubicin)). In certain embodiments, the step of complexing of Method C further comprises crosslinking the macromer, before or after the step of complexing, in the presence of a crosslinking agent (crosslinker). In certain embodiments, the crosslinker is a norbornene crosslinker (e.g., tri-norbornene crosslinker).

The step(s) of the methods of preparing the nanostructures, supramolecular complexes, and/or compositions (e.g., gels) described herein may be performed under any suitable conditions. A suitable condition is a combination of physical and chemical parameters under which an intended product (e.g., a nanostructure, supramolecular complex, or composition (e.g., gel) described herein) or intermediate may be formed using the methods.

A suitable condition may include the absence of a solvent (i.e., neat). A suitable condition may include a suitable solvent. In certain embodiments, the suitable solvent is an organic solvent. In certain embodiments, the suitable solvent is an inorganic solvent (e.g., water). In certain embodiments, the suitable solvent is an aprotic organic solvent (e.g., acetonitrile, N,N-dimethylformamide (DMF), N,N-dimethylacetamide (DMA), N-methyl-2-pyrrolidone (NMP), dimethyl sulfoxide (DMSO), tetrahydrofuran (THF), 2-methyl-tetrahydrofuran, tetrahydropyran, dioxane, diethyl ether, methyl t-butyl ether (MTBE), dimethoxyethane (DME), diglyme, acetone, butanone, dichloromethane, chloroform, carbon tetrachloride, or 1,2-dichloroethane). In certain embodiments, the suitable solvent is DMSO. In certain embodiments, the suitable solvent is acetonitrile. In certain embodiments, the suitable solvent is a protic organic solvent (e.g., an alcohol, such as methanol, ethanol, propanol, or butanol). In certain embodiments, the suitable solvent is a mixture of two or more solvents (e.g., a mixture of water and DMSO). In certain embodiments, the suitable solvent is commercially available.

A suitable condition may also include a suitable concentration of a ligand of Formula (A) or macromer of Formula (B) or (C) in a fluid or suitable solvent. In certain embodiments, the concentration of a ligand of Formula (A) or macromer of Formula (B) or (C), or a salt thereof, in a fluid or suitable solvent is at least about 1, at least about 3, at least about 10, at least about 15, at least about 25, at least about 50, at least about 100, at least about 250, at least about 500, or at least about 1,000 millimoles per liter of the fluid or suitable solvent. In certain embodiments, the concentration of the a ligand of Formula (A) or macromer of Formula (B) or (C), or a salt thereof, in a fluid or suitable solvent is not more than about 1,000, not more than about 500, not more than about 250, not more than about 100, not more than about 50, not more than about 25, not more than about 15, not more than about 10, not more than about 3, or not more than about 1 millimoles per liter of the fluid or suitable solvent. Combination of the above ranges (e.g., between about 5 and about 500 millimoles per liter of the fluid or suitable solvent, inclusive) is also within the scope of the present disclosure. In certain embodiments, the concentration of a ligand of Formula (A) or macromer of Formula (B)

or (C), or a salt thereof, in a fluid or suitable solvent is between 5 and 500, between 5 and 100, between 10 and 500, between 15 and 500, inclusive, or at least about 10 or about 15 millimoles per liter of the fluid or suitable solvent, inclusive.

A suitable condition may also include a suitable molar ratio of (1) the ligand of Formula (A) or macromer of Formula (B) or (C) to (2) the transition metal salt. In certain embodiments, the molar ratio of the ligand of Formula (A) to the transition metal salt is about 2:1. In certain embodiments, the molar ratio of the macromer of Formula (B) or (C) to the transition metal salt is about 1:1.

A suitable condition may also include a suitable temperature under which a step of a method of preparing a nanostructure, supramolecular complex, or composition (e.g., gel) described herein is performed. In certain embodiments, the suitable temperature is at least about 20° C., at least about 40° C., at least about 60° C., at least about 70° C., at least about 80° C., at least about 100° C., at least about 120° C., or at least about 140° C. In certain embodiments, the suitable temperature is not more than about 140° C., not more than about 120° C., not more than about 100° C., not more than about 80° C., not more than about 70° C., not more than about 60° C., not more than about 40° C., or not more than about 20° C. Combinations of the above-referenced ranges (e.g., between about 20° C. and about 120° C., inclusive) are also within the scope of the disclosure. In certain embodiments, the suitable temperature is between about 20° C. and about 30° C., inclusive. In certain embodiments, the suitable temperature is about 23° C. In certain embodiments, the suitable temperature is between about 60° C. and about 80° C., inclusive. In certain embodiments, the suitable temperature is about 70° C. In certain embodiments, the suitable temperature is about 80° C. In certain embodiments, the suitable temperature is about 120° C. A suitable temperature may be a variable temperature (e.g., from 20° C. to about 70° C.) during a step of a method described herein.

A suitable condition may also include a suitable pressure under which a step of a method described herein is performed. In certain embodiments, the suitable pressure is about 1 atmosphere.

A suitable condition may also include a suitable atmosphere under which a step of a method described herein is performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that a step of a method described herein lasts. In certain embodiments, the suitable time duration is in the order of minutes (e.g., about 30 minutes), hours (e.g., about 1 hour, about 2 hours, about 4 hours, about 6 hours, or about 12 hours), or days (e.g., about 1 day, 2 days, or 3 days). In certain embodiments, the suitable time duration is between about 12 hours to about 2 days, inclusive (e.g., about 1 day).

The nanostructures, supramolecular complexes, and compositions (e.g., gels) prepared by the methods described herein may be isolated and/or purified using methods known in the art, such as chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying.

Another aspect of the present disclosure relates to nanostructures, supramolecular complexes, and compositions (e.g., gels) prepared by a method described herein. In certain embodiments, described herein are supramolecular complexes prepared by Method B, wherein the macromer is of Formula (B-1), (B-2), (B-3), or (B-4); and optionally the transition metal salt is a Pd(II) salt (e.g., $Pd(NO_3)_2$), Ni(II) salt (e.g., $Ni(ClO_4)_2$), Fe(II) salt (e.g., $Fe(ClO_4)_2$), or a solvate or hydrate thereof, and optionally the molar ratio of the macromer to the transition metal salt is about 1:1. In certain embodiments, described herein are supramolecular complexes prepared by Method B, wherein the macromer is of Formula (C-1) or (C-2); and optionally the transition metal salt is a Pd(II) salt (e.g., $Pd(NO_3)_2$), Ni(II) salt (e.g., $Ni(ClO_4)_2$), Fe(II) salt (e.g., $Fe(ClO_4)_2$), or a solvate or hydrate thereof; and optionally the molar ratio of the macromer to the transition metal salt is about 1:1.

In certain embodiments, described herein are gels prepared by Method C. In certain embodiments, the gel is a gel prepared by method C, wherein the macromer is of Formula (B-1), (B-2), (B-3), or (B-4); and optionally the transition metal salt is a Pd(II) salt (e.g., $Pd(NO_3)_2$), Ni(II) salt (e.g., $Ni(ClO_4)_2$), Fe(II) salt (e.g., $Fe(ClO_4)_2$), or a solvate or hydrate thereof; and optionally the molar ratio of the macromer to the transition metal salt is about 1:1; and optionally the fluid is water, DMSO, acetonitrile, or a mixture thereof (e.g., an about 1:1 (v:v) mixture of water and acetonitrile); and optionally the concentration of the macromer is between about 5 and about 500 millimoles per liter of the fluid (e.g., between about 5 and about 100 millimoles per liter of the fluid), inclusive; and optionally the step of complexing is performed at a temperature of between about 20° C. and about 100° C. (e.g., between about 20° C. and about 80° C.), inclusive.

In certain embodiments, the gel is a gel prepared by method C, wherein the macromer is of Formula (B-1); and optionally the transition metal salt is a Pd(II) salt (e.g., $Pd(NO_3)_2$, $[(MeCN)_4Pd^{2+}](BF_4^-)_2$, or a Pd(II) salt that is not $Pd(OAc)_2$), a Ni(II) salt, or a solvate or hydrate thereof; and optionally the molar ratio of the macromer to the transition metal salt is about 1:1; and optionally the fluid is DMSO, water, acetonitrile, or a mixture thereof and optionally the concentration of the macromer is at least 5 millimoles per liter of the fluid (e.g., between 5 and 100 millimoles per liter of the fluid, inclusive; or between 15 and 100 millimoles per liter of the fluid, inclusive); and optionally the step of complexing is performed at a temperature of between 60° C. and 80° C., inclusive (e.g., about 70° C.).

In certain embodiments, the gel is a gel prepared by method C, wherein the macromer is of Formula (B-2); and optionally the transition metal salt is a Pd(II) salt (e.g., $Pd(NO_3)_2$, $[(MeCN)_4Pd^{2+}](BF_4^-)_2$, or a Pd(II) salt that is not $Pd(OAc)_2$), a Ni(II) salt, or a solvate or hydrate thereof; and optionally the molar ratio of the macromer to the transition metal salt is about 1:1; and optionally the fluid is DMSO, water, acetonitrile, or a mixture thereof; and optionally the concentration of the macromer is at least 5 millimoles per liter of the fluid (e.g., between 5 and 100 millimoles per liter of the fluid, inclusive; or between 15 and 100 millimoles per liter of the fluid, inclusive); and optionally the step of complexing is performed at a temperature of between 60° C. and 80° C., inclusive (e.g., about 70° C.).

In certain embodiments, the gel is a gel prepared by method C, wherein the macromer is of Formula (B-3); and optionally the transition metal salt is a Pd(II) salt (e.g., $Pd(NO_3)_2$), or a solvate or hydrate thereof, and optionally the molar ratio of the macromer to the transition metal salt is about 1:1; and optionally the fluid is water, and optionally the concentration of the macromer is at least 14 millimoles per liter of the fluid (e.g., between 14 and 100 millimoles per liter of the fluid, inclusive); and optionally the step of complexing is performed at a temperature of between 20° C. and 30° C., inclusive (e.g., about 23° C.).

In certain embodiments, the gel is a gel prepared by method C, wherein the macromer is of Formula (B-4); and optionally the transition metal salt is a Pd(II) salt (e.g., Pd(NO$_3$)$_2$), or a solvate or hydrate thereof; and optionally the molar ratio of the macromer to the transition metal salt is about 1:1; and optionally the fluid is water, and optionally the concentration of the macromer is at least 9.5 millimoles per liter of the fluid (e.g., between 9.5 and 100 millimoles per liter of the fluid, inclusive); and optionally the step of complexing is performed at a temperature of between 20° C. and 30° C., inclusive (e.g., about 23° C.).

In certain embodiments, the gel is a gel prepared by method C, wherein the macromer is of Formula (B-4); and optionally the transition metal salt is a Pd(II) salt (e.g., Pd(NO$_3$)$_2$), or a solvate or hydrate thereof; and optionally the molar ratio of the macromer to the transition metal salt is about 1:1; and optionally the fluid is water, and optionally the concentration of the macromer is at least 9.5 millimoles per liter of the fluid (e.g., between 9.5 and 100 millimoles per liter of the fluid, inclusive); and optionally the step of complexing is performed at a temperature of between 60° C. and 80° C., inclusive (e.g., about 70° C.).

In certain embodiments, the gel is a gel prepared by method C, wherein the macromer is of Formula (C-1) or (C-2); and optionally the transition metal salt is a Pd(II) salt (e.g., Pd(NO$_3$)$_2$), Ni(II) salt (e.g., Ni(ClO$_4$)$_2$), Fe(II) salt (e.g., Fe(ClO$_4$)$_2$), or a solvate or hydrate thereof; and optionally the molar ratio of the macromer to the transition metal salt is about 1:1; and optionally the fluid is water, DMSO, acetonitrile, or a mixture thereof (e.g., an about 1:1 (v:v) mixture of water and acetonitrile); and optionally the concentration of the macromer is between about 5 and about 500 millimoles per liter of the fluid (e.g., between about 10 and about 100 millimoles per liter of the fluid), inclusive; and optionally the step of complexing is performed at a temperature of between about 40° C. and about 100° C. (e.g., between about 60° C. and about 80° C.), inclusive.

In certain embodiments, the gel is a gel prepared by method C, wherein the macromer is of Formula (C-1); and optionally the transition metal salt is a Ni(II) salt (e.g., Ni(ClO$_4$)$_2$), or a solvate or hydrate thereof; and optionally the molar ratio of the macromer to the transition metal salt is about 1:1; and optionally the fluid is acetonitrile; and optionally the concentration of the macromer is at least 10 millimoles per liter of the fluid (e.g., between about 10 and about 100 millimoles per liter of the fluid), inclusive; and optionally the step of complexing is performed at a temperature of between about 20° C. and about 30° C., inclusive (e.g., about room temperature).

In certain embodiments, the gel is a gel prepared by method C, wherein the macromer is of Formula (C-1) or (C-2); and optionally the transition metal salt is a Ni(II) salt (e.g., Ni(ClO$_4$)$_2$), Fe(II) salt (e.g., Fe(ClO$_4$)$_2$), or a solvate or hydrate thereof; and optionally the molar ratio of the macromer to the transition metal salt is about 1:1; and optionally the fluid is acetonitrile.

In certain embodiments, the gel is a gel prepared by method C, wherein the macromer is of Formula (C-1) or (C-2); and optionally the transition metal salt is a Ni(II) salt (e.g., Ni(ClO$_4$)$_2$), Fe(II) salt (e.g., Fe(ClO$_4$)$_2$), or a solvate or hydrate thereof; and optionally the molar ratio of the macromer to the transition metal salt is about 1:1; and optionally the fluid is an about 1:1 (v:v) mixture of water and acetonitrile.

In certain embodiments, described herein are gels prepared by Method C, wherein the step of complexing of Method C further comprises the presence of an agent (e.g., a small molecule, such as an anticancer agent (e.g., doxorubicin)). The nanostructures, supramolecular complexes, and gels described herein may also be modified to covalently attach to a -linker- agent moiety, and the resulting modified nanostructures, supramolecular complexes, and gels are also within the scope of the present disclosure. In certain embodiments, the linker is a diradical of a peptide (e.g., a peptide of not more than 5, not more than 10, not more than 30, or not more than 100 amino acid residues). In certain embodiments, the linker is biodegradable. In certain embodiments, the linker is cleavable by an enzyme under physiological conditions. In certain embodiments, the linker is -Ile-Phe-Gly-. In certain embodiments, the agent is a monoradical of a pharmaceutical agent (e.g., therapeutic agent or diagnostic agent). In certain embodiments, the pharmaceutical agent is an pharmaceutical agent approved by the FDA for use in a human or animal.

Methods of Treatment and Uses

One of the major problems in the development of formulations of pharmaceutical agents (e.g., anti-cancer agents) is the delivery of the pharmaceutical agents with adequately high bioavailability for therapeutic intentions. Using conventional delivery techniques, many pharmaceutical agents cannot be delivered effectively to the target tissues or target cells. Gels, such as hydrogels, have emerged as an important class of materials for biomedical applications due to their unique properties that bridge the gap between solid and liquid states. The gels described herein are advantageous over conventional gels that typically include a covalently cross-linked polymer network at least because the molecular network of a gel described herein is formed at least by non-covalent interactions, such as complexation of a ligand and a transition metal ion, and thus is thermoreversible, able to flow (e.g., under a high shear stress), and able to self-heal when damaged. An agent may be encapsulated in a gel described herein (e.g., encapsulated in a nanostructure moiety of a supramolecular complex of the gel) and is delivered to a tissue or cell (e.g., a target tissue or target cell). The gel may dissociate in the tissue or cell to release the agent to the tissue or cell. In certain embodiments, a nanostructure moiety of a supramolecular complex of the gel dissociates (e.g., by breaking the coordination bonds between (1) the ligands of Formula (A) or macromers of Formula (B) or (C) and (2) the transition metal ions, and optionally by breaking divalent linkers Y by, e.g., hydrolysis) to release the agent that was encapsulated in the nanostructure moiety before the dissociation. The gels described herein are also advantageous over conventional nanoparticles at least because the gels described herein are more robust and has higher storage modulus than the conventional nanoparticles.

In another aspect, the present disclosure provides methods of delivering an agent described herein (e.g., small molecule) to a subject, tissue, or cell. In certain embodiments, described herein are methods of delivering the agent to a target tissue or target cell described herein. In certain embodiments, described herein are methods of selectively delivering the agent to a target tissue, compared to a non-target tissue. In certain embodiments, described herein are methods of selectively delivering the agent to a target cell, compared to a non-target cell. In certain embodiments, the agent is delivered into the subject, tissue, or cell by the methods described herein. In certain embodiments, the agent is selectively delivered into the target tissue or target cell by the methods described herein, compared to a non-target tissue or non-target cell, respectively.

Another aspect of the present disclosure relates to methods of increasing the delivery of an agent to a subject, tissue, or cell. In certain embodiments, the delivery of the agent to the subject, tissue, or cell is increased by a method described herein. In certain embodiments, the delivery of the agent to the subject, tissue, or cell by a method described herein is increased compared to the delivery of the agent to the subject, tissue, or cell by a control method that does not involve a composition described herein.

In another aspect, the present disclosure provides methods of treating a disease described herein in a subject in need thereof.

In another aspect, the present disclosure provides methods of preventing a disease described herein in a subject in need thereof.

In certain embodiments, a disease described herein is a genetic disease. In certain embodiments, the disease is a proliferative disease. In certain embodiments, the disease is cancer. In certain embodiments, the disease is a benign neoplasm. In certain embodiments, the disease is pathological angiogenesis. In certain embodiments, the disease is an inflammatory disease. In certain embodiments, the disease is an autoimmune disease. In certain embodiments, the disease is a hematological disease. In certain embodiments, the disease is a neurological disease. In certain embodiments, the disease is a gastrointestinal disease. In certain embodiments, the disease is a liver disease. In certain embodiments, the disease is a spleen disease. In certain embodiments, the disease is a respiratory disease. In certain embodiments, the disease is a lung disease. In certain embodiments, the disease is a painful condition. In certain embodiments, the painful condition is inflammatory pain. In certain embodiments, the painful condition is associated with an inflammatory disorder and/or an autoimmune disorder. In certain embodiments, the disease is a genitourinary disease. In certain embodiments, the disease is a musculoskeletal condition. In certain embodiments, the disease is an infectious disease. In certain embodiments, the disease is a psychiatric disorder. In certain embodiments, the disease is a metabolic disorder. In certain embodiments, the disease is hepatic carcinoma. In certain embodiments, the disease is hypercholesterolemia. In certain embodiments, the disease is refractory anemia. In certain embodiments, the disease is familial amyloid neuropathy.

Another aspect of the present disclosure relates to methods of genetically engineering a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites).

In certain embodiments, a method described herein includes administering to the subject a composition described herein. In certain embodiments, a method described herein includes administering to the subject an effective amount of a composition described herein.

In certain embodiments, a method described herein includes contacting the tissue with a composition described herein. In certain embodiments, a method described herein includes contacting the tissue with an effective amount of a composition described herein.

In certain embodiments, a method described herein includes contacting the cell with a composition described herein. In certain embodiments, a method described herein includes contacting the cell with an effective amount of a composition described herein.

In certain embodiments, a subject described herein is a human. In certain embodiments, the subject is an animal. In certain embodiments, the subject is a non-human animal. The animal may be of either sex and may be at any stage of development. In certain embodiments, the subject is a fish. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a human with a disease described herein. In certain embodiments, the subject is a human suspected of having a disease described. In certain embodiments, the subject is a human at risk of developing a disease described herein.

In certain embodiments, a cell described herein is in vivo. In certain embodiments, a cell described herein is in vitro.

Another aspect of the present disclosure relates to uses of a nanostructure described herein in a method described herein (e.g., uses for delivering an agent to a subject, tissue, or cell; uses for treating a disease in a subject in need thereof; and uses for preventing a disease in a subject).

Another aspect of the present disclosure relates to uses of a supramolecular complex described herein in a method described herein (e.g., uses for delivering an agent to a subject, tissue, or cell; uses for treating a disease in a subject in need thereof; and uses for preventing a disease in a subject).

Another aspect of the present disclosure relates to uses of a composition (e.g., gel) described herein in a method described herein (e.g., uses for delivering an agent to a subject, tissue, or cell; uses for treating a disease in a subject in need thereof; and uses for preventing a disease in a subject).

EXAMPLES

In order that the invention described herein may be more fully understood, the following examples are set forth. The synthetic and biological examples described in this application are offered to illustrate the nanostructures, supramolecular complexes, pharmaceutical compositions, and methods provided herein and are not to be construed in any way as limiting their scope.

Preparation of the Nanostructures, Supramolecular Complexes, and Compositions (e.g., Gels)

The nanostructures, supramolecular complexes, and compositions (e.g., gels) described herein can be prepared from readily available starting materials using the following general methods and procedures (e.g., the methods shown in any one of Schemes 1 to 4). It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization.

Scheme 1. Exemplary synthesis of the ligands of Formula (A)
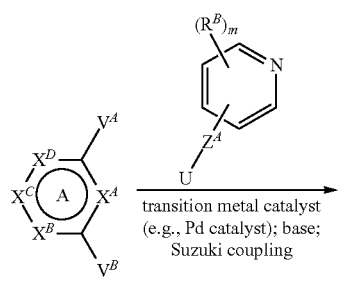
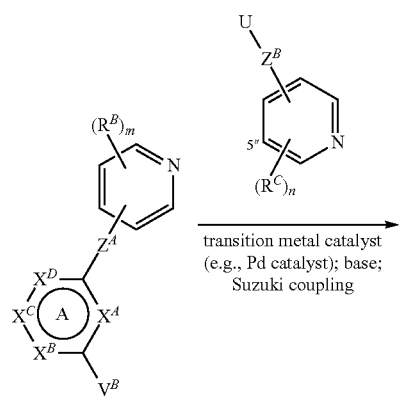
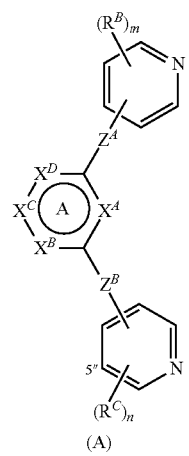
In Scheme 1, each instance of U is independently an organoboron moiety (e.g., —B(OH)$_2$, a borate moiety
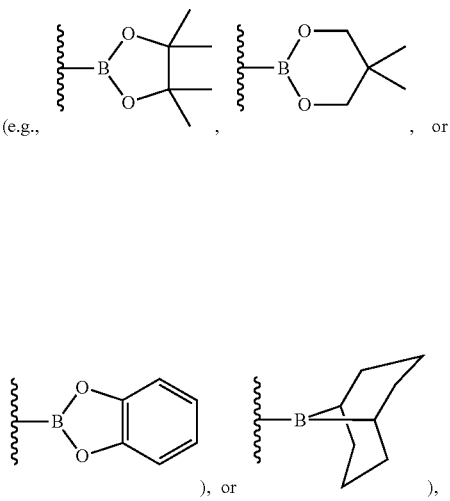
and each instance of V$^A$ and V$^B$ is independently halogen (e.g., Cl, Br, or I) or —OTf.
Scheme 2. Exemplary synthesis of exemplary macromers of Formula (B)
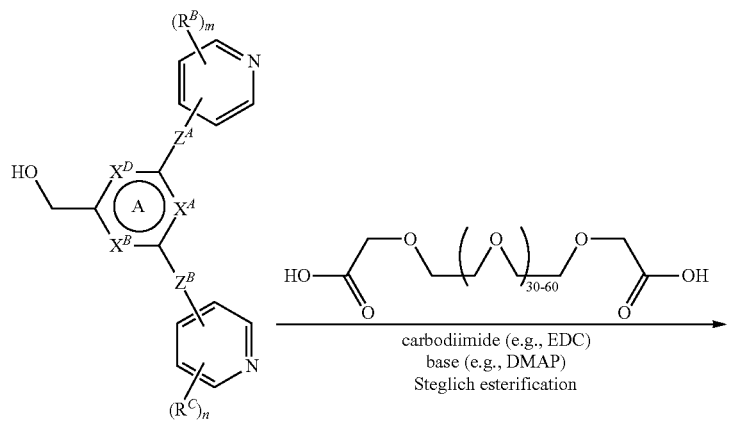

-continued
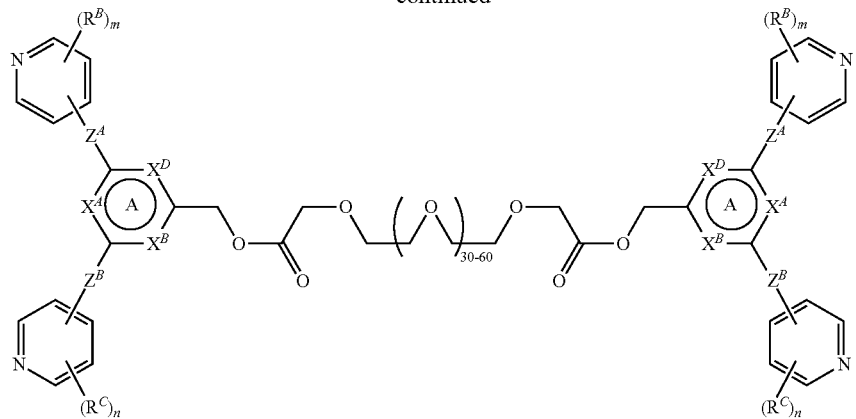
Scheme 3. Exemplary synthesis of exemplary nanostructures described herein
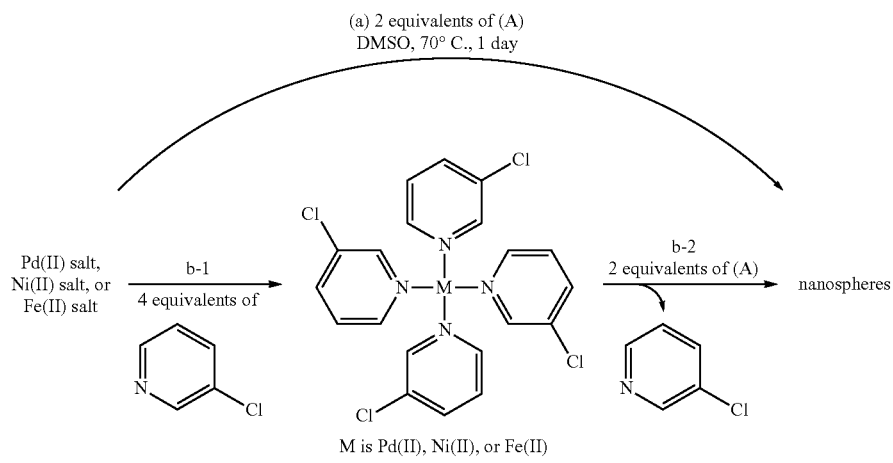
Scheme 4. Exemplary synthesis of exemplary supramolecular complexes and gels described herein
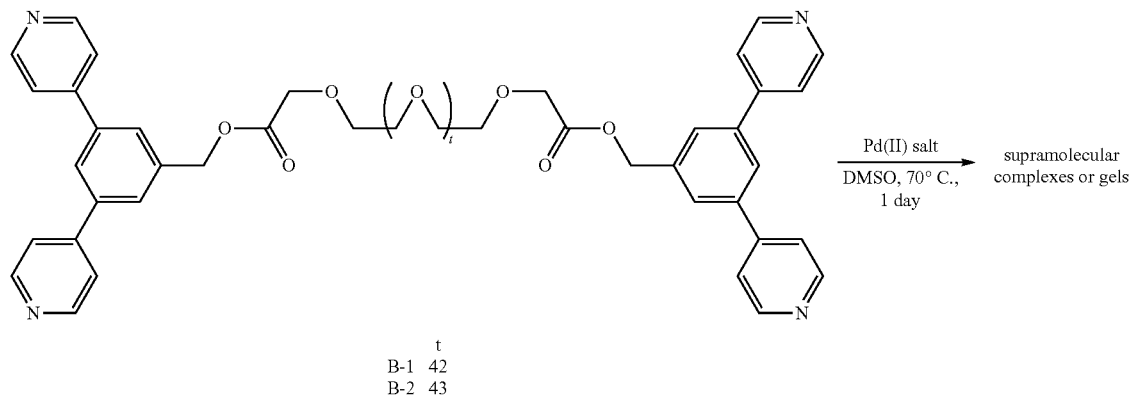
| | t |
|---|---|
| B-1 | 42 |
| B-2 | 43 |

Example 1. Preparation and Characterization of Ligand B-1

In an exemplary set of experiments, diacids

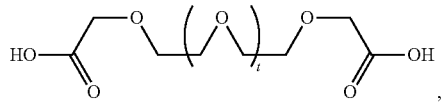

such as

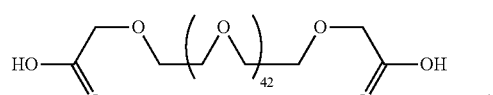
and
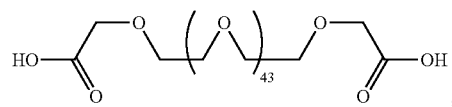, were synthesized according to the method shown in Scheme 5 (see, e.g., U.S. Pat. No. 8,067,505), wherein the number-average molecular weight ($M_n$) of the PEG moiety

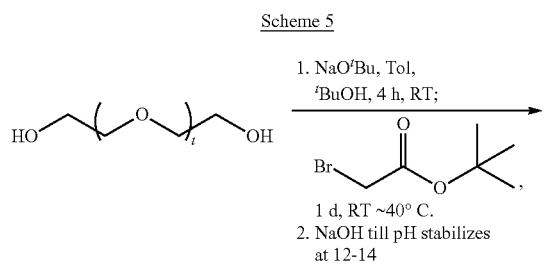

was about 2 kDa, 4.6 kDa, 6 kDa, 10 kDa, 25 kDa, and 35 kDa. The yields were at least about 80%.

Scheme 5

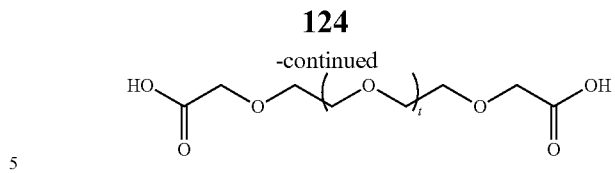

In an exemplary set of experiments, diacid

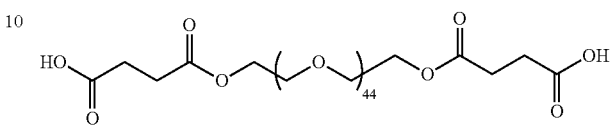

was synthesized according to the method shown in Scheme 6 in a 92.4% yield, and the product was pure by $^1$H NMR and mass spectroscopy (MALDI-TOF).

Scheme 6

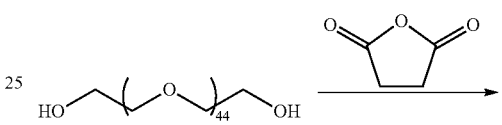

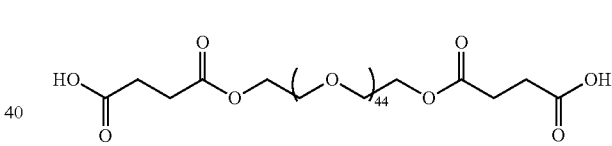

In an exemplary set of experiments, telechelic bromo-poly(n-butyl acrylate) (telechelic bromo-pNBA) with a $M_n$ of 4.2 kDa (degree of polymerization (DP) was about 30; and polydispersity (PDI) was about 1.13 as determined by GPC) or 13.9 kDa (DP was about 106); and PDI was about 1.08 as determined by GPC).

In an exemplary set of experiments, ligand B-1 was prepared according to the method shown in Scheme 7. An exemplary $^1$H NMR spectrum (DMSO-d$_6$, 400 MHz) is shown in FIG. 12.

Scheme 7. Exemplary synthesis of ligand B-1

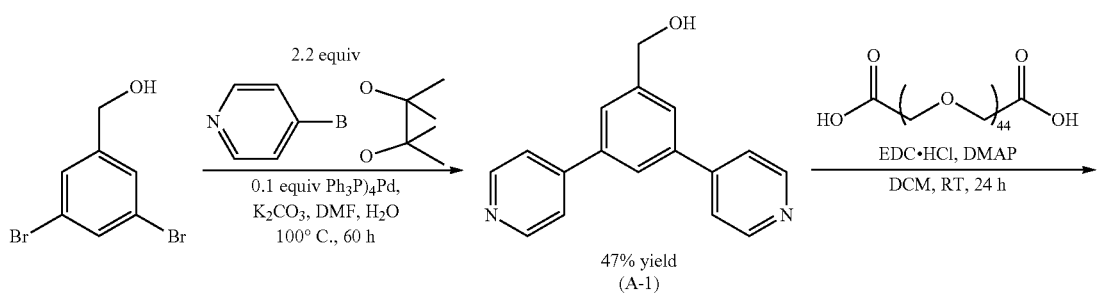

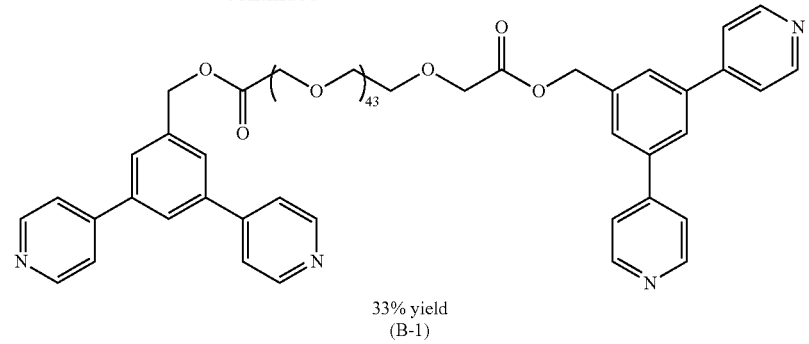

33% yield
(B-1)

Example 2. Preparation and Characterization of Nanosphere I-1

In an exemplary set of experiments, nanosphere I-1 was prepared according to the method in Scheme 3, steps (b-1) and (b-2), wherein the ligand of Formula (A) was ligand A-1, and the Pd(II) salt was Pd(NO$_3$)$_2$. To a 2-mL vial with A-1 (13.13 mg, 0.05006 mmol) dissolved in 366.7 µL of DMSO-d$_6$ was added via micropipette a solution of Pd(NO$_3$)$_2$·2H$_2$O (6.67 mg, 0.02503 mmol) in 133.3 µL of DMSO-d$_6$. The head-space of the vial was briefly purged with argon, the vial was closed with a screw-cap, and the resultant mixture was immediately vortexed, giving rise to a light-yellow liquid with small gelatinous pieces dispersed in it. The mixture was heated at 70° C. for 8 h, during the course of which, it became a light yellow homogeneous solution. A liquid was formed, which contained predominantly one supramolecular species. An exemplary $^1$H NMR spectrum (DMSO-d$_6$) of the resulting nanosphere I-1 evidenced the formation of nanospheres. Exemplary MTT proliferation assay results of nanosphere I-1 using HeLa cells are shown in FIG. 14, which indicate that nanosphere I-1 was toxic to HeLa cells with an IC$_{50}$ of 7.9 µM.

Example 3. Preparation and Characterization of Supramolecular Complexes and Gels In another exemplary set of experiments, supramolecular complexes and gels were prepared according to the method of FIG. 1A. The formation of the supramolecular complexes and gels were evidenced by $^1$H NMR (FIG. 1C). Gelation was virtually instantaneous at the sites where the reactants came into contact. After the reaction mixture was heated at 70° C. for 8 hours or 80° C. for 4 hours, it became homogeneous. When ligand B-2 and Pd(NO$_3$)$_2$ were combined at a concentration of 0.01 M with a 15% excess of ligand B-2, the reaction mixture became a homogeneous liquid after heating at 100° C. overnight; the $^1$H NMR spectrum of the resulting mixture suggested formation of nanospheres. The rate of gelation can be tuned by adjusting the reactivity of the transition metal (e.g., Pd(II)) salt. In some cases, the more labile the counterion of the transition metal salt, the more rapid the gelation is. Pd(NO$_3$)$_2$ and [(MeCN)$_4$Pd$^{2+}$](BF$_4^-$)$_2$ resulted in rapid gelation, while no gelation was observed seen when Pd(OAc)$_2$ was used. In some cases, the counterion of the transition metal salt is a non-coordinating counterion. In some cases, the counterion of the transition metal salt provides a sufficient kinetic barrier to reduce the rate of gelation. For instance, is was observed that 3-chloropyridine can be used as such an auxiliary ligands that can be used with a Pd(II) salt. See, e.g., Scheme 3. From the frequency sweeps spanning 0.1 and 100 rad/s, shortly after mixing of all the reaction components, a storage modulus G' of about 16-21 kPa and a about 15-fold lower G" (0.74-1.4 kPa) were observed (FIGS. 21A and 5B), confirming that the observed gelation had, indeed, taken place. During the subsequent heating stage at 70° C., G' dropped, reaching a plateau after 5 hours at 8.8-11 kPa; G", on the other hand, increased to 3.7-5.5 kPa. Thus, the reaction mixture remained a gel, but it lost a significant amount of elasticity and became more liquid-like. These observations are consistent with the hypothesis that upon mixing ligand B-2 and Pd(NO$_3$)$_2$, a largely random network is formed, and during the heating stage, this network transformed to linked nanospheres through reversible coordination of the Pd(II) ions with the nitrogen atoms labeled with 1' and 1" of the pyridinyl moieties. Because of the small size of the PEG2000 divalent linkers and the relatively large size of the nanospheres, as well as the fact that there were 24 PEG2000 divalent linkers extending from each nanosphere, it may be very difficult to have each chain link two different nanospheres. Thus, loopy nanospheres may have formed, which led to a reduced G' and elevated G".

In another exemplary set of experiments, supramolecular complexes and gels were prepared according to the method of FIG. 2C, where the concentration of ligand B-2 in DMSO-d$_6$ was 0.025 M. The reaction (gelation) was monitored by measuring the rheology (e.g., shear storage modulus and shear loss modulus) of the reaction mixture using equipment shown in FIG. 2B. The results were shown in FIG. 2A, where the shear rate was 10 rad/s, and the reaction temperature was 70° during the duration of the experiment. The results of the reaction mixture at 70° C. were fitted to exponential curves.

In another exemplary set of experiments, supramolecular complexes and gels were prepared according to the method of FIG. 1A, wherein the reaction temperature and time duration were according to FIGS. 3A and 3B. The formation of the supramolecular complexes and gels were evidenced by $^1$H NMR (FIGS. 3A and 3B).

In another exemplary set of experiments, supramolecular complexes and gels were prepared according to the method of FIG. 1A, wherein the concentration of ligand B-2 were as provided in FIGS. 4A and 4B, and the reaction temperature was room temperature (FIG. 4A) and 70° C. (FIG. 4B). Also shown in FIGS. 4A and 4B are images of the reaction mixtures, which indicate that reaction mixtures containing 15 mM or 25 mM of ligand B-2 in DMSO-d$_6$ were able to form gels, whereas reaction mixtures containing 10 mM or 5 mM of ligand B-2 in DMSO-$d_6$ were not able to form gels. FIG. 4C shows the rheology of gels formed from different concentrations of ligand B-2.

In another exemplary set of experiments, supramolecular complexes and gels were prepared according to the method of FIG. 1A, wherein ligand B-2 was partially replaced with ligand A-1, wherein the mole amount of ligand A-1 was twice the mole amount of ligand B-2 that was replaced by ligand A-1. Exemplary modulus and shear viscosity results are shown in FIGS. 5B and 5C. Even replacement of 80% of ligand B-2 with 2 equivalents of ligand A-1, a gel was still formed.

In another exemplary set of experiments, supramolecular complexes and gels were prepared according to the method in Scheme 4, wherein the Pd(II) salt was Pd(NO$_3$)$_2$, and the concentration of ligand B-1 in DMSO was 5 mM (gel III-5), 10 mM (gel III-6), or 100 mM (gels III-1 to III-4). Exemplary $^1$H NMR spectra are shown in FIG. 9A (gel III-5) to 9B (gel III-6). Differential scanning calorimetry (DSC) experiments were performed on the gels prepared from 100 mM solutions. The reaction mixtures were quenched at 0 min (gel III-1), 2.5 h (gel III-2), 5.5 h (gel III-3), and 8.5 h (gel III-4), respectively, by addition of diethyl ether to the reaction mixtures to extract DMSO and provide a poor solvent. The DSC graphs showed a melting transition for gel III-1 at about 40° C., corresponding to PEG melting. No melting transition was observed for gels III-2 to III-4. The gels (gel III-5) obtained from a 5 mM solution was dialyzed against water (2×700 mL). The gels all turned from purple to orange upon addition of an aqueous solution of Ni(ClO$_4$)$_2$. Similar results were obtained when B-2 was used instead of B-1.

In another exemplary set of experiments, supramolecular complexes and gels were prepared according to the method in FIG. 15A. The concentration of ligand C-1 in acetonitrile was 10 mM. Initial rheology measurements indicated that gelation was completed within seconds. Oscillatory rheology measurements in a frequency sweep from 0.1-628 rad/s over 100 minutes showed that G' had already crossed G" before the first measurement (FIG. 15B). After mixing all the reactants and reagents, a storage modulus was measured to be close to 1×10$^6$ Pa, and a loss modulus was measured to be 1×10$^5$ Pa, which are high moduli for networks whose junctions are presumably dynamic. The increase in G' and G" after 43.9 minutes may be attributed to evaporation of the solvent. The supramolecular complexes and gels may be formed through junction self-assembly as shown in FIG. 15C. The gelation as indicated by the shear viscosity of the reaction mixture over reaction time is shown in FIG. 11A. FIG. 11A indicates that the gel formed at different rates for different solvents (immediately for MeCN and after about 2 hrs for water). The frequency sweep as indicated by a plot of shear storage modulus (G') and shear loss modulus (G") of the gel versus the strain (ω) is shown in FIG. 11B. FIGS. 11A and 11B indicate that the different solvents affected the kinetics of the gel formation (e.g., the kinetics of forming the secondary structure of the gel) but did not show a clear effect on the frequency behavior of the gel.

In another exemplary set of experiments, supramolecular complexes or gels were not formed using the method in Scheme 4, wherein the Pd(II) salt was replaced with a Zn(II) salt (e.g., Zn(ClO$_4$)$_2$), and the molar ratio of ligand B-1 or B-2 to the Zn(II) salt was 2:1 or 3:1.

Example 4. Preparation and Characterization of Loopy Nanospheres

In another exemplary set of experiments, loopy nanospheres were prepared according to the method in FIG. 13A, wherein the concentration of ligand B-1 in DMSO-$d_6$ was below 10 mM. The formation of loopy nanospheres was evidenced by $^1$H NMR and DLS results (FIG. 13B). The average diameter Dh of the PEG moieties of ligands B-1 was about 2.5 nm, and the average diameter of the nanosphere without the PEG moieties was about 2.8 nm.

Example 5. Preparation and Characterization of Supramolecular Complexes and Gels, Each of which Contained Doxorubicin Bright red supramolecular complexes and gels were formed by heating in DMSO-$d_6$ at 70° C. for 1 day a solution of ligand B-2 (100 mM) and Pd(NO$_3$)$_2$.H$_2$O in the presence of doxorubicin (100 mM). An image of the resulting gel is shown in FIG. 6B. The gel of FIG. 6B four times with DMSO-$d_6$ (4×300 mL) an image of the gel after the extractions is shown in FIG. 6C, and images of the four extracts are shown in FIG. 6D. Unencapsulated doxorubicin was removed by extraction with fresh DMSO-$d_6$, leaving a light-red gel with encapsulated doxorubicin. While the color of the first DMSO-$d_6$ extract was bright red, the subsequent extracts had virtually identical faint-orange color, indicating that an approximately constant low level of doxorubicin was released each time after the first wash. This observation is consistent with expected encapsulation and subsequent slow release of the doxorubicin from the nanospheres in the formed supramolecular complexes and gels.

Example 6. Solution Assembly of Ligands L1 and L2

Prior to the formation of suprametallogels, it was first sought to confirm that L1 and L2 form the expected Pd$_{12}$L$_{24}$ and Pd$_2$L$_4$ assemblies, respectively. Exposure of L1 to Pd(NO$_3$)$_2$. 2H$_2$O in DMSO-$d^6$ (0.100 M) initially provided a gelatinous mixture characterized by highly broadened downfield-shifted peaks in the $^1$H NMR spectrum (FIG. 17A). This mixture transformed into a clear light-yellow solution upon heating for 8 h at 70° C. The $^1$H NMR spectrum of this solution contained one set of broad ligand-based resonances consistent with a highly symmetric nanoscopic assembly (FIG. 17A); the resonances in the aromatic region were shifted downfield compared to those of L1, and the corresponding chemical shifts were virtually identical to those reported previously by Fujita and coworkers for methanofullerene-functionalized spheres constructed from the same ligand.[50]

Likewise, upon mixing L2 with Pd(NO$_3$)$_2$.2H$_2$O in DMSO-$d^6$ (0.100 M), a mixture of different L2-Pd$^{2+}$ species was obtained as gathered from the presence of many sets of ligand-based resonances in the aromatic region of the $^1$H NMR spectrum (FIG. 17B). Remarkably, upon annealing for 2 h at 70° C., this mixture coalesced into a single highly symmetric small assembly, as inferred from the single set of slightly broadened ligand-based resonances in the $^1$H NMR spectrum (FIG. 17B). Annealing for 8 h at 100° C. afforded an identical spectrum, implying that the assembly is stable under these conditions. Fourier transform ion cyclotron resonance (FT-ICR) electron spray ionization mass spectrometry (ESI-MS) exhibited a dominant species with mass/charge (m/z) corresponding to the triply cationic paddle-wheel mono-nitrate. X-ray crystallography confirmed the M$_2$L$_4$ paddlewheel connectivity of this assembly (FIG. 17C).[69] Considered collectively, these data confirm that both L1 and L2 initially form complex mixtures of assemblies upon exposure to Pd(NO$_3$)$_2$.2H$_2$O in DMSO-$d^6$ at room temperature, and that these mixtures quantitatively convert to well-defined assemblies under thermodynamic control.

Example 7. Preparation of Suprametallogels Using (1) B-3 or B-4 and (2) $Pd(NO_3)_2 \cdot 2H_2O$; and Annealing Experiments of the Suprametallogels L1 and L2 were coupled onto the ends of carboxylic acid terminated 2.2 kDa polyethylene glycol (PEG) to generate macromers B-3 and B-4, respectively (FIG. 16C). Exposure of B-3 to $Pd(NO_3)_2 \cdot 2H_2O$ at in DMSO-$d_6$ 23° C. resulted in immediate gelation when $[Pd^{2+}]=[B-3] \geq 14$ mM (0.043 g/mL). Macromer B-4 formed gels at all concentrations tested above 9.5 mM (0.026 g/mL).

In an exemplary preparation, to a 1-dram scintillation vial was added 20.25 mg (7.5 μmol) of macromer (B-3 or B-4) and then 210.0 μL DMSO-$d^6$. In a 2-mL scintillation vial, a stock solution of $Pd(NO_3)_2 \cdot 2H_2O$ in DMSO-$d^6$ was prepared at a concentration of 11.1 mg $Pd(NO_3)_2 \cdot 2H_2O$ per 1.00 mL DMSO-$d^6$ (after vortexing for ~1 min, a clear orange solution forms). 90 μL of this solution was transferred via micropipette to the solution of the macromer, and gelation was observed immediately, although the gel coloration is inhomogeneous. The headspace of the vial is briefly purged with argon, the vial is sealed, and heated at 80° C. for 4 h to give rise to a homogeneous light-yellow gel (translucent if derived from B-4, opaque if derived from B-3). Molarity of macromer in the gel (in this case 24 mM) was determined by dividing the number of moles of the macromer used by the total volume of the gel, accounting for the non-negligible contribution of the polymer to the total volume.

The observation that the paddlewheel-former B-4 gels at a significantly lower concentration compared to B-3 suggests that that even upon initial mixing, gels derived from B-3 and B-4 have fundamentally different network structures despite their identical composition.

Based on the solution assembly studies described above, it was expected that gels formed upon immediate mixing of B-3 or B-4 and $Pd^{2+}$ at room temperature are crosslinked through a complex mixture of branched coordination polymers rather than the well-defined target assemblies. Thus, these gels were annealed under conditions similar to those used to induce self-assembly of the free ligands. The annealing process was monitored by variable temperature $^1H$ solid state NMR (VT $^1H$ ssNMR) spectroscopy (FIGS. 18 and 19). In the case of paddlewheel-former B-4, the spectra revealed a transformation similar to that observed for free ligand L2: prior to annealing there were multiple sets of ligand-derived resonances in the $^1H$ ssNMR spectrum, which coalesced and sharpened into single resonances that mapped closely onto the solution $^1H$ NMR spectrum of the L2-based paddlewheels. These data suggest that the network junctions are converted into symmetric, paddlewheel structures within 1 h at 70° C.

In the case of gels prepared from macromer B-3, structural changes upon thermal annealing by ssNMR could not be resolved due to significant peak broadening (FIG. 19B). However, the peaks of these resonances have the same chemical shifts as those observed in solution $^1H$ NMR spectra of spheres formed from free L1 after annealing (FIG. 17A) and also soluble, nanoscale coordination polymers formed from mixing B-3 with $Pd^{2+}$ at very high dilution followed by annealing (FIG. 19A, inset cryo-TEM image shows nanoscale coordination polymers of B-3 and $Pd^{2+}$ formed at high dilution). Nevertheless, while the self-assembly of $M_{12}L_{24}$ cage-like junctions may occur in these gels,[70] this cannot be confirmed conclusively from ssNMR. Branched assemblies, which may consist of sphere fragments or larger (>24 ligand) clusters, could lead to similar ssNMR spectra. Regardless, these data clearly demonstrate that the choice of meta-versus para-pyridine ligands gives rise to networks with significantly different structure.

Example 8. Simulations of Assembly and Gelation Processes

To gain deeper insight into the impact of ligand identity on network assembly, it was turned to computer simulation (FIGS. 20A and 16B). Our approach extended the molecular dynamics simulations of Yoneya and Fujita[71,72] in which the details of metal-ligand binding were captured empirically through Coulombic interactions, and mediated by an implicit solvent. This model[71] have been adapted to include the meta-substituted version of the bis-pyridine ligand and the ability to simulate the case where individual pairs of ligands are attached to each other via a long flexible polymer chain. Our scheme for generating trajectories, which was chosen to mimic the sudden introduction of $Pd^{2+}$ into a well-mixed solution of ligands, involved propagating a randomly distributed mixture of metal ions and ligand molecules under experimental conditions (e.g., temperature and concentration). As illustrated in FIG. 20A, simulations consisted of 98 metal ions and 192 bis-pyridine ligand molecules (or 96 ligand-terminated macromers) in a periodically replicated cubic simulation box with a volume of 6540 $nm^3$. Five different trajectory ensembles were generated corresponding to the assembly of cage-forming ligands (L-para), paddlewheel-forming ligands (L-meta), L1-terminated 2.2 kDa PEG (macromer B-3), and L2-terminated 2.2 kDa PEG (macromer B-4). A more detailed description of our simulations, which are nearly identical to those presented in Reference 71,[71] are presented in the supporting information. In our analysis, cluster size was refer to in terms of the number of ligands in a given metal-ligand cluster, denoted with the quantity y as in $M_xL_y$. Our particular focus is on the relationship between ligand identity (i.e., meta- or para-substituted bis-pyridine) and metal-ligand cluster formation, how that relationship is affected by the linking of monomers by flexible polymer chains, and finally in characterizing the inter-cluster connectivity (as it relates to gelation) that accompanies the spontaneous assembly of tethered ligand dimers. Below, the solution assembly of $Pd^{2+}$ and ligand monomers are described, and the network-forming consequence of linking monomers with flexible polymer chains is discussed.

Example 9. Solution Assembly of Free Ligands L-Para and L-Meta

Trajectories initialized with randomly distributed ligand and metal ion positions exhibit the rapid formation of relatively unstable metal-ligand clusters followed by the slow annealing of the cluster morphology as the system evolves towards a more thermodynamically favorable configuration. This behavior is illustrated in FIG. 20B, which contain plots of the time-dependent (over 1 μs) average cluster size, $$\bar{y}(t) = \frac{1}{N(t)} \sum_{i=1}^{N(t)} y_i(t),$$

where the summation is taken over all of the N(t) clusters that exist at time t, and $y_i(t)$ is the number of ligands present in the $i^{th}$ cluster at time t. More specifically, the black and grey lines correspond to the average cluster size in solutions containing L-para and L-meta ligands, respectively. While both systems exhibit a clear separation of timescales between initial cluster formation (t≤100 ns) and the subsequent annealing of network morphology (t≥200 ns), the average cluster size for the sphere-forming L-para ligand (40±20) is significantly larger than that of the paddlewheel-forming L-meta ligands (6.3±0.5). The origin of this difference can be understood by considering the cluster size distributions (FIG. 20C). FIG. 20C shows histograms of the probability, $P_y$, that at time t≈1 μs, a given ligand belongs to a cluster with size y. The results for the cage-forming L-para ligand (shown in black), indicate that there is not a particularly strong preference for the formation of the schematic target $M_{12}L_{24}$ cluster (such as the one shown in FIG. 16B), which is consistent with the findings of Yoneya and Fujita.[71] In fact, the distribution of cluster sizes for L-para clusters after 1 μs is broad and, for the concentration that has been considered, predicts the prevalence of very large clusters such as those shown in FIG. 20A, far left. In stark contrast, for the paddlewheel-forming L-meta ligand $P_y$ is narrowly distributed and peaked at y=4 (see FIG. 20C), which corresponds to the schematic target $M_2L_4$ paddlewheel shown in FIG. 16B. Such clusters are also readily observed in FIG. 20A, second from the left. Taken together, these simulated results support the key notion underlying our suprametallogel design: the geometry of L-para facilitates the formation of large clusters while L-meta exhibits a strong preference for small $M_2L_4$ clusters. It should be noted, however, that it has been observed the occasional presence of system-spanning L-pra clusters, which is an indication that our results may contain artifacts due to system size effects, for example in the preferential stabilization of clusters that are large enough to interact with themselves through the periodic boundaries of our simulation. Indeed when simulations were perform at lower concentration (larger simulation cell), a significantly reduced probability for the formation of large (y>60) clusters was observed. These effects, combined with our inability to simulate the long timescales associated with the real assembly process, contribute to a lower than expected yield of $M_{12}L_{24}$ clusters based on experimental observation. In fact, our simulations more likely reflect the experimental systems prior to annealing (FIGS. 17A to 17C).

Example 10. Simulating the Assembly of Suprametallogels

To investigate suprametallogel formation, simulations were performed in which pairs of ligand monomers were tethered together via a model flexible polymer chain (see FIG. 20A, right). The polymer chain was described implicitly in the form of a ligand-ligand pair potential that exerted a bias on the relative position of bound ligands. This bias potential, equal to the potential of mean force governing the end-to-end distance of a three-dimensional self-avoiding random walk, was chosen to mimic details of the PEG chains used in our experiments (e.g., macromers B-3 and B-4). Similar to the free ligand simulations described above, trajectories were initiated from configurations with randomly distributed metal ions and macromers whose end-ligands were initially separated by the mean end-to-end distance of the model polymer chains. FIG. 20A shows snapshots of suprametallogels derived from macromers B-3 and B-4.

The average cluster size $\bar{y}$ and the cluster size distributions $P_y$ for macromers B-3 and B-4 are shown along side the free ligand results in FIGS. 20B and 20C. It was found that the qualitative difference between $\bar{y}$ for the para- and meta-pyridine based ligands, specifically on the tendency for para- to form a broad distribution of larger clusters and meta- to form a narrow distribution of small clusters, is preserved upon the addition of a flexible polymer tether. For both species, however, the presence of a polymer linker tends to favor the formation of smaller clusters (relative to the free ligands) and thereby lower $\bar{y}$ (FIG. 20B); after 1 μs networks comprised of macromers B-3 and B-4 display $\bar{y}$ values ($\bar{y}_1$ and $\bar{y}_2$, respectively) of 21±6 and 5.3±0.7. It is clear from FIG. 20B, however, that the L-para based systems are not in a state of dynamic equilibrium after 1 μs. Thus, it cannot be distinguished whether the decrease in average cluster size upon addition of a polymer linker is the result of a thermodynamic shift in cluster size distribution or rather due to retardation of network relaxation. Based upon the results from L-meta based clusters, it was hypothesized that the effect is kinetic in nature, but ultimately the resolution requires longer simulations. Nonetheless, these results confirm that the assembly preferences between para-versus meta-substituted pyridine ligands effectively translate into suprametallogels, and corroborate the NMR results discussed above.

Example 11. Analysis of Network Connectivity and Elastically Inactive Defects

To explain the unique mechanical properties of suprametallogels, simulations were expanded to include analysis of key network defects that impact bulk mechanical properties. Specifically, the interconnectivity of metal-ligand clusters was computed, and quantifying the elastically inactive primary cyclic, or "loop" defects, was focused on, that are formed when both ligand ends of a single macromer belong to the same assembled metal-ligand cluster. For a given cluster with y ligands, the quantity $\rho_L$ has been computed, which is the density of ligands in that cluster that are members of loop defects. FIG. 20D shows plots of the average value of $\rho_L$ as a function of cluster size for macromers B-3 and B-4. Our simulations have a finite number of macromers, and thus there is a trivial correlation between loop density and cluster size that can be understood by considering clusters composed of randomly selected ligands. In this case, loop density is expected to scale linearly with cluster size between the trivial end points, $\rho_L=0$ for y=1 and $\rho_L=1$ for y=192 (black curve, FIG. 20D). In suprametallogels comprised of B-3 and B-4 it was found that loop formation increases rapidly with cluster size. Furthermore, there is a slightly greater prevalence of loops for B-3 compared to B-4. Keeping in mind that networks comprised of B-3 contain a broad range of cluster sizes, including very large ones, and that networks comprised of B-4 feature small, fairly uniform clusters, the data presented in FIG. 20D provides a critical insight: networks comprised of B-3 have a much greater prevalence of elastically inactive loop defects compared to networks comprised of B-4 (see arrows, FIG. 20D).

Example 12. Mechanical Properties of Suprametallogels

The data described above supports our initial hypothesis that metallosupramolecular assembly induced gelation of polymers bearing isomeric bis-pyridine ligands can provide suprametallogels with dramatically different structure based on tuning the average cluster size, e.g., branch functionality. It was next sought to assess the impact of these structural differences on bulk suprametallogel mechanical properties. Oscillatory rheology was used to monitor the storage and loss moduli (G' and G", respectively) for 6.3 wt. % gels derived from B-3 and B-4 as a function of oscillation angular frequency (w) and strain both before and after thermal annealing.

As shown in FIGS. 21A to 21D, these gels behaved as elastic solids—their G' values were always larger than their G" values—over the entire range of tested frequencies both before and after annealing. Thus, these suprametallogels do not display a viscous flow regime at low frequencies at 25° C. Despite this similarity, other mechanical properties of the gels were strikingly different. For example, prior to thermal annealing, the high-frequency G' of gels based on sphere-former B-3 (12±3 kPa, FIG. 21A) was a factor of four greater than that of gels based on paddlewheel-former B-4 (3.0±0.5 kPa, FIG. 21B). This observation implies a significantly greater average elastically active junction functionality, e.g., cluster size, in gels based on B-3 prior to annealing, which agrees well with our NMR and molecular dynamics simulations.[73]

Upon thermal annealing, a decrease was observed in the high frequency G' value for both sets of gels; the final G' values were 5.2±0.3 kPa and 1.9±0.2 kPa for suprametallogels derived from B-3 and B-4, respectively (FIGS. 21A and 21B, grey curves). Notably, this decrease is greater for networks derived from B-3. Our simulations show that systems based on para-ligands initially have a broad distribution of cluster sizes with many clusters that can be much larger than the target 24 ligands, whereas those based on meta-ligands are more narrowly distributed near the target 4 ligands. Thus, assuming that thermal annealing drives these systems towards the target cluster size (as shown in FIGS. 17 and 18), suprametallogels based on para ligands should experience a greater decrease in cluster size and a corresponding greater decrease in G'. Our simulations also show that as cluster size decreases, the number of elastically inactive loops should decrease; this effect should provide a compensatory increase in the bulk modulus. Based on our data, the cluster size effect on G' outweighs possible changes in the loop fraction. The relationship between loop defect formation and cluster structure in suprametallogels will provide an interesting avenue for future experimental and theoretical research.

Strain sweeps in oscillatory shear at 10 rad/s performed into the nonlinear regime illustrate that the bite angle of the ligand and the state of assembly (before or after annealing) both have a significant impact on the yield behavior of the gels (FIGS. 21C and 21D). The yield stress of gels derived from B-4 (2,570±400 Pa, FIG. 21D) was comparable to that for suprametallogels derived from B-3 prior to annealing (2,080±840 Pa, FIG. 21C). However, while the former showed only a 28% (to 1840±140 Pa) decrease in yield stress after annealing, the latter exhibited an 87% decrease (to 260±110 Pa). Furthermore, while the yield strain of suprametallogels derived from B-3 exhibited a decrease from ~18% to ~6.3% after annealing (FIG. 21C), the yield strain of gels derived from B-4 increased after annealing from ~83% to ~110% (FIG. 21D). Notably, suprametallogels derived from B-4 could withstand more than 17 times as much strain as those derived from B-3. These data agree with our picture of suprametallogel structure. Though macromer B-3 provides somewhat stiffer materials due to an increase in f(5.2±0.3 kPa for B-3 versus 1.9±0.2 kPa for B-4), the presence of large clusters in these networks and the fact that the 2.2 kDa PEG chains have roughly the same radius as the target $M_{12}L_{24}$ cages lead to brittle materials; the PEG chains in networks of B-3 are either elastically inactive (in loops), or highly extended to bridge the large clusters. These extended PEG chains cannot bear significant stress. In contrast, the PEG chains in networks comprised of B-4 are less extended and more capable of bearing stress. In future studies, increasing the PEG chain length should facilitate enhancements in yield stress in networks build form para-pyridine ligands.

Lastly, it was sought to assess whether networks comprised of B-3 or B-4 could self-heal upon thermal annealing (FIGS. 22A to 22F). Samples of suprametallogels derived from B-3 (FIG. 22A) and B-4 (FIG. 22D) were cut with a razor blade to introduce macroscopic fractures (FIGS. 22B and 22E, fractures labeled with arrows). These samples were then subjected to heating for 4 h at 80° C., and healing was assessed based on macroscopic observation, e.g., did the two separated gel pieces become one uniform piece after annealing? Note that no additional solvent was added, and no pressure was applied to bring the two pieces into contact. Based on the collective data presented above, it was expected that networks comprised of B-3 would be more difficult to heal, since healing in these materials would require complete reassembly of large clusters; loop defect shuffling within disconnected clusters could be more rapid than inter-cluster healing. The smaller junctions in networks prepared from B-4 would facilitate the bridging of gaps formed during the fracture. Indeed, it was found that suprametallogels prepared from B-3 were unable to heal under these conditions (FIG. 22C), while those from B-4 completely recovered their initial state.

A major advantage of the suprametallogels described herein is the ability to program nano-scale architectures within a polymeric network, which could give rise to emergent, unexpected properties. When the swelling behavior of suprametallogels comprising B-3 or B-4 was examined, it was surprised to find that the suprametallogels comprising B-4 were capable of absorbing a remarkable 157±9 times their own weight in solvent (DMSO), whereas the suprametallogels comprising B-3 absorbed only 23±2 times their own weight (FIG. 22G). The latter value (23±2) is typical for a covalent network whereas the former value (157±9) is on par with the best superabsorbent polymers known (Chen, J., Park, H. & Park, K. Synthesis of superporous hydrogels: Hydrogels with fast swelling and superabsorbent properties. Journal of biomedical materials research 44, 53-62, (1999). These observations suggest that suprametallogels derived from B-4 and other paddlewheel forming ligands could have promising applications as super-absorbent materials.

Example 13. Preparation of Macromer C-2

A telechelic bis-pyridyl-tetrazine macromer (C-2) was synthesized by appending the bptz moiety on the ends of poly(ethylene glycol) (MW: 2000 Da) with a carbon spacer, through modified procedures of published work (Cok, A. M.; Zhou, H.; Johnson, J. A. *Macromolecular Symposia* 2013, 329, 108; Zhou, H.; Woo, J.; Cok, A. M.; Wang, M.; Olsen, B. D.; Johnson, J. A. *Proceedings of the National Academy of Sciences* 2012).

Example 14. Preparation of Gels Using (1) Macromer C-1 and (2) $Ni(ClO_4)_2$ Hydrate or $Fe(CO_4)_2$ Hydrate; and Characterizations of the Gels Mixing macromer C-1 with $Ni(ClO_4)_2$ hydrate or $Fe(ClO_4)_2$ hydrate in a 1:1 metal to ligand ratio in acetonitrile (100 mg/mL of C-1 at room temperature) resulted in qualitatively fast formation of gels with an accompanying color change. This observation leads to the conclusion that the bptz end-groups and metal ions must be aggregating in some higher order; otherwise, the macromer would merely undergo linear extension and not form a gel. A solution of C-1 does not gel on its own, which means that these gels are not merely physical gels from π-π stacking or other interactions.

To demonstrate that the metal-ligand bonds are responsible for the gelation, gels (FIG. 23A) were first formed with C-1 and iron perchlorate or nickel perchlorate in acetonitrile; none of the components form gels independently. Then, 25 µL of a 0.05 M $K_4$EDTA aqueous solution was added to the gels, and upon vortexing, the gels immediately dissolved and formed a liquid mixture (FIG. 23B).

The mechanical properties of gels formed from C-1 and Ni(ClO$_4$)$_2$ and Fe(ClO$_4$)$_2$ in acetonitrile were characterized by oscillatory rheology. Exemplary results are shown in FIGS. 24A and 24B. Frequency sweeps for both gels showed storage moduli of approximately 22 kPa for nearly the entire frequency range. Strain sweeps of the two gels displayed a difference in crossover point between G' and G"; the gel made using $Fe^{2+}$ becomes more fluid-like at about 18% strain, while the gel made using $Ni^{2+}$ retains its network structure until approximately 42% strain.

Also studied were the effect of solvents on gelation of the $Ni^{2+}$ coordinated gels. Exemplary results are shown in FIGS. 25A and 25B. As in the original condition, a 1:1 ratio of metal and ligand in acetonitrile results in fast gelation; the G'/G" crossover point lies beyond the leftmost point on the frequency axis. Performing the reaction in water results in slower gelation, although the value for G' approaches that of the gelation in acetonitrile at the highest frequencies tested. Interestingly, gelation in 1:1 acetonitrile/water results in a higher frequency crossover point for G' and G" than for either water or acetonitrile alone. This is unexpected, as it was predicted that the crossover point for the solvent mixture to lie between the two solvents separately.

Example 15. Preparation of Gels with Mixed Crosslinking Modalities and Characterizations of the Gels The capability of the bptz moiety to react with strained alkenes as well as metals led us to examine the mechanical properties of gels with mixed crosslinking modalities. By using a tris-norbornene crosslinker, 25% or 50% of the tetrazines were crosslinked to form soluble hyperbranched networks. Then, the remaining tetrazines were reacted with an amount of Ni(ClO$_4$)$_2$ such that the metals and ligands were in a 1:1 ratio. The metal-ligand crosslinking and tetrazine-norbornene crosslinking could not be done simultaneously; the metal-ligand coordination is much faster than the tetrazine-norbornene reaction and the latter cannot occur at a high enough efficiency after gelation. Furthermore, solution-state $^1$H-NMR experiments showed that after coordination of metal to the unfunctionalized bptz ligand, a model norbomene compound did not react with bptz with any detectable conversion.

Oscillatory rheology of these gels showed a slight increase in the storage and loss moduli due to the addition of the covalent crosslinker (FIG. 26). Interestingly, the gel with 50% covalent crosslinks has similar mechanical properties to the gel made with 25% covalent crosslinks (FIG. 26).

Example 16. Cytotoxicity Against HeLa Cells

Because C-2 forms gels with $Fe^{2+}$ salts, which are biocompatible, these gels may have applications as therapeutic devices. First, the cytotoxicity of these gels was tested on HeLa cells to determine the effect of the components of the gels on cell viability. Due to the difficulty in assessing the toxicity of gel materials, the components of the gels were tested separately. The iron and macromer show little cytotoxicity compared to MILLIQ water, which was used as a control (FIG. 27).

Example 17. Preparation of Gels that Contain Covalently Attached Doxorubicin Due to the biocompatibility of $Fe^{2+}$ salts, it was sought to create a metallogel that could serve as a drug-releasing therapeutic. For this purpose, a photocleavable doxorubicin-conjugated, norbornene-terminated PEG macromer was used and reacted with 10% of the available tetrazines of C-2 to produce a statistical mixture of bifunctionalized (1%), monofunctionalized (18%), and unfunctionalized (81%) macromer (FIG. 28). However, since most of C-2 remained unfunctionalized after the reaction, it was predicted that the doxorubicin-loaded macromers would simply become dangling ends on a gel that was structurally supported by unfunctionazlied C-2. The macromer mixture was dried out and redissolved in water and then reacted with an amount of Fe(ClO4)$_2$ such that the metal to remaining tetrazine was 1:1. Gelation, as determined by the vial inversion test, occurred within seconds (FIG. 28, inset).

Example 18. Release of Doxorubicin from the Gel of Example 17

To test the release of doxorubicin, the gel was covered with 100 µL of water, then irradiated with a UV lamp, and its extract was removed and replaced with water at various time intervals. The release was tracked by LCMS by observing absorbance at 490 nm and mass over time. Exemplary results are shown in FIG. 10. At 0 minutes, the gel shows no release of doxorubicin, and after 10 minutes, begins to show release of doxorubicin at an elution time of approximately 4 minutes; its identity was confirmed by the corresponding m/z from the negative ion mode trace of the ESI-MS. After 105 minutes, the gel continued to show release of doxorubicin. The peak with the greatest absorbance at an elution time of approximately 5 minutes is the macromer mixture, which is slowly released by the gel. Though the material remained a gel for the duration of the experiment, when the gel was layered with water and left to stand, the entire mixture eventually dissolved within a week.

The release of doxorubicin was slow for two reasons. Because the coordination of iron to the bipyridyl tetrazines produces colored complexes, the penetration of light into the gel beyond the surface is minimal. In addition, once the doxorubicin is released from the gel, it must diffuse through the gel into the water to be observed by LCMS. Nevertheless, slow doxorubicin release was observed for 105 minutes after exposure to UV light and extraction by water.

Example 18. Preparation of Gels that Contain Covalently Attached Biodegradable Peptide-Tryptamine A demonstration of another method of functionalizing the gel described herein is the appendage of a biodegradable peptide and its subsequent cleavage by an enzyme. Molecule X, which contains the peptide sequence Ile-Phe-Gly and is terminated by tryptamine, was used to functionalize 10 mol % of the tetrazines on macromer C-2. This mixture was combined in a 1:1 metal-ligand ratio with $FeSO_4.7H_2O$, which resulted in qualitatively quick gelation. Iron sulfate also formed gels in water with a similar storage modulus as that of iron perchlorate in acetonitrile.

Example 19. Release of Tryptamine Glycnamide from the Gel of Example 18

The potentially biocompatible gel of Example 18 was placed in 100 μL of a buffered solution (100 mM Tris, 10 mM $CaCl_2$, pH 7.8) and treated with chymotrypsin, at a concentration of 1.9 μM in enzyme. After 45 minutes, the release of tryptamine glycnamide was observed by LC-MS (observed $[M+1]^+$: 218.0, expected $[M+1]^+$: 218.1), confirming the cleavage of the peptide between phenylalanine and glycine (FIG. 7). Though tryptamine glycinamide has no known biological function, in principle, any amine can be coupled to the N-terminus of the peptide chain and be released by a chymotrypsin digest of the gel.

CONCLUSIONS

Herein, a novel strategy has been introduced for gelation that makes use of metallosupramolecular assembly of ligands appended to the ends of polymer chains. Using this approach, the average junction size and architecture is encoded in the bite angles of the ligands and the coordination geometry of the metal ions. Solid-state NMR, rheometry, and molecular dynamics simulations reveal that these differences are a direct consequence of the preference for these meta- and para-substituted ligands to self-assemble into $Pd_2L_4$ paddlewheel or $Pd_{12}L_{24}$ cage-like assemblies, respectively. Compared to conventional metallogels, the suprametallogels behave as elastic solids at oscillatory angular frequencies as low as 0.1 rad/s, and they exhibit high storage moduli (1.9±0.2 and 5.2±0.7 kPa) at 10-fold lower concentration of pyridine ligands for the same concentration of palladium(II) and 1.6 times lower mass fraction of the polymer network. Suprametallogels bridge the gap between conventional "soft" metallogels and "hard" crystalline supramolecular architectures. It has been confirmed that assembly, indeed, takes place within the gels during the course of thermal annealing at moderate temperatures (70-80° C.), and that the size of the self-assembled cages at the junctions dictates the mechanical properties of the materials. Lastly, the ability of suprametallogels to undergo self-healing of extensive macroscopic fractures has been demonstrated, thanks to the reversible nature of coordination bonding. Hence, it is anticipated that the implementation of the present strategy is to become a vital tool for the synthesis of novel robust, yet dynamic materials with novel properties.

REFERENCES

1 Xing, B., Choi, M.-F. & Xu, B. A stable metal coordination polymer gel based on a calix[4]arene and its "uptake" of non-ionic organic molecules from the aqueous phase. *Chemical Communications*, 362-363, doi:10.1039/B111245G (2002).
2 J. H. Hafkamp, R. et al. Organogel formation and molecular imprinting by functionalized gluconamides and their metal complexes. *Chemical Communications*, 545-546, doi:10.1039/A608266A (1997).
3 Xing, B., Choi, M.-F., Zhou, Z. & Xu, B. Spontaneous Enrichment of Organic Molecules from Aqueous and Gas Phases into a Stable Metallogel. *Langmuir* 18, 9654-9658, doi:10.1021/1a0256580 (2002).
4 Xing, B., Choi, M.-F. & Xu, B. Design of Coordination Polymer Gels as Stable Catalytic Systems. *Chemistry—A European Journal* 8, 5028-5032, doi:10.1002/1521-3765 (20021104)8:21<5028::AID-CHEM5028>3.0.CO; 2-1 (2002).
5 Westhaus, E. & Messersmith, P. B. Triggered release of calcium from lipid vesicles: a bioinspired strategy for rapid gelation of polysaccharide and protein hydrogels. *Biomaterials* 22, 453-462, doi: dx.doi.org/10.1016/S0142-9612(00)00200-3 (2001).
6 Fullenkamp, D. E., He, L., Barrett, D. G., Burghardt, W. R. & Messersmith, P. B. Mussel-Inspired Histidine-Based Transient Network Metal Coordination Hydrogels. *Macromolecules* 46, 1167-1174, doi:10.1021/ma301791n (2013).
7 Holten-Andersen, N. et al. pH-induced metal-ligand cross-links inspired by mussel yield self-healing polymer networks with near-covalent elastic moduli. *Proceedings of the National Academy of Sciences* 108, 2651-2655, doi: 10.1073/pnas. 1015862108 (2011).
8 Holten-Andersen, N. et al. Metal-coordination: using one of nature's tricks to control soft material mechanics. *Journal of Materials Chemistry B* 2, 2467-2472, doi: 10.1039/C3TB21374A (2014).
9 Harrington, M. J., Masic, A., Holten-Andersen, N., Waite, J. H. & Fratzl, P. Iron-Clad Fibers: A Metal-Based Biological Strategy for Hard Flexible Coatings. *Science* 328, 216-220, doi:10.1126/science. 1181044 (2010).
10 Zhao, Y., Beck, J. B., Rowan, S. J. & Jamieson, A. M. Rheological Behavior of Shear-Responsive Metallo-Supramolecular Gels. *Macromolecules* 37, 3529-3531, doi: 10.1021/ma0497005 (2004).
11 Weng, W., Beck, J. B., Jamieson, A. M. & Rowan, S. J. Understanding the Mechanism of Gelation and Stimuli-Responsive Nature of a Class of Metallo-Supramolecular Gels. *Journal of the American Chemical Society* 128, 11663-11672, doi:10.1021/ja063408q (2006).
12 Weng, W., Jamieson, A. M. & Rowan, S. J. Structural origin of the thixotropic behavior of a class of metallo-supramolecular gels. *Tetrahedron* 63, 7419-7431, doi: dx.doi.org/10.1016/j.tet.2007.03.119 (2007).
13 Weng, W., Li, Z., Jamieson, A. M. & Rowan, S. J. Control of Gel Morphology and Properties of a Class of Metallo-Supramolecular Polymers by Good/Poor Solvent Environments. *Macromolecules* 42, 236-246, doi:10.1021/ma801046w (2008).
14 Weng, W., Li, Z., Jamieson, A. M. & Rowan, S. J. Effect of monomer structure on the gelation of a class of metallo-supramolecular polymers. *Soft Matter* 5, 4647-4657, doi:10.1039/B911166B (2009).
15 Beck, J. B. & Rowan, S. J. Multistimuli, Multiresponsive Metallo-Supramolecular Polymers. *Journal of the American Chemical Society* 125, 13922-13923, doi:10.1021/ja038521k (2003).
16 Rowan, S. J. & Beck, J. B. Metal-ligand induced supramolecular polymerization: A route to responsive materials. *Faraday Discussions* 128, 43-53, doi:10.1039/B403135K (2005).
17 Bumworth, M., Mendez, J. D., Schroeter, M., Rowan, S. J. & Weder, C. Decoupling Optical Properties in Metallo-Supramolecular Poly(p-phenylene ethynylene)s. *Macromolecules* 41, 2157-2163, doi:10.1021/ma702712e (2008).

18 McKenzie, B. M. & Rowan, S. J. in *Molecular Recognition and Polymers* 157-178 (John Wiley & Sons, Inc., 2008).
19 Buerkle, L. E. & Rowan, S. J. Supramolecular gels formed from multi-component low molecular weight species. *Chemical Society Reviews* 41, 6089-6102, doi: 10.1039/C2CS35106D (2012).
20 Xu, D. & Craig, S. L. Scaling Laws in Supramolecular Polymer Networks. *Macromolecules* 44, 5465-5472, doi: 10.1021/ma200096s (2011).
21 Xu, D. & Craig, S. L. Strain Hardening and Strain Softening of Reversibly Cross-Linked Supramolecular Polymer Networks. *Macromolecules* 44, 7478-7488, doi: 10.1021/ma201386t (2011).
22 Xu, D., Hawk, J. L., Loveless, D. M., Jeon, S. L. & Craig, S. L. Mechanism of Shear Thickening in Reversibly Cross-Linked Supramolecular Polymer Networks. *Macromolecules* 43, 3556-3565, doi:10.1021/ma100093b (2010).
23 Loveless, D. M., Jeon, S. L. & Craig, S. L. Chemoresponsive viscosity switching of a metallo-supramolecular polymer network near the percolation threshold. *Journal of Materials Chemistry* 17, 56-61, doi:10.1039/B614026B (2007).
24 Yount, W. C., Loveless, D. M. & Craig, S. L. Small-Molecule Dynamics and Mechanisms Underlying the Macroscopic Mechanical Properties of Coordinatively Cross-Linked Polymer Networks. *Journal of the American Chemical Society* 127, 14488-14496, doi:10.1021/ja054298a (2005).
25 Yount, W. C., Loveless, D. M. & Craig, S. L. Strong Means Slow: Dynamic Contributions to the Bulk Mechanical Properties of Supramolecular Networks. *Angewandte Chemie International Edition* 44, 2746-2748, doi:10.1002/anie.200500026 (2005).
26 Loveless, D. M., Jeon, S. L. & Craig, S. L. Rational Control of Viscoelastic Properties in Multicomponent Associative Polymer Networks. *Macromolecules* 38, 10171-10177, doi:10.1021/ma0518611 (2005).
27 Kean, Z. S. et al. Increasing the Maximum Achievable Strain of a Covalent Polymer Gel Through the Addition of Mechanically Invisible Cross-Links. *Adv. Mater. (Weinheim, Ger.)*, n/a-n/a, doi:10.1002/adma.201401570 (2014).
28 Nair, K. P., Breedveld, V. & Weck, M. Modulating mechanical properties of self-assembled polymer networks by multi-functional complementary hydrogen bonding. *Soft Matter* 7, 553-559, doi:10.1039/C0SM00795A (2011).
29 Nair, K. P., Breedveld, V. & Weck, M. Multiresponsive Reversible Polymer Networks Based on Hydrogen Bonding and Metal Coordination. *Macromolecules* 44, 3346-3357, doi:10.1021/ma102462y (2011).
30 Hackelbusch, S., Rossow, T., van Assenbergh, P. & Seiffert, S. Chain Dynamics in Supramolecular Polymer Networks. *Macromolecules* 46, 6273-6286, doi:10.1021/ma4003648 (2013).
31 Hackelbusch, S., Rossow, T., Becker, H. & Seiffert, S. Multiresponsive Polymer Hydrogels by Orthogonal Supramolecular Chain Cross-Linking. *Macromolecules* 47, 4028-4036, doi:10.1021/ma5008573 (2014).
32 Zhang, Y. et al. Active Cross-Linkers that Lead to Active Gels. *Angewandte Chemie International Edition* 52, 11494-11498, doi:10.1002/anie.201304437 (2013).
33 Rubinstein, M. & Colby, R. *Polymers Physics*. (Oxford, 2003).
34 Cordier, P., Toumilhac, F., Soulie-Ziakovic, C. & Leibler, L. Self-healing and thermoreversible rubber from supramolecular assembly. *Nature* 451, 977-980, doi: www.nature.com/nature/journal/v451/n7181/suppinfo/nature06669_S1.html (2008).
35 Sun, W.-Y., Yoshizawa, M., Kusukawa, T. & Fujita, M. Multicomponent metal-ligand self-assembly. *Current Opinion in Chemical Biology* 6, 757-764, doi: dx.doi.org/10.1016/S1367-5931(02)00358-7 (2002).
36 Harris, K., Fujita, D. & Fujita, M. Giant hollow MnL2n spherical complexes: structure, functionalisation and applications. *Chemical Communications* 49, 6703-6712, doi:10.1039/C3CC43191F (2013).
37 Leininger, S., Olenyuk, B. & Stang, P. J. Self-Assembly of Discrete Cyclic Nanostructures Mediated by Transition Metals. *Chem. Rev. (Washington, D.C., U. S.)* 100, 853-908, doi:10.1021/cr9601324 (2000).
38 Meyer, C. D. et al. The Dynamic Chemistry of Molecular Borromean Rings and Solomon Knots. *Chemistry—A European Journal* 16, 12570-12581, doi:10.1002/chem.201001806 (2010).
39 Forgan, R. S., Sauvage, J.-P. & Stoddart, J. F. Chemical Topology: Complex Molecular Knots, Links, and Entanglements. *Chem. Rev. (Washington, D.C., U. S.)* 111, 5434-5464, doi:10.1021/cr200034u (2011).
40 Chambron, J.-C. & Sauvage, J.-P. Topologically complex molecules obtained by transition metal templation: it is the presentation that determines the synthesis strategy. *New Journal of Chemistry* 37, 49-57, doi:10.1039/C2NJ40555E (2013).
41 Ronson, T. K., Zarra, S., Black, S. P. & Nitschke, J. R. Metal-organic container molecules through subcomponent self-assembly. *Chemical Communications* 49, 2476-2490, doi:10.1039/C2CC36363A (2013).
42 Smulders, M. M. J., Riddell, I. A., Browne, C. & Nitschke, J. R. Building on architectural principles for three-dimensional metallosupramolecular construction. *Chemical Society Reviews* 42, 1728-1754, doi:10.1039/C2CS35254K (2013).
43 Castilla, A. M., Ramsay, W. J. & Nitschke, J. R. Stereochemistry in Subcomponent Self-Assembly. *Accounts of Chemical Research* 47, 2063-2073, doi:10.1021/ar5000924 (2014).
44 Campos-Fernández, C. S., Clérac, R. & Dunbar, K. R. A One-Pot, High-Yield Synthesis of a Paramagnetic Nickel Square from Divergent Precursors by Anion Template Assembly. *Angewandte Chemie International Edition* 38, 3477-3479, doi:10.1002/(SICI) 1521-3773(19991203)38: 23<3477::AID-ANIE3477>3.0.CO; 2-P (1999).
45 Campos-Fernández, C. S., Clérac, R., Koomen, J. M., Russell, D. H. & Dunbar, K. R. Fine-Tuning the Ring-Size of Metallacyclophanes: A Rational Approach to Molecular Pentagons. *Journal of the American Chemical Society* 123, 773-774, doi:10.1021/ja002960r (2001).
46 Chifotides, H. T. & Dunbar, K. R. Anion-π Interactions in Supramolecular Architectures. *Accounts of Chemical Research* 46, 894-906, doi:10.1021/ar300251k (2013).
47 Holliday, B. J. & Mirkin, C. A. Strategies for the Construction of Supramolecular Compounds through Coordination Chemistry. *Angewandte Chemie International Edition* 40, 2022-2043, doi:10.1002/1521-3773 (20010601)40:11<2022::AID-ANIE2022>3.0.CO; 2-D (2001).
48 Yoshizawa, M. & Klosterman, J. K. Molecular architectures of multi-anthracene assemblies. *Chemical Society Reviews* 43, 1885-1898, doi:10.1039/C3CS60315F (2014).

49 Sun, Q.-F. et al. Self-Assembled M24L48 Polyhedra and Their Sharp Structural Switch upon Subtle Ligand Variation. *Science (Washington, D.C., U. S.)* 328, 1144-1147, doi:10.1126/science.1188605 (2010).

50 Tominaga, M. et al. Finite, spherical coordination networks that self-organize from 36 small components. *Angew. Chem., Int. Ed.* 43, 5621-5625, doi:10.1002/anie.200461422 (2004).

51 Chand, D. K., Biradha, K. & Fujita, M. Self-assembly of a novel macrotricyclic Pd(metallocage encapsulating a nitrate ion. *Chemical Communications*, 1652-1653, doi: 10.1039/B104853H (2001).

52 Owens, T. D., Hollander, F. J., Oliver, A. G. & Ellman, J. A. Synthesis, Utility, and Structure of Novel Bis(sulfinyl)imidoamidine Ligands for Asymmetric Lewis Acid Catalysis. *Journal of the American Chemical Society* 123, 1539-1540, doi:10.1021/ja005635c (2001).

53 Su, C.-Y., Cai, Y.-P., Chen, C.-L., Zhang, H.-X. & Kang, B.-S. Coordination-directed assembly of trigonal and tetragonal molecular boxes encapsulating anionic guests. *Journal of the Chemical Society, Dalton Transactions*, 359-361, doi:10.1039/B010118O (2001).

54 Liu, Z.-M. et al. Assembly of Trigonal and Tetragonal Prismatic Cages from Octahedral Metal Ions and a Flexible Molecular Clip. *Inorganic Chemistry* 46, 5814-5816, doi:10.1021/ic062270+ (2007).

55 Desmarets, C., Policar, C., Chamoreau, L.-M. & Amouri, H. Design, Self-Assembly, and Molecular Structures of 3D Copper(II) Capsules Templated by BF4-Guest Anions. *European Journal of Inorganic Chemistry* 2009, 4396-4400, doi:10.1002/ejic.200900606 (2009).

56 Liu, H.-K. et al. Discrete M2L2 metallacycle and M2L4 cage frameworks and anion competitive reactions of Cu2L4 type receptor. *Inorganic Chemistry Communications* 12, 457-460, doi: dx.doi.org/10.1016/j.inoche.2009.03.017 (2009).

57 Liao, P. et al. Two-component control of guest binding in a self-assembled cage molecule. *Chemical Communications* 46, 4932-4934, doi:10.1039/C0CC00234H (2010).

58 Kishi, N., Li, Z., Yoza, K., Akita, M. & Yoshizawa, M. An M2L4 Molecular Capsule with an Anthracene Shell: Encapsulation of Large Guests up to 1 nm. *Journal of the American Chemical Society* 133, 11438-11441, doi: 10.1021/ja2037029 (2011).

59 Li, Z., Kishi, N., Hasegawa, K., Akita, M. & Yoshizawa, M. Highly fluorescent M2L4 molecular capsules with anthracene shells. *Chemical Communications* 47, 8605-8607, doi:10.1039/C1CC12946E (2011).

60 Li, Z., Kishi, N., Yoza, K., Akita, M. & Yoshizawa, M. Isostructural M2L4 Molecular Capsules with Anthracene Shells: Synthesis, Crystal Structures, and Fluorescent Properties. *Chemistry—A European Journal* 18, 8358-8365, doi:10.1002/chem.201200155 (2012).

61 Barbour, L. J., Orr, G. W. & Atwood, J. L. An intermolecular (H2O)10 cluster in a solid-state supramolecular complex. *Nature* 393, 671-673, doi: www.nature.com/nature/journal/v393/n6686/suppinfo/393671a0_S1.html (1998).

62 Yue, N. L. S., Eisler, D. J., Jennings, M. C. & Puddephatt, R. J. Macrocyclic and Lantern Complexes of Palladium (II) with Bis(amidopyridine) Ligands: Synthesis, Structure, and Host-Guest Chemistry. *Inorganic Chemistry* 43, 7671-7681, doi:10.1021/ic048893+ (2004).

63 Amouri, H. et al. Host-Guest Interactions: Design Strategy and Structure of an Unusual Cobalt Cage That Encapsulates a Tetrafluoroborate Anion. *Angewandte Chemie International Edition* 44, 4543-4546, doi:10.1002/anie.200500786 (2005).

64 Clever, G. H., Tashiro, S. & Shionoya, M. Inclusion of Anionic Guests inside a Molecular Cage with Palladium (II) Centers as Electrostatic Anchors. *Angewandte Chemie International Edition* 48, 7010-7012, doi:10.1002/anie.200902717 (2009).

65 Hirakawa, T. et al. Removal of Perchlorate Anion from an Aqueous Solution by Encapsulation in an Anion-templated Self-assembled Molecular Capsule. *Chemistry Letters* 38, 290-291, doi:10.1246/cl.2009.290 (2009).

66 Yan, X. et al. Responsive Supramolecular Polymer Metallogel Constructed by Orthogonal Coordination-Driven Self-Assembly and Host/Guest Interactions. *Journal of the American Chemical Society* 136, 4460-4463, doi: 10.1021/ja412249k (2014).

67 Yan, X. et al. Hierarchical Self-Assembly: Well-Defined Supramolecular Nanostructures and Metallohydrogels via Amphiphilic Discrete Organoplatinum(II) Metallacycles. *Journal of the American Chemical Society* 135, 14036-14039, doi:10.1021/ja406877b (2013).

68 Yan, X. et al. Supramolecular polymers with tunable topologies via hierarchical coordination-driven self-assembly and hydrogen bonding interfaces. *Proceedings of the National Academy of Sciences* 110, 15585-15590, doi:10.1073/pnas.1307472110 (2013).

69 Crystals were obtained by vapor diffusion of ethyl acetate into DMSO-$d^6$ at 23° C.

70 The chemical shifts and symmetric nature of the broad resonances mapped well onto the solution $^1$H NMR spectra of the L1-spheres and soluble polymer network fragments derived from B-3.

71 Yoneya, M., Tsuzuki, S., Yamaguchi, T., Sato, S. & Fujita, M. Coordination-Directed Self-Assembly of M12L24 Nanocage: Effects of Kinetic Trapping on the Assembly Process. *ACS Nano* 8, 1290-1296, doi:10.1021/nn404595j (2014).

72 Yoneya, M., Yamaguchi, T., Sato, S. & Fujita, M. Simulation of Metal-Ligand Self-Assembly into Spherical Complex M6L8. *J. Am. Chem. Soc.* 134, 14401-14407, doi:10.1021/ja303542r (2012).

73 Greater junction functionality translates into smaller $\mu$ for the same v in the phantom network model equation $G'_{phantom} = RT(v-\mu)\varphi \cdot 1/3$.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A macromer of Formula (B):

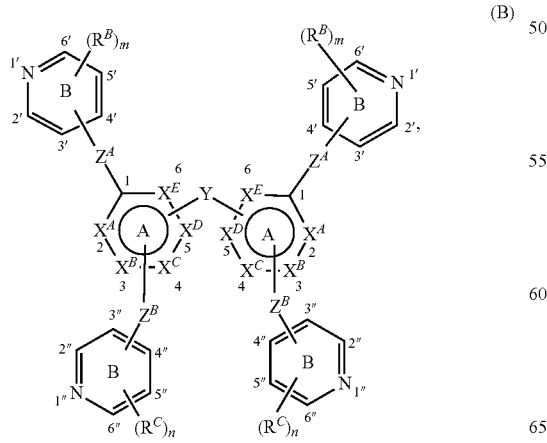

or a salt thereof, wherein:
each of

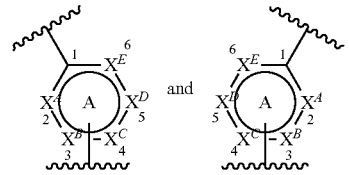

is Ring A, wherein Ring A is of the formula:

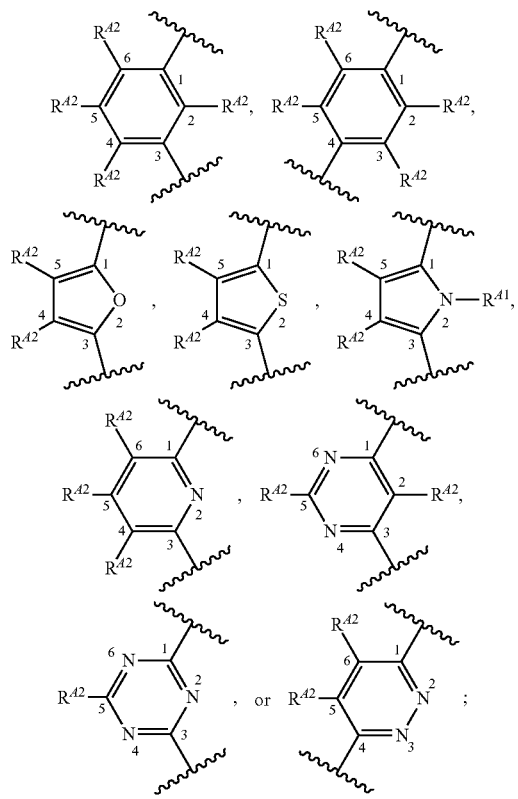

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)O$R^a$, —C(=O)N($R^a$)$_2$, or a nitrogen protecting group;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —NR$^a$C(=O)$R^a$, —NR$^a$C(=O)O$R^a$, —NR$^a$C(=O)N($R^a$)$_2$, —OC(=O)$R^a$, —OC(=O)O$R^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

m is 0, 1, 2, 3, or 4;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

n is 0, 1, 2, 3, or 4;

$Z^A$ is a bond or a saturated or unsaturated, $C_{1-4}$ hydrocarbon chain, optionally wherein one or more chain atoms of the saturated or unsaturated, $C_{1-4}$ hydrocarbon chain are independently replaced with —O—, —S—, —$NR^{ZA}$—, —N=, or =N—, wherein each instance of $R^{ZA}$ is independently hydrogen, unsubstituted $C_{1-6}$ alkyl, or a nitrogen protecting group, and optionally wherein one or more chain atoms of the saturated or unsaturated, $C_{1-4}$ hydrocarbon chain are independently substituted with one or more substituents independently selected from the group consisting of =O and halogen;

$Z^B$ is a bond or a saturated or unsaturated, $C_{1-4}$ hydrocarbon chain, optionally wherein one or more chain atoms of the saturated or unsaturated, $C_{1-4}$ hydrocarbon chain are independently replaced with —O—, —S—, —$NR^{ZB}$—, —N=, or =N—, wherein each instance of $R^{ZB}$ is independently hydrogen, unsubstituted $C_{1-6}$ alkyl, or a nitrogen protecting group, and optionally wherein one or more chain atoms of the saturated or unsaturated, $C_{1-4}$ hydrocarbon chain are independently substituted with one or more substituents independently selected from the group consisting of =O and halogen; and Y is a saturated or unsaturated, $C_{30-3000}$ hydrocarbon chain, optionally wherein one or more chain atoms of the saturated or unsaturated, $C_{30-3000}$ hydrocarbon chain are independently replaced with —O—, —S—, —$NR^Y$—, =N—, or —N=, wherein each instance of $R^Y$ is independently hydrogen, unsubstituted $C_{1-6}$ alkyl, or a nitrogen protecting group, and optionally wherein one or more chain atoms of the saturated or unsaturated, $C_{30-3000}$ hydrocarbon chain are independently substituted with one or more substituents independently selected from the group consisting of =O, halogen, and unsubstituted $C_{1-6}$ alkyl.

2. The macromer of claim 1, wherein the macromer is of the formula:

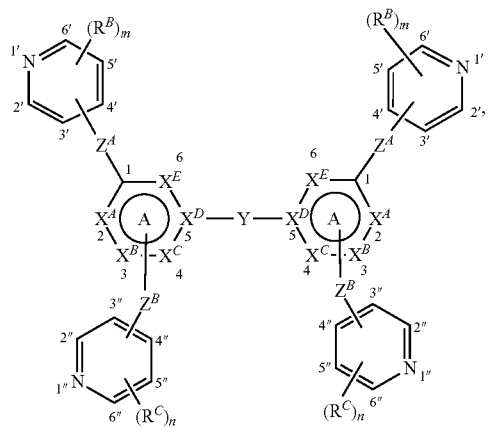

or a salt thereof.

3. The macromer of claim 1, wherein the macromer is of the formula:

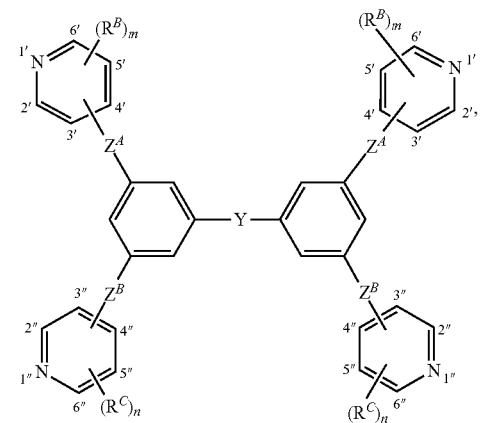

or a salt thereof.

4. The macromer of claim 1, wherein the macromer is of the formula:
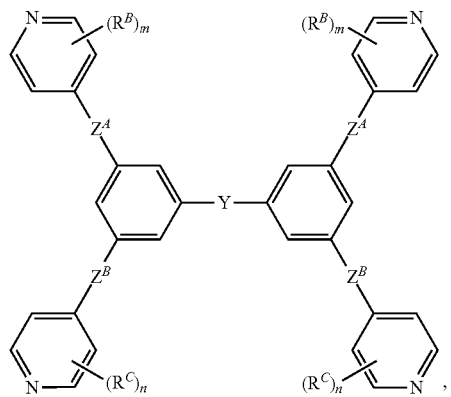
or a salt thereof.
5. The macromer of claim 1, wherein the macromer is of the formula:
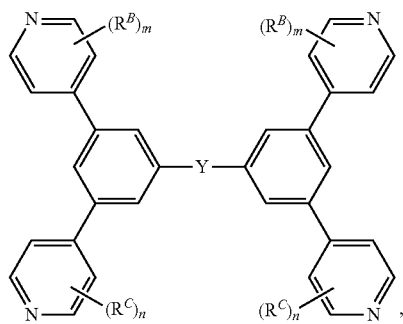
or a salt thereof.
6. The macromer of claim 1, wherein the macromer is of the formula:
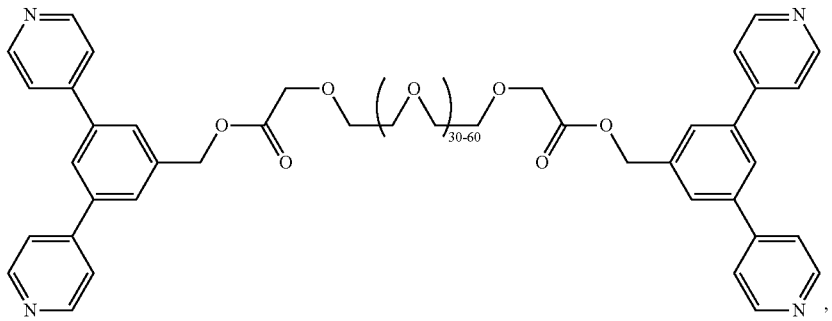
or a salt thereof.
7. A macromer of the formula:
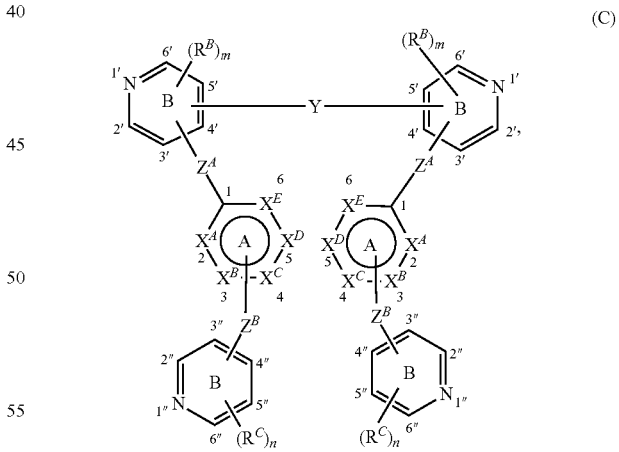
(C)
each of
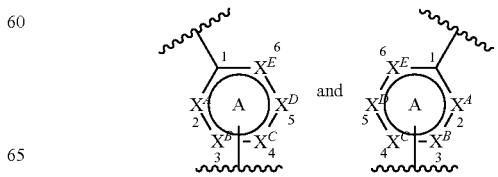
and is Ring A, wherein Ring A is of the formula:

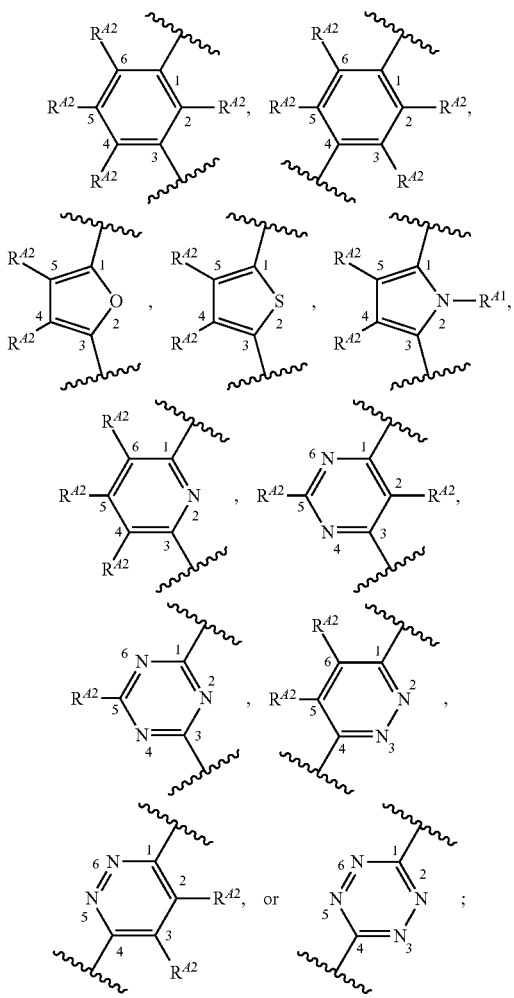

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)O$R^a$, —C(=O)N($R^a$)$_2$, or a nitrogen protecting group;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$), —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

m is 0, 1, 2, or 3;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C(=O)O$R^a$, —N$R^a$C(=O)N($R^a$)$_2$, —OC(=O)$R^a$, —OC(=O)O$R^a$, or —OC(=O)N($R^a$)$_2$;

n is 0, 1, 2, 3, or 4;

$Z^A$ is a bond or a saturated or unsaturated, $C_{1-4}$ hydrocarbon chain, optionally wherein one or more chain atoms of the saturated or unsaturated, $C_{1-4}$ hydrocarbon chain are independently replaced with —O—, —S—, —NR$^{ZA}$—, —N=, or =N—, wherein each instance of $R^{ZA}$ is independently hydrogen, unsubstituted $C_{1-6}$ alkyl, or a nitrogen protecting group, and optionally wherein one or more chain atoms of the saturated or unsaturated, $C_{1-4}$ hydrocarbon chain are independently substituted with one or more substituents independently selected from the group consisting of =O and halogen;

$Z^B$ is a bond or a saturated or unsaturated, $C_{1-4}$ hydrocarbon chain, optionally wherein one or more chain atoms of the saturated or unsaturated, $C_{1-4}$ hydrocarbon chain are independently replaced with —O—, —S—, —NR$^{ZB}$—, —N=, or =N—, wherein each instance of $R^{ZB}$ is independently hydrogen, unsubstituted $C_{1-6}$ alkyl, or a nitrogen protecting group, and optionally wherein one or more chain atoms of the saturated or unsaturated, $C_{1-4}$ hydrocarbon chain are independently substituted with one or more substituents independently selected from the group consisting of =O and halogen; and Y is a saturated or unsaturated, $C_{30-3000}$ hydrocarbon chain, optionally wherein one or more chain atoms of the saturated or unsaturated, $C_{30-3000}$ hydrocarbon chain are independently replaced with —O—, —S—, —NR$^Y$—, =N—, or —N=, wherein each instance of $R^Y$ is independently hydrogen, unsubstituted $C_{1-6}$ alkyl, or a nitrogen protecting group, and optionally wherein one or more chain atoms of the saturated or unsaturated, $C_{30-3000}$ hydrocarbon chain are independently substituted with one or more substituents independently selected from the group consisting of =O, halogen, and unsubstituted $C_{1-6}$alkyl:

or a salt thereof.

8. The macromer of claim 1, or a salt thereof, wherein Ring A is of the formula:

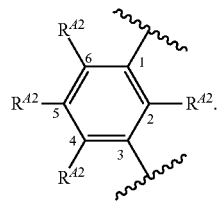

9. The macromer of claim 1, or a salt thereof, wherein Ring A is of the formula:

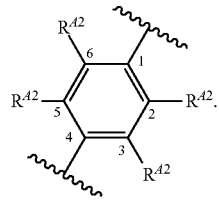

10. The macromer of claim 1, or a salt thereof, wherein Ring A is of the formula:

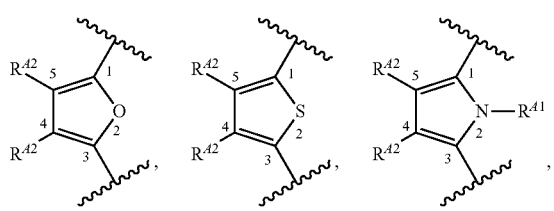

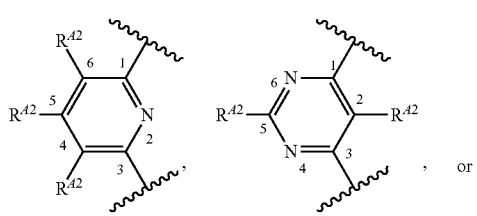

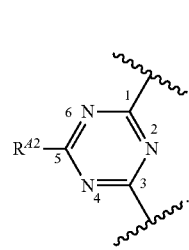

11. The macromer of claim 1, or a salt thereof, wherein Ring A is of the formula:

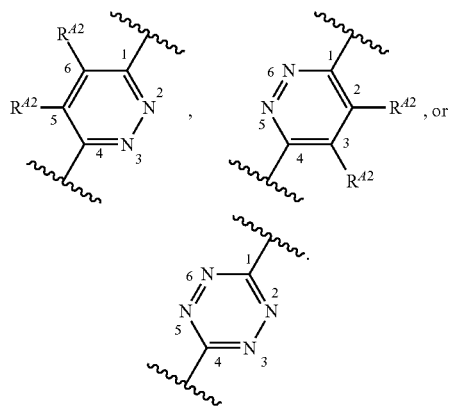

12. The macromer of claim 1, or a salt thereof, wherein Ring B is of the formula:

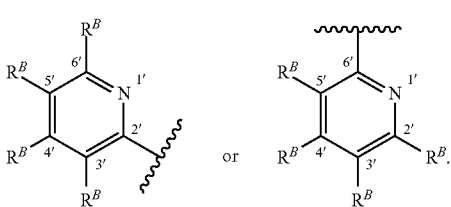

13. The macromer of claim 1, or a salt thereof, wherein Ring B is of the formula:

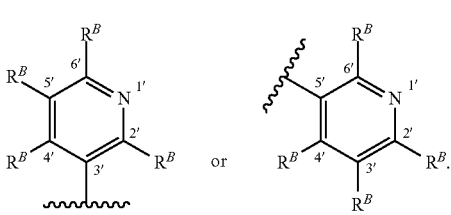

14. The macromer of claim 1, or a salt thereof, wherein Ring B is of the formula:

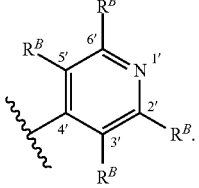

15. The macromer of claim 1, or a salt thereof, wherein each instance of $R^{A1}$ is hydrogen, and each instance of $R^{A2}$ is hydrogen.

16. The macromer of claim 1, or a salt thereof, wherein each one of m and n is 0.

17. The macromer of claim 1, or a salt thereof, wherein each one of $Z^A$ and $Z^B$ is a bond.

18. The macromer of claim 1, or a salt thereof, wherein each one of $Z^A$ and $Z^B$ is —C≡C—, —C≡C—C≡C—, or a moiety of the formula:

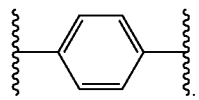 [SMILES: *c1ccc(*)cc1]

19. The macromer of claim 1, or a salt thereof, wherein Y is a saturated or unsaturated, $C_{80-1500}$ hydrocarbon chain, optionally wherein not more than one half of all instances of the chain atoms of the saturated or unsaturated, $C_{80-1500}$ hydrocarbon chain are independently replaced with —O—, —S—, or —NR$^Y$—, and optionally wherein one or more chain atoms of the saturated or unsaturated, $C_{80-1500}$ hydrocarbon chain are independently substituted with one or more substituents independently selected from the group consisting of =O, halogen, and unsubstituted $C_{1-6}$ alkyl.

20. The macromer of claim 1, or a salt thereof, wherein Y is of the formula:

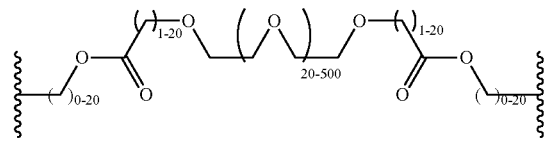

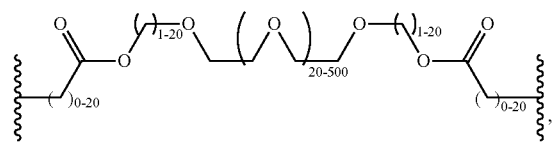

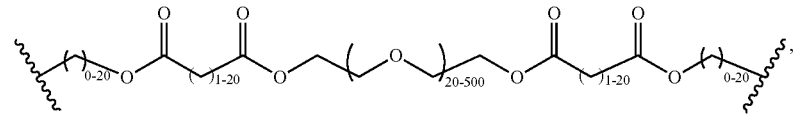

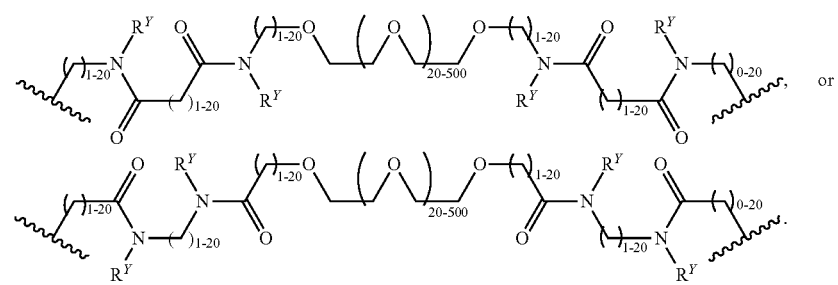

or

21. The macromer of claim 1, or a salt thereof, wherein each chain atom, with any substituents thereon, of Y is independently —CH$_2$—, —CH(unsubstituted $C_{1-6}$ alkyl)-, —C(unsubstituted $C_{1-6}$ alkyl)$_2$-, —C(=O)—, —O—, —NH—, —N(unsubstituted $C_{1-6}$ alkyl)-, —N(nitrogen protecting group)-, or —CF$_2$—.

22. The macromer of claim 7, wherein the macromer is of the formula:

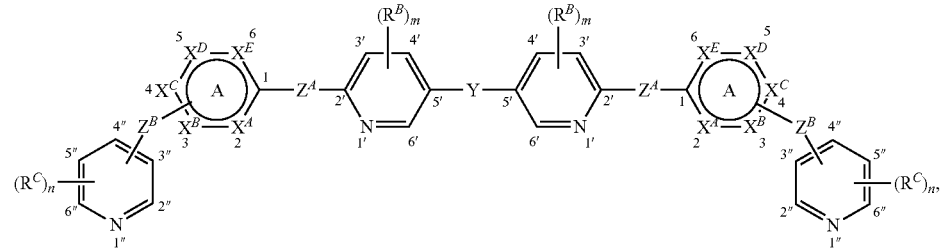

or a salt thereof.

23. The macromer of claim 7, wherein the macromer is of the formula:

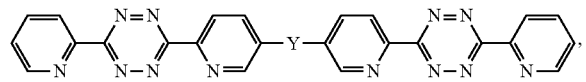

or a salt thereof.

24. The macromer of claim 7, or a salt thereof, wherein Ring A is of the formula:

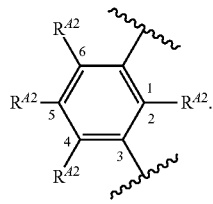

25. The macromer of claim 7, or a salt thereof, wherein Ring A is of the formula:

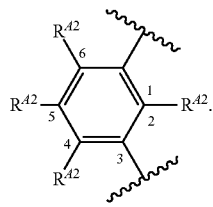

26. The macromer of claim 7, or a salt thereof, wherein Ring A is of the formula:

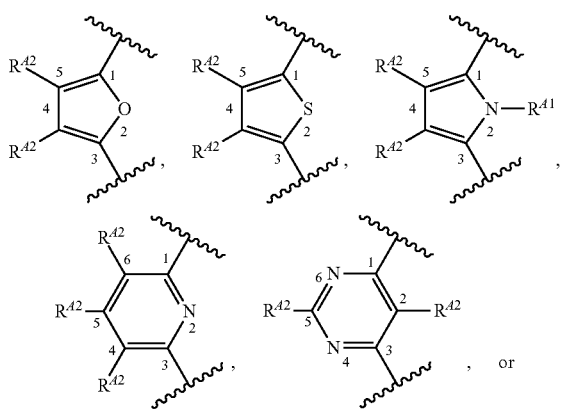

27. The macromer of claim 7, or a salt thereof, wherein Ring A is of the formula:

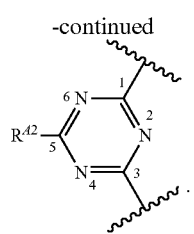

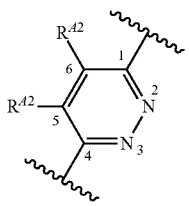

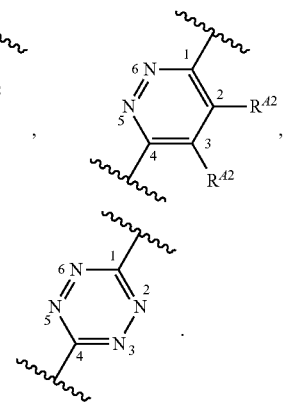

28. The macromer of claim 7, or a salt thereof, wherein each instance of $R^{A1}$ is hydrogen, and each instance of $R^{A2}$ is hydrogen.
29. The macromer of claim 7, or a salt thereof, wherein each one of m and n is 0.
30. The macromer of claim 7, or a salt thereof, wherein each one of $Z^A$ and $Z^B$ is a bond.
31. The macromer of claim 7, or a salt thereof, wherein each one of $Z^A$ and $Z^B$ is —C≡C—, —C≡C—C≡C—, or a moiety of the formula:

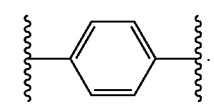 [SMILES: *c1ccc(*)cc1]

32. The macromer of claim 7, or a salt thereof, wherein Y is a saturated or unsaturated, $C_{80-1500}$ hydrocarbon chain, optionally wherein not more than one half of all instances of the chain atoms of the saturated or unsaturated, $C_{80-1500}$ hydrocarbon chain are independently replaced with —O—, —S—, or —$NR^Y$—, and optionally wherein one or more chain atoms of the saturated or unsaturated, $C_{80-1500}$ hydrocarbon chain are independently substituted with one or more substituents independently selected from the group consisting of =O, halogen, and unsubstituted $C_{1-6}$ alkyl.
33. The macromer of claim 7, or a salt thereof, wherein Y is of the formula:

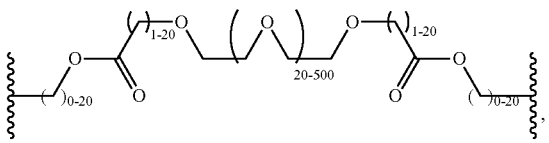

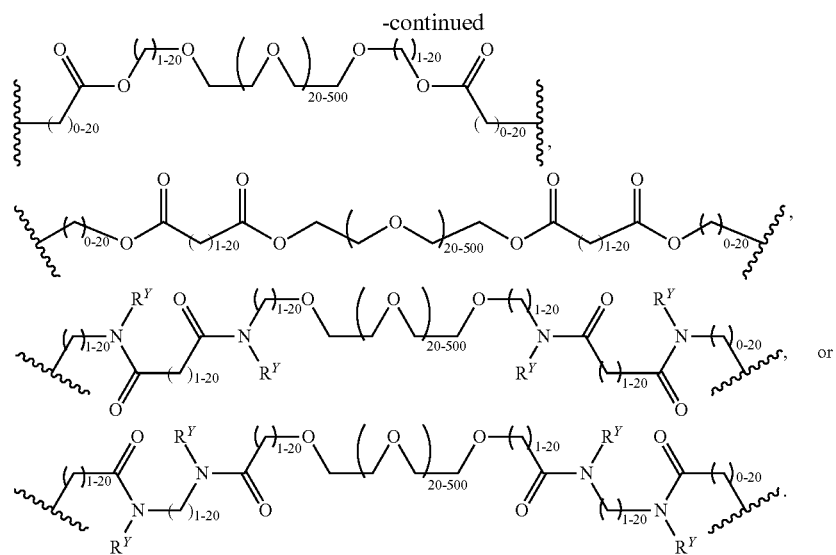
34. The macromer of claim 7, or a salt thereof, wherein each chain atom, with any substituents thereon, of Y is independently —$CH_2$—, —CH(unsubstituted $C_{1-6}$ alkyl)—, —C (unsubstituted $C_{1-6}$ alkyl)$_2$—, —C(=O)—, —O—, —NH—, —N(unsubstituted $C_{1-6}$ alkyl)—, —N(nitrogen protecting group)—, or —$CF_2$—.
35. The macromer of claim 7, wherein the macromer is of the formula:
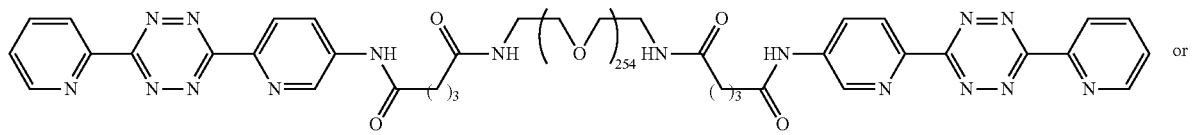
(C-1)
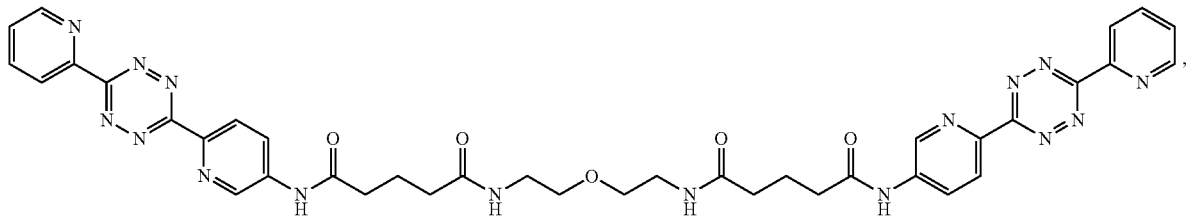
(C-2)
or a salt thereof.